(12) United States Patent
Sun et al.

(10) Patent No.: US 9,222,113 B2
(45) Date of Patent: *Dec. 29, 2015

(54) MICROORGANISMS AND METHODS FOR THE COPRODUCTION 1,4-BUTANEDIOL AND GAMMA-BUTYROLACTONE

(71) Applicant: Genomatica, Inc., San Diego, CA (US)

(72) Inventors: Jun Sun, San Diego, CA (US); Mark J. Burk, San Diego, CA (US); Anthony P. Burgard, Bellefonte, PA (US); Robin E. Osterhout, San Diego, CA (US); Wei Niu, Lincoln, NE (US); John D. Trawick, La Mesa, CA (US); Robert Haselbeck, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/936,878

(22) Filed: Jul. 8, 2013

(65) Prior Publication Data

US 2014/0162327 A1 Jun. 12, 2014

Related U.S. Application Data

(63) Continuation of application No. 12/940,021, filed on Nov. 4, 2010, now Pat. No. 8,530,210.

(60) Provisional application No. 61/264,598, filed on Nov. 25, 2009.

(51) Int. Cl.
*C12P 7/18* (2006.01)
*C12P 17/04* (2006.01)
*C12N 1/20* (2006.01)

(52) U.S. Cl.
CPC . *C12P 17/04* (2013.01); *C12N 1/20* (2013.01); *C12P 7/18* (2013.01)

(58) Field of Classification Search
IPC ................................................ C12P 7/18,17/04
See application file for complete search history.

(56) References Cited

U.S. PATENT DOCUMENTS

| | | |
|---|---|---|
| 4,048,196 A | 9/1977 | Broecker et al. |
| 4,301,077 A | 11/1981 | Pesa et al. |
| 4,430,430 A | 2/1984 | Momose et al. |
| 4,652,685 A | 3/1987 | Cawse et al. |
| 4,876,331 A | 10/1989 | Doi |
| 5,164,309 A | 11/1992 | Gottschalk et al. |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,413,922 A | 5/1995 | Matsuyama et al. |
| 5,461,139 A | 10/1995 | Gonda et al. |
| 5,475,086 A | 12/1995 | Tobin et al. |
| 5,478,952 A | 12/1995 | Schwartz |
| 5,502,273 A | 3/1996 | Bright et al. |
| 5,516,883 A | 5/1996 | Hori et al. |
| 5,534,432 A | 7/1996 | Peoples et al. |
| 5,563,239 A | 10/1996 | Hubbs et al. |
| 5,602,321 A | 2/1997 | John |
| 5,608,146 A | 3/1997 | Frommer et al. |
| 5,610,041 A | 3/1997 | Somerville et al. |
| 5,650,555 A | 7/1997 | Somerville et al. |
| 5,663,063 A | 9/1997 | Peoples et al. |
| 5,674,978 A | 10/1997 | Tobin et al. |
| 5,705,626 A | 1/1998 | Tobin et al. |
| 5,747,311 A | 5/1998 | Jewell |
| 5,750,848 A | 5/1998 | Krüger et al. |
| 5,770,435 A | 6/1998 | Donnelly et al. |
| 5,830,716 A | 11/1998 | Kojima et al. |
| 5,846,740 A | 12/1998 | Tobin et al. |
| 5,849,894 A | 12/1998 | Clemente et al. |
| 5,869,301 A | 2/1999 | Nghiem et al. |
| 5,908,924 A | 6/1999 | Burdette et al. |
| 5,942,660 A | 8/1999 | Gruys et al. |
| 5,958,745 A | 9/1999 | Gruys et al. |
| 5,994,478 A | 11/1999 | Asrar et al. |
| 5,998,366 A | 12/1999 | Tobin et al. |
| 6,010,870 A | 1/2000 | Pelzer et al. |
| 6,011,139 A | 1/2000 | Tobin et al. |
| 6,011,144 A | 1/2000 | Steinbuchel et al. |
| 6,022,729 A | 2/2000 | Steinbuchel et al. |

(Continued)

FOREIGN PATENT DOCUMENTS

| | | |
|---|---|---|
| GB | 1230276 | 4/1971 |
| GB | 1314126 | 4/1973 |

(Continued)

OTHER PUBLICATIONS

Abe et al., "Biosynthesis from gluconate of a random copolyester consisting of 3-hydroxybutyrate and medium-chain-length 3-hydroxyalkanoates by *Pseudomonas* sp. 61-3," *Int. J. Biol. Macromol.* 16(3):115-119 (1994).

Aberhart and Hsu, "Stereospecific hydrogen loss in the conversion of [2H7]isobutyrate to beta-hydroxyisobutyrate in Pseudomonas putida. The stereochemistry of beta-hydroxyisobutyrate dehydrogenase," *J. Chem. Soc. Perkin1.* 6:1404-1406 (1979).

Abiko et al., "Localization of NAD-isocitrate dehydrogenase and glutamate dehydrogenase in rice roots: candidates for providing carbon skeletons to NADH-glutamate synthase," *Plant Cell Physiol.* 46(10):1724-1734 (2005).

Adams and Kletzin, "Oxidoreductase-type enzymes and redox proteins involved in fermentative metabolisms of hyperthermophilic Archaea," *Adv. Protein Chem.* 48:101-180 (1996).

(Continued)

*Primary Examiner* — Rosanne Kosson
(74) *Attorney, Agent, or Firm* — Jones Day

(57) ABSTRACT

The invention provides non-naturally occurring microbial organisms comprising 1,4-butanediol (14-BDO) and gamma-butyrolactone (GBL) pathways comprising at least one exogenous nucleic acid encoding a 14-BDO and GBL pathway enzyme expressed in a sufficient amount to produce 14-BDO and GBL. The invention additionally provides methods of using such microbial organisms to produce 14-BDO and GBL.

8 Claims, 11 Drawing Sheets

(56) References Cited

U.S. PATENT DOCUMENTS

| | | | |
|---|---|---|---|
| 6,080,562 A | 6/2000 | Byrom et al. |
| 6,091,002 A | 7/2000 | Asrar et al. |
| 6,111,658 A | 8/2000 | Tabata |
| 6,117,658 A | 9/2000 | Dennis et al. |
| 6,156,852 A | 12/2000 | Asrar et al. |
| 6,159,738 A | 12/2000 | Donnelly et al. |
| 6,204,341 B1 | 3/2001 | Asrar et al. |
| 6,228,579 B1 | 5/2001 | Zyskind et al. |
| 6,228,623 B1 | 5/2001 | Asrar et al. |
| 6,248,862 B1 | 6/2001 | Asrar et al. |
| 6,277,586 B1 | 8/2001 | Tobin et al. |
| 6,280,986 B1 | 8/2001 | Hespell et al. |
| 6,316,262 B1 | 11/2001 | Huisman et al. |
| 6,329,183 B1 | 12/2001 | Skraly et al. |
| RE37,543 E | 2/2002 | Krüger et al. |
| 6,361,983 B1 | 3/2002 | Ames |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,682,906 B1 | 1/2004 | Tobin et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,897,055 B2 | 5/2005 | Möckel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,067,300 B2 | 6/2006 | Emptage et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,256,021 B2 | 8/2007 | Hermann |
| 7,309,597 B2 | 12/2007 | Liao et al. |
| 7,314,974 B2 | 1/2008 | Cao et al. |
| 7,393,676 B2 | 7/2008 | Gokarn et al. |
| 7,504,250 B2 | 3/2009 | Emptage et al. |
| 7,858,350 B2 | 12/2010 | Burk et al. |
| 7,947,483 B2 | 5/2011 | Burgard et al. |
| 8,067,214 B2 | 11/2011 | Burk et al. |
| 8,530,210 B2 * | 9/2013 | Sun et al. ............... 435/158 |
| 2002/0012939 A1 | 1/2002 | Palsson |
| 2002/0164729 A1 | 11/2002 | Skraly et al. |
| 2002/0168654 A1 | 11/2002 | Maranas et al. |
| 2003/0059792 A1 | 3/2003 | Palsson et al. |
| 2003/0203459 A1 | 10/2003 | Chen et al. |
| 2003/0224363 A1 | 12/2003 | Park et al. |
| 2003/0233218 A1 | 12/2003 | Schilling |
| 2003/0233675 A1 | 12/2003 | Cao et al. |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0090645 A1 | 4/2005 | Asakura |
| 2005/0164342 A1 | 7/2005 | Tobin |
| 2005/0170480 A1 | 8/2005 | Huisman |
| 2005/0221466 A1 | 10/2005 | Liao et al. |
| 2005/0239179 A1 | 10/2005 | Skraly et al. |
| 2005/0287655 A1 | 12/2005 | Tabata et al. |
| 2006/0041152 A1 | 2/2006 | Cantrell et al. |
| 2006/0046288 A1 | 3/2006 | Ka-Yiu et al. |
| 2006/0084155 A1 | 4/2006 | Huisman |
| 2006/0134760 A1 | 6/2006 | Rieping et al. |
| 2006/0141594 A1 | 6/2006 | San et al. |
| 2007/0072279 A1 | 3/2007 | Meynial-Salles et al. |
| 2007/0087425 A1 | 4/2007 | Ohto |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0292927 A1 | 12/2007 | Donaldson et al. |
| 2008/0120732 A1 | 5/2008 | Elliot |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0229451 A1 | 9/2008 | Cao et al. |
| 2008/0261230 A1 | 10/2008 | Liao et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2008/0293125 A1 | 11/2008 | Subbian et al. |
| 2009/0023182 A1 | 1/2009 | Schilling |
| 2009/0047719 A1 | 2/2009 | Burgard et al. |
| 2009/0075351 A1 | 3/2009 | Burk et al. |
| 2009/0100536 A1 | 4/2009 | Adams et al. |
| 2009/0158452 A1 | 6/2009 | Johnson et al. |
| 2009/0246842 A1 | 10/2009 | Hawkins et al. |
| 2009/0253192 A1 | 10/2009 | Emptage et al. |
| 2009/0275096 A1 | 11/2009 | Burgard et al. |
| 2010/0099925 A1 | 4/2010 | Kharas |
| 2010/0184171 A1 | 7/2010 | Jantama et al. |
| 2010/0304453 A1 | 12/2010 | Trawick et al. |
| 2010/0330634 A1 | 12/2010 | Park et al. |
| 2011/0014669 A1 | 1/2011 | Madden et al. |
| 2011/0045575 A1 | 2/2011 | Van Dien et al. |
| 2011/0129904 A1 | 6/2011 | Burgard et al. |
| 2011/0190513 A1 | 8/2011 | Lynch |

FOREIGN PATENT DOCUMENTS

| | | | |
|---|---|---|---|
| GB | 1344557 | 1/1974 | |
| GB | 1512751 | 6/1978 | |
| JP | 62285779 | 12/1987 | |
| KR | 1020060011345 A | 2/2006 | |
| KR | 100676160 B1 | 1/2007 | |
| KR | 100679638 B1 | 1/2007 | |
| KR | 1020070021732 A | 2/2007 | |
| KR | 1020070096348 A | 10/2007 | |
| KR | 10-2009-0025902 | 3/2009 | |
| WO | WO 82/03854 | 11/1982 | |
| WO | WO 91/00917 | 1/1991 | |
| WO | WO 92/19747 | 11/1992 | |
| WO | WO 93/02187 | 2/1993 | |
| WO | WO 93/02194 | 4/1993 | |
| WO | WO 93/06225 | 4/1993 | |
| WO | WO 94/11519 | 5/1994 | |
| WO | WO 94/12014 | 6/1994 | |
| WO | WO 95/11985 | 5/1995 | |
| WO | WO 99/06532 | 2/1999 | |
| WO | WO 99/14313 | 3/1999 | |
| WO | WO 00/61763 | 10/2000 | |
| WO | WO 02/055995 | 7/2002 | |
| WO | WO 02/061115 | 8/2002 | |
| WO | WO 03/008603 | 1/2003 | |
| WO | WO 03/106998 | 12/2003 | |
| WO | WO 2004/018621 | 3/2004 | |
| WO | WO 2004/029235 | 4/2004 | |
| WO | WO 2005/026338 | 3/2005 | |
| WO | WO 2005/052135 | 6/2005 | |
| WO | WO 2007/030830 | 3/2007 | |
| WO | WO 2007/141208 | 12/2007 | |
| WO | WO 2008/018930 | 2/2008 | |
| WO | WO 2008/027742 | 6/2008 | |
| WO | WO 2008/115840 | 9/2008 | |
| WO | WO 2008115840 A2 * | 9/2008 | ............... C12N 1/21 |
| WO | WO 2008/131286 | 10/2008 | |
| WO | WO 2008/144626 | 11/2008 | |

(56) References Cited

FOREIGN PATENT DOCUMENTS

| WO | WO 2009/011974 | 1/2009 |
|---|---|---|
| WO | WO 2009/023493 | 2/2009 |
| WO | WO 2009/031766 | 3/2009 |
| WO | WO 2009/049274 | 4/2009 |
| WO | WO 2009/094485 | 7/2009 |
| WO | WO 2009/103026 | 8/2009 |
| WO | WO 2009/111513 | 9/2009 |
| WO | WO 2009/131040 | 10/2009 |
| WO | WO 2010/006076 | 1/2010 |
| WO | WO 2010/085731 | 7/2010 |
| WO | WO 2011/137192 | 11/2011 |

OTHER PUBLICATIONS

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Aidoo et al., "Cloning, sequencing and disruption of a gene from Streptomyces clavuligerus Involved in clavulanic acid biosynthesis," *Gene* 147(1):41-46 (1994).

Alber et al., "Malonyl-coenzyme a reductase in the modified 3-hydroxypropionate cycle for autotrophic carbon fixation in archaeal *Metallosphaera* and *Sulfolobus* spp.," *J. Bacteriol.* 188:8551-8559 (2006).

Alberty, "Biochemical thermodynamics," *Biochim. Biophys. Acta* 1207:1-11 (1994).

Alhapel et al., "Molecular and functional analysis of nicotinate catabolism in Eubacterium barkeri," *Proc. Natl. Acad. Sci. U.S.A.* 103(33)12341-12346 (2006).

Allen et al., "DNA sequence of the putA gene from *Salmonella typhimurium*: a bifunctional membrane-associated dehydrogenase that binds DNA," *Nucleic Acids Res.* 21:1676 (1993).

Amarasingham and Davis, "Regulation of alpha-ketoglutarate dehydrogenase formation in *Escherichia coli*," *J. Biol. Chem.* 240: 3664-3668 (1965).

Amos and McInerey, "Composition of poly-.beta.-hydroxyalkanoate from Syntrophomonas wottei grown on unsaturated fatty acid substrates," *Arch. Microbiol.* 155:103-106 (1991).

Amuro et al., "Isolation and characterization of the two distinct genes for human glutamate dehydrogenase," *Biochem. Biophys. Acta.* 1049:216-218 (1990).

Andersen and Hansen, "Cloning of the lysA gene from *Mycobacterium tuberculosis*," *Gene* 124:105-109 (1993).

Andersen et al., "A gene duplication led to specialized gamma-aminobutyrate and beta-alaine aminotransferase in yeast," *FEBS J.* 274(7):1804-1817 (2007).

Andre and Jauniaux, "Nucleotide sequence of the yeast UGA1 gene encoding GABA transaminase," *Nucleic Acids Res.* 18:3049 (1990).

Aneja and Charles, "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).

Ansorge and Kula, "Production of Recombinant L-Leucine Dehydrogenase from Bacillus cereus in Pilot Scale Using the Runaway Replication System *E. coli*[pIET98]," *Biotechnol. Bioeng.* 68(5):557-562 (2000).

Aoshima and Igarashi, "A novel biotin protein required for reductive carboxylation of 2-oxoglutarate by isocitrate dehydrogenase in Hydrogenobacter thermophilus TK-6," *Mol. Microbiol.* 51(3):791-798 (2004).

Aoshima et al., "A novel oxalosuccinate-forming enzyme involved in the reductive carboxylation of 2-oxoglutarate in Hydrogenobacter thermophilus TK-6," *Mol. Microbiol.* 62(3):748-759 (2006).

Aragon and Lowenstein, "A survey of enzymes which generate or use acetoacetyl thioesters in rat liver," *J. Biol. Chem.* 258(8):4725-4733 (1983).

Arikawa et al., "Soluble fumarate reductase isoenzymes from *Saccharomyces cerevisiae* are required for anaerobic growth," *FEMS Microbiol. Lett.* 165:111-116 (1998).

Arps et al., "Genetics of Serine Pathway Enzymes in Methylobacterium extorquens AM1: Phosphoenolpyruvate Carboxylase and Malyl Coenzyme A Lyase," *J. Bacteriol.* 175(12):3776-3783 (1993).

Asano and Kato, "Crystalline 3-methylaspartase from a facultative anaerobe, *Escherichia coli* strain YG1002," *FEMS Microbiol. Lett.* 118(3):255-258 (1994).

Asano et al., "Alteration of substrate specificity of aspartase by directed evolution," *Biomol. Eng.* 22:95-101 (2005).

Asaoka et al., "Production of 1,4-butanediol from bacillus which is fermented on sugar substrate, from which production is recovered," *Chiyoda Chem. Eng. Constr. Co.* (Official Publication Date 1987). Database WPI Week 198804 Thomson Scientific, London, GB; AN 1988-025175.

Asuncion et al., "Overexpression, purification, crystallization and data collection of 3-methylaspartase from Clostridium tetanomorphum," *Acta Crystallogr.D. Biol. Crystallogr.* 57:731-733 (2001).

Asuncion et al., "The Structure of 3-Methylaspartase from Clostridium tetanomorphum Functions via the Common Enolase Chemical Step," *J. Biol. Chem.* 277(10):8306-8311 (2002).

Atsumi et al., "Non-fermentative pathways for synthesis of branched-chain higher alcohols as biofuels," *Nature* 451(7174):86-89 (2008).

Baba et al., "Construction of *Escherichia coli* K-12 in-frame, single-gene knockout mutants: the Keio collection," *Mol. Syst. Biol.* 2:2006. 0008 (2006).

Baker and van der Drift, "Purification and properties of L-erythro-3,5-diaminohexanoate dehydrogenase from Clostridium sticklandii," *Biochemistry* 13(2):292-299 (1974).

Baker et al., "Purification and properties of L-erythro-3,5-diaminohexanoate dehydrogenase from a lysine-fermenting Clostirdium," *J. Biol. Chem.* 247(23):7724-7734 (1972).

Barker et al., "Butyryl-CoA:acetoacetate CoA-transferase from a lysine-fermenting Clostridium," *J. Biol. Chem.* 253(4):1219-1225 (1978).

Barker et al., "Pathway of Lysine Degradation in Fusobacterium nucleatum," *J. Bacteriol.* 152(1):201-207 (1982).

Barrowman et al., "Immunological comparison of microbial TPP-dependent non-oxidative alpha-keto acid decarboxylase," *FEMS Microbiology Lett.* 34:57-60 (1986).

Barthelmebs et al., "Expression of *Escherichia coli* of Native and Chimeric Phenolic Acid Decarboxylases with Modified Enzymatic activites and Method for Scrreening recombinant *E. coli* Strains Expressing These Enzymes," *Appl. Environ. Microbiol.* 67:1063-1069 (2001).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172:7035-7042 (1990).

Baum et al., "A plant glutamate decarboxylase containing a calmodulin binding domain, Cloning, sequence, and functional analysis," *J. Biol. Chem.* 268:19610-19617 (1993).

Benachenhou-Lahfa et al., "PCR-mediated cloning and sequencing of the gene encoding glutamate dehydrogenase from the archaeon Sulfolobus shilbatae: Identification of putative amino-acid signatures for extremophilic adaptation," *Gene* 140:17-24 (1994).

Berg et al., "A 3-Hydroxypropionate/4-Hydroxybutyrate Autotrophic Carbon Dioxide Assimilation Pathway in Archaea," *Science* 318:1782-1786 (2007).

Bergquist and Gibbs, "Degenerate oligonucleotide gene shuffling," *Methods Mol. Biol.* 352:191-204 (2007).

Bergquist et al., "Degenerate oligonucleotide gene shuffling (DOGS) and random drift mutagenesis (RNDN): two complementary techniques for enzyme evolution," *Biomol. Eng.* 22:63-72 (2005).

Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).

Bermejo et al., "Expression of Clostridium acetobutylicum ATCC 824 Genes in *Escherichia coli* for Acetone Production and Acetate Detoxification," *Appl. Environ. Microbiol.* 64(3):1079-1085 (1998).

(56) References Cited

OTHER PUBLICATIONS

Biellmann et al., "Aspartate-beta-semialdehyde dehydrogenase from *Escherichia coli*. Purification and general properties," *Eur. J. Biochem.* 104(1):53-58 (1980).
Biello, "Turning Bacteria into Plastic Factories," *Scientific American* 1-2 (2008). (Printed Feb. 17, 2011).
Binstock and Shulz, "Fatty acid oxidation complex from *Escherichia coli*," *Methods Enzymol.* 71 Pt C:403-411 (1981).
Birrer et al., "Electro-transformation of Clostridium beijerinckii NRRL B-592 with shuttle plasmid pHR106 and recombinant derivatives," *Appl. Microbiol. Biotechnol.* 41(1):32-38.
Bisswanger, "Substrate Specificity of the Pyruvate Dehydrogenase Complex from *Escherichi coli*," *J. Biol. Chem.* 256(2):815-822 (1981).
Blanco et al., "Critical catalytic functional groups in the mechanims of aspartate-β-semialdehyde dehydrogenase," *Acta Crystallogr. D. Biol. Crystallogr.* 60:1808-1815 (2004).
Blanco et al., "The role of substrate-binding roups in the mechanism of asparte-β-semialdehyde dehydrogenase," *Acta Crystallogr. D. Biol. Crystallog.* 60:1388-1395 (2004).
Blattner et al., "The complete genome sequence of *Escherichia coli* K-12," *Science* 277:1453-1462 (1997).
Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).
Bonnarme et al., "Itaconate biosynthesis in Aspergillus terreus," *J. Bacteriol.* 177(12):3573-3578 (1995).
Bonner and Bloch, "Purification and Properties of Fatty Acyl Thiesterase I from *Escherichia coli*," *J. Biol. Chem.* 247(10) 3123-3133 (1972).
Botsford et al., "Accumulation of glutamate by *Salmonella typhimurium* in response to osmotic stress," *Appl. Environ. Microbiol.* 60:2568-2574 (1994).
Boning et al., "Substrate Specificity of the 3-Methylaspartate Ammonia-Lyase Reaction: Observation of Differential Relative Reaction rates for Substrate-Product Pairs," *Biochemistry* 27:2953-2955 (1988).
Bower et al., "Cloning, Sequencing, and Characterization of the Bacillus subtilis Biotin Biosynthetic Operon," *J. Bacteriol.* 178(14):4122-4130 (1996).
Boynton et al., "Cloning, sequencing, and expression of clustered genes encoding beta-hydroxybutyryl-coenzyme A (CoA) dehydrogenase, crotonase, and butyryl-CoA dehydrogenase from Clostridium acetobutylicum ATCC 824," *J. Bateriol.* 178(11):3015-3024 (1996).
Branden et al., "Introduction to Protein Structure," *Garland Publishing Inc.*, New York, p. 247 (1991).
Brandt et al., "Ability of the phototrophic bacterium Rhodospirillum rubrum to produce various poly (beta-hydroxyalkanoates): potential sources for biodegradable polyesters," *Int. J. Biol. Macromol.* 11:49-55 (1989).
Branlant and Branlant, "Nucleotide sequence of the *Escherichia coli* gap gene. Differente evolutionay behaviour of the Nad+-binding domain and of the catalytic domain of D-glyceraldehyde-3-phosphate dehydrogenase," *Eur. J. Biochem.* 150(1):61-66 (1985).
Brasen and Schonheit, "Unusual ADP-forming acetyl-coenzyme A synthetases from the mesophilic halophilic eurarchaeon Haloarcula marismortui and from the hyperthermophilic crenarchaeon Pyrobaculum aerophilum," *Arch. Microbiol.* 182:277-287 (2004).
Bravo et al., "Reliable, sensitive, rapid and quantitative enzyme-based assay for gamma-hydroxybutyric acid (GHB)," *J. Forensic Sci.* 49:379-387 (2004).
Breitkreuz et al., "A novel gamma-hydroxybutyrate dehydrogenase: identification and expression of an Arabidopsis cDNA and potential role under oxygen deficiency," *J. Biol. Chem.* 278:41552-41556 (2003).
Bremer, "Pyruvate Dehydrogenase, Substrate Specificity and Product Inhibition," *Eur. J. Biochem.* 8:535-540 (1969).

Bridger et al., "The subunits of succinyl-coenzyme. A synthetase—function and assembly," In Krebs' Citric Acid Cycle—Half a Century and Still Turning, *Biochem. Soc. Symp.* 54:103-111.
Brosch et al., "Genome plasticity of BCG and impact on vaccine efficacy," *Proc. Natl. Acad. Sci. U.S.A.* 104(13):5596-5601 (2007).
Bu et al., "Two human glutamate decarboxylases, 65-kDa GAD and 67-kDa GAD, are each encoded by a single gene," *Proc. Natl. Acad. Sci. U.S.A.* 89(6):2115-2119 (1992).
Bu, et al., "The exon-intron organization of the genes (GAD1 and GAD2) encoding two human glutamate decarboxylases (GAD67 and GAD65) suggests that they derive from a common ancestral GAD," *Genomics* 21:222-228 (1994).
Buck and Guest, "Overexpression and site-directed mutagenesis of the succinyl-CoA synthetase of *Escherichia coli* and nucleotide sequence of a gene (g30) that is adjacent to the suc operon," *Biochem. J.* 260(3):737-747 (1989).
Buck et al., "Primary Structure of the Succinyl-CoA Synthetase of *Escherichia coli*," *Biochemistry* 24:6245-6252 (1985).
Buck et al., "Cloning and expression of the succinyl-CoA synthetase genes of *Escherichia coli* K12," *J. Gen. Microbiol.* 132(6):1753-1762 (1986).
Buckel et al., "Glutaconate CoA-Transferase from Acidaminococcus fermentans," *Eur. J. Biochem.* 118:315-321 (1981).
Bult et al., "Complete genome sequence of the methanogenic archaeon, Methanococcus jannaschii," *Science* 273:1058-1073 (1996).
Burgard and Maranas, "Probing the Performance Limits of the *Escherichia coli* Metabolic Network Subject to Gene Additions or Deletions," *Biotechnol. Bioeng.* 74(5):364-375 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burke et al, "The Isolation, Characterization, and Sequence of the Pyruvate Kinase Gene of *Saccharomyces cerevisiae*," *J. Biol. Chem.* 258(4):2193-2201 (1983).
Buu et al., "Functional Characterization and Localization of Acetyl-CoA Hydrolase, Ach1p, in *Saccharomyces cerevisiae*," *J. Biol. Chem.* 278(19):17203-17209 (2003).
Campbell et al., "A new *Escherichia coli* metabolic competency: growth on fatty acids by a novel anaerobic β-oxidation pathway," *Mol. Microbiol.* 47(3):793-805 (2003).
Cary et al., "Cloning and expression of Clostridium acetobutylicum ATCC 824 acetoacetyl-coenzyme A:acetate/butyrate:coenzyme A-transferase in *Escherichia coli*," *Appl. Environ. Microbiol.* 56(6):1576-1583 (1990).
Cary et al., "Cloning and expression of Clostridium acetobutylicum phosphotransbutyrylase and butyrate kinase genes in *Escherichia coli*," *J. Bacteriol.* 170(10):4613-4618 (1988).
Caspi et al., "MetaCyc: a multiorganism database of metabolic pathways and enzymes," *Nucleic Acids Res.* 34(Database issue):D511-D516 (2006).
Causey et al., "Engineering *Escherichia coli* for efficient conversion of glucose to pyruvate," *Proc. Natl. Acad. Sci. U.S.A.* 101:2235-2240 (2004).
Cha and Parks, Jr., "Succinic Thiokinase. I. Purification of the Enzyme from Pig Heart," *J. Biol. Chem.* 239:1961-1967 (1964).
Chandra Raj et al., "Pyruvate decarboxylase: a key enzyme for the oxidative metabolism of lactic acid by Acetobacter pasteruianus," *Arch. Microbiol.* 176:443-451 (2001).
Chavez et al., "The NADP-glutamate dehydrogenase of the cyanobacterium Synechocystis 6803: cloning, transcriptional analysis and disruption of the gdhA gene," *Plant Mol. Biol.* 28:173-188 (1995).
Chen and Hiu, "Acetone-Butanol-Isopropanol Production by Clostridium beijerinckii (Synonym, Clostridium butylicum)," *Biotechnology Letters* 8(5):371-376 (1986).
Chen and Lin, "Regulation of the adhE gene, which encodes ethanol dehydrogenase in *Escherichia coli*," *J. Bacteriol.* 173(24):8009-8013 (1991).

(56) References Cited

OTHER PUBLICATIONS

Chen et al., "A novel lysine 2,3-aminomutase encoded by the yodO gene of Bacillus subtilis: characterization and the observation of organic radical intermediates," *Biochem. J.* 348:539-549.

Chen et al., "Cloning, Sequencing, Heterologous Expression, Purification, and Characterization of Adenosylcobalamin-dependent D-Ornithine Aminomutase from Clostridium sticklandii," *J. Biol. Chem.* 276:44744-44750 (2001).

Chicco et al., "Regulation of Gene Expression of Branched-chain Keto Acid Dehydrogenase Complex in Primary Cultured Hepatocytes by Dexamethasone and cAMP Analog," *J. Biol. Chem.* 269(30):19427-19434 (1994).

Chirpich et al., "Lysine 2,3-Aminomutase. Purification and properties of a pyridoxal phosphate and S-adenosylmethionine-activated enzyme," *J. Biol. Chem.* 245(7):1778-1789 (1970).

Cho et al., "Critical residues for the coenzyme specificity of NAD+-deptendent 15-hydroxyprtaglandin dehydrogenase," *Arch. Biochem. Biophys.* 419(2): 139-146 (2003).

Chowdhury et al., "Cloning and Overexpression of the 3-Hydroxyisobutyrate Dehydrogenase Gene from Pseudomonas putida E23," *Biosci. Biotechnol. Biochem.* 67(2):438-441 (2003).

Chowdhury et al., "3-Hydroxyisobutyrate dehydrogenase from Pseudomonas putida E23: purification and characterization," *Biosci. Biotechnol. Biochem.* 60(12):2043-2047 (1996).

Christenson et al., "Kinetic analysis of the 4-methylideneimidazole-5-one-containing tyrosine aminomutase in enediyne antitumor antibiotic C-1027 biosynthesis," *Biochemistry* 42(43):12708-12718 (2003).

Chu et al., "Enzymatically active truncated cat brain glutamate decarboxylase: expression, purification, and absorption spectrum," *Arch. Biochem. Biophys.* 313:287-295 (1994).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-hydroxyacid dehydrogenase with new substrate specificity," *Biochem. Biophys. Res. Commun.* 148:15-23 (1987).

Clausen et al., "PAD1 encodes phenylacrylic acid decarboxylase which confers resistance to cinnamic acid in *Saccharomyces cerevisiae*," *Gene* 142:107-112 (1994).

Cock et al., "A nuclear gene with many introns encoding ammonium-inductible chloroplastic NADP-specific glutamate dehydrogenase(s) in Chlorella sorokiniana," *Plant Mol. Biol.* 17:1023-1044 (1991).

Coco et al., "DNA shuffling method for generating highly recombined genes and evolved enzymes," *Nat. Biotechnol.* 19(4):354-359 (2001).

Cogoni et al., "*Saccharomyces cerevisiae* has a single glutamate synthase gene coding for a plant-like high-molecular-weight polypeptide," *J. Bacteriol.* 177:792-798 (1995).

Colby and Chen, "Purification and properties of 3-Hydroxybutyryl-Coenzyme A Dehydrogenase from Clostridium beijerinckii (Clostridium butylicum:) NRRL B593," *Appl. Environ. Microbiol.* 58:3297-3302 (1992).

Cole et al., "Deciphering the biology of *Mycobacterium tuberculosis* from the complete genome sequence," *Nature* 393:537-544 (1998).

Coleman et al., "Expression of a glutamate decarboxylase homologue is required for normal oxidative stress tolerance in *Saccharomyces cerevisiae*," *J. Biol. Chem.* 276:244-250 (2001).

Cooper, "Glutamate-γ-aminobutyrate transaminase," *Methods Enzymol.* 113:80-82 (1985).

Corthesy-Theulaz et al., "Cloning and characterization of Helicobacter pylori succinyl CoA:acetoacetate CoA-transferase, a novel prokaryotic member of the CoA-transferase family," *J. Biol. Chem.* 272(41):25659-25667 (1997).

Creaghan and Guest, "Succinate dehydrogenase-dependent nutritional requirement for succinate in mutants of *Escherichia coli* K12," *J. Gen. Microbiol.* 107(1):1-13 (1978).

Cukalovic et al., "Feasibility of production method for succinic acid derivatives: a marriage of renewable resources and chemical technology," *Biofuels Bioprod. Bioref.* 2:505-529 (2008).

Cunningham and Guest, "Transcription and transcript processing in the sdhCDAB-sucABCD operon of *Escherichia coli*," *Microbiology* 144:2113-2123 (1998).

Darlison et al., "Nucleotide sequence of the sucA gene encoding the 2-oxoglutarate dehydrogenase of *Escherichia coli* K12," *Eur. J. Biochem.* 141(2):351-359 (1984).

Datsenko and Wanner, "One-step inactivation of chromosomal genes in *Escherichia coli* K-12 using PCR products," *Proc. Natl. Acad. Sci. U.S.A.* 97(12):6640-6645 (2000).

Davie et al., "Expression and Assembly of a Functional E1 Component (α2β2) of Mammalian Branched-Chain α-Ketoacid Dehydrogenase Complex in *Escherichia coli*," *J. Biol. Chem.* 267:16601-16606 (1992).

De Biase et al., "Isolation, overexpression, and biochemical characterization of the two isoforms of glutamic acid decarboxylase from *Escherichia coli*," *Protein Expr. Purif.* 8:430-438 (1996).

de la Torre et al., "Identification and functional analysis of prokaryotic-type aspartate aminotransferase: implications for plant amino acid metabolism," *Plant J.* 46(3):414-425 (2006).

Deana, "Substrate specificity of a dicarboxyl-CoA: dicarboxylic acid coenzyme A transferase from rat liver mitochondria," *Biochem. Int.* 26(4):767-773 (1992).

Deckert et al., "The complete genome of the hyperthermophilic bacterium Aquifex aeolicus," *Nature* 392:353-358 (1998).

Diao et al., "Crystal Structure of Butyrate Kinase 2 from Thermotoga maritima, a Member of the ASKHA Superfamily of Phosphotransferases," *J. Bacteriol.* 191(8):2521-2529 (2009).

Diao et al., "Crystallization of butyrate kinase 2 from Thermotoga maritima medicated by varpor diffusion of acetic acid," *Acta Crystallogr. D. Crystallogr.* 59:1100-1102 (2003).

Diaz et al., "Gene cloning, heterologous overexpression and optimized refolding of the NAD-glutamate dehydrogenase from haloferax mediterranei," *Extremophiles* 10(2):105-115 (2006).

Diderichsen et al., "Cloning of aldB, which encodes alpha-acetolactate decarboxylase, an exoenzyme from Bacillus brevis," *J. Bacteriol.* 172(8):4315-4321 (1990).

Diruggiero et al., "Expression and in vitro assembly of recombinant glutamate dehydrogenase from the hyperthermophilic archaeon Pyrococcus turiosus," *Appl. Environ. Microbiol.* 61:159-164 (1995).

Doi et al., "Biosynthesis and characterization of poly(3-hydroxybutyrate-co-4-hydroxybutyrate) in Alcaligenes eutrophus," *Int. J. Biol. Macromol.* 12:106-111 (1990).

Doi et al., "Nuclear Magnetic Resonance Studies on Unusual Bacterial Copolyesters of 3-Hydroxybutyrate and 4-Hydroxybutyrate," *Macromolecules* 21:2722-2727 (1988).

Doi, "Microbial Synthesis, Physical Properties, and Biodegradability of Polyhydroxyalkanoates," *Macromol. Symp.* 98:585-599 (1995).

Dombek and Ingram, "Ethanol production during batch fermentation with *Saccharomyces cerevisiae*: changes in glycolytic enzymes and internal pH," *Appl. Environ. Microbiol.* 53:1286-1291 (1987).

Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561.

Donnelly and Cooper, "Two succinic semialdehyde dehydrogenases are induced when *Escherichia coli* K-12 is grown on gamma-aminobutyrate," *J. Bacteriol.* 145:1425-1427 (1981).

Dover et al., "Genetic analysis of the gamma-aminobutyrate utilization pathway in *Escherichia coli* K-12," *J. Bacteriol.* 117(2):494-501 (1974).

Doyle et al., "Structural basis for a change in substrate specificity: crystal structure of S113E isocitrate dehydrogenase in a complex with isopropylmalate, Mg2+, and NADP," *Biochemistry* 40(14):4234-4241 (2001).

Drake, "Acetogenesis, acetogenic bacteria, and the acetyl-CoA "Wood/Ljungdahl" pathway: past and current perspectives," In H.L. Drake (ed.), *Acetogenesis* pp. 3-60 Chapman and Hall, New York (1994).

Drewke et al., "4-O-Phosphoryl-L-threonine, a substrate of the pdxC(serC) gene product involved in vitamin $B_6$ biosynthesis," *FEBS Lett.* 390:179-182 (1996).

(56) References Cited

OTHER PUBLICATIONS

Duncan et al., "Acetate utilization and butyryl coenzyme A (CoA):acetate-CoA transferase in butyrate-producing bacteria from the human large intestine," *Appl. Environ. Microbiol* 68(10):5186-5190 (2002).

Duncan et al., "Purification and properties of NADP-dependent glutamate dehydrogenase from Ruminococcus flavefaciens FD-1," *Appl. Environ. Microbiol.* 58:4032-4037 (1992).

Dürre et al., "Solventogenic enzymes of Clostridium acetobutylicum: catalytic properties, genetic organization, and transcriptional regulation," *FEMS Microbiol. Rev.* 17(3):251-262.

Edwards and Palsson, "Systems properties of the Haemophilus influenzae Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533.

Edwards et al., "In Silico Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol. Bioeng.* 99:1392-1406 (2008).

Eggen et al., "The glutamate dehydrogenase-encoding gene of the hyperthermophilic archaeon Pyrococcus furiosus: sequence, transcription and analysis of the deduced amino acid sequence," *Gene* 132:143-148 (1993).

Enomoto et al., "Cloning and sequencing of the gene encoding the soluble fumarate reductase from *Saccharomyces cerevisiae*," *DNA Res.* 3:263-267 (1996).

Estevez et al., "X-ray crystallographic and kinetic correlation of a clinically observed human fumarase mutation," *Protein Sci.* 11:1552-1557 (2002).

Faehnle et al., "A New Branch in the Family: Structure of Aspartate-β-semialdehyde dehydrogenase from Methanococcus jannaschii," *J. Mol. Biol.* 353:1055-1068 (2005).

Feist et al., "The growing scope of applications of genome-scale metabolic reconstructions using *Escherichia coli*," *Nat. Biotechnol.* 26(6):659-667 (2008).

Fell and Small, "Fat Synthesis in Adipose Tissue. An Examination of Stoichiometric Constraints," *Biochem. J.* 238(3):781-786 (1986).

Fernandez-Valverde et al., "Purification of Pseudomonas putida Acyl coenzyme a Ligase Active with a Range of Aliphatic and Aromatic Substrates," *Appl. Environ. Microbiol.* 59:1149-1154.

Filetici et al., "Sequence of the GLT1 gene from Saccharomyces cerevisiae reveals the domain structure of yeast glutamate synthase," *Yeast* 12:1359-1366 (1996).

Fischer and Sauer, "Metabolic flux profiling of *Escherichi coli* mutants in central carbon metabolism using GC-MS," *Eur. J. Biochem.* 270(5) 880-891 (2003).

Fishbein and Bessman, "Purification and properties of an enzyme in human blood and rat liver microsomes catalyzing the formation and hydrolysis of gamma-lactones. I. Tissue localization, stoichiometry, specificity, distinction from esterase," *J. Biol. Chem.* 241(21):4835-4841 (1966).

Fishbein and Bessman, "Purification and properties of an enzyme in human blood and rat liver microsomes catalyzing the formation and hydrolysis of γ-lactones. II. Metal ion effects, kinetics, and equilibra," *J. Biol. Chem.* 241(21):4842-4847 (1966).

Föllner et al., "Analysis of the PHA granule-associate proteins GA20 and GA11 in Methylobacterium extorquens and Methylobacterium rhodesianum," *J. Basic Microbiol.* 37(1):11-21 (1997).

Fong and Palsson, "Metabolic gene-deletion strains of *Escherichia coli* evolve to computationally predicted growth phenotypes," *Nat. Genet.* 36(10):1056-1058 (2004).

Fong et al., "Description and interpretation of adaptive evolution of *Escherichia coli* K-12 MG1655 by using a genome-scale in silico metabolic model," *J. Bacteriol.* 185(21):6400-6408 (2003).

Fontaine et al, "A New Type of Glucose Fermentation by *Clostridium thermoaceticum* N.sp.," *J. Bacteriol.* 43:701-715 (1943).

Fontaine et al., "Molecular characterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.* 184(3):821-830 (2002).

Ford, et al., "Molecular properties of the lys1+ gene and the regulation of alpha-aminoadipate reductase in Schizosaccharomyces pombe," *Curr. Genet.* 28(2):131-137 (1995).

Forster et al., "Genome-scale reconstruction of the *Saccharomyces cerevisiae* metabolic network," *Genome Res.* 13(2):244-253 (2003).

Friedrich et al., "The complete stereochemistry of the enzymatic dehydration of 4-hydroxybutyryl coenzyme A to crotonyl coenzyme A," *Angew. Chem. Int. Ed. Engl.* 47:3254-3257 (2008).

Fries et al., "Reaction Mechanism of the Heteroameric (α2β2) E1 Component of 2-Oxo Acid Dehydrogenase Multienzyme Complexes," *Biochemistry* 42:6996-7002 (2003).

Fuhrer, et al., "Computational prediction and experimental verification of the gene encoding the NAD+/NADP+-dependent succinate semialdehyde dehydrogenase in *Escherichia coli*," *J. Bacteriol.* 189:8073-8078 (2007).

Fujii et al., "Characterization of L-lysine 6-aminotransferase and its structural gene from Favobacterium lutescens IFO3084," *J. Biochem.* 128(3):391-397 (2000).

Fujii et al., "Error-prone rolling circle amplification: the simplest random mutagenesis protocol," *Nat. Protoc.* 1(5):2493-2497 (2006).

Fujii et al., "One-step random mutagenesis by error-prone rolling circle amplification," *Nucleic. Acids Res.* 32(19):e145 (2004).

Fujita et al., "Novel Substrate Specificity of designer3-Isopropylmalate Dehydrogenase Derived from thermus thermophilus HB1," *Biosci. Biotechnol. Biochem.* 65(12):2695-2700 (2001).

Fukao et al., "Succinyl-coA:3-Ketoacid CoA Transferase (SCOT): Cloning of the Human SCOT Gene, Tertiary Structural Modeling of the Human SCOT Monomer, and Characterization of Three Pathogenic Mutations," *Genomics* 68:144-151 (2000).

Fukuda and Wakagi, "Substrate recognition by 2-oxoacid:ferredoxin oxidoreductase from *Sulfolobus* sp. Strain 7," *Biochim. Biophys. Acta* 1597:74-80 (2002).

Fukuda et al., "Role of a highly conserved YPITP motif in 2-oxoacid:ferredoxin oxidoreductase," *Eur. J. Biochem.* 268:5639-5646 (2001).

Gallego et al., "A role for glutamate decarboxylase during tomato ripening: the characterisation of a cDNA encoding a putative glutamate decarboxylase with a calmodulin-binding site," *Plant Mol. Biol.* 27:1143-1151 (1995).

Gay et al., "Cloning Structural Gene sacB, Which codes for Exoenzyme Levansucrase of Bacillus subtilis: Epxresion of the Gene in *Escherichia coli*," *J. Bacteriol.* 153:1424-1431 (1983).

Gerhardt et al., "Fermentation of 4-aminobutyrate by Clostridium aminobutyricum: cloning of two genes involved in the formation and dehydration of 4-hydroxybutyryl-CoA," *Arch. Microbiol.* 174:189-199 (2000).

Gerngross and Martin, "Enzyme-catalyzed synthesis of poly((R)-(−)-3-hydroxybutyrate): formation of macroscopic granules in vitro," *Proc. Natl. Acad. Sci. U.S.A.* 92:6279-6783 (1995).

Gerngross, et al., "Overexpression and purification of the soluble polyhydroxyalkanoate synthase from Alcalligenes eutrophus: evidence for a required posttranslational modification for catalytic activity," *Biochemistry* 33:9311-9320 (1994).

Gibbs et al., "Degenerate oligonucleotide gene shuffling (DOGS): a method for enhancing the frequency of recombination with family shuffling," *Gene.* 271:13-20 (2001).

Giesel and Simon, "On the occurrence of enoate reductase and 2-oxocarboxylate reductase in clostridia and some observations on the amino acid fermentation by Peptostreptococcus anaerobius," *Arch. Microbiol.* 135(1):51-57 (1983).

Girbal, et al., "Regulation of metabolic shifts in Clostridium acetobutylicum ATCC 824," *FEMS Microbiol. Rev.* 17:287-297 (1995).

Goda et al., "Cloning, Sequencing, and Expression in *Escherichia coli* of the *Clostridium tetanomorphum* Gene Encoding β-Methylaspartase and Characterization of the Recombinant Protein," *Biochemistry* 31:10747-10756 (1992).

(56) References Cited

OTHER PUBLICATIONS

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
Gonzalez, et al., "Cloning of a yeast gene coding for the glutamate synthase small subunit (GUS2) by complementation of *Saccharomyces cerevisiae* and *Escherichia coli* glutamate auxotrophs," *Mol. Microbiol.* 6:301-308 (1992).
Gonzalez-Pajuelo et al., "Metabolic engineering of Clostridium acetobutylicum for the industrial production of 1,3-propanediol from glycerol," *Met. Eng.* 7:329-336 (2005).
Goupil et al., "Imbalance of leucine flux in Lactoccus lactis and its use for the isolation of diacetyl-overproducing strains," *Appl. Environ. Microbiol.* 62(7):2636-2640 (1996).
Goupil-Feuillerat et al., "Transcriptional and translational regulation of alpha-acetolactate decarboxylase of *Lactococcus lactis* subsp. *lactis*," *J. Bacteriol.* 182(19):5399-5408 (2000).
Green et al., "Catabolism of α-Ketoglutarate by a sucA Mutant of Bradyrhizobium japonicum: Evidence for an Alternative Tricarboxylic Acid Cycle," *J. Bacteriol.* 182(10):2838-2844 (2000).
Gregerson, et al., "Molecular characterization of NADH-dependent glutamate synthase from alfalfa nodules," *Plant Cell* 5:215-226 (1993).
Guirard and Snell, "Purification and properties of ornithine decarboxylase from *Lactobacillus* sp. 30a," *J. Biol. Chem.* 255(12):5960-5964 (1980).
Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from Schizosaccharomyces pombe," *Yeast* 21(15):1279-1288 (2004).
Guo et al., "Site-directed mutational analysis of the novel catalytic domains of alpha-aminoadipate reductase (Lys2p) from Candida albicans," *Mol. Genet. Genomics* 269(2):271-279 (2003).
Guzman et al., "Tight regulation, modulation, and high-level expression by vectors containing the arabinose PBAD promoter," *J. Bacteriol.* 177:4121-4130 (1995).
Guzman, et al., "Tight regulation, modulation and high-level expression by vectors containing the arabinose PBAD promoter," J. Bacteriol. 177(14):4121-4130 (1995).
Hadfield et al., "Active site analysis of the potential antimicrobial target aspartate semialdehyde dehydrogenase," *Biochemistry* 40(48):14475-14483 (2001).
Hadfield et al., "Structure of aspartate-beta-semialdehyde dehydrogenase from *Escherichia coli*, a key enzyme in the aspartate family of amino acid biosynthesis," *J. Mol. Biol.* 289(4):991-1002 (1999).
Hammer and Bode, "Purification and characterization of an inducible L-lysine:2-oxoglutarate 6-aminostransferase from Dandida utilis," *J. Basic Microbiol.* 32:21-27 (1992).
Hanai et al., "Engineered synthetic pathway for isopropanol production in *Escherichia coli*," *Appl. Environ. Microbiol.* 73:7814-7818 (2007).
Hansford, "Control of mitochondrial substrate oxidation," *Curr. Top. Bioenerg.* 10:217-278 (1980).
Hasegawa et al., "Transcriptional regulation of ketone body-utilizing enzyme, acetoacetyl-CoA synthetase, by C/EBPα during adipocyte differentiation," *Biochim Biophys. Acta* 1779:414-419 (2008).
Hashidoko et al., "Cloning of a DNA Fragment Carrying the 4-Hydroxycinnamate Decarboxylase (pofK) Gene from Klebsiella oxtoca, and Its Constitutive Expression in *Escherichia coli* JM109 Cells," *Biosci. Biotech. Biochem.* 58(1):217-218 (1994).
Hashimoto et al., "Activation of L-Lysine ε-Dehydrogenase from Agrobacterium tumefaciens by Several Amino Acids and Monocarboxylates," *J. Biochem.* 106:76-80 (1989).
Hasson et al., "The Crystal Structure of Benzoylformate Decarboxylase at 1.6 Å Resolution: Diversity of Catalytic Residues in thiamin Diphosphate-Dependent Enzymes," *Biochemistry* 37:9918-9930 (1998).

Hawes et al., "Mammalian 3-hydroxyisobutyrate dehydrogenase," *Methods Enzymol.* 324:218-228 (2000).
Hayden et al., "Glutamate dehydrogenase of Halobacterium salinarum: evidence that the gene sequence currently assigned to the NADP+-dependent enzyme is in fact that of the NAD+-dependent glutamate dehydrogenase," *FEMS Microbiol. Lett.* 211:37-41 (2002).
Hayes et al., "Combining computational and experimental screening for rapid optimization of protein properties," *Proc. Natl. Acad. Sci. U.S.A.* 99(25):15926-15931 (2002).
Hein, et al., "Biosynthesis of poly(4-hydroxybutyric acid) by recombinant strains of *Escherichia coli*," *FEMS Microbiol. Lett.* 153(2):411-418 (1997).
Henne, et al., "Construction of environmental DNA libraries in *Escherichia coli* and screening for the presence of genes conferring utilization of 4-hydroxybutyrate," *Appl. Environ. Microbiol.* 65(9):3901-3907 (1999).
Hennessy, et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).
Henning et al., "Identification of Novel enzoylformate Decarboxlyases by Growth Selection," *App. Environ. Microbiol.* 72(12)7510-7517 (2006).
Hermes et al., "Searching sequence space by definably random mutagenesis: Improving the catalytic potency of an enzyme," *Proc. Natl. Acad. Sci. U.S.A.* 87:696-700 (1990).
Herrmann et al., "Two beta-alanyl-CoA:ammonia lyases in Clostridium propionicum," *FEBS J.* 272:813-821 (2005).
Hesslinger et al., "Novel keto acid formate-lyase and propionate kinase enzymes are components of an anaerobic pathway in *Escherichia coli* that degrades L-threonine to propionate," *Mol. Microbiol* 27:477-492 (1998).
Hester et al., "Purification of active E1 alpha 2 beta 2 of Pseudomonas putida branched-chain-oxoacid dehydrogenase," *Eur. J. Biochem.* 233(3):828-836 (1995).
Heydari et al., "Highly Stable L-Lysine 6-Dehydrogenase from the Thermophile Geobacillus stearothemophilus Isolated from a Japanese Hot Spring: Characterization, gene Cloning and Sequencing, and Expression," *Appl. Environ. Microbiol.* 70:937-942 (2004).
Hezayen et al., "Biochemical and enzymological properties of the polyhydroxybutyrate synthase from the extremely halophilic archaeon strain 56," *Arch. Biochem. Biophys.* 403(2):284-291 (2002).
Hibbert et al. "Directed evolution of biocatalytic processes," *Biomol. Eng.* 22:11-19 (2005).
Hijarrubia et al., "Domain Structure characterization of the Multifunctional α-Aminoadipate Reductase from Penicillium chrysogenum by Limited Proteolysis," *J. Biol. Chem.* 278:8250-8256 (2003).
Hillmer and Gottschalk, "Solubilization and partial characterization of particulate dehydrogenases from Clostridium kluyveri," *Biochim. Biophys. Acta* 334:12-23 (1974).
Hiramitsu, et al., "Production of Poly(3-hydroxybutyrate-co-4-hydroxybutyrate) by Alcallgenes latus," *Biotechnol Lett.* 15:461-464 (1993).
Hirano et al., "Purification and Characterization of the alcohol dehydrogenase with a broad substrate specificity originated from 2-phenylethanol-assimilating *Brevibacterium* sp. KU 1390," *J. Biosci. Bioeng.* 100(3):318-322 (2005).
Hiser et al., "ERG10 from *Saccharomyces cerevisiae* encodes acetoacetyl-CoA thiolase," *J. Biol. Chem.* 269:31383-31389 (1994).
Hoffineister et al., "Mitochondrial trans-2-enoyl-CoA reductase of wax ester fermentation from Euglena gracilis defines a new family of enzymes involved in lipid synthesis," *J. Biol. Chem.* 280:4329-4338 (2005).
Hogan et al., "Improved specificity toward substrates with ositively charged side chains by site-directed mutagenesis of the L-lactate dehydrogenase of Bacillus stearothermophilus," *Biochemistry* 34(13):4225-4230 (1995).

(56) References Cited

OTHER PUBLICATIONS

Hong and Lee, "Enhanced Production of Succinic Acid by Metabolically Engineered *Escherichia coli* with Amplified Activities of Malic Enzyme and Fumarase," *Biotechnol Bioprocess Eng.* 9:252-255 (2004).

Hong, et al., "The genome sequence of the capnophilic rumen bacterium *Mannheimia succiniciproducens*," *Nat. Biotechnol.* 22(10):1275-1281 (2004).

Huang et al., "Identification and Characterization of a Second Butyrate Kinase from Clostridium acetobutylicum ATCC 824, " *J. Mol. Microbiol. Biotechnol.* 2(1):33-38 (2000).

Huang et al., "Purification and Characterization of a Ferulic Acid Decarboxylase from Pseudomonas fluorescens," *J. Bacteriol.* 176(19):5912-5918 (1994).

Hughes et al., "Evidence for Isofunctional Enzymes in the Degradation of Phenol, *m*- and *p*-Toulate, and *p*-Cresol via Catechol meta-Cleavage Pathways in Alcaligenes eutrophus," *J. Bacteriol.* 158:79-83 (1984).

Hugler et al., "Malonyl-coenzyme A reductase from Chloroflexus aurantiacus, a key enzyme of the 3-hydroxypropionate cycle for autotrophic CO(2) fixation," *J.Bacteriol.* 184:2404-2410 (2002).

Huh et al., "Global analysis of protein localization in budding yeast," *Nature* 425:686-691 (2003).

Huisman and Lalonde, "Ch. 30: Enzyme Evolution for Chemical Process Applications," In R N. Patel (ed.), *Biocatalysis in the pharmaceutical and biotechnology industries*, CRC Press, Boca Raton, FL, p. 717-742 (2007).

Huo and Viola, "Substrate specificity and identification of functional groups of homoserine kinase from *Escherichia col*," *Biochemistry* 35(50):16180-16185 (1996).

Ibarra et al., "*Escherichia coli* K-12 undergoes adaptive evolution to achieve in silico predicted optimal growth," *Nature* 420(6912):186-189 (2002).

Iffland et al., "Directed molecular evolution of cytochrome c peroxidase," *Biochemistry* 39(25):10790-10798 (2000).

Ikai and Yamamoto, "Identification and Analysis of a Gene Encoding L-2,4-Diaminobutyrate:2-Ketoglutarate 4-Aminotransferase Invloved in the 1,3-Diaminopropane Production Pathway in Acinetobacter baumanni," *J. Bacteriol.* 179(16):5118-5125 (1997).

Imai and Ohno, "Measurement of yeast intracellular pH by image processing and the change it undergoes during growth phase," *J. Biotechnol.* 38:165-172 (1995).

Ingoldsby et al., "The discovery of four distinct glutamate dehydrogenase genes in a strain of Halobacterium salinarum," *Gene* 349:237-244 (2005).

Ishida et al., "Efficient production of L-Lactic acid by metabolically engineered *Saccharomyces cerevisiae* with a genome-integrated L-lactate dehydrogenase gene." *Appl. Envirom. Microbiol.* 71:1964-1970 (2005).

Ishige et al., "Wax ester production from n-alkanes by *Acinetobacter* sp. strain M-1: ultrastructure of cellular inclusions and role of acyl coenzyme A reductase," *Appl. Environ. Microbiol.* 68(3):1192-1195 (2002).

Ismaiel et al., "Purification and characterization of a primary-secondary alcohol dehydrogenase from two strains of Clostridium beijerinckii," *J. Bacteriol.* 175(16):5097-5105 (1993).

Ismail et al., "Functional genomics by NMR spectroscopy Phenylacetate catabolism in *Escherichia coli*," *Eur. J. Biochem.* 270:3047-3054 (2003).

Ito et al., "D-3-hydroxybutyrate dehydrogenase from Pseudomonas fragi: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Jeon et al., "Heterologous expression of the alcohol dehydrogenase (adhI) gene from *Geobacillus thermoglucosidasius* strain M10EXG," *J. Biotechnol.* 135:127-133 (2008).

Jesudason and Marchessault, "Synthetic Poly[(R,S)-.beta.-hydroxyalkanoates] with Butyl and Hexyl Side Chains," *Macromolecules* 27:2595-2602 (1994).

Jewell et al., "Bioconversion of propionic, valeric and 4-hydroxybutyric acids into the corresponding alcohols by Clostridium acetobutylicum NRRL 527," *Curr. Microbiol.* 13(4):215-219 (1986).

Jiang et al., "De novo computational design of retro-aldol enzymes," *Science* 319(5868):1387-1391 (2008).

Johnson et al., "Alteration of a single amino acid changes the substrate specificity of dihydroflavonol 4-reductase," *Plant J.* 25(3):325-333 (2001).

Johnston et al., "Complete nucleotide sequence of *Saccharomyces cerevisiae* chromosome VIII," *Science* 265:2077-2082 (1994).

Jones and Woods,"Acetone-butanol fermentation revisited," *Microbiol. Rev.* 50(4):484-524 (1986).

Jones et al., "Purification and characterization of D-b-hydroxybutyrate dehydrogenase expressed in *Escherichia coli*," *Biochem. Cell Biol.* 71(7-8):406-410 (1993).

Kakimoto et al., "β-Aminoisobutyrate-α-ketoglutarate transaminase in relation to β-aminoisobutyric aciduria," *Biochim. Biophys. Acta.* 156(2):374-380 (1968).

Kaneko et al., "Sequence analysis of the genome of the unicellular cyanobacterium *Synechocystis* sp. strain PCC6803, II. Sequence determination of the entire genome and assignment of potential protein-coding regions," *DNA Res.* 3:109-136 (1996).

Kapatral et al., "Genome Sequence and Analysis of the Oral Bacterium Fusobacterium nucleatum Strain Atcc 25586," *J. Bacteriol.* 184(7):2005-2018 (2002).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Kato et al., "Open reading frame 3 of the barotolerant bacterium strain DSS12 is complementary with cydD in *Escherichia coli*: cydD functions are required for cell stability at high pressure," *J. Biochem.* 120:301-305 (1996).

Kato et al., "Production of a novel copolyester of 3-hydroxybutyric acid with a medium-chain-length 3-hydroxyalkanoic acids by *Pseudomonas* sp. 61-3 from sugars," *Appl. Microbiol. Biotechnol.* 45:363-370 (1996).

Kazahaya et al, "Aerobic Dissimilation of Glucose by Heterolactic Bacteria," *J. Gen. Appl. Microbiol.* 18(1):43-55 (1972).

Keng and Viola, "Specificity of Aspartokinase III from *Escherichia coli* and an Examination of Important Catalytic Residues," *Arch. Biochem. Biophys.* 335:73-81 (1996).

Kessler et al., "Pyruvate-formate-lyase-deactivase and acetyl-CoA reductase activities of *Escherichia coli* reside on a polymeric protein particle encoded by adhE," *FEBS. Lett.* 281:59-63 (1991).

Khan et al., "Molecular properties and enhancement of thermostability by random mutagenesis of glutamate ehydrogenase from Bacillus subtilis," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al., "Construction of an *Escherichia coli* K-12 Mutant for Homoethanologenic Fermentation of glucose or Xylose without Foreign Genes, " *Appl. Environ. Microbiol.* 73:1766-1771 (2007).

Kim et al., "Dihydrolipoamide Dehydrogenase Mutation Alters the NADH Sensitivity of Pyruvate Dehydrogenase Complex of *Escherichi coli* K-12," *J. Bacteriol.* 190:3851-3858 (2008).

Kim et al., "Effect of overexpression of Actinobacillus succinogenes phosphoenolpyruvate carboxykinase on succinate production in *Escherichia coli*," Appl. Environ. Microbiol. 70:1238-1241 (2004).

Kim, "Purification and Propertis of a mine α-Ketoglutarate Transaminase from *Escherichia coli*," *J. Biol. Chem.* 239:783-786 (1964).

Kimura et al., "Production of Poly(3-hydroxybutyrate-co-4-hydroxybutyrate) by Pseudomonas acidovorans," *Biotechnol. Lett.* 14(6):445-450 (1992).

Kinnaird et al., "The complete nucleotide sequence of the Neurospora crassa am (NADP-specific glutamate dehydrogenase) gene," *Gene* 26:253-260 (1983).

Kino et al., "Synthesis of DL-tryptophan by modified broad specificity amino acid racemase from Pseudomonas putida IFO 12996," *Appl. Microbiol. Biotechnol.* 73(6):1299-1305 (2007).

(56) References Cited

OTHER PUBLICATIONS

Kinoshita, "Purification of two alcohol dehydrogenases from Zymomonas mobilis and their properties," *Appl. Microbiol. Biotechnol.* 22:249-254 (1985).

Kirby et al., "Purification and properties of rabbit brain and liver 4-aminobutyrate aminotransferases isolated by monoclonal-antibody Immunoadsorbent chromatography," *Biochem. J.* 230:481-488 (1985).

Kizer et al., "Application of Functional Genomics to Pathway Optimization for Increased Isoprenoid Production," *Appl. Environ. Microbiol.* 74(10):3229-3241 (2008).

Klatt et al., "Comparative genomics provides evidence for the 3-hydroxypropionate autotrophic pathway in filamentous anoxygenic phototrophic bacteria and in hot spring microbial mats," Environ. Microbiol. 9(8):2067-2078 (2007).

Klenk et al., "The complete genome sequence of the hyperthermophilic, sulphate-reducing archaeon Archaeoglobus fulgidus," *Nature* 390:364-370 (1997).

Knapp et al., "Crystal Structure of the Truncated Cubic Core Component of the *Escherichia coli* 2-Oxoglutarate Dehydrogenase Multienzyme Complex," *J. Mol. Biol.* 289:655-668 (1998).

Knappe and Sawers, "A radical-chemical route to acetyl-CoA: the anaerobically induced pyruvate formate-lyase system of *Escherichia coli*," *FEMS Microbiol. Rev.* 75:383-398 (1990).

Kobayashi et al., "Frementative Production of 1,4-Butanediol from Sugars by *Bacillus* sp.," *Agric. Biol. Chem.* 51(6):1689-1690 (1987).

Kobayashi et al., "Physiochemical, Catalytic, and Immunochemical Properties of Fumarases Crystallized Separately from Mitochondrial and Cytosolic Fractions of Rat Liver," *J. Biochem.* 89:1923-1931 (1981).

Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).

Korbert et al., "Crystallization of the NADP+-dependent Glutamate Dehydrogenase from *Escherichia coli*," *J. Mol. Biol.* 234:1270-1273 (1993).

Korolev et al., "Autotracing of *Escherichia coli* acetate CoA-transferase α-subunit structure using 3.4 Å MAD and 1.9 Å native data," *Acta. Cryst.* D58:2116-2121 (2002).

Kort et al., "Glutamate dehydrogenase from the hyperthermophilic bacterium Thermotoga maritima: molecular characterization and phylogenetic implications," *Extremophiles* 1:52-60.

Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kreimeyer et al., "Identification of the Last Unknown Genes in the fermentation Pathway of Lysine," *J. Biol. Chem.* 282:7191-7197 (2007).

Kretz et al., "Gene site saturation mutagenesis: a comprehensive mutagenesis approach," *Methods Enzymol.* 388:3-11 (2004).

Krieger et al., "Pyruvate decarboxylase from Kluyveromyces lactis an enzyme with an extraordinary substrate activation behaviour," *Eur. J. Biochem.* 269:3256-3263 (2002).

Kumamaru et al., "Enhanced degradation of polychlorinated biphenyls by directed evolution of biphenyl dioxgenase," *Nat. Biotechnol.* 16(7)663-666 (1998).

Kunioka et al., "New bacterial copolyesters produced in Alcaligenes eutrophus from organic acids," *Polym. Commun.* 29:174-176 (1988).

Kurihara et al., "A Novel Putrescine Utilization Pathway Involves γ-Glutamylated Intermediates of *Escherichia coli* K-12," *J. Biol. Chem.* 280(6) 4602-4608 (2005).

Kuznetsova et al., "Enzyme genomics: Application of general enzymatic screens to discover new enzymes," *FEMS Microbiol. Rev.* 29:263-279 (2005).

Kwok and Hanson, "GFP-labelled Rubisco and aspartate aminotransferase are present in plastid stromules and traffic between plastids, " *J. Exp. Bot.* 55:(397)595-604 (2004).

Kwon et al., "Brain 4-aminobutyrate aminotransferase. Isolation and sequence of a cDNA encoding the enzyme," *J. Biol. Chem.* 267:7215-7216 (1992).

Kwon et al., "Influence of gluconeogenic phosphoenolpyruvate carboxykinase (PCK) expression on succinic acid fermentation in *Escherichia coli* under high bicarbonate condition," *J. Microbiol. Biotechnol.* 16(9):1448-1452 (2006).

Lageveen, et al., "Formation of Polyesters by Pseudomonas oleovorans: Effect of Substrates on Formation and Composition of Poly-(R)-3-Hydroxyalkanoates and Poly-(R)-3-Hydroxyalkenoates," *Appl. Environ. Microbiol.* 54:2924-2932 (1988).

Laivenieks et al., "Cloning sequencing, and overexpression of the Anaerobiospirillum succiniproducens phosphoenolpyruvate carboxykinase (pckA) gene," *Appl Environ. Microbiol.* 63:2273-2280 (1997).

Lam and Winkler, "Metabolic Relationships between Pyridoxine (vitamin B6) and Serine Biosynthesis in *Escherichia coli* K-12," *J. Bacteriol.* 172(11):6518-6528 (1990).

Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395:147-155 (2006).

Lamed and Zeikus, "Novel NAP-linked alcohol-aldehyde/ketone oxidoreductase in thermophilic ethanologenic bacteria," *Biochem. J.* 195:183-190 (1981).

Lebbink et al., "Engineering activity and stability of *Thermotoga maritima* Glutamate Dydrogenase. I. Introduction of a Six-residue Ion-pair Network in the Hinge Region," *J. Mol. Biol.* 280:287-296 (1998).

Lebbink et al., "Engineering activity and stability of *Thermotoga maritima* glutamate dehydrogenase. II: construction of a 16-residue ion-pair network at the subunit interface," *J. Mol. Biol.* 289(2):357-369 (1999).

Leduc et al., "The Hotdog Thiesterase EntH (YbdB) Plays a Role in Vivo in Optimal Enterobactin biosynthesis by Interacting with the ArCP Domain of EntB," *J. Bacteriol.* 189(19):7112-7126 (2007).

Lee and Cho, "Identification of essential active-site residues in ornithine decarboxylase of Nicotiana glutinosa decarboxylating both L-ornithine and L-lysine," *Biochem. J.* 360(Pt 3):657-665 (2001).

Lee et al., "Biosynthesis of enantiopure (s)-3-hydroxybutyric acid in metabolically engineered *Escherichia coli*," *Appl. Microbiol. Biotechnol.* 79(4):633-641 (2008).

Lee et al., "Cloning and Characterization of Mannheimia succiniciproducens MBEL55E Phosphoenolpyruvate Carboxykinase (pckA) Gene," *Biotechnol. Bioprocess Eng.* 7:95-99 (2002).

Lee et al., "Phylogenetic diversity and the structural basis of substrate specificity in the beta/alpha-barrel fold basic amino acid decarboxylases," *J. Biol. Chem.* 282(37):27115-27125 (2007).

Lee et al., "A new approach to directed gene evolution by recombined extension on truncated templates (RETT)," *J. Molec. Catalysis* 26:119-129 (2003).

Lee et al., "Biosynthesis of copolyesters consisting of 3-hydroxybutyric acid and medium-chain-length 3-hydroxyalkanoic acids from 1,3-butanediol or from 3-hydroxybutyrate by Pseudomonas sp. A33," *Appl. Microbiol. Biotechnol.* 42: 901-909 (1995).

Lee et al., "Enhanced biosynthesis of P(3HB-3HV) and P(3HB-4HB) by amplification of the cloned PHB biosynthesis genes in Alcatigenes eutrophus," *Biotechnol. Lett.* 19:771-774 (1997).

Lemoigne and Rouklehman, "Fermentation b-Hydroxybutyrique," *Annales des Fermentations* 5:527-536 (1925).

Lemonnier and Lane, "Expression of the second lysine decarboxylase gene of *Escherichia coli*," *Microbiology* 144(Pt 3):751-760 (1998).

Lepore et al., "The x-ray crystal structure of lysine-2,3-aminomutase from Clostridium subterminale," *Proc. Natl. Acad. Sci. U.S.A.* 102:13819-13824 (2005).

(56) References Cited

OTHER PUBLICATIONS

Li and Jordan, "Effecrts of Substitution of Tryptophan 412 in the Substrate Activation Pathway of Yeast Pyruvate Decarboxylase," *Biochemistry* 38:10004-10012 (1999).

Li, Guang-Shan, "Development of a reporter system for the study of gene expression for solvent production in Clostridium beijerinckii NRRL B592 and Clostridium acetobutylicum ATCC 824," Dissertation, Department of Biochemestry, Virginia Polytechnic Institute and State University (Sep. 1998).

Lian and Whitman, "Sterochemical and Isotopic Labeling Studies of 4-Oxalocrotonate Decarboxylase and Vinylpyruvate Hydratase: Analysis and Mechanistic Implications," *J. Am. Chem. Soc.* 116:10403-10411 (1994).

Liebergesell and Steinbuchel, "Cloning and nucleotide sequences of genes relevant for biosynthesis of poly(3-hydroxybutyric acid) in Chromatium vinosum strain D," *Eur. J. Biochem.* 209(1):135-150 (1992).

Lin et al., "Fed-batch culture of a metabolically engineered *Escherichia coli* strain designed for high-level succinate production and yield under aerobic conditions," *Biotechnol. Bioeng.* 90(6):775-779 (2005).

Lin et al., "Functional expression of horseradish peroxidase in *E. coli* by directed evolution," *Biotechnol. Prog.* 15(3):467-471 (1999).

Lingen et al., "Alteration of the Substrate Specificity of Benzoylformate Decarboxylase from Pseudomonas putida by Directed Evolution," *Chembiochem* 4:721-726 (2003).

Lingen et al., "Improving the carboligase activity of benzoylformate decarboxylase from Pseudomonas putida by a combination of directed evolution and site-directed mutagenesis," *Protein Eng.* 15:585-593 (2002).

Link et al., "Methods for generating precise deletions and insertions in the genome of wild-type *Escherichia coli*: application to open reading frame characterization," *J. Bacteriol.* 179:6228-6237 (1997).

Liu and Steinbuchel, "Exploitation of butyrate kinase and phosphotransbutyrylase from Clostridium acetobutylicum for the in vitro biosynthesis of poly (hydroxyalkanoic acid)," *Appl. Microbiol. Biotechnol.* 53(5):545-552 (2000).

Liu et al., "Crystal Structures of Unbound and Aminoxyacetate-Bound *Escherichia coli* Y-Aminobutyrate Aminotransferase," *Biochemistry* 43:10896-10905 (2004).

Liu et al., "Kinetic and crystallographic analysis of active site mutants of *Escherichia coli* gamma-aminobutyrate aminotransferase," *Biochemistry* 44:(8):2982-2992 (2005).

Ljungdahl and Andreesen, "Formate dehydrogenase, a selenium—tungsten enzyme from Clostridium thermoaceticum," *Methods Enzymol.* 53:360-372 (1978).

Lokanath et al., "Crystal Structure of novel NADP-dependent 3-Hydroxyisobutyrate Dehydrogenase from Thermus thermophilus HB8," *J. Mol Biol.* 352:905-917 (2005).

Louie and Chan, "Cloning and characterization of the gamma-glutamyl phosphate reductase gene of Campylobacter jejuni," *Mol. Gen. Genet.* 240:29-35 (1993).

Louis et al., "Restricted Distribution of the Butyrate Kinase Pathway among Butyrate-Producing Bacteria from the Human Colon," *J. Bacteriol.* 186(7):2099-2106 (2004).

Low et al., "Mimicking somatic hypermutation: affinity maturation of antibodies displayed on baceriophage using a bacterial mutator strain," *J. Mol. Biol.* 260(3):359-368 (1996).

Lu et al, "Functional analysis and regulation of the divergent spuABCDEFG-spuI operons for polyamine uptake and utilization in Pseudomonas aeruginosa PA01," *J. Bacteriol.* 184:3765-3773 (2002).

Lu et al., "Enhanced production of poly(3-hydroxybutyrate-co-3-hydroxyhexanoate) via manipulating the fatty acid beta-oxidation pathway in *E. coli*," *FEMS Microbiol. Lett.* 221(1):97-101 (2003).

Lu et al., "Molecular cloning of polyhydroxyalkanoate synthesis operon from Aeromonas hydrophilia and its expression in *Escherichia coli*," *Biotechnol. Prog.* 20(5):1332-1336 (2004).

Lutke-Eversloh and Steinbuchel, "Biochemical and molecular characterization of a succinate semialdehyde dehydrogenase involved in the catabolism of 4-hydroxybutyric acid in Ralstonia eutropha," *FEMS Microbiol. Lett.* 181:63-71 (1999).

Lutz and Bujard, "Independent and tight regulation of transcriptional units in *Escherichia coli* via the LacR/O, the TetR/O and AraC/I1-I2 regulatory elements," *Nucleic Acids Res.* 25:1203-1210 (1997).

Lutz et al., "Creating multiple-crossover DNA libraries independent of sequence identity," *Proc. Natl. Acad. Sci. U.S.A.* 98(20):11248-11253 (2001).

Lutz et al., "Rapid generation of incremental truncation libraries for protein engineering using α-phosphothioate nucleotides," *Nucleic Acids Res.* 15:29(4):e16 (2001).

Ma et al., "Induced Rebuilding of Aspartase Confromation," *Ann. N.Y. Acad. Sci.* 672:60-65 (1992).

Mack and Buckel, "Conversion of glutaconate CoA-transferase from Acidaminococcus fermentas into an acyl-CoA hydrolase by site-directed mutagenesis," *FEBS Lett.* 405:209-212 (1997).

Mack et al., "Location of the two genes encoding glutaconate coenzyme A-transferase at the beginning of the hydroxyglutarate operon in Acidaminococcus fermentans," *Eur. J. Biochem.* 226:41-51 (1994).

Mahadevan and Schilling, "The effects of alternate optimal solutions in constraint-based genome-scale metabolic models," *Metab. Eng.* 5(4):264-276 (2003).

Mahadevan et al., "Applications of metabolic modeling to drive bioprocess development for the production of value-added chemicals," *Biotechnol. Bioprocess Eng.* 10(5):408-417 (2005).

Mahan and Csonka, "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.* 156(3):1249-1262 (1983).

Majewski and Domach, "Simple Constrained-Optimization View of Acete Overflow in *E. coli*," *Biotechnol. Bioeng.* 35(7):732-738 (1990).

Majumdar et al., "Functional consequences of substitution in the active site (phosphor) histidine residue of *Escherichia coli* succinyl-CoA synthetase," *Biochim. Biophys. Acta.* 1076:86-90 (1991).

Mandal and Ghosh, "Isolation of a glutamate synthase (GOGAT)-negative, pleiotropically N utilization-defective mutant of Azospirillum brasilense: cloning and partial characterization of GOGAT structural gene," *J. Bacteriol.* 175:8024-8029 (1993).

Manning and Pollitt, "Tracer studies of the interconversion of R- and S-methylmalonic semialdehydes in man," *Biochem. J.* 231:481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170(2):991-994 (1988).

Marks et al., "Molecular Cloning and Characterization of (R)-3-Hydroxybutyrate Dehydrogenase from Human Heart," *J. Biol. Chem.* 267:15459-15463 (1992).

Martin et al., "Engineering a mevalonate pathway in *Escherichia coli* for production of terpenoids," *Nat. Biotechnol.* 21:796-802 (2003).

Martinez-Blanco et al., "Purification and Biochemical Characterization of Phenylacetyl-CoA Ligase from Pseudomonas putida," *J. Biol. Chem.* 265(12):7084-7090 (1990).

Mat-Jan et al., "Anaerobic growth defects resulting from gene fusions affecting succinyl-CoA synthetase in *Escherichia coli* K12," *Mol. Gen. Genet.* 215:276-280 (1989).

Mattevi et al., "Atomic structure of the cubic core of the pyruvate dehydrogenase multienzyme complex," *Science* 255:1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.* 58(5):1435-1439 (1992).

Mavrovouniotis, "Estimation of standard Gibbs energy changes of biotransformations," *J. Biol. Chem.* 266:14440-14445 (1991).

McKinlay et al., "Prospects for a bio-based succinate industry," *Appl. Microbiol. Biotechnol.* 76(4):727-740 (2007).

(56) References Cited

OTHER PUBLICATIONS

McLaggan et al., "Interdependence of K+ and glutamate accumulation during osmotic adaptation of *Escherichia coli*," *J. Biol. Chem.* 269:1911-1917 (1994).
McPherson and Wootton, "Complete nucleotide sequence of the *Escherichia coli* gdhA gene," *Nucleic Acids Res.* 11(15):5257-5266 (1983).
Melchiorsen et al., "The level of pyruvate-formate lyase controls the shift from homolactic to mixed-acid product formation in Lactoccus lactis," *Appl. Microbiol. Biotechnol.* 58(3):338-344 (2002).
Meng and Chuang, "Site-Directed Mutagenesis and functional Analysis of the Active-Site Residues of the E2 Component of Bovine Branched-Chain α-Keto Acid Dehydrogenase Complex," *Biochemistry* 33:12879-12885 (1994).
Menzel et al., "Enzymatic evidence for an involvement of pyruvate dehydrogenase in the anaerobic glycerol metabolism of Klebsiella pneumoniae," *J. Biotechnol.* 56:135-142 (1997).
Menzel et al., "Kinetic, dynamic, and pathway studies of glycerol metabolism by Klebsiella pneumoniae in anaerobic continuous culsutre: IV. Enzynmes and fluxes of pyruvate metabolism," *Biotechnol. Bioeng.* 60(5):617-626 (1998).
Mermelstein et al., "Metabolic Engineering of Clostridium acetobutylicum ATCC 824 for Increased Solvent Production by Enhancement of Acetone Formation Enzyme Activities Using a Synthetic Acetone Operon," *Biotechnol. Bioeng.* 42(9):1053-1060 (1993).
Metz et al., "Purification of a jojoba embryo fatty acyl-coenzyme A reductase and expression of its cDNA in high erucic acid rapeseed," *Plant Physiol.* 122(3):635-644 (2000).
Metzer and Halpern, "In vivo cloning and characterization of the gabCTDP gene cluster of *Escherichia coli* K-12," *J. Bacteriol.* 172:3250-3256 (1990).
Metzer et al., "Isolation and properties of *Escherichia coli* K-12 mutants impaired in the utilization of gamma-aminobutyrate," *J. Bacteriol.* 137(3):1111-1118 (1979).
Miles and Guest, "Molecular genetic aspects of the citric acid cycle of *Escherichia coli*," *Biochem. Soc. Symp.* 54:45-65 (1987).
Miller and Brenchly, "Cloning and characterization of gdhA, the structural gene for glutamate dehydrogenase of *Salmonella typhimurium*," *J. Bacteriol.* 157:171-178 (1984).
Misono and Nagasaki, "Occurrence of L-Lysine ε-Dehydrogenase in Agrobacterium tumefaciens," *J. Bacteriol.* 150(1):398-401 (1982).
Miyamoto and Katsuki, "Possible physiological roles of aspartase, NAD- and NADP-requiring glutamate dehydrogenases of Pseudomonas fluorescens," *J. Biochem.* 112:52-56 (1992).
Miyazaki et al., "α-Aminoadipate aminotransferase from an extremely thermophilic bacterium, Thermus thermophilus," *Microbiology* 150:2327-2334 (2004).
Mizobata et al., "Purification and Characterization of a thermostable Class II Fumarase from Thermus thermophilus," *Arch. Biochem. Biophys.* 355:49-55 (1998).
Momany et al., "Crystallographic Structures of a PLP-Dependent Ornithine Decarboxylase from Lactobacillus 30a to 3.0 Å Resolution," *J. Mol. Biol.* 242:643-655 (1995).
Monnet et al., "Regulation of branched-chain amino acid biosynthesis by α-acetolactate decarboxylase in Streptococcus thermophilus," *Lett. Appl. Microbiol.* 36(6):399-405 (2003).
Moore et al., "Expression and Purification of Aspartate β-Semialdehyde Dehydrogenase from Infectious Microorganisms," *Protein Expr. Purif.* 25:189-194 (2002).
Morris et al., "Nucleotide sequence of the LYS2 gene of Saccharomyces cerevisiae: homology to Bacillus brevis tyrocidine synthetase1," *Gene* 98:141-145 (1991).
Mountain et al., "The Klebsiella aerogenes glutamate dehydrogenase (gdnA) gene: cloning, high-level expression and hybrid enzyme formation in *Escherichia coli*," *Mol. Gen. Genet.* 199:141-145 (1985).
Muh et al., "4-Hydroxybutyryl-CoA dehydratase from Clostridium aminobutyricum: characterization of FAD and iron-sulfur clusters involved in an overall non-redox reaction," *Biochemistry* 35:11710-11718 (1996).

Muh et al., "Mossbauer study of 4-hydroxybutyryl-CoA dehydratase—probing the role of an iron-sulfur cluster in an overall non-redox reaction," *Eur. J. Biochem.* 248:380-384 (1997).
Muller et al., "Nucleotide exchange and excision technology (NExT) DNA shuffling: a robust method for DNA fragmentation and directed evolution," *Nucleic Acids Res.* 33(13):e117.
Mullins et al., "A specialized citric acid cycle requiring succinyl-coenzyme A (CoA):acetate CoA-transferase (AarC) confers acetic acid resistance on the acidophile Acetobacter aceti," *J. Bacteriol.* 190:4933-4940 (2008).
Muratsubaki and Enomoto, "One of the fumarate reductase isoenzymes from *Saccharomyces cerevisiae* is encoded by the OSM1 gene," *Arch. Biochem. Biophys.* 352(2):175-181 (1998).
Musfeldt and Schonheit, "Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcus jannaschii," *J. Bacteriol.* 184(3):636-644 (2002).
Nagasu et al., "Nucleotide Sequence of the GDH gene coding for the NADP-specific glutamate dehydrogenase of *Saccharomyces cerevisiae*," *Gene* 37:247-253 (1985).
Naggert et al., "Cloning, Sequencing, and Characterization of *Escherichia coli* thioesterasell," *J. Biol. Chem.* 266(17):11044-11050 (1991).
Najmudin et al., "Purification, crystallization and preliminary X-ray crystallographic studies on acetolactate decarboxylase," *Acta. Crystallogr. D. Biol. Crystallog.* 59:1073-1075 (2003).
Nakahigashi and Inokuchi, "Nucleotide sequence of the fadA and fadB genes from *Escherichia coli*," *Nucleic Acids Res.* 18(16):4937 (1990).
Nakano et al., "Characterization of Anaerobic Fermentative Growth of *Bacillus subtilis*: Identification of Fermentation End Products and Genes Required for Growth," *J. Bacteriol.* 179(21):6749-6755 (1997).
Namba et al., "Coenzyme A and Nicotinamide Adenine dinucleotide-deptendent Branched Chain α-Keto Acid Dehydrogenase," *J. Biol. Chem.* 244:4437-4447 (1969).
Ness et al., "Synthetic shuffling expands functional protein diversity by allowing amino acids to recombine independently," *Nat. Biotechnol.* 20(12):1251-1255 (2002).
Nexant, "1,4-Butanediol/THF—PERP Program New Report Alert," Nexant ChemSystems PERP Report 02/03-7, p. 1-5 (Jan. 2004).
Niegemann et al., "Molecular organization of the *Escherichia coli* gab cluster: nucleotide sequence of the structural genes gabD and gabP and expression of the GABA permease gene," *Arch. Microbiol.* 160:454-460 (1993).
Nishizawa et al., "Gene expression and characterization of two 2-oxoacid:ferredoxin oxidoreductases from Aeropyrum pernix K1," *FEBS. Lett.* 579:2319-2322 (2005).
Niu et al., "Benzene-free synthesis of adipic acid," *Biotechnol. Prog.* 18:201-211 (2002).
Nolling et al., "Genome sequence and comparative analysis of the solvent-producing bacterium Clostridium acetobutylicum," *J. Bacteriol.* 183(16):4823-4838 (2001).
Nowicki et al., "Recombinant tyrosine aminotransferase from Trypanosoma cruzi: structural characterization and site directed mutagenesis of a broad substrate specificity enzyme," *Biochim. Biophys. Acta* 1546(2):268-281 (2001).
Ohgami et al., "Expression of acetoacetyl-CoA synthetase, a novel cytosolic ketone body-utilizing enzyme, in human brain," *Biochem. Pharmacol.* 65:989-994 (2003).
Ohsugi et al., "Metabolism of L-β-Lysine by a Pseudomonas, Purification and Properties of a Deacetylase-Thiolesterase utilizing 4-Acetamidobutyrl CoA and Related Compounds," *J. Biol. Chem.* 256:7642-7651 (1981).
Okino et al., "An efficient succinic acid production process in a metabolically engineered Corynebacterium glutamicum strain," *Appl. Microbiol. Biotechnol.* 81(3):459-464 (2008).
Oku and Kaneda, "Biosynthesis of Branched-chain Fatty Acids in Bacillis subtilis," *J. Biol. Chem.* 263:18386-18396 (1988).
Okuno et al., "2-Aminoadipate-2-oxoglutarate aminotransferase isoenzymes in human liver: a plausible physiological role in lysine and tryptophan metabolism," *Enzyme Protein* 47(3):136-148 (1993).

(56) References Cited

OTHER PUBLICATIONS

Oliver et al., "Determination of the nucleotide sequence for the glutamate synthase structural genes of *Escherichia coli* K-12," *Gene* 60:1-11 (1987).

Olivera et al., "Molecular characterization of the phenylacetic acid catabolic pathway in Pseudomonas putida U: The phenylacetyl-CoA catabolon," *Proc. Natl. Acad. Sci. U.S.A.* 95:6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

O'Reilly and Devine, "Sequence and analysis of the citrulline biosynthetic operon argC-F from Bacillus subtilis," *Microbiology* 140:1023-1025 (1994).

Orencio-Trejo et al., "Metabolic regulation analysis of an ethanologenic *Escherichia coli* strain based on RT-PCR and enzymatic activities," *Biotechnol. Biofuels* 1:8 (2008).

Ostermeier et al., "A combinatorial approach to hybrid enzymes independent of DNA homology," *Nat. Biotechnol.* 17(12):1205-1209 (1999).

Ostermeier et al., "Combinatorial protein engineering by incremental truncation," *Proc. Natl. Acad. Sci. U.S.A.* 96(7):3562-3567 (1999).

O'Sullivan, et al., "Purification and characterisation of acetolactate decarboxylase from Leuconostoc lactis NCW1," *FEMS Microbiol. Lett.* 194(2):245-249 (2001).

Otten and Quax, "Directed evolution: selecting today's biocatalysts," *Biomol. Eng.* (22):1-9 (2005).

Palosaari and Rogers, "Purification and properties of the inducible coenzyme A-linked butyraldehyde dehydrogenase from Clostridium acetobutylicum," *J. Bacteriol.* 170(7):2971-2976 (1988).

Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).

Park and Lee, "Identification and Characterization of a New Enoyl coenzyme A Hydratase involved in biosynthesis of Medium-Chain-Length Polyhdroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng.* 86:681-686 (2004).

Park et al., "Regulation of succinate dehydrogenase (sdhCDAB) operon expression ion *Escherichia coli* in response to carbon supply and anaerobiosis: role of ArcA and Fnr," *Mol. Microbiol.* 15:473-482 (1995).

Park et al., "Aerobic regulation of the sucABCD genes of *Escherichia coli*, which encode alpha-ketoglutarate dehydrogenase and succinyl coenzyme A synthetase: roles of ArcA, Fnr, and the upstream sdhCDAB promoter," *J. Bacteriol.* 179:4138-4142 (1997).

Park et al., "Isolation and characterization of recombinant mitochondrial 4-aminobutyrate aminotransferase," *J. Biol. Chem.* 268:7636-7639 (1993).

Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene*. 68(2): 275-283 (1988).

Pauwels et al., "The N-acetylglutamate synthase? N-acetylglutamate kinase metabolon of *Saccharomyces cerevisiae* allows cor-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Pelanda et al., "Glutamate synthase genes of the diazotroph Azospirillum brasillense. Cloning, sequencing, and analysis of functional domains," *J. Biol. Chem.* 268:3099-3106 (1993).

Peoples and Sinskey, "Fine structural analysis of the Zoogloea ramigera phhA-phhB locus encoding beta-ketothiolase and acetoacetyl-CoA reductase: nucleotide sequence of phbB," *Mol. Microbiol.* 3:349-357 (1989).

Pereira et al., "Active site mutants of Escherichia coli citrate synthase. Effects of mutations on catalytic and allosteric properties," *J. Biol. Chem.* 269:412-417 (1994).

Peretz and Burstein, "Amino Acid Sequence of Alcohol Dehydrogenase from the Thermophilic Bacterium Thermoanaerobium brockii," *Biochemistry* 28:6549-6555 (1989).

Peretz et al., "Molecular cloning, nucleotide sequencing, and expression of genes encoding alcohol dehydrogenases from the thermophile Thermoanaerobacter brockii and the mesophile Clostridium beijerinckii," *Anaerobe* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior et al., "Reactivity of lactones and GHB formation," *J. Org. Chem.* 70(2):420-426 (2005).

Petitdemange et al., "Regulation of the NADH and NADPH-ferredoxin oxidoreductases in clostridia of the butyric group," *Biochim Biophys. Acta.* 421(2):334-337 (1976).

Phalip et al., "Purification and properties of the alpha-acetolactate decarboxylase from *Lactococcus lactis* subsp. Lactis NCDO 2118," *FEBS Lett.* 351:95-99 (1994).

Pharkya et al., "Exploring the overproduction of amino acids using the bilevel optimization framework OptKnock," *Biotechnol. Bioeng.* 84(7):887-899 (2003).

Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.* 174:177-182 (1988).

Pohl et al., "Remarkably broad substrate tolerance of malonyl-CoA synthetase, an enzyme capable of intracellular synthesis of polyketide precursors," *J. Am. Chem Soc.* 123(24): 5822-5823 (2001).

Pohlmann et al., "Genome sequence of the bioplastic-producing "Knallgas" bacterium Ralstonia eutropha H16," *Nat. Biotechnol.* 24(10):1257-1262 (2006).

Poirier et al., "Polyhydroxybutyrate, a Biodegradable Thermoplastic Produced in Transgenic Plants," *Science* 256:520-523 (1992).

Polovnikova et al., "Structural and Kinetic Analysis of Catalysis by a thiamin diphosphate-Dependent Enzyme, Benzoylformate Decarboxylase," *Biochemistry* 42:1820-1830 (2003).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175:377-385 (1993).

Presecan et al., "The Bacillus subtillis genome from gerBC (311 degrees) to licR (334 degrees)," *Microbiology* 143:3313-3328 (1997).

Price et al., "Genome-scale models of microbial cells: evaluating the consequences of constraints," *Nat. Rev. Microbiol.* 2(11):886-897 (2004).

Pritchard et al., "A general model of error-prone PCR," *J. Theor. Biol.* 234:497-509 (2005).

Purnell et al., "Modulation of higher-plant NAD(H)-dependent glutamate dehydrogenase activity in transgenic tobacco via alteration of beta subunit levels," *Planta* 222:167-180 (2005).

Qi et al., "Functional expression of prokaryotic and eukaryotic genes in *Escherichia coli* for conversion of glucose to p-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4)651-662 (2009).

Qiu et al., "Metabolic engineering for the production of copolyesters consisting of 3-hydroxybutyrate and 3-hydroxyhexanoate by Aeromonas hydrophilia," *Macromol. Biosci.* 4(3):255-261 (2004).

Radhakrishnan et al., "Applications of metabolic modeling to drive bioprocess development for the production of value-added chemicals," *Biotechnol. Bioprocess. Eng.* 10:408-417 (2005).

Rajpal et al., "A general method for greatly improving the affinity of antibodies by using combinatorial libraries," *Proc. Natl. Acad. Sci. U.S.A.* 102(24):8466-8471 (2005).

(56) References Cited

OTHER PUBLICATIONS

Ramon-Maiques et al., "Structure of Acetylglutamate Kinase, a Key Enzyme for Arginine Biosynthesis and a Prototype for the Amino Acid Kinase Enzyme Family, during Catalysis," *Structure* 10:329-342 (2002).
Ramos et al., "Mutations affecting the enzymes involved in the utilization of 4-aminobutyric acid as nitrogen source by the yeast *Saccharomyces cerevisiae*," *Eur. J. Biochem.* 149:401-404 (1985).
Rathinasabapathi, "Propionate, a source of β-alanine, is an inhibitor of β-alanine methylation in Limonium latifolium, Plumbaginaceae," *J. Plant Physiol.* 159:671-674 (2002).
Recasens et al., "Cysteine Sulfinate Aminotransferase and Aspartate Aminotransferase Isoenzymes of Rat Brain. Purification, Characterization, and Further Evidence for Identity," *Biochemistry* 19:4583-4589 (1980).
Redenbach et al., "A set of ordered cosmids and a detailed genetic and physical map for the 8 Mb Streptomyces coelicolor A3(2) chromosome," *Mol. Microbiol.* 21:77-96 (1996).
Reed et al., "An expanded genome-scale model of *Escherichia coli* K-12 (iJR904 GSM/GPR)," *Genome. Biol.* 4(9):R54 (2003).
Reetz and Carballeria, "Iterative saturation mutagenesis (ISM) for rapid directed evolution of functional enzymes," *Nat. Protoc.* 2(4):891-903 (2007).
Reetz et al., "Creation of Enantioselective biocatalysts for Organic Chemistry by In Vitro Evolution," *Agnew. Chem. Int. Ed. Engl.* 36:2830-2832 (1997).
Reetz et al., "Directed Evolution of an Enantioselective Enzyme through Combinatorial Multiple-Cassette Mutagenesis," *Agnew. Chem. Int. Ed. Engl.* 40:3589-3591 (2001).
Reetz et al., "Expanding the Range of Substrate Acceptance of Enzymes: Combinatorial Active-site saturation test," *Agnew. Chem.* 117:4264-4268 (2005).
Reetz et al., "Iterative Saturation Mutagenesis on the Basis of B Factors as a Strategy for Increasing Protein Thermostability," *Agnew. Chem. Int. Ed. Engl.* 45:7745-7751 (2006).
Reidhaar-Olson and Sauer, "Combinatorial cassette mutagenesis as a probe of the informational content of protein sequences," *Science* 241(4861):53-57 (1988).
Reidhaar-Olson et al., "Random mutagenesis of protein sequences using oligonucleotide cassettes," *Methods Enzymol.* 208:564-586 (1991).
Reiser and Somerville, "Isolation of mutants of Acinetobacter calcoaceticus deficient in wax ester synthesis and complementation of one mutation with a gene encoding a fatty acyl coenzyme A reductase," *J. Bacteriol.* 179(9):2969-2975 (1997).
Reitzer, "Ammonia Assimillation and the Biosynthesis of Glutamine, Glutamate, Aspartate, Asparagine, 1-Alanine, and d-Alanine," In Neidhardt (Ed.), *Escherichia coli and Salmonella: Cellular and Molecular Biology*, ASM Press: Washington, DC, p. 391-407 (1996).
Repetto and Tzagoloff, "Structure and Regulation of KGD1, the Structural Gene for Yeast α-Ketoglutarate Dehydrogenase," *Mol. Cell.* 9:2695-2705 (1989).
Resnekov et al., "Organization and regulation of the Bacillus subtilis odhAB operon, which encodes two of the subenzymes of the 2-oxoglutarate dehydrogenase complex," *Mol. Gen. Genet.* 234(2):285-296 (1992).
Ribeiro et al., "Microbial reduction of α-acetyl-γ-butyrolactone," *Tetrahedron: Asymmetry* 17(6):984-988 (2006).
Rigden et al., "A cofactor-dependent phosphoglycerate mutase homolog from Bacillus stearothermophilus is actually a broad specificity phosphatase," *Protein Sci.* 10:1835-1846 (2001).
Riondet et al., "Measurement of the intracellular pH in *Escherichia coli* with the internally conjugated fluorescent probe 5- (and 6-)carboxyfluorescein succinimidyl ester," *Biotechnol. Tech.* 11:735-738 (1997).
Riviere et al., "Acetyl:Succinate CoA-transferase in Procyclic Trypanosoma brucei," *J. Biol Chem.* 279(44):45337-45346 (2004).
Robinson et al., "Studies on Rat Brain Acyl-Coenzyme a Hydrolase (Short Chain)," *Biochem. Biophys. Res. Commun.* 71:959-965 (1976).

Roca et al., "Metabolic engineering of ammonium assimilation in xylose-fermenting *Saccharmyces cerevisiae* improves ethanol production," *Appl. Environ. Microbiol.* 69(8):4732-4736 (2003).
Rodriguez et al., "Characterization of the p-coumaric acid decarboxylase from Lactobacillus plantarum CECT 748(T)," *J. Agric. Food Chem.* 56(9):3068-3072 (2008).
Rohdich et al., "Enoate reductases of Clostridia. Cloning, sequencing, and expression," *J. Biol. Chem.* 276(8):5779-5787 (2001).
Romero et al., "Partial purification, characterization and nitrogen regulation of the lysine epsilon-aminotransferase of Streptomyces clavuligerus," *J. Ind. Microbiol. Biotechnol.* 18(4):241-246 (1997).
Rose and Weaver, "The role of the allosteric B site in the fumarase reaction," *Proc. Natl. Acad. Sci. U.S.A.* 101:3393-3397 (2004).
Rose et al., "Enzymatic phosphorylation of acetate," *J. Biol. Chem.* 211(2):737-756 (1954).
Roy and Dawes, "Cloning and Characterization of the Gene Encoding Lipamide Dehydrogenase in *Saccharomyces cerevisiae*," *J. Gen. Microbiol.* 133:925-933 (1987).
Ruldeekulthamrong et al., "Molecular characterization of lysine 6-dehydrogenase from Achromobacter denitrificans," *BMB Rep.* 41:790-795 (2008).
Sabo et al., "Purification and Physical Properties of Inducible *Escherichia coli* Lysine Decarboxylase," *Biochemistry* 13(4):662-670 (1974).
Saito and Doi, "Microbial synthesis and properties of poly(3-hydroxybutyrate-co-4-hydroxybutyrate) in Comamonas acidovorans," *Int. J. Biol. Macromol.* 16:99-104 (1994).
Saito et al., "Microbial Synthesis and properties of Poly(3-hydroxybutyrate-co-4-hydroxybutyrate)," *Polym. Int.* 39:169-174 (1996).
Sakakibara et al., "Isolation and characterization of a cDNA that encodes maize glutamate dehydrogenase," *Plant Cell Physiol.* 36:789-797 (1995).
Salmon et al., "Global gene expression profiling in *Escherichia coli* K12: effects of oxygen availability and ArcA," *J. Biol. Chem.* 280(15):15084-15096 (2005).
Samsonova et al., "Molecular cloning and characterization of *Escherichia coli* K12 ygjG gene," *BMC Microbiol.* 3:2 (2003).
Sanchez et al., "Properties and functions of two succinic-semialdehyde dehydrogenases from Pseudomonas putida," *Biochim. Biophys. Acta.* 953(3):249-257 (1988).
Sanchez et al., "Purification and properties of two succinic semialdehyde dehydrogenases from Klebsiella pneumoniae," *Biochim. Biophys. Acta.* 990(3):225-231 (1989).
Sato et al., "Poly[(R)-3-Hydroxybutyrate] Formation in *Escherichia coli* from Glucose through an Enoyl-CoA Hydratase-Mediated Pathway," *J. Biosci. Bioeng.* 103(1):38-44 (2007).
Scherf and Buckel, "Purification and properties of 4-hydroxybutyrate coenzyme A transferase from Clostridium aminobutyricum," *Appl. Environ. Microbiol.* 57(9):2699-2702 (1991).
Scherf and Buckel, "Purification and properties of an iron-sulfur and FAD-containing 4-hydroxybutyryl-CoA dehydratase/vinylacetyl-CoA Δ3-Δ2-isomerase from Clostridium aminobutyricum," *Eur. J. Biochem.* 215:421-429 (1993).
Scherf et al., "Suffinate-ethanol fermentation in Clostridium kluyveri: purification and characterisation of 4-hydroxybutyryl-CoA dehydratase/vinylacetyl-CoA delta 3-delta 2-isomerase," *Arch. Microbiol.* 161:239-245 (1994).
Schilling et al., "Combining Pathway Analysis with Flux Balance Analysis for the Comprehensive Study of Metabolic Systems," *Biotechnol. Bioeng.* 71(4):286-306 (2000-2001).
Schilling et al., "Theory for the Systematic Definition of Metabolic Pathways and Their Use in Interpreting Metabolic Function from a Pathway-Oriented Perspective," *J. Theor. Biol.* 203(3):229-248 (2000).
Schilling et al., "Toward Metabolic Phenomics: Analysis of Genomic Data Using Flux Balances," *Biotechnol. Prog.* 15(3):288-295 (1999).
Schneider et al., "The *Escherichia coli* gabDTPC operon: specific γ-aminobutyrate catabolism and nonspecific induction," *J. Bacteriol.* 184:6976-6986 (2002).

(56) References Cited

OTHER PUBLICATIONS

Schulz et al., "Stereopsecific Production of the Herbicide Phosphinothricin (Glufosinate) by Transamination: Isolation and Characterization of a Phosphinothricin-Specific Transaminase from *Escherichia coli*," *Appl. Environ. Microbiol.* 56:1-6 (1990).

Scott and Jakoby, "Soluble γ-Aminobutyric-Glutamic Transaminase from Pseudomonas fluorescens," *J. Biol. Chem.* 234:932-936 (1959).

Seedorf et al., "The genome of Clostridium kluyveri, a strict anaerobe with unique metabolic features," Proc. Natl. Acad. Sci. U.S.A. 105(6):2128-2133 (2008).

Seffernick et al., "Melamine deaminase and atrazine chlorohydrolase: 98 percent identical but functionally different," *J. Bacteriol.* 183(3):2405-2410 (2001).

Selifonova et al., "Rapid evolution of novel traits in microorganisms," *Appl. Environ. Microbiol.* 67(8):3645-3649 (2001).

Sen et al., "Developments in directed evolution for improving enzyme functions," *Appl. Biochem. Biotechnol.* 143(3):212-223 (2007).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanon et al., "Effect of ArcA and FNR on the expression of genes related to the oxygen regulation and the glycolysis pathway in *Eschericiha coli* under microaerobic growth conditions," *Biotechnol. Bioeng.* 92(2):147-159 (2005).

Shames et al., "Interaction of aspartate and aspartate-derived antimetabolites with the enzymes of the threonine biosynthetic pathway of *Escherichia ecoli*," *J. Biol. Chem.* 259(24):15331-15339 (1984).

Shao et al., "Random-priming in vitro recombination: an effective tool for directed evolution," *Nucleic Acids Res.* 26(2):681-683 (1998).

Shi et al., "The structure of L-aspartate ammonia-lyase from *Escherichia coli*," *Biochem.* 36(30):9136-9144 (1997).

Shigeoka and Nakano, "Characterization and molecular properties of 2-oxoglutarate decarboxylase from Euglena gracilis," *Arch. Biochem. Biophys.* 288:22-28 (1991).

Shigeoka and Nakano, "The effect of thiamin on the activation of thiamin pyrophosphate-dependent 2-oxoglutarate decarboxylase in Euglena gracilis," *Biochem. J.* 292 (Pt 2):463-467 (1993).

Shigeoka et al., "Effect of L-glutamate on 2-oxoglutarate decarboxylase in Euglena gracilis," *Biochem. J.* 282 ( Pt 2):319-323 (1992).

Shimomura et al., "3-Hydroxyisobutyryl-CoA Hydrolase," *Meth. Enzymol.* 324:229-240 (2000).

Shimomura et al., "Purification and Partial Characterization of 3-Hydroxyisobutyryl-coenzyme A Hydrolase of Rat Liver," *J. Biol. Chem.* 269:14248-14253 (1994).

Shingler et al., "Nucleotide Sequence and Functional Analysis of the Complete Phenol/3,4-Dimethylphenol Catabolic Pathway of *Pseudomonas* sp. Strain CF600," *J. Bacteriol.* 174(3):711-724 (1992).

Shiraki et al., "Fermentative production of (R)-(-)-(3) hydroxybutyrate using 3-hydroxybutyrate dehydrogenase null mutant of Ralstonia eutropha and recombinant *Escherichia coli*," *J. Biosci. Bioeng.* 102(6):529-534 (2006).

Shukla et al., "Production of D(-)-lactate from sucrose and molasses," *Biotechnol. Lett.* 26(9):689-693 (2004).

Sieber et al., "Libraries of hybrid proteins from distantly related sequences," *Nat. Biotechnol.* 19(5):456-460 (2001).

Siegert et al., "Exchanging the substrate specificities of pyruvate decarboxylase from Zymomonas mobilis and benzoylase from *Pseudomonas putida*," *Protein Eng. Des. Sel.* 18:345-357 (2005).

Simonov et al.,"Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Sinclair et al, "Purification and characterization of the branched chain α-ketoacid dehydrogenase complex from *Saccharomyces cerevisiae*," *Biochem. Mol. Biol. Int.* 31(5):911-922 (1993).

Sivaraman et al., "Codon choice in genes depends on flanking sequence information—implications for theoretical reverse translation," *Nucleic Acids Res.* 36(3):e16 (2008).

Sjostrom et al., "Purification and characterisation of a plasminogen-binding protein from Haemophilus influenzae. Sequence determination reveals identity with aspartase," *Biochim. Biophys. Acta.* 1324:182-190 (1997).

Skarstedt and Silverstein, "*Escherichia coli* Acetate Kinase Mechanism Studied by Net Initial Rate, Equilibriu, and Independent Isotopic Exchange Kinetics," *J. Biol. Chem.* 251:6775-6783 (1976).

Skinner and Cooper, "An *Escherichia coli* mutant defective in the NAD-dependent succinate semialdehyde dehydrogenase," *Arch. Microbiol.* 132(3):270-275 (1982).

Smit et al., "Identification, Cloning, and Characterization of a Lactococcus lactis Branched-Chain α-Keto Acid Decarboxylase Involved in Flavor Formation," *Appl. Environ. Microbiol.* 71:303-311 (2005).

Smith et al., "Fumarate metabolism and the microaerophily of Campylobacter species," *Int. J. Biochem. Cell Biol.* 31:961-975 (1999).

Smith et al., "Purification and characteristics of a gamma-glutamyl kinase involved in *Escherichia coli* proline biosynthesis," *J.Bacteriol.* 157:545-551 (1984).

Smith et al., "Complete genome sequence of Methanobacterium thermoautotrophicum deltaH: functional analysis and comparative genomics," *J. Bacteriol.* 179:7135-7155 (1997).

Snedecor et al., "Selection, expression, and nucleotide sequencing of the glutamate dehydrogenase gene of Peptostreptococcus asaccharolyticus," *J. Bacteriol.* 173:6162-6167.

Soda and Misono, "L-Lysine:alpha-ketoglutarate aminotransferase. II. Purification, crystallization, and properties," *Biochemistry* 7(11):4110-4119 (1968).

Sohling and Gottschalk, "Molecular analysis of the anaerobic succinate degradation pathway in Clostridium kluyveri.," *J. Bacteriol.* 178(3):871-880 (1996).

Söhling and Gottschalk, "Purification and characterization of a Coenzyme-A-dependent succinate-semialdehyde dehydrogenase from Clostridium kluyveri," *Eur. J. Biochem.* 212:121-127 (1993).

Sohling et al., "Molecular analysis of the anaerobic succinate degradation pathway in Clostridium kluyveri," *J. Bacteriol.* 178(3):871-880 (1996).

Sokatch et al., "Purification of a Branched-Chain Keto Acid Dehydrogenase from Pseudomonas putida," *J. Bacteriol.* 647-652 (1981).

Song et al., "Construction of recombinant *Escherichia coli* strains producing poly (4-hydroxybutyric acid) homopolyester from glucose," Wei Sheng Wu Xue.Bao. 45:382-386 (2005). (In Chinese, includes English abstract).

Song et al., "Structure, Function, and Mechanism of the Phenylacetate Pathway Hot Dog-fold Thioesterase PaaI," *J. Biol. Chem.* 281(16):11028-11038 (2006).

Spencer and Guest, "Transcription analysis of the sucAB, aceEF and lpd genes of *Escherichia coli*," *Mol. Gen. Genetics* 200:145-154 (1985).

Spencer et al., "Nucleotide sequence of the sucB gene encoding the dihydrolipoamide succinyltransferase of *Escherichia coli* K12 and homology with the corresponding acetyltransferase," *Eur. J. Biochem.* 141(2):361-374 (1984).

Stadtman, "The enzymatic synthesis of β-alanyl coenzyme A," *J. Am. Chem. Soc.* 77:5765-5766 (1955).

Stanley et al., "Expression and stereochemical and isotope effect studies of active 4-oxalocrotonate decarboxylase," *Biochemistry* 39(12):3514 (2000).

Stanley et al., "Expression and Sterochemical and Isotope Effect Studies of Active 4-Oxalocrotonate Decarboxylase," *Biochemistry* 39:(4):718-726 (2000).

Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," *Microbiology* 151(Pt 11):3793-3801 (2005).

(56) References Cited

OTHER PUBLICATIONS

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005). (Epub May 17, 2005).
Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Steinbuchel and Schlegel, "A multifunctional fermentative alcohol dehydrogenase from the strict aerobe Alcaligenes eutrophus: purification and properties," *Eur. J. Biochem.* 141:555-564 (1984).
Steinbuchel and Schlegel, "Physiology and molecular genetics of poly(beta-hydroxy-alkanoic acid) synthesis in Alcaligenes eutrophus," *Mol. Microbiol.* 5(3):535-542 (1991).
Steinbuchel and Valentin, "Diversity of bacterial polyhydroxyalkanoic acids," *FEMS Microbiol. Lett.* 128:219-228 (1995).
Steinbuchel et al., "A *Pseudomonas* strain accumulating polyesters of 3-hydroxybutyric acid and medium-chain-length 3-hydroxyalkanoic acids," *Appl. Microbiol. Biotechnol.* 37:691-697 (1992).
Stemmer, "DNA Shuffling by random fragmentation and reassembly: in vitro recombination for molecular evolution," *Proc. Natl. Acad. Sci. U.S.A.* 91(22):10747-10751 (1994).
Stemmer, "Rapid evolution of a protein in vitro by DNA shuffling," *Nature* 370:389-391 (1994).
Stokell et al., "Probing the roles of key residues in the unique regulatory NADH binding site of type II citrate synthase of *Escherichia coli*," *J. Biol. Chem.* 278(37):35435-35443 (2003).
Stols et al., "New vectors for co-expression of proteins: Structure of Bacillus subtilis ScoAB obtained by high-throughput protocols," *Protein Expr. Purif.* 53:396-403 (2007).
Stoyan et al., "Cloning, sequencing and overexpression of the leucine dehydrogenase gene from *Bacillus cereus*," *J. Biotechnol.* 54:77-80 (1997).
Strauss and Fuchs, "Enzymes of a novel autotrophic CO2 fixation pathway in the phototrophic bacterium Chloroflexus aurantiacus, the 3-hydroxypropionate cycle," *Eur. J. Biochem.* 215:633-643 (1993).
Suda et al., "Purification and properties of alpha-keoadipate reductase, a newly discovered enzyme from human placenta," *Arch. Biochem. Biophys.* 176(2):610-620 (1976).
Suda et al., "Subcellular Localization and tissue Distribution of α-Ketodaipate Reduction and Oxidation in the Rat," *Biochem. Biophys. Res. Commun.* 77:586-591 (1977).
Suematsu et al., "Molecular cloning and functional expression of rat liver cytosolic acetyl-CoA hydrolase," *Eur. J. Biochem.* 268(9):2700-2709 (2001).
Sulzenbacher et al., "Crystal structure of *E.coli* alcohol dehydrogenase YqhD: evidence of a covalently modified NADP coenzyme," *J. Mol. Biol.* 342(2):489-502 (2004).
Suthers et al., "Metabolic flux elucidation for large-scale models using 13C labeled isotopes," *Metab. Eng.* 9(5-6):387-405 (2007).
Suzuki et al., "GriC and GriD Constitute a carboxylic acid reductase involved in grixazone biosynthesis in Streptomyces griseus," *J. Antibiot.* 60(6):380-387 (2007).
Suzuki, "Phosphotransacetylase of *Escherichia coli* B, activation by pyruvate and inhibition by NADH and certain nucleotides," *Biochim Biophys. Acta* 191(3):559-569 (1969).
Syntichaki et al., "The amino-acid sequence similarity of plant glutamate dehydrogenase to the extremophilic archaeal enzyme conforms to its stress-related function," *Gene.* 168:87-92.
Takagi and Kisumi, "Isolation of a Versatile Serratia marcescens Mutant as a Host and Molecular Cloning of the Aspartase Gene," *J. Bacteriol.* 161(1):1-6 (1985).
Takagi et al., "Purfication, Crystallization, and Molecular Properties of Aspartase from Pseudomonas fluorescens," *J. Biochem.* 96:545-552 (1984).
Takahashi et al., "Metabolic Pathways for Cytoxic End Product Formation from Glutamate- and Aspartate-Containing Peptides by Porphyromonas gingivalis," *J. Bacteriol.* 182(17):4704-4710 (2000).

Takahashi-Abbe et al., "Biochemical and functional properties of a pyruvate formate-lyase (PFL)-activating system in *Streptococcus mutans*," *Oral Microbiol. Immunol.* 18(5)293-297 (2003).
Takanashi et al., "Characterization of a novel 3-hydroxybutyrate dehydrogenase from Ralstonia pickettii T1," *Antonie van Leeuwnhoek* 95(3):249-262 (2009).
Takatsuka et al., "Gene cloning and molecular characterization of lysine decarboxylase from Selenomonas ruminantium delineate its evolutionary relationship to ornithine decarboxylases from eukaryotes," *J. Bacteriol.* 182(23):6732-6741 (2000).
Takatsuka et al., "Identification of the amino acid residues conferring substrate specificity upon selenomonas ruminantium lysine decarboxylase," *Biosci. Biotechnol. Biochem.* 63(10):1843-1846 (1999).
Takigawa et al., "Probabilistic path ranking based on adjacent pairwise coexpression for metabolic transcripts analysis," *Bioinformatics* 24(2):250-257 (2008).
Tamaki et al., "Purification, Properties, and Sequencing of Aminisobutyrate Aminotransferases from Rat Liver," *Meth. Enzymol.* 324:376-389 (2000).
Tanaka et al., "Cloning and characterization of a human orthologue of testis-specific succinyl CoA:3-oxo acid CoA transferase (Scot-t) cDNA," *Mol. Hum. Reprod.* 8:16-23 (2001.).
Tanaka et al., "Lysine decarboxylase of Vibrio parahaemolyticus: kinetics of transcription and role in acid resistance," *J. Appl. Microbiol.* 104(5):1283-1293 (2007).
Tang et al., "Identification of a novel pyridoxal 5'-phosphaste binding site in adenosylcobalamin-dependent lysine 5,6-aminomutase from Porphyromonas gingivalis," *Biochemistry* 41(27):8767-8776 (2002).
Tani et al., "Thermostable NADP(+)-dependent medium-chain alcohol dehydrogenase from *Acinetobacter* sp strain M-1: Purification and characterization and gene expression in *Escherichia coli*," *Appl. Environ. Microbiol.* 66:5231-5235 (2000).
Teller et al., "The glutamate dehydrogenase gene of Clostridium symbiosum, Cloning by polymerase chain reaction sequence analysis and over-expression in *Escherichia coli*," *Eur. J. Biochem.* 206:151-159 (1992).
Ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," *Appl. Environ. Microbiol.* 64(4):1303-1307 (1998).
Thakur et al., "Changes in the Electroencephalographic and .gamma.-Aminobutyric Acid Transaminsase and Succinic Semialdehyde Dehydrogenase in the Allergen Induced Rat Brain," *Biochem. Int.* 16:235-243 (1998).
Thauer, "Microbiology. A fifth pathway of carbon fixation," *Science* 318:1732-1733 (2007).
Tian et al., "Variant tricarboxylic acid cycle in *Mycobacterium tuberculosis*: identification of alpha-ketoglutarate decarboxylase," *Proc. Natl. Acad. Sci. U.S.A.* 102(30):10670-10675 (2005).
Tobin et al., "Localization of the lysine epsilon-aminotransferase (lat) and delta- (L-alphaaminoadipyl)-L-cysteinyl-D-Valine synthetase (pcbAB) genes from Streptomyces clavuligerus and production of lysine epsilon-aminotransferase activity in *Escherichia coli*," *J. Bacteriol.* 173(19):6223-6229 (1991).
Tomb et al., "The complete genome sequence of the gastric pathogen Helicobacter pylori," *Nature* 388:539 (1997).
Toth et al., "The ald gene, encoding a coenzyme A-acylating aldehyde dehydrogenase, distinguishes Clostridium beijerinckii and two other solvent-producing clostridia from Clostridium acetobutylicum," *Appl. Environ. Microbiol.* 65(11):4973-4980 (1999).
Tretter and Adam-Vizi, "Alpha-ketoglutarate dehydrogenase: a target and generator of oxidative stress," *Philos. Trans. R. Soc. Lond B. Biol. Sci.* 360:2335-2345 (2005).
Tseng et al., "Metabolic engineering of Escherichia coli for enhanced production of (R)- and (S)-3-hydroxybutyrate," *Appl. Environ. Microbiol.* 75(10):3137-3145 (2009).
Tucci and Martin, "A novel prokaryotic trans-2-enoyl-CoA reductase from the spirochete Treponema denticola," *FEBS Lett.* 581:1561-1566 (2007).

(56) References Cited

OTHER PUBLICATIONS

Twarog and Wolfe, "Role of Buyryl Phosphate in the Energy Metabolism of Clostridium Tetanomorphum," *J. Bacteriol.* 86:112-117 (1963).
Tzimagiorgis et al., "Molecular cloning, structure and expression analysis of a full-length mouse brain glutamate dehydrogenase cDNA," *Biochem. Biophys. Acta.* 1089:250-253 (1991).
Tzimagiorgis et al., "Structure and expression analysis of a member of the human glutamate dehydrogenase (GLUD) gene gamily mapped to chromosome 10p11.2," *Hum. Genet.* 91:433-438 (1993).
Uchiyama et al., "Identification of the4-Hydroxycinnamate Decarboxylase (PAD) Gene of Klebsiella oxytoca," *Biosci. Biotechnol. Biochem.* 72:116-123 (2008).
Umeda et al., "Cloning and sequence analysis of the poly(3-hydroxyalkanoic acid)-synthesis genes of Pseudomonas acidophila," *Appl. Biochem. Biotechnol.* 70-72:341-352 (1998).
Uttaro and Opperdoes, "Purification and characterisation of a novel iso-propanol dehydrogenase from *Phytomonas* sp," *Mol. Biochem. Parasitol.* 85:213-219 (1997).
Valdes-Hevia and Gancedo, "Isolation and characterization of the gene encoding phosphoenolpyruvate carboxykinase from *Saccharomyces cerevisiae*," *FEBS Lett.* 258(2):313-316 (1989).
Valentin et al., "Indentication of 4-hydroxyhexanoic acid as a new constituent of biosynthetic polyhydroxyalkanoic acids from bacteria," *Appl. Microbiol. Biotechnol.* 40:710-716 (1994).
Valentin et al., "Identification of 4-hydroxyvaleric acid as a constituent of biosynthetic polyhydroxyalkanoic acids from bacteria," *Appl. Microbiol. Biotechnol.* 36:507-514 (1992).
Valentin et al., "Identification of 5-hydroxyhexanoic acid, 4-hydroxyaheptanoic acid and 4-hydroxyoctanoic acid as new constituents of bacterial polyhydroxyalkanoic acids," *Appl. Microbiol. Biotechnol.* 46:261-267 (1996).
Valentin et al., "Metabolic pathway for biosynthesis of poly(3-hydroxybutyrate-co-4-hydroxybutyrate) from 4-hydroxybutyrate by Alcaligenes eutrophus," *Eur. J. Biochem.* 227(1-2):43-60 (1995).
Valentin et al., "Poly(3-hydroxybutyrate-co-4-hydroxybutyrate) formation from gamma-aminobutyrate and glutamate," *Biotechnol Bioeng.* 67(3):291-299 (2000).
Valentin et al., "Production of poly(3-hydroxybutyrate-co-4-hydroxybutyrate) in recombinant *Escherichia coli* grown on glucose," *J. Biotechnol.* 58:33-38 (1997).
Valentine and Wolfe, "Purification and role of phosphotransbutyrylase," *J. Biol. Chem.* 235:1948-1952 (1960).
Valle et al., "Complete nucleotide sequence of the glutamate dehydrogenase gene from *Escherichia coli* K-12," *Gene* 27:193-199 (1984).
Valle et al., "Nucleotide sequence of the promotor and amino-terminal coding region of the glutamate dehydrogenase structural gene of *Escherichia coli*," *Gene* 23:199-209 (1983).
Vamecq et al., "The microsomal dicarboxylyl-CoA synthetase," *Biochem. J.* 230:683-693 (1985).
van der Rest et al., "Functions of the membrane-associated and cytoplasmic malate dehydrogenases in the citric acid cycle of *Escherichia coli*," *J. Bacteriol.* 182(24):6892-6899 (2000).
van der Voorhorst et al., "Genetic and biochemcial characterization of a short-chain alcohol dehydrogenase from the hyperthermophilic archaeon Pyrococcus furiosus," *Eur. J. Biochem.* 268:3062-3068 (2001).
Van Grinsven et al., "Acetate:Succinate CoA-transferase in the Hydrogenosomes of Trichomonas vaginalis," *J. Biol. Chem.* 283:1411-1418 (2008).
Vanderwinkel et al., "Growth of *Escherichia coli* on Fatty Acids: Requirement for Coenzyme a Transferase Activity," *Biochem. Biophys. Res. Commun.* 33:902-908 (1968).
Vanrolleghem et al., "Validation of a Metabolic Network for *Saccharomyces cerevisiae* Using Mixed Substrate Studies," *Biotechnol. Prog.* 12(4):434-448 (1996).
Varma and Palsson, "Metabolic Flux Balancing: Basic Concepts, Scientific and Practical Use," *Biotechnology* 12:994-998 (1994).
Varma and Palsson, "Stoichiometric flux balance models quantitatively predict growth and metabolic by-product secretion in wild-type *Escherichia coli* W3110," *Appl. Environ. Microbiol.* 60:3724-3731 (1994).
Vazquez et al., "Phosphotransbutyrylase Expression in Bacillus megaterium," *Curr. Microbiol.* 42:345-349 (2001).
Venkitasubramanian et al. Biocatalysis in the Pharmaceutical and Biotechnology Industries, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol Chem.* 282:478-485.
Vernal et al., "Cloning and heterologous expression of a broad specificity aminotransferase of leishmania mexicana promastigotes1," *FEMS Microbiol. Lett.* 229(2):217-222 (2003).
Vernal et al., "Isolation and partial characterization of a broad specificity aminotransferase from Leishmania mexicana promastigotes," *Mol. Biochem. Parasitol.* 96(1-2):83-92 (1998).
Vey et al., "Structural basis for glycyl radical formation by pyruvate formate-lyase activating enzyme," *Proc. Natl. Acad. Sci. U.S.A.* 105(42):16137-16141 (2008).
Viola, "L-aspartase: new tricks from an old enzyme," *Adv. Enzymol. Relat. Areas. Mol. Biol.* 74:295-341 (2000).
Vita et al., "Disulfide bond-dependent mechanism of protection against oxidative stress in pyruvate-ferredoxin oxidoreductase of anaerobic Desulfovibrio bacteria," *Biochemistry.* 47(3):957-964 (2008).
Volkov et al., "Random chimeragenesis by heteroduplex recombination," *Methods Enzymol.* 328:456-463 (2000).
Volkov et al., "Recombination and chimeragenesis by in vitro heteroduplex formation and in vivo repair," *Nucleic Acids Res.* 27(18):e18 (1999).
Wakil et al., "Studies on the Fatty Acid Oxidizing System of Animal Tissues," *J. Biol. Chem.* 207:631-638 (1954).
Walter et al., "Sequence and arrangement of two genes of the butyrate-synthesis pathway of Clostridium acetobutylicum ATCC 824," *Gene* 134:107-111 (1993).
Walter et al., "Molecular characterization of two Clostridium acetobutylicum ATCC 824 butanol dehydrogenase isozyme genes," *J. Bacteriol.* 174(22):7149-7158 (1992).
Wang et al., "Molecular cloning and functional identification of a novel phenylacetyl-CoA ligase gene from Penicillium chrysogenum," *Biochem. Biophys. Res. Commun.* 360(2):453-458 (2007).
Wang et al., "The primary structure of branched-chain a-oxo acid dehydrogenase from Bacillus subtilis and its similarity to other α-oxo acid dehydrogenases," *Eur. J. Biochem.* 213:1091-1099 (1993).
Wang et al., "Isolation of poly-3-hydroxybutyrate metabolism genes from complex microbial communities by phenotypic complementation of bacterial mutants," *Appl. Environ. Microbiol.* 72(1):384-391 (2006).
Wang et al., "Screening microorganisms for utilization of furfural and possible intermediates in its degradative pathway," *Biotechnol. Lett.* 16(9):977-982 (1994).
Ward et al., "Molecular analysis of the role of two aromatic aminotransferases and a broad-specificity aspartate aminotransferase in the aromatic amino acid metabolism of Pyrococcus furiosus," *Archaea* 1:133-141 (2002).
Weaver, "Structure of free fumarase C from *Eschericiha coli*," *Acta. Crystallog. D. Biol. Crystallogr.* 61:1395-1401 (2005).
Weidner and Sawers, "Molecular Characterization of the Genes Encoding Pyruvate Formate-Lyase and Its Activating Enzyme of Clostridium pasteruianum," *J. Bacteriol.* 178(8):2440-2444 (1996).
Welch et al., "Purification and characterization of the NADH-dependent butanol dehydrogenase from Clostridium acetobutylicum (ATCC 824)," *Arch. Biochem. Biophys.* 273(2):309-318 (1989).
Werpy et al., "Top Value Added Chemicals from Biomass. vol. I—Results of Screening for Potential Candidates from Sugars and Synthesis Gas," *DOE Report* (2004).
Westin et al., "The Identification of Succinyl-CoA Thioesterase Suggests a Novel Pathway for Succinate Production in Peroxisomes," *J. Biol. Chem.* 280(46):38125-38132 (2005).

(56) References Cited

OTHER PUBLICATIONS

Wexler et al., "A wide host-range metagenomic library from a waste water treatment plant yields a novel alcohol/aldehyde dehdrogenase," *Environ. Microbiol.* 7:1917-1926 (2005).
Whalen and Berg, "Analysis of an avtA::Mu d1(Ap lac) Mutant: Metabolic role of Transaminase C," *J. Bacteriol.* 150(2):739-746 (1982).
Whalen and Berg, "Gratuitous Repression of avtA in *Escherichia coli* and *Salmonella typhimurium*," *J. Bacteriol.* 158(2):571-574 (1984).
Wiesenborn et al., "Coenzyme A Transferase from Clostridium acetobutylicum ATC 824 and Its Role in the Uptake of Acids," *Appl. Environ. Microbiol.* 55:323-329 (1989).
Wilkie and Warren, "Recombinant Expression, Purification, and Characterization of Three Isoenzymes of Aspartate Aminotrannsferase from *Arabidopsis thaliana*," *Protein Expr. Purif.* 12:381-389 (1998).
Wilks et al., "A specific, highly active malate dehydrogenase by redesign of a lactate dehydrogenase framework," *Science* 242(4885):1541-1544 (1988).
Wilks et al., "Design for a broad substrate specificity keto acid dehydrogenase," *Biochemistry* 29(37)8587-8591 (1990).
Wilks et al., "Design of a specific phenyllactate dehydrogenase by peptide loop exchange on the Bacillus stearothermophilus lactate dehydrogenase framework," *Biochemistry* 31(34):7802-7806 (1992).
Willadsen and Buckel, "Assay of 4-hydroxybutyryl-CoA dehydrasate from Clostridium aminobutyricum," *FEMS Microbiol. Lett.* 70:187-191 (1990).
Williams et al., "Biodegradable plastics from plants," *CHEMTECH* 26:38-44 (1996).
Willke and Vorlop, "Biotechnological production of itaconic acid," *Appl. Microbiol. Biotechnol.* 56:289-295 (2001).
Winzer et al., "Differential regulation of two thiolase genes from Clostridium acetobutylicum DSM 792," *J. Mol. Microbiol. Biotechnol.* 2:531-541 (2000).
Witkowski et al., "Conversion of a β-ketoacyl synthase to a malonyl decarboxylase by replacement of the active-site cysteine with glutamine," *Biochemistry* 38(36):11643-11650 (1999).
Wolff and Kenealy, "Purification and characterization of the oxygen-sensitive 4-hydroxybutanoate dehydrogenase from Clostridium kluyveri," *Protein Expr. Purif.* 6:206-212 (1995).
Wolff et al., "Dehydrogenases involved in the conversion of succinate to 4-hydroxybutanoate by Clostridium kluyven," *Appl. Environ. Microbiol.* 59:1876-1882 (1993).
Wong et al., "Sequence satruation mutagenesis with tunable mutation frequencies," *Anal. Biochem.* 341:187-189 (2005).
Wong et al., "Sequence saturation mutagenesis (SeSaM): a novel method for directed evolution," *Nucleic Acids Res.* 32(3):e26 (2004).
Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).
Wynn et al., "Chaperonins GroEL and GroES Promote Assembly of Heterotramers (α2β2) of Mammalian Mitochondrial Branched-chain α-Keto Acid Decarboxylase in *Escherichia coli*," *J. Biol. Chem.* 267(18):12400-12403 (1992).
Wynn et al., "Cloning and Expression in *Escherichia coli* of a Mature E1β Subunit of Bovine Mitochondrial Branched-chain α-Keto Acid Dehydrogenase Complex," *J. Biol Chem.* 267(3):1881-1887 (1992).
Yagi et al., "Aspartate: 2-0xoglutarate Aminotransferase from Bakers' Yeast: Crystallization and Characterization," *J. Biochem.* 92:35-43 (1982).
Yagi et al., "Crystallization and Properties of Aspartate Aminotransferase from *Escherichi coli* B," *FEBS Lett.* 100(1)81-84 (1979).
Yagi et al., "Glutamate-Aspartate Transaminase from Microorganisms," *Meth. Enzymol.* 113:83-89 (1985).
Yakunin and Hallenbeck, "Purification and characterization of pyruvate oxidoreductase from the photosynthetic bacterium Rhodobacter capsulatus," *Biochim. Biophys. Acta.* 1409(1):39-49 (1998).
Yamamoto et al., "Carboxylation reaction catalyzed by 2-oxoglutarate:ferredoxin oxidoreductases from Hydrogenobacter thermophilus," *Extremophiles* 14:79-85 (2010).
Yamamoto et al., "Purification and properties of NADP-dependent formate dehydrogenase from Clostridium thermoaceticum, a tungsten-selenium-iron protein," *J. Biol. Chem.* 258(3):1826-1832 (1983).
Yang et al, "Nucleotide Sequence of the fadA Gene. Primary structure of 3-ketoacyl-coenzyme A thiolase from *Escherichia coli* and the structural organization of the fadAB operon," *J. Biol. Chem.* 265(18):10424-10429 (1990) with correction in *J. Biol. Chem.* 266(24):16255 (1991).
Yang et al., "Aspartate Dehydrogenase, a Novel Enzyme Idnetified from Structural and Functional Studies of TM16343," *J. Biol. Chem.* 278:8804-8808 (2003).
Yang et al., "Nucleotide sequence of the promoter and fadB gene of the fadBA operon and primary structure of the multifunctional fatty acid oxidation protein from *Escherichia coli*," *Biochemistry* 30(27):6788-6795 (1991).
Yano et al., "Directed evolution of an aspartate aminotransferase with new substrate specificities," *Proc. Natl. Acad. Sci. U.S.A.* 95:5511-5515 (1998).
Yarlett et al., "Trichomonas vaginalis: characterization of ornithine decarboxylase," *Biochem. J.* 293:487-493 (1993).
Yee et al., "Isolation and characterization of a NADP-dependent glutamate dehydrogenase gene from the primitive eucaryote Giardia lamblia," *J. Biol. Chem.* 267:7539-7544 (1992).
Yoshida et al., "The structures of L-rhamnose isomerase from Pseudomonas stutzeri in complexes with L-rhamnose and D-allose provide insights into broad substrate specificity," *J. Mol. Biol.* 365(5):1505-1516 (2007).
Youngleson et al., "Homology between hydroxybutyryl and hydroxyacyl coenzyme A dehydrogenase enzymes from Clostridium acetobutylicum fermentation and vertebrate fatty acid beta-oxidation pathways," *J. Bacteriol.* 171(12):6800-6807 (1989).
Yu et al., "sucAB and sucCD are mutually essential genes in *Escherichia coli*," *FEMS Microbiol. Lett.* 254(2):245-250 (2006).
Yun et al., "The genes for anabolic 2-oxoglutarate: ferredoxin oxidoreductse from hydrogenobacter thermophilus TK-6," *Biochem. Biophys. Res. Commun.* 282(2):589-594.
Yun et al., "ω-Amino acid:pyruvate transaminase from Alcaligenes denitrificans Y2k-2: a new catalyst for kinetic resolution of β-amino acids and amines," *Appl. Environ. Microbiol.* 70(4):2529-2534 (2004).
Zeiher and Randall, "Identification and Characterization of Mitochondrial Acetyl-Coenzyme A Hydrolase from Pisum sativum L. Seedlings," *Plant Physiol.* 94:20-27 (1990).
Zhang et al., "2-Oxoacid: Ferredoxin Oxidoreductase from the Thermoacidophilic Archaeon, *Sulfolobus* sp. Strain 7," *J. Biochem.* 120:587-599 (1996).
Zhang et al., "Directed evolution of a fucosidase from a galactosidase by DNA shuffling and screening," *Proc. Natl. Acad. Sci. U.S.A.* 94:4504-4509 (1997).
Zhang et al., "Isolation and Properties of a levo-lactonase from Fusarium proliferatum ECD2002: a robust biocatalyst for production of chiral lactones," *App. Microbiol. Biotechnol.* 75(5):1087-1094 (2007).
Zhang, et al., "Kinetic and mechanistic characterization of the polyhydroxybutyrate synthase from Ralstonia eutropha," *Biomacromolecules* 1(2):244-251 (2000).
Zhao et al., "Molecular evolution by staggered extension process (StEP) in vitro recombination," *Nat. Biotechnol.* 16(3):258-261 (1998).
Zhou et al., "Engineering a native homoethanol pathway in *Escherichia coli* B for ethanol production," Biotechnol. Lett. 30:335-342 (2008).
Zhou et al., "The remarkable structural and functional organization of the eukaryotic pyruvate dehydrogenase complexes," *Proc. Natl. Acad. Sci. U.S.A.* 98:14802-14807 (2001).

(56) References Cited

OTHER PUBLICATIONS

Zhou et al., "Functional replacement of the *Escherichia coli* D-(−)-lactate dehydrogenase gene (ldhA) with the L-(+)-lactate dehydrogenase gene (ldhL) from Pediococcus acidilactici," *Appl. Environ. Micro.* 69:2237-2244 (2003).

Zhuang et al., "The YbgC protein encoded by the ybgC gene of the tol-pal gene cluster of Haemophilus influenzae catalyzes acyl-coenzyme A thioester hydrolysis," *FEBS Lett.* 516:161-163 (2002).

Four pages from URL: shigen.nig.ac.jp/ecoli/pec/genes.List.DetailAction.do (Printed Dec. 21, 2009).

Two pages from URL: www.genome.jp/dbget-bin/www_bget?cdf:CD2966 (Printed Dec. 21, 2009).

Two pages from URL: www.genome.jp/dbget-bin/www_bget?cpe:CPE2531 (Printed Dec. 21, 2009).

Two pages from URL: www.genome.jp/dbget-bin/www_bget?ctc:CTC01366 (Printed Dec. 21, 2009).

Two pages from URL: www.genome.jp/dbget-bin/www_bget?cth:Cthe_0423 (Printed Mar. 4, 2010).

Two pages from URL: Openwetware.org/wiki/Synthetic_Biology:BioBricks, Synthetic Biology:BioBricks, portal for information relating to the Resistry of Standard Biological Parts (Printed Dec. 21, 2009).

\* cited by examiner

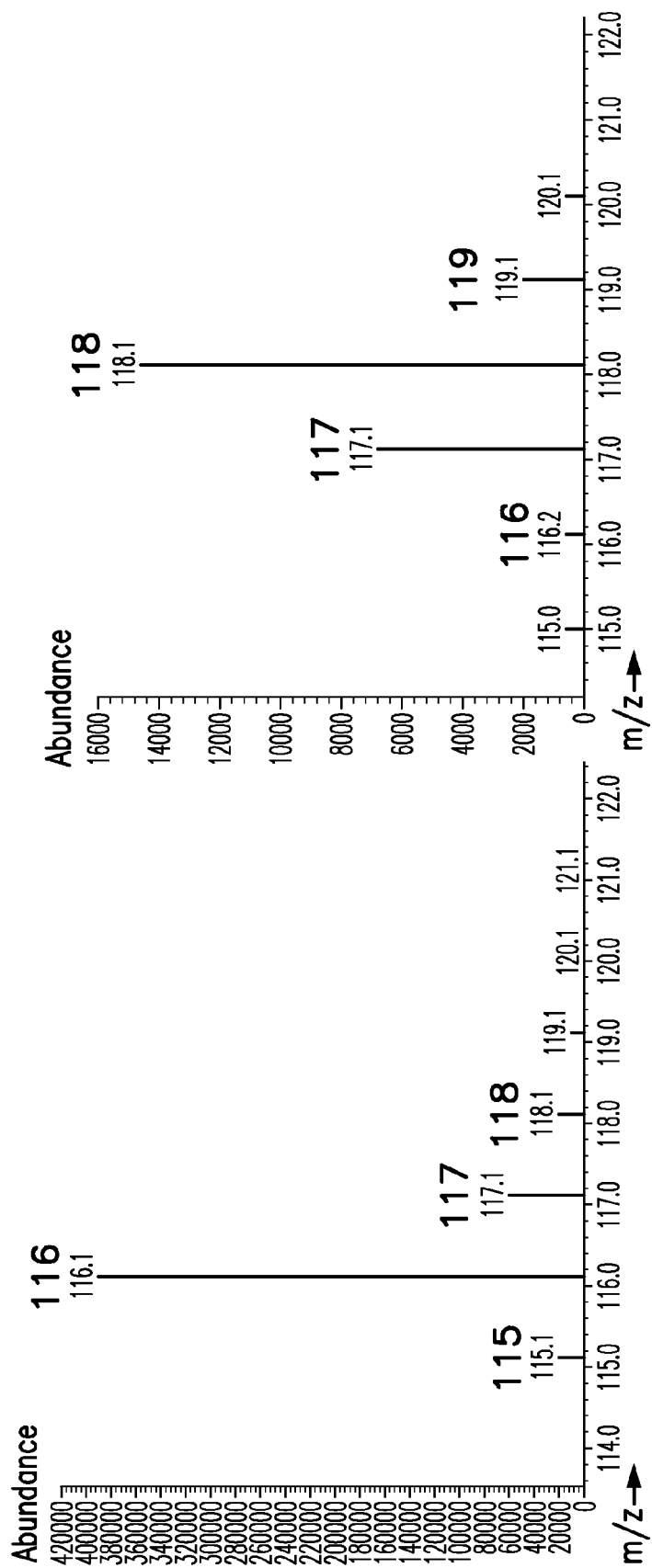

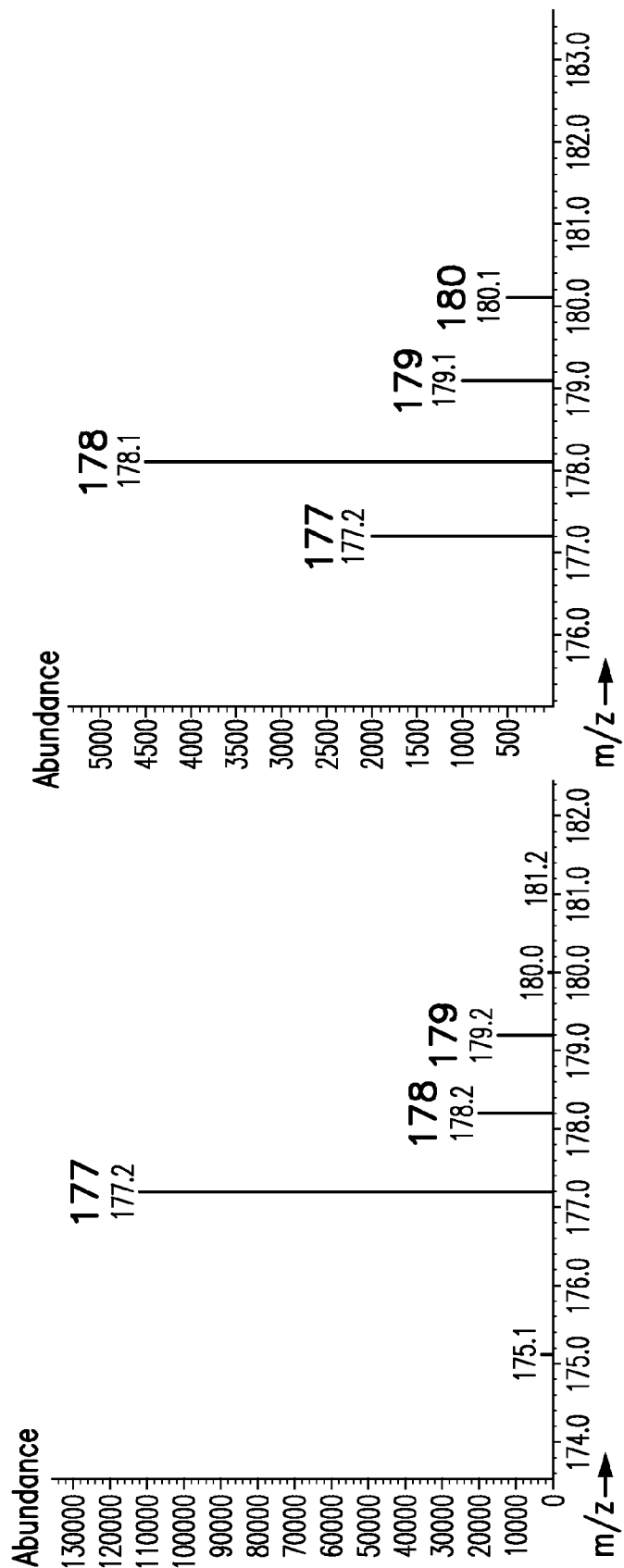

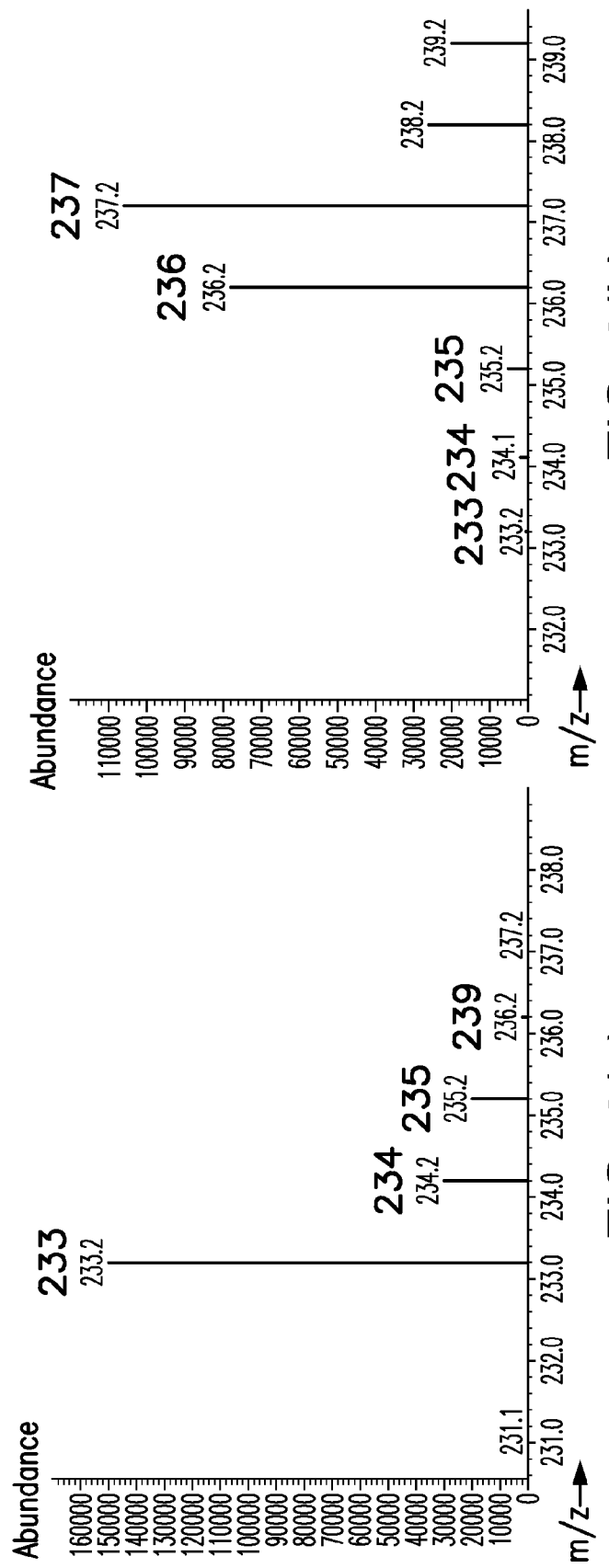

A.

ATGAAAGCTGCAGTAGTAGAGCAATTTAAGGAACCATTAAAAATTAAAGAAGTGGAAAAGCCATC
TATTTCATATGGCGAAGTATTAGTCCGCATTAAAGCATGCGGTGTATGCCATACGGACTTGCACG
CCGCTCATGGCGATTGGCCAGTAAAACCAAAACTTCCTTTAATCCCTGGCCATGAAGGAGTCGGA
ATTGTTGAAGAAGTCGGTCCGGGGGTAACCCATTTAAAAGTGGGAGACCGCGTTGGAATTCCTTG
GTTATATTCTGCGTGCGGCCATTGCGAATATTGTTTAAGCGGACAAGAAGCATTATGTGAACATC
AACAAAACGCCGGCTACTCAGTCGACGGGGGTTATGCAGAATATTGCAGAGCTGCGCCAGATTAT
GTGGTGAAAATTCCTGACAACTTATCGTTTGAAGAAGCTGCTCCTATTTTCTGCGCCGGAGTTAC
TACTTATAAAGCGTTAAAAGTCACAGGTACAAAACCGGGAGAATGGGTAGCGATCTATGGCATCG
GCGGCCTTGGACATGTTGCCGTCCAGTATGCGAAAGCGATGGGGCTTCATGTTGTTGCAGTGGAT
ATCGGCGATGAGAAACTGGAACTTGCAAAAGAGCTTGGCGCCGATCTTGTTGTAAATCCTGCAAA
AGAAAATGCGGCCCAATTTATGAAAGAGAAAGTCGGCGGAGTACACGCGGCTGTTGTGACAGCTG
TATCTAAACCTGCTTTTCAATCTGCGTACAATTCTATCCGCAGAGGCGGCACGTGCGTGCTTGTC
GGATTACCGCCGGAAGAAATGCCTATTCCAATCTTTGATACGGTATTAAACGGAATTAAAATTAT
CGGTTCCATTGTCGGCACGCGGAAAGACTTGCAAGAAGCGCTTCAGTTCGCTGCAGAAGGTAAAG
TAAAAACCATTATTGAAGTGCAACCTCTTGAAAAAATTAACGAAGTATTTGACAGAATGCTAAAA
GGAGAAATTAACGGACGGGTTGTTTTAACGTTAGAAAATAATAATTAA

B.

MKAAVVEQFKEPLKIKEVEKPSISYGEVLVRIKACGVCHTDLHAAHGDWPVKPKLPLIPGHEGVG
IVEEVGPGVTHLKVGDRVGIPWLYSACGHCEYCLSGQEALCEHQQNAGYSVDGGYAEYCRAAPDY
VVKIPDNLSFEEAAPIFCAGVTTYKALKVTGTKPGEWVAIYGIGGLGHVAVQYAKAMGLHVVAVD
IGDEKLELAKELGADLVVNPAKENAAQFMKEKVGGVHAAVVTAVSKPAFQSAYNSIRRGGTCVLV
GLPPEEMPIPIFDTVLNGIKIIGSIVGTRKDLQEALQFAAEGKVKTIIEVQPLEKINEVFDRMLK
GEINGRVVLTLENNN

FIGURE 7

SEQUENCE LISTING

<160> NUMBER OF SEQ ID NOS: 5

<210> SEQ ID NO 1
<211> LENGTH: 1023
<212> TYPE: DNA
<213> ORGANISM: Geobacillus thermoglucosidasius
<220> FEATURE:

<223> OTHER INFORMATION: nucleotide sequence of adh1 gene

<400> SEQUENCE: 1

```
atgaaagctg cagtagtaga gcaatttaag gaaccattaa aaattaaaga agtggaaaag      60
ccatctattt catatggcga agtattagtc cgcattaaag catgcggtgt atgccatacg     120
gacttgcacg ccgctcatgg cgattggcca gtaaaaccaa aacttccttt aatccctggc     180
catgaaggag tcggaattgt tgaagaagtc ggtccggggg taacccattt aaaagtggga     240
gaccgcgttg gaattccttg gttatattct gcgtgcggcc attgcgaata ttgtttaagc     300
ggacaagaag cattatgtga acatcaacaa aacgccggct actcagtcga cgggggttat     360
gcagaatatt gcagagctgc gccagattat gtggtgaaaa ttcctgacaa cttatcgttt     420
gaagaagctg ctcctatttt ctgcgccgga gttactactt ataaagcgtt aaaagtcaca     480
ggtacaaaac cgggagaatg ggtagcgatc tatggcatcg gcggccttgg acatgttgcc     540
gtccagtatg cgaaagcgat ggggcttcat gttgttgcag tggatatcgg cgatgagaaa     600
ctggaacttg caaaagagct tggcgccgat cttgttgtaa atcctgcaaa agaaaatgcg     660
gcccaattta tgaaagagaa agtcggcgga gtacacgcgg ctgttgtgac agctgtatct     720
aaacctgctt ttcaatctgc gtacaattct atccgcagag gcggcacgtg cgtgcttgtc     780
ggattaccgc cggaagaaat gcctattcca atctttgata cggtattaaa cggaattaaa     840
attatcggtt ccattgtcgg cacgcggaaa gacttgcaag aagcgcttca gttcgctgca     900
gaaggtaaag taaaaaccat tattgaagtg caacctcttg aaaaaattaa cgaagtattt     960
gacagaatgc taaaggagaa aattaacgga cgggttgttt taacgttaga aaataataat    1020
taa                                                                   1023
```

<210> SEQ ID NO 2
<211> LENGTH: 340
<212> TYPE: PRT
<213> ORGANISM: Geobacillus thermoglucosidasius
<220> FEATURE:
<223> OTHER INFORMATION: amino acid sequence of adh1 gene

<400> SEQUENCE: 2

```
Met Lys Ala Ala Val Val Glu Gln Phe Lys Glu Pro Leu Lys Ile Lys
1               5                   10                  15

Glu Val Glu Lys Pro Ser Ile Ser Tyr Gly Glu Val Leu Val Arg Ile
            20                  25                  30

Lys Ala Cys Gly Val Cys His Thr Asp Leu His Ala Ala His Gly Asp
        35                  40                  45

Trp Pro Val Lys Pro Lys Leu Pro Leu Ile Pro Gly His Glu Gly Val
    50                  55                  60

Gly Ile Val Glu Glu Val Gly Pro Gly Val Thr His Leu Lys Val Gly
65                  70                  75                  80

Asp Arg Val Gly Ile Pro Trp Leu Tyr Ser Ala Cys Gly His Cys Glu
                85                  90                  95

Tyr Cys Leu Ser Gly Gln Glu Ala Leu Cys Glu His Gln Gln Asn Ala
            100                 105                 110

Gly Tyr Ser Val Asp Gly Gly Tyr Ala Glu Tyr Cys Arg Ala Ala Pro
        115                 120                 125

Asp Tyr Val Val Lys Ile Pro Asp Asn Leu Ser Phe Glu Glu Ala Ala
    130                 135                 140

Pro Ile Phe Cys Ala Gly Val Thr Thr Tyr Lys Ala Leu Lys Val Thr
145                 150                 155                 160
```

```
Gly Thr Lys Pro Gly Glu Trp Val Ala Ile Tyr Gly Ile Gly Gly Leu
                165                 170                 175
Gly His Val Ala Val Gln Tyr Ala Lys Ala Met Gly Leu His Val Val
            180                 185                 190
Ala Val Asp Ile Gly Asp Glu Lys Leu Glu Leu Ala Lys Glu Leu Gly
        195                 200                 205
Ala Asp Leu Val Val Asn Pro Ala Lys Glu Asn Ala Ala Gln Phe Met
    210                 215                 220
Lys Glu Lys Val Gly Gly Val His Ala Ala Val Val Thr Ala Val Ser
225                 230                 235                 240
Lys Pro Ala Phe Gln Ser Ala Tyr Asn Ser Ile Arg Arg Gly Gly Thr
                245                 250                 255
Cys Val Leu Val Gly Leu Pro Pro Glu Glu Met Pro Ile Pro Ile Phe
            260                 265                 270
Asp Thr Val Leu Asn Gly Ile Lys Ile Ile Gly Ser Ile Val Gly Thr
        275                 280                 285
Arg Lys Asp Leu Gln Glu Ala Leu Gln Phe Ala Ala Glu Gly Lys Val
    290                 295                 300
Lys Thr Ile Ile Glu Val Gln Pro Leu Glu Lys Ile Asn Glu Val Phe
305                 310                 315                 320
Asp Arg Met Leu Lys Gly Glu Ile Asn Gly Arg Val Val Leu Thr Leu
                325                 330                 335
Glu Asn Asn Asn
            340

<210> SEQ ID NO 3
<211> LENGTH: 20
<212> TYPE: PRT
<213> ORGANISM: Euglena gracilis
<220> FEATURE:
<223> OTHER INFORMATION: first 20 amino acids sequence from the
      N-terminus of
      KDC gene

<400> SEQUENCE: 3

Met Thr Tyr Lys Ala Pro Val Lys Asp Val Lys Phe Leu Leu Asp Lys
1               5                   10                  15
Val Phe Lys Val
            20

<210> SEQ ID NO 4
<211> LENGTH: 59
<212> TYPE: DNA
<213> ORGANISM: Artificial Sequence
<220> FEATURE:
<223> OTHER INFORMATION: one of the primer pair used to PCR amplify
      lacZ-alpha fragment
      from pUC19 vector

<400> SEQUENCE: 4
gacgaattcg ctagcaagag gagaagtcga catgtccaat tcactggccg tcgttttac        59

<210> SEQ ID NO 5
<211> LENGTH: 47
<212> TYPE: DNA
<213> ORGANISM: Artificial Sequence
<220> FEATURE:
<223> OTHER INFORMATION: one of the primer pair used to PCR amplify
      lacZ-alpha fragment
      from pUC19 vector
```

```
<400> SEQUENCE: 5
gaccctagga agctttctag agtcgaccta tgcggcatca gagcaga                47
```

MICROORGANISMS AND METHODS FOR THE COPRODUCTION 1,4-BUTANEDIOL AND GAMMA-BUTYROLACTONE

This application is a continuation of U.S. Non-provisional application Ser. No. 12/940,021, filed Nov. 4, 2010, which claims the benefit of priority of U.S. Provisional Application No. 61/264,598, filed Nov. 25, 2009, the entire contents of which are incorporated herein by reference.

BACKGROUND OF THE INVENTION

The instant application contains a Sequence Listing which has been submitted in ASCII format via EFS-Web and is hereby incorporated by reference in its entirety. Said ASCII copy, created on Jun. 28, 2013, is named 12956-298-999_Sequence_Listing.txt and is 5,629 bytes in size.

The present invention relates generally to biosynthetic processes, and more specifically to organisms having 1,4-butanediol and gamma-butyrolactone biosynthetic capability.

1,4-Butanediol (14-BDO) is a polymer intermediate and industrial solvent with a global market of about 3 billion lb/year. 14-BDO is currently produced from petrochemical precursors, primarily acetylene, maleic anhydride, and propylene oxide. For example, acetylene is reacted with 2 molecules of formaldehyde in the Reppe synthesis reaction (Kroschwitz and Grant, *Encyclopedia of Chem. Tech.*, John Wiley and Sons, Inc., New York (1999)), followed by catalytic hydrogenation to form 1,4-butanediol. Downstream, 14-BDO can be further transformed; for example, by oxidation to gamma-butyrolactone (GBL) or hydrogenolysis to tetrahydrofuran (THF). These compounds have varied uses as polymer intermediates, solvents, and additives, and have a combined market of nearly 2 billion lb/year.

Gamma-butyrolactone (GBL) is a chemical intermediate and common solvent with a global market of about 0.5 billion lb/year. GBL has wide applications. GBL serves as a chemical intermediate in the manufacture of pyrrolidones that are widely used in the pharmaceutical industry. It can be used in the production of pesticides, herbicides and plant growth regulators. GBL is also used as an aroma compound, as a stain remover, as a superglue remover, as a paint stripper, and as a solvent in some wet aluminum electrolytic capacitors. Currently, GBL is mainly synthesized through 14-BDO from crude oil and/or natural gas derived feedstocks by the Reppe acetylene chemistry.

Microbial organisms and methods for effectively co-producing commercial quantities of 14-BDO and GBL are described herein and include related advantages.

SUMMARY OF INVENTION

The invention provides non-naturally occurring microbial organisms containing 1,4-butanediol (14-BDO) and gamma-butyrolactone (GBL) pathways comprising at least one exogenous nucleic acid encoding a 14-BDO pathway enzyme and at least one exogenous nucleic acid encoding a GBL pathway enzyme each expressed in a sufficient amount to produce 14-BDO and GBL. The invention additionally provides methods of using such microbial organisms to produce 14-BDO and GBL, which in some embodiments includes the non-enzymatic lactonization of 4-hydroxybutyryl-phosphate or 4-hydroxybutyryl-CoA to form GBL.

BRIEF DESCRIPTION OF THE DRAWINGS

FIG. 7A shows the nucleotide sequence (SEQ ID NO: 1) of the adh1 gene from *Geobacillus thermoglucosidasius*, and FIG. 7B shows the encoded amino acid sequence (SEQ ID NO: 2).

FIG. 8A shows the expression of the *Geobacillus thermoglucosidasius* adh1 gene in *E. coli*. Either whole cell lysates or supernatants were analyzed by SDS-PAGE and stained with Coomassie blue for plasmid with no insert, plasmid with 083 (*Geotrichum capitatum* N-benzyl-3-pyrrolidinol dehydrogenase) and plasmid with 084 (*Geobacillus thermoglucosidasius* adh1) inserts.

FIG. 8B shows the activity of 084 with butyraldehyde (diamonds) or 4-hydroxybutyraldehyde (squares) as substrates.

DETAILED DESCRIPTION OF THE INVENTION

Figure 1:
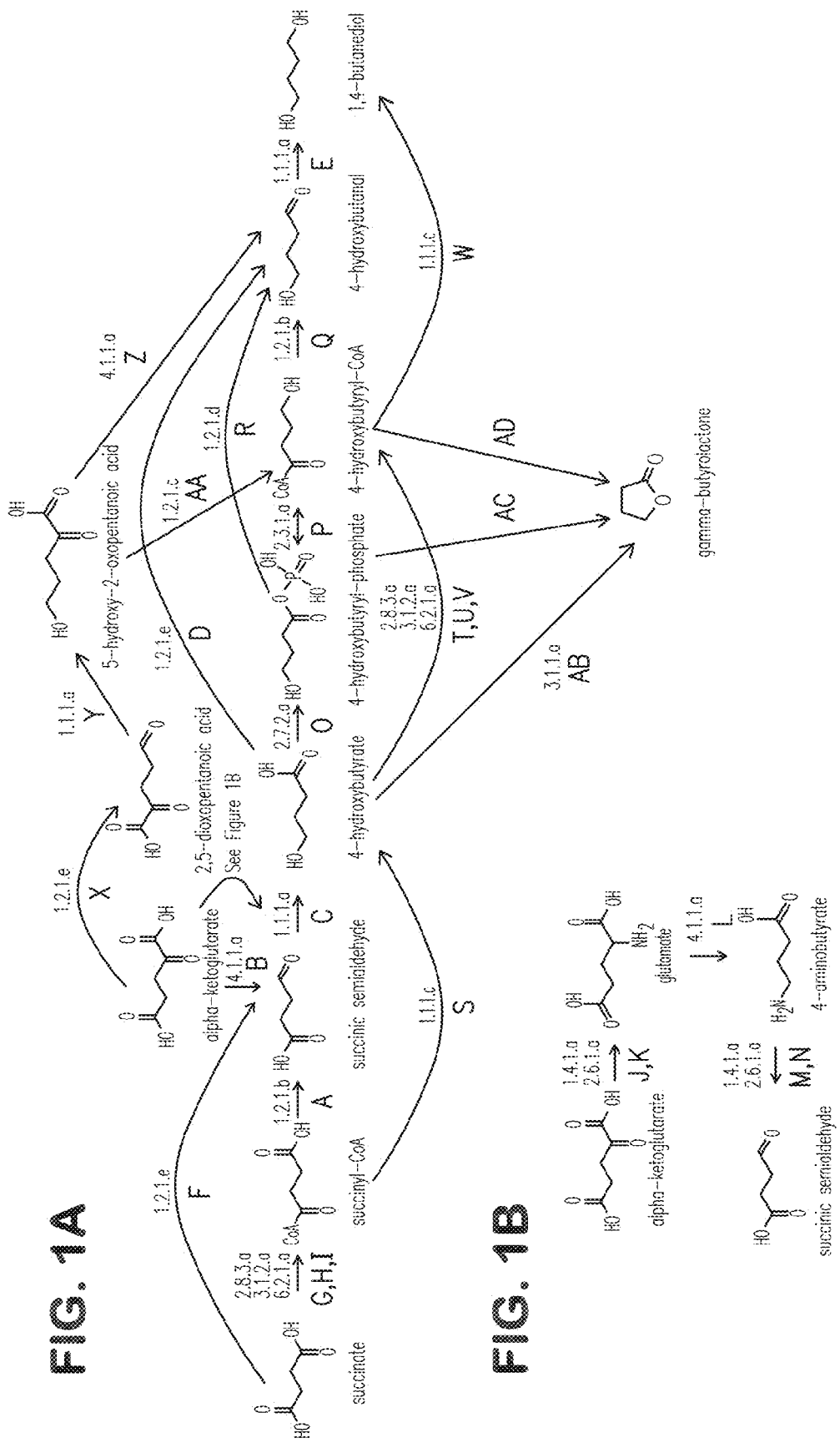
FIGS. 1A and 1B show exemplary pathways for co-production of 14-BDO and GBL. Enzymes for transformation of identified substrates to products include: A) succinyl-CoA reductase (aldehyde forming), B) alpha-ketoglutarate decarboxylase, C) 4-hydroxybutyrate dehydrogenase, D) 4-hydroxybutyrate reductase, E) 1,4-butanediol dehydrogenase, F) succinate reductase, G) succinyl-CoA transferase, H) succinyl-CoA hydrolase, I) succinyl-CoA synthetase (or succinyl-CoA ligase), J) glutamate dehydrogenase, K) glutamate transaminase, L) glutamate decarboxylase, M) 4-aminobutyrate dehydrogenase, N) 4-aminobutyrate transaminase, O) 4-hydroxybutyrate kinase, P) phosphotrans-4-hydroxybutyrylase, Q) 4-hydroxybutyryl-CoA reductase (aldehyde forming), R) 4-hydroxybutyryl-phosphate reductase, S) succinyl-CoA reductase (alcohol forming), T) 4-hydroxybutyryl-CoA transferase, U) 4-hydroxybutyryl-CoA hydrolase, V) 4-hydroxybutyryl-CoA synthetase (or 4-hydroxybutyryl-CoA ligase), W) 4-hydroxybutyryl-CoA reductase (alcohol forming), X) alpha-ketoglutarate reductase, Y) 5-hydroxy-2-oxopentanoate dehydrogenase, Z) 5-hydroxy-2-oxopentanoate decarboxylase, AA) 5-hydroxy-2-oxopentanoate dehydrogenase (decarboxylation), AB) 4-hydroxybutyrate lactonase, AC) non-enzymatic 4-hydroxybutyryl-phosphate lactonization, and AD) non-enzymatic 4-hydroxybutyryl-CoA lactonization.

The present invention is directed to the design and production of cells and organisms having biosynthetic production capabilities for 1,4-butanediol (14-BDO) and gamma-butyrolactone (GBL). The invention, in particular, relates to the design of microbial organisms capable of producing 14-BDO and GBL by introducing one or more nucleic acids encoding a 14-BDO and GBL pathway enzyme.

In one embodiment, the invention utilizes in silico stoichiometric models of *Escherichia coli* metabolism that identify metabolic designs for biosynthetic production of 14-BDO and GBL. The results described herein indicate that metabolic pathways can be designed and recombinantly engineered to achieve the biosynthesis of 14-BDO and GBL in *Escherichia coli* and other cells or organisms. Biosynthetic production of 14-BDO and GBL, for example, for the in silico designs can be confirmed by construction of strains having the designed metabolic genotype. These metabolically engineered cells or organisms also can be subjected to adaptive evolution to further augment 14-BDO and GBL biosynthesis, including under conditions approaching theoretical maximum growth.

In certain embodiments, the 14-BDO and GBL biosynthesis characteristics of the designed strains make them genetically stable and particularly useful in continuous bioprocesses. Separate strain design strategies were identified with incorporation of different non-native or heterologous reaction capabilities into *E. coli* or other host organisms leading to 14-BDO and GBL producing metabolic pathways from either succinate, succinyl-CoA or alpha-ketoglutarate. In silico metabolic designs were identified that resulted in the biosynthesis of 14-BDO and GBL in microorganisms from each of these metabolic intermediates. Embodiments of the invention include the controlled production of 14-BDO and GBL at a predetermined ratio. As described herein, this ratio can be regulated by, for example, introducing an exogenous nucleic acid encoding an enzyme or protein with an increased or decreased activity or specificity for one or more intermediates in the respective 14-BDO or GBL pathways or modulating the expression of an enzyme or protein in a 14-BDO or GBL pathway, thereby regulating the production of 14-BDO and GBL.

Strains identified via the computational component of the platform can be put into actual production by genetically engineering any of the predicted metabolic alterations which lead to the biosynthetic production of 14-BDO and GBL or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

Embodiments of the invention also provide methods for co-production of 14-BDO and GBL. Co-production of 14-BDO and GBL is attractive due to the following advantages: 1) co-production will satisfy the needs of both chemicals and reduce the cost and environmental impact of the transformation of 14-BDO to GBL; 2) construction of a single large regional facility for co-production will save capital investment and reduce fixed cost comparing to separate productions; 3) separating the two co-products from fermentation broth can be easily achieve through distillation due to their boiling points (14-BDO at 230° C. and GBL at 204° C.).

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a 14-BDO and GBL biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "1,4-butanediol" is intended to mean an alcohol derivative of the alkane butane, carrying two hydroxyl groups which has the chemical formula $C_4H_{10}O_2$ and a molecular mass of 90.12 g/mol. The chemical compound 1,4-butanediol also is known in the art as 14-BDO or BDO and is a chemical intermediate or precursor for a family of compounds referred to herein as BDO family of compounds As used herein, the term "gamma-butyrolactone" is intended to mean a lactone having the chemical formula $C_4H_6O_2$ and a molecular mass of 86.089 g/mol. The chemical compound gamma-butyrolactone also is know in the art as GBL, butyrolactone, 1,4-lactone, 4-butyrolactone, 4-hydroxybutyric acid lactone, and gamma-hydroxybutyric acid lactone. The term as it is used herein is intended to include any of the compound's various salt forms.

As used herein, the term "4-hydroxybutanoic acid" is intended to mean a 4-hydroxy derivative of butyric acid having the chemical formula $C_4H_8O_3$ and a molecular mass of 104.11 g/mol (126.09 g/mol for its sodium salt). The chemical compound 4-hydroxybutanoic acid also is known in the art as 4-HB, 4-hydroxybutyrate, gamma-hydroxybutyric acid or GHB. The term as it is used herein is intended to include any of the compound's various salt forms and include, for example, 4-hydroxybutanoate and 4-hydroxybutyrate. Specific examples of salt forms for 4-HB include sodium 4-HB and potassium 4-HB. Therefore, the terms 4-hydroxybutanoic acid, 4-HB, 4-hydroxybutyrate, 4-hydroxybutanoate, gamma-hydroxybutyric acid and GHB as well as other art recognized names are used synonymously herein.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation. Coenzyme A can also function as an activating group for a spontaneous intramolecular chemical reaction, such as, circulazation or lactonization.

As used herein, the term "phosphate" is intended to mean an inorganic chemical ion of the empirical formula $PO^{3-}_4$ and a molar mass of 94.973 g/mol. A phosphate can act as a functional group when added to a compound. A phosphate can function as an activating group for a spontaneous intramolecular chemical reaction, such as, cirulazation or lactonization.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "predetermined ratio" when used in reference to the amount of one compound relative to the amount of another compound is intended to mean a ratio of compounds that is established in advance that can be produced by a non-naturally occurring microorganism described herein through prior experimental determination for each compound separately or in combination. A predetermined ratio can also be established in advance by determining the maximum theoretical yield for a non-naturally occurring microorganism to produce 14-BDO and GBL as described herein. Embodiments described herein include that the predetermined ratio intends there is at least some detectable amount of one product relative to the amount of a second, third, or fourth product up to any number of products or intermediate compounds in a 14-BDO or GBL pathway produced by a non-naturally occurring microorganism described herein. Embodiments described herein include the amount of intracellular 14-BDO or GBL produced by the microorganisms is at least 0.001 mM, or alternatively at least 0.01 mM, or alternatively at least 0.1 mM, or alternatively at least 1.0 mM or alternatively at least 10 mM or alternatively at least 100 mM, or alternatively at least 1M. Embodiments described herein also include the amount of intracellular 14-BDO or GBL produced by the microorganisms is at least 1%, or alternatively at least 5%, or alternatively at least 10%, or alternatively at least 15%, or alternatively at least 20%, or alternatively at least 25%, or alternatively at least 30%, or alternatively at least 35%, or alternatively at least 40%, or alternatively at least 45%, or alternatively at least 50%, or alternatively at least 55%, or alternatively at least 60%, or alternatively at least 65%, or alternatively at least 70%, or alternatively at least 75%, or alternatively at least 80%, or alternatively at least 85%, or alternatively at least 90%, or alternatively at least 95%, or alternatively at least 98%, or alternatively at least 100% of the maximum theoretical yield. Embodiments described herein include the predetermined ratio of intracellular 14-BDO to GLB produced by the microorganisms is 1:1, or alternatively 1:2, or alternatively 1:3, or alternatively 1:4, or alternatively 1:5, or alternatively 1:6, or alternatively 1:7, or alternatively 1:8, or alternatively 1:9, or alternatively 1:10, or alternatively 1:15, or alternatively about 1:20, or alternatively 1:25, or alternatively 1:30, or alternatively 1:35, or alternatively 1:40, or alternatively 1:45, or alternatively about 1:50, or alternatively 1:60, or alternatively 1:70, or alternatively 1:80, or alternatively 1:90, or alternatively 1:100. Embodiments described herein include the predetermined ratio of intracellular 14-BDO to GLB produced by the microorganisms is 2:1, or alternatively 3:1, or alternatively 4:1, or alternatively 5:1, or alternatively 6:1, or alternatively 7:1, or alternatively 8:1, or alternatively 9:1, or alternatively 10:1, or alternatively 15:1, or alternatively about 20:1, or alternatively 25:1, or alternatively 30:1, or alternatively 35:1, or alternatively 40:1, or alternatively 45:1, or alternatively about 50:1, or alternatively 60:1, or alternatively 70:1, or alternatively 80:1, or alternatively 90:1, or alternatively 100:1.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 14-BDO and GBL biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a non-naturally occurring microbial organism, comprising a microbial organism having a 1,4-butanediol (14-BDO) pathway and a gamma-butyrolactone (GBL) pathway, said 14-BDO pathway comprising at least one exogenous nucleic acid encoding a 14-BDO pathway enzyme expressed in a sufficient amount to produce 14-BDO, said 14-BDO pathway comprising a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase, a 4-hydroxybutyryl-CoA reductase (alcohol forming), an alpha-ketoglutarate reductase, a 5-hydroxy-2-oxopentanoate dehydrogenase, a 5-hydroxy-2-oxopentanoate decarboxylase or a 5-hydroxy-2-oxopentanoate dehydrogenase (decarboxylation) (see FIG. 1, steps A, B, C, D, E, F, G, H, I, J, K, L, M, N, O, P, Q, R, S, T, U, V, W, X, Y, Z, AA), said GBL pathway comprising at least one exogenous nucleic acid encoding an GBL pathway enzyme expressed in a sufficient amount to produce GBL, said GBL pathway comprising a succinyl-CoA reductase (aldehyde forming), an alpha-ketoglutarate decarboxylase, a 4-hydroxybutyrate dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a succinyl-CoA reductase (alcohol forming) or a 4-hydroxybutyrate lactonase (see FIG. 1, steps A, B, C, F, G, H, I, J, K, L, M, N, S, AB).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, A, C, O, P, Q, E).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase (see FIG. 1, steps G/H/I, A, C, O, R, E).

In a further embodiment, the non-naturally occurring microbial organism has a 14-BDO pathway comprising a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, A, C, T/U/V, Q, E).

In a further embodiment, the non-naturally occurring microbial organism has a 14-BDO pathway comprising a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming (see FIG. 1, steps G/H/I, A, C, T/U/V, W).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps G/H/I, A, C, O, P, W).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase (see FIG. 1, steps G/H/I, S, D, E).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, S, O, P, Q, E).

In a further embodiment, the non-naturally occurring microbial organism has a 14-BDO pathway comprising a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase (see FIG. 1, steps G/H/I, S, O, R, E).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, S, T/U/V, Q, E).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, S, T/U/V, W).

In a further embodiment, the non-naturally occurring microbial organism has a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming) (see FIG. 1, steps G/H/I, S, O, P, W).

In a further embodiment, the non-naturally occurring microbial organism has a 14-BDO pathway comprising a succinate reductase; a 4-hydroxybutyrate dehydrogenase; a 4-hydroxybutyrate reductase; and 1,4-butanediol dehydrogenase (see FIG. 1, steps F, C, D, E).

In a further embodiment, the non-naturally occurring microbial organism has a 14-BDO pathway comprising a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps F, C, O, P, Q, E).

In a further embodiment, the non-naturally occurring microbial organism has a 14-BDO pathway comprising a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps F, C, O, P, W).

In a further embodiment, the non-naturally occurring microbial organism has a 14-BDO pathway comprising a succinate reductase; a 4-hydroxybutyrate dehydrogenase; a 4-hydroxybutyrate kinase; a 4-hydroxybutyryl-phosphate reductase; and 1,4-butanediol dehydrogenase (see FIG. 1, steps F, C, O, R, E).

In a further embodiment, the non-naturally occurring microbial organism has a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase (see FIG. 1, steps F, C, T/U/V, Q, E).

In a further embodiment, the non-naturally occurring microbial organism has a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps F, C, T/U/V, W).

In a further embodiment, the non-naturally occurring microbial organism has a 14-BDO pathway comprising an alpha-ketoglutarate decarboxylase; a 4-hydroxybutyrate dehydrogenase; a 4-hydroxybutyrate reductase; and 1,4-butanediol dehydrogenase (see FIG. 1, steps B, C, D, E).

In a further embodiment, the non-naturally occurring microbial organism has a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps B, C, O, P, Q, E).

In a further embodiment, the non-naturally occurring microbial organism has a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming) (see FIG. 1, steps B, C, O, P, W).

In a further embodiment, the non-naturally occurring microbial organism has a 14-BDO pathway comprising. an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps B, C, O, R, E).

In a further embodiment, the non-naturally occurring microbial organism has a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase (see FIG. 1, steps B, C, T/U/V, Q, E).

In a further embodiment, the non-naturally occurring microbial organism has a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming) (see FIG. 1, steps B, C, T/U/V, W).

In a further embodiment, the non-naturally occurring microbial organism has a 14-BDO pathway comprising a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase (see FIG. 1, steps J/K, L, M/N, C, D, E).

In a further embodiment, the non-naturally occurring microbial organism has a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase (see FIG. 1, steps J/K, L, M/N, C, O, P, Q, E).

In a further embodiment, the non-naturally occurring microbial organism has a 14-BDO pathway comprising a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps J/K, L, M/N, C, O, P, W), In a further embodiment, the non-naturally occurring microbial organism has a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps J/K, L, M/N, C, O, R, E).

In a further embodiment, the non-naturally occurring microbial organism has a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps J/K, L, M/N, C, T/U/V, Q, E).

In a further embodiment, the non-naturally occurring microbial organism has a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps J/K, L, M/N, C, T/U/V, W).

In a further embodiment, the non-naturally occurring microbial organism has a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase (see FIG. 1, steps X, Y, AA, Q, E).

In a further embodiment, the non-naturally occurring microbial organism has a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming) (see FIG. 1, steps X, Y, AA, and W).

In a further embodiment, the non-naturally occurring microbial organism has a 14-BDO pathway comprising an alpha-ketoglutarate reductase; a 5-hydroxy-2-oxopentanoate dehydrogenase; a 5-hydroxy-2-oxopentanoate decarboxylase; and a 1,4-butanediol dehydrogenase (see FIG. 1, steps X, Y, Z, E).

In a further embodiment, the non-naturally occurring microbial organism has a GBL pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyrate lactonase (see FIG. 1, steps G/H/I, A, C, AB).

In a further embodiment, the non-naturally occurring microbial organism has a GBL pathway comprising a succinyl-CoA transferase, a succinyl-CoA hydrolase and a succinyl-CoA synthetase; a succinyl-CoA reductase (alcohol forming); and a 4-hydroxybutyrate lactonase (see FIG. 1, steps G/H/I, S, AB).

In a further embodiment, the non-naturally occurring microbial organism has a GBL pathway comprising a succinate reductase; a 4-hydroxybutyrate dehydrogenase; and a 4-hydroxybutyrate lactonase (see FIG. 1, steps F, C, AB).

In a further embodiment, the non-naturally occurring microbial organism has a GBL pathway comprising an alpha-ketoglutarate decarboxylase, a 4-hydroxybutyrate dehydrogenase and a 4-hydroxybutyrate lactonase (see FIG. 1, steps B, C, AB).

In a further embodiment, the non-naturally occurring microbial organism has a GBL pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; and a 4-hydroxybutyrate lactonase (see FIG. 1, steps J/K, L, M/N, C, AB).

In one embodiment, the invention provides a non-naturally occurring microbial organism, comprising a microbial organism having a 1,4-butanediol (14-BDO) pathway and a gamma-butyrolactone (GBL) pathway, said 14-BDO pathway comprising a first set of exogenous nucleic acids encoding 14-BDO pathway enzymes expressed in a sufficient amount to produce 14-BDO, wherein said first set is selected from the group consisting of: [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase)] (see FIG. 1, steps G/H/I, A, C, D, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, A, C, O, P, Q, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps G/H/I, A, C, O, R, E); [a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, A, C, T/U/V, Q, E); [a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, A, C, T/U/V, W]; [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps G/H/I, A, C, O, P, W); [a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase] (see FIG. 1, steps G/H/I, S, D, E); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, S, O, P, Q, E); [a succinyl-CoA transferase, a succinyl-CoA hydrolase or succinyl-CoA synthetase; a succinyl-CoA reductase (alcohol forming), a 4-hydroxybutyrate kinase; a 4-hydroxybutyryl-phosphate reductase; and a 1,4-butanediol dehydrogenase] (see FIG. 1, steps G/H/I, S, O, R, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, S, T/U/V, Q, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, S, T/U/V, W); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming)] (see FIG. 1, steps G/H/I, S, O, P, W); [a succinate reductase; a 4-hydroxybutyrate dehydrogenase; a 4-hydroxybutyrate reductase; and 1,4-butanediol dehydrogenase]; [a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps F, C, O, P, Q, E); [a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps F, C, O, P, W); [a succinate reductase; a 4-hydroxybutyrate dehydrogenase; a 4-hydroxybutyrate kinase; a 4-hydroxybutyryl-phosphate reductase; and 1,4-butanediol dehydrogenase] (see FIG. 1, steps F, C, O, R, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase] (see FIG. 1, steps F, C, T/U/V, Q, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps F, C, T/U/V, W); [an alpha-ketoglutarate decarboxylase; a 4-hydroxybutyrate dehydrogenase; a 4-hydroxybutyrate reductase; and 1,4-butanediol dehydrogenase]; [an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps B, C, O, P, Q, E); [an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming)] (see FIG. 1, steps B, C, O, P, W); [an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps B, C, O, R, E); [an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase] (see FIG. 1, steps B, C, T/U/V, W); [an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming)] (see FIG. 1, steps B, C, T/U/V, W); [a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase] (see FIG. 1, steps J/K, L, M/N, C, D, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase] (see FIG. 1, steps J/K, L, M/N, C, O, P, Q, E); [a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps J/K, L, M/N, C, O, P, W); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps J/K, L, M/N, C, O, R, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps J/K, L, M/N, C, T/U/V, Q, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps J/K, L, M/N, C, T/U/V, W); [an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase] (see FIG. 1, steps X, Y, AA, Q, E); [an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming)] (see FIG. 1, steps X, Y, AA, and W); and [an alpha-ketoglutarate reductase; a 5-hydroxy-2-oxopentanoate dehydrogenase; a 5-hydroxy-2-oxopentanoate decarboxylase; and a 1,4-butanediol dehydrogenase] (see FIG. 1, steps X, Y, Z, E), said GBL pathway comprising a second set of exogenous nucleic acid encoding an GBL pathway enzyme expressed in a sufficient amount to produce GBL, said second set is selected from the group consisting of [a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyrate lactonase] (see FIG. 1, steps G/H/I, A, C, AB); [a succinyl-CoA transferase, a succinyl-CoA hydrolase and a succinyl-CoA synthetase; a succinyl-CoA reductase (alcohol forming); and a 4-hydroxybutyrate lactonase] (see FIG. 1, steps G/H/I, S, AB); [a succinate reductase; a 4-hydroxybutyrate dehydrogenase; and a 4-hydroxybutyrate lactonase] (see FIG. 1, steps F, C, AB); [an alpha-ketoglutarate decarboxylase, a 4-hydroxybutyrate dehydrogenase and a 4-hydroxybutyrate lactonase] (see FIG. 1, steps B, C, AB); and [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; and a 4-hydroxybutyrate lactonase] (see FIG. 1, steps J/K, L, M/N, C, AB).

In a further aspect of each of the above embodiments, the exogenous nucleic acid is a heterologous nucleic acid.

In a further aspect of each of the above embodiments, the non-naturally occurring microbial organism is in a substantially anaerobic culture medium.

In a further aspect of each of the above embodiments, the 14-BDO and GBL products are produced at a predetermined ratio. In some aspects of the invention, the predetermined ratio of 14-BDO to GBL is 1:1, or alternatively 1:2, or alternatively 1:3, or alternatively 1:4, or alternatively 1:5, or alternatively 1:6, or alternatively 1:7, or alternatively 1:8, or alternatively 1:9, or alternatively 1:10, or alternatively 1:15, or alternatively about 1:20, or alternatively 1:25, or alternatively 1:30, or alternatively 1:35, or alternatively 1:40, or alternatively 1:45, or alternatively about 1:50, or alternatively 1:60, or alternatively 1:70, or alternatively 1:80, or alternatively 1:90, or alternatively 1:100. In some aspects of the invention, the predetermined ratio of 14-BDO to GBL is 2:1, or alternatively 3:1, or alternatively 4:1, or alternatively 5:1, or alternatively 6:1, or alternatively 7:1, or alternatively 8:1, or alternatively 9:1, or alternatively 10:1, or alternatively 15:1, or alternatively about 20:1, or alternatively 25:1, or alternatively 30:1, or alternatively 35:1, or alternatively 40:1, or alternatively 45:1, or alternatively about 50:1, or alternatively 60:1, or alternatively 70:1, or alternatively 80:1, or alternatively 90:1, or alternatively 100:1.

It is understood by one of skill in the art that the non-naturally occurring microorganisms described herein, having a 14-BDO and a GBL pathway, can have exogenous nucleic acids encoding enzymes or proteins of more than one pathway described herein. For example, a microorganism can have exogenous nucleic acids encoding enzymes or proteins for steps G/H/I, A, C, O, P, Q, and E of FIG. 1 and steps J/K, L, M/N, C, O, P and W of FIG. 1 for production of 14-BDO. It is also understood that exogenous nucleic acids encoding enzymes or proteins of the 14-BDO pathway can also satisfy the enzymes or proteins of the GBL pathway, and vice versa. For example, an exogenous nucleic acid encoding the enzyme succinate reductase in the 14-BDO pathway is also encoding the succinate reductase for the GBL pathway for co-production of 14-BDO and GBL.

In an additional embodiment, the invention provides a non-naturally occurring microbial organism having a 14-BDO and GBL pathway, wherein the non-naturally occurring microbial organism comprises at least one exogenous nucleic acid encoding an enzyme or protein that converts a substrate to a product selected from the group consisting of succinate to succinyl-CoA, succinate to succinic semialdehyde, succinyl-CoA to succinic semialdehyde, succinyl-CoA to 4-hydroxybutyrate, succinic semialdehyde to 4-hydroxybutyrate, alpha-ketoglutarate to succinic semialdehyde, alpha-ketoglutarate to glutamate, glutamate to 4-aminobutyrate, 4-aminobutyrate to succinic semialdehyde, alpha-ketoglutarate to 2,5-dioxopentanoic acid, 2,5-dioxopentanoic acid to 5-hydroxy-2-oxopentanoic acid, 5-hydroxy-2-oxopentanoic acid to 4-hydroxybutanal, 4-hydroxybutyrate to 4-hydroxybutanal, 4-hydroxybutyrate to 4-hydroxybutyryl-phosphate, 4-hydroxybutyryl-phosphate to 4-hydroxybutyryl-CoA, 4-hydroxybutyryl-phosphate to 4-hydroxybutanal, 5-hydroxy-2oxopentanoic acid to 4-hydroxybutyryl-CoA, 4-hydroxybutyryl-CoA to 4-hydroxybutanal, 4-hydroxybutyrate to 4-hydroxybutyryl-CoA, 4-hydroxybutyryl-CoA to 1,4-butanediol, 4-hydroxybutanal to 1,4-butanediol and 4-hydroxybutyrate to gamma-butyrolactone. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a 14-BDO and GBL pathway, such as that shown in FIG. 1.

While generally described herein as a microbial organism that contains a 14-BDO and GBL pathway, it is understood that the invention additionally provides a non-naturally occurring microbial organism comprising at least one exogenous nucleic acid encoding a 14-BDO or GBL pathway enzyme expressed in a sufficient amount to produce an intermediate of a 14-BDO or GBL pathway. For example, as disclosed herein, 14-BDO and GBL pathways are exemplified in FIG. 1. Therefore, in addition to a microbial organism containing a 14-BDO and GBL pathway that produces 14-BDO and GBL, the invention additionally provides a non-naturally occurring microbial organism comprising at least one exogenous nucleic acid encoding a 14-BDO or GBL pathway enzyme, where the microbial organism produces a 14-BDO or GBL pathway intermediate, for example, succinyl-CoA, succinic semialdehyde, 4-hydroxybutyrate, 4-hydroxybutyryl-phosphate, 4-hydroxybutyryl-CoA, 4-hydroxybutanal, glutamate, 4-aminobutyrate, succinic semialdehyde, 2,5-dioxopentanoic acid or 5-hydroxy-2oxopentanoic acid.

It is understood that any of the pathways disclosed herein, as described in the Examples and exemplified in the Figures, including the pathways of FIGS. 1A and 1B, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 14-BDO or GBL pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

Exemplary alcohol and aldehyde dehydrogenases that can be used for in vivo conversions described herein from 4-HB to 14-BDO are listed below in Table 1.

TABLE 1

Alcohol and Aldehyde Dehydrogenases for Conversion of 4-HB to 14-BDO.

ALCOHOL DEHYDROGENASES

| | |
|---|---|
| ec: 1.1.1.1 | alcohol dehydrogenase |
| ec: 1.1.1.2 | alcohol dehydrogenase (NADP+) |
| ec: 1.1.1.4 | (R,R)-butanediol dehydrogenase |
| ec: 1.1.1.5 | acetoin dehydrogenase |
| ec: 1.1.1.6 | glycerol dehydrogenase |
| ec: 1.1.1.7 | propanediol-phosphate dehydrogenase |
| ec: 1.1.1.8 | glycerol-3-phosphate dehydrogenase (NAD+) |
| ec: 1.1.1.11 | D-arabinitol 4-dehydrogenase |
| ec: 1.1.1.12 | L-arabinitol 4-dehydrogenase |
| ec: 1.1.1.13 | L-arabinitol 2-dehydrogenase |
| ec: 1.1.1.14 | L-iditol 2-dehydrogenase |
| ec: 1.1.1.15 | D-iditol 2-dehydrogenase |
| ec: 1.1.1.16 | galactitol 2-dehydrogenase |
| ec: 1.1.1.17 | mannitol-1-phosphate 5-dehydrogenase |
| ec: 1.1.1.18 | inositol 2-dehydrogenase |
| ec: 1.1.1.21 | aldehyde reductase |
| ec: 1.1.1.23 | histidinol dehydrogenase |
| ec: 1.1.1.26 | glyoxylate reductase |
| ec: 1.1.1.27 | L-lactate dehydrogenase |
| ec: 1.1.1.28 | D-lactate dehydrogenase |
| ec: 1.1.1.29 | glycerate dehydrogenase |
| ec: 1.1.1.30 | 3-hydroxybutyrate dehydrogenase |
| ec: 1.1.1.31 | 3-hydroxyisobutyrate dehydrogenase |
| ec: 1.1.1.35 | 3-hydroxyacyl-CoA dehydrogenase |
| ec: 1.1.1.36 | acetoacetyl-CoA reductase |
| ec: 1.1.1.37 | malate dehydrogenase |
| ec: 1.1.1.38 | malate dehydrogenase (oxaloacetate-decarboxylating) |
| ec: 1.1.1.39 | malate dehydrogenase (decarboxylating) |
| ec: 1.1.1.40 | malate dehydrogenase (oxaloacetate-decarboxylating) (NADP+) |
| ec: 1.1.1.41 | isocitrate dehydrogenase (NAD+) |
| ec: 1.1.1.42 | isocitrate dehydrogenase (NADP+) |
| ec: 1.1.1.54 | allyl-alcohol dehydrogenase |
| ec: 1.1.1.55 | lactaldehyde reductase (NADPH) |
| ec: 1.1.1.56 | ribitol 2-dehydrogenase |
| ec: 1.1.1.59 | 3-hydroxypropionate dehydrogenase |
| ec: 1.1.1.60 | 2-hydroxy-3-oxopropionate reductase |
| ec: 1.1.1.61 | 4-hydroxybutyrate dehydrogenase |
| ec: 1.1.1.66 | omega-hydroxydecanoate dehydrogenase |
| ec: 1.1.1.67 | mannitol 2-dehydrogenase |
| ec: 1.1.1.71 | alcohol dehydrogenase [NAD(P)+] |
| ec: 1.1.1.72 | glycerol dehydrogenase (NADP+) |
| ec: 1.1.1.73 | octanol dehydrogenase |
| ec: 1.1.1.75 | (R)-aminopropanol dehydrogenase |

TABLE 1-continued

Alcohol and Aldehyde Dehydrogenases for Conversion of 4-HB to 14-BDO.

| | |
|---|---|
| ec: 1.1.1.76 | (S,S)-butanediol dehydrogenase |
| ec: 1.1.1.77 | lactaldehyde reductase |
| ec: 1.1.1.78 | methylglyoxal reductase (NADH-dependent) |
| ec: 1.1.1.79 | glyoxylate reductase (NADP+) |
| ec: 1.1.1.80 | isopropanol dehydrogenase (NADP+) |
| ec: 1.1.1.81 | hydroxypyruvate reductase |
| ec: 1.1.1.82 | malate dehydrogenase (NADP+) |
| ec: 1.1.1.83 | D-malate dehydrogenase (decarboxylating) |
| ec: 1.1.1.84 | dimethylmalate dehydrogenase |
| ec: 1.1.1.85 | 3-isopropylmalate dehydrogenase |
| ec: 1.1.1.86 | ketol-acid reductoisomerase |
| ec: 1.1.1.87 | homoisocitrate dehydrogenase |
| ec: 1.1.1.88 | hydroxymethylglutaryl-CoA reductase |
| ec: 1.1.1.90 | aryl-alcohol dehydrogenase |
| ec: 1.1.1.91 | aryl-alcohol dehydrogenase (NADP+) |
| ec: 1.1.1.92 | oxaloglycolate reductase (decarboxylating) |
| ec: 1.1.1.94 | glycerol-3-phosphate dehydrogenase [NAD(P)+] |
| ec: 1.1.1.95 | phosphoglycerate dehydrogenase |
| ec: 1.1.1.97 | 3-hydroxybenzyl-alcohol dehydrogenase |
| ec: 1.1.1.101 | acylglycerone-phosphate reductase |
| ec: 1.1.1.103 | L-threonine 3-dehydrogenase |
| ec: 1.1.1.104 | 4-oxoproline reductase |
| ec: 1.1.1.105 | retinol dehydrogenase |
| ec: 1.1.1.110 | indolelactate dehydrogenase |
| ec: 1.1.1.112 | indanol dehydrogenase |
| ec: 1.1.1.113 | L-xylose 1-dehydrogenase |
| ec: 1.1.1.129 | L-threonate 3-dehydrogenase |
| ec: 1.1.1.137 | ribitol-5-phosphate 2-dehydrogenase |
| ec: 1.1.1.138 | mannitol 2-dehydrogenase (NADP+) |
| ec: 1.1.1.140 | sorbitol-6-phosphate 2-dehydrogenase |
| ec: 1.1.1.142 | D-pinitol dehydrogenase |
| ec: 1.1.1.143 | sequoyitol dehydrogenase |
| ec: 1.1.1.144 | perillyl-alcohol dehydrogenase |
| ec: 1.1.1.156 | glycerol 2-dehydrogenase (NADP+) |
| ec: 1.1.1.157 | 3-hydroxybutyryl-CoA dehydrogenase |
| ec: 1.1.1.163 | cyclopentanol dehydrogenase |
| ec: 1.1.1.164 | hexadecanol dehydrogenase |
| ec: 1.1.1.165 | 2-alkyn-1-ol dehydrogenase |
| ec: 1.1.1.166 | hydroxycyclohexanecarboxylate dehydrogenase |
| ec: 1.1.1.167 | hydroxymalonate dehydrogenase |
| ec: 1.1.1.174 | cyclohexane-1,2-diol dehydrogenase |
| ec: 1.1.1.177 | glycerol-3-phosphate 1-dehydrogenase (NADP+) |
| ec: 1.1.1.178 | 3-hydroxy-2-methylbutyryl-CoA dehydrogenase |
| ec: 1.1.1.185 | L-glycol dehydrogenase |
| ec: 1.1.1.190 | indole-3-acetaldehyde reductase (NADH) |
| ec: 1.1.1.191 | indole-3-acetaldehyde reductase (NADPH) |
| ec: 1.1.1.192 | long-chain-alcohol dehydrogenase |
| ec: 1.1.1.194 | coniferyl-alcohol dehydrogenase |
| ec: 1.1.1.195 | cinnamyl-alcohol dehydrogenase |
| ec: 1.1.1.198 | (+)-borneol dehydrogenase |
| ec: 1.1.1.202 | 1,3-propanediol dehydrogenase |
| ec: 1.1.1.207 | (−)-menthol dehydrogenase |
| ec: 1.1.1.208 | (+)-neomenthol dehydrogenase |
| ec: 1.1.1.216 | farnesol dehydrogenase |
| ec: 1.1.1.217 | benzyl-2-methyl-hydroxybutyrate dehydrogenase |
| ec: 1.1.1.222 | (R)-4-hydroxyphenyllactate dehydrogenase |
| ec: 1.1.1.223 | isopiperitenol dehydrogenase |
| ec: 1.1.1.226 | 4-hydroxycyclohexanecarboxylate dehydrogenase |
| ec: 1.1.1.229 | diethyl 2-methyl-3-oxosuccinate reductase |
| ec: 1.1.1.237 | hydroxyphenylpyruvate reductase |
| ec: 1.1.1.244 | methanol dehydrogenase |
| ec: 1.1.1.245 | cyclohexanol dehydrogenase |
| ec: 1.1.1.250 | D-arabinitol 2-dehydrogenase |
| ec: 1.1.1.251 | galactitol 1-phosphate 5-dehydrogenase |
| ec: 1.1.1.255 | mannitol dehydrogenase |
| ec: 1.1.1.256 | fluoren-9-ol dehydrogenase |
| ec: 1.1.1.257 | 4-(hydroxymethyl)benzenesulfonate dehydrogenase |
| ec: 1.1.1.258 | 6-hydroxyhexanoate dehydrogenase |
| ec: 1.1.1.259 | 3-hydroxypimeloyl-CoA dehydrogenase |
| ec: 1.1.1.261 | glycerol-1-phosphate dehydrogenase [NAD(P)+] |
| ec: 1.1.1.265 | 3-methylbutanal reductase |
| ec: 1.1.1.283 | methylglyoxal reductase (NADPH-dependent) |
| ec: 1.1.1.286 | isocitrate-homoisocitrate dehydrogenase |
| ec: 1.1.1.287 | D-arabinitol dehydrogenase (NADP+) butanol dehydrogenase |

TABLE 1-continued

Alcohol and Aldehyde Dehydrogenases
for Conversion of 4-HB to 14-BDO.

ALDEHYDE DEHYDROGENASES

| | |
|---|---|
| ec: 1.2.1.2 | formate dehydrogenase |
| ec: 1.2.1.3 | aldehyde dehydrogenase (NAD+) |
| ec: 1.2.1.4 | aldehyde dehydrogenase (NADP+) |
| ec: 1.2.1.5 | aldehyde dehydrogenase [NAD(P)+] |
| ec: 1.2.1.7 | benzaldehyde dehydrogenase (NADP+) |
| ec: 1.2.1.8 | betaine-aldehyde dehydrogenase |
| ec: 1.2.1.9 | glyceraldehyde-3-phosphate dehydrogenase (NADP+) |
| ec: 1.2.1.10 | acetaldehyde dehydrogenase (acetylating) |
| ec: 1.2.1.11 | aspartate-semialdehyde dehydrogenase |
| ec: 1.2.1.12 | glyceraldehyde-3-phosphate dehydrogenase (phosphorylating) |
| ec: 1.2.1.13 | glyceraldehyde-3-phosphate dehydrogenase (NADP+) (phosphorylating) |
| ec: 1.2.1.15 | malonate-semialdehyde dehydrogenase |
| ec: 1.2.1.16 | succinate-semialdehyde dehydrogenase [NAD(P)+] |
| ec: 1.2.1.17 | glyoxylate dehydrogenase (acylating) |
| ec: 1.2.1.18 | malonate-semialdehyde dehydrogenase (acetylating) |
| ec: 1.2.1.19 | aminobutyraldehyde dehydrogenase |
| ec: 1.2.1.20 | glutarate-semialdehyde dehydrogenase |
| ec: 1.2.1.21 | glycolaldehyde dehydrogenase |
| ec: 1.2.1.22 | lactaldehyde dehydrogenase |
| ec: 1.2.1.23 | 2-oxoaldehyde dehydrogenase (NAD+) |
| ec: 1.2.1.24 | succinate-semialdehyde dehydrogenase |
| ec: 1.2.1.25 | 2-oxoisovalerate dehydrogenase (acylating) |
| ec: 1.2.1.26 | 2,5-dioxovalerate dehydrogenase |
| ec: 1.2.1.27 | methylmalonate-semialdehyde dehydrogenase (acylating) |
| ec: 1.2.1.28 | benzaldehyde dehydrogenase (NAD+) |
| ec: 1.2.1.29 | aryl-aldehyde dehydrogenase |
| ec: 1.2.1.30 | aryl-aldehyde dehydrogenase (NADP+) |
| ec: 1.2.1.31 | L-aminoadipate-semialdehyde dehydrogenase |
| ec: 1.2.1.32 | aminomuconate-semialdehyde dehydrogenase |
| ec: 1.2.1.36 | retinal dehydrogenase |
| ec: 1.2.1.39 | phenylacetaldehyde dehydrogenase |
| ec: 1.2.1.41 | glutamate-5-semialdehyde dehydrogenase |
| ec: 1.2.1.42 | hexadecanal dehydrogenase (acylating) |
| ec: 1.2.1.43 | formate dehydrogenase (NADP+) |
| ec: 1.2.1.45 | 4-carboxy-2-hydroxymuconate-6-semialdehyde dehydrogenase |
| ec: 1.2.1.46 | formaldehyde dehydrogenase |
| ec: 1.2.1.47 | 4-trimethylammoniobutyraldehyde dehydrogenase |
| ec: 1.2.1.48 | long-chain-aldehyde dehydrogenase |
| ec: 1.2.1.49 | 2-oxoaldehyde dehydrogenase (NADP+) |
| ec: 1.2.1.51 | pyruvate dehydrogenase (NADP+) |
| ec: 1.2.1.52 | oxoglutarate dehydrogenase (NADP+) |
| ec: 1.2.1.53 | 4-hydroxyphenylacetaldehyde dehydrogenase |
| ec: 1.2.1.57 | butanal dehydrogenase |
| ec: 1.2.1.58 | phenylglyoxylate dehydrogenase (acylating) |
| ec: 1.2.1.59 | glyceraldehyde-3-phosphate dehydrogenase (NAD(P)+) (phosphorylating) |
| ec: 1.2.1.62 | 4-formylbenzenesulfonate dehydrogenase |
| ec: 1.2.1.63 | 6-oxohexanoate dehydrogenase |
| ec: 1.2.1.64 | 4-hydroxybenzaldehyde dehydrogenase |
| ec: 1.2.1.65 | salicylaldehyde dehydrogenase |
| ec: 1.2.1.66 | mycothiol-dependent formaldehyde dehydrogenase |
| ec: 1.2.1.67 | vanillin dehydrogenase |
| ec: 1.2.1.68 | coniferyl-aldehyde dehydrogenase |
| ec: 1.2.1.69 | fluoroacetaldehyde dehydrogenase |
| ec: 1.2.1.71 | succinylglutamate-semialdehyde dehydrogenase |

Other exemplary enzymes and pathways are disclosed herein (see Examples). Furthermore, it is understood that enzymes can be utilized for carry out reactions for which the substrate is not the natural substrate. While the activity for the non-natural substrate may be lower than the natural substrate, it is understood that such enzymes can be utilized, either as naturally occurring or modified using the directed evolution or adaptive evolution, as disclosed herein.

14-BDO and GBL production through any of the pathways disclosed herein are based, in part, on the identification of the appropriate enzymes for conversion of precursors to 14-BDO and GBL. A number of specific enzymes for several of the reaction steps have been identified. For those transformations where enzymes specific to the reaction precursors have not been identified, enzyme candidates have been identified that are best suited for catalyzing the reaction steps. Enzymes have been shown to operate on a broad range of substrates, as discussed below. In addition, advances in the field of protein engineering also make it feasible to alter enzymes to act efficiently on substrates, even if not a natural substrate. Described below are several examples of broad-specificity enzymes from diverse classes suitable for a 14-BDO and GBL pathway as well as methods that have been used for evolving enzymes to act on non-natural substrates.

A key class of enzymes in 14-BDO and GBL pathways is the oxidoreductases that interconvert ketones or aldehydes to alcohols (1.1.1). Numerous exemplary enzymes in this class can operate on a wide range of substrates. An alcohol dehydrogenase (1.1.1.1) purified from the soil bacterium *Brevibacterium* sp KU 1309 (Hirano et al., *J. Biosc. Bioeng.* 100: 318-322 (2005)) was shown to operate on a plethora of aliphatic as well as aromatic alcohols with high activities. Table 2 shows the activity of the enzyme and its $K_m$ on different alcohols. The enzyme is reversible and has very high activity on several aldehydes also (Table 3).

TABLE 2

Relative activities of an alcohol dehydrogenase from *Brevibacterium* sp KU to oxidize various alcohols.

| Substrate | Relative Activity (0%) | $K_m$ (mM) |
|---|---|---|
| 2-Phenylethanol | 100* | 0.025 |
| (S)-2-Phenylpropanol | 156 | 0.157 |
| (R)-2-Phenylpropanol | 63 | 0.020 |
| Bynzyl alcohol | 199 | 0.012 |
| 3-Phenylpropanol | 135 | 0.033 |
| Ethanol | 76 | |
| 1-Butanol | 111 | |
| 1-Octanol | 101 | |
| 1-Dodecanol | 68 | |
| 1-Phenylethanol | 46 | |
| 2-Propanol | 54 | |

*The activity of 2-phenylethanol, corresponding to 19.2 U/mg, was taken as 100%.

TABLE 3

Relative activities of an alcohol dehydrogenase from *Brevibacterium* sp KU 1309 to reduce various carbonyl compounds.

| Substrate | Relative Activity (%) | $K_m$ (mM) |
|---|---|---|
| Phenylacetaldehyde | 100 | 0.261 |
| 2-Phenylpropionaldehyde | 188 | 0.864 |
| 1-Octylaldehyde | 87 | |
| Acetophenone | 0 | |

Lactate dehydrogenase (1.1.1.27) from *Ralstonia eutropha* is another enzyme that has been demonstrated to have high activities on several 2-oxoacids such as 2-oxobutyrate, 2-oxopentanoate and 2-oxoglutarate (a C5 compound analogous to 2-oxoadipate) (Steinbuchel and Schlegel, *Eur. J. Biochem.* 130:329-334 (1983)). Column 2 in Table 4 demonstrates the activities of ldhA from *R. eutropha* (formerly *A. eutrophus*) on different substrates (Steinbuchel and Schlegel, supra, 1983).

TABLE 4

The in vitro activity of R. eutropha ldhA (Steinbuchel and Schlegel, supra, 1983) on different substrates and compared with that on pyruvate.

| Substrate | Activity (%) of | | |
|---|---|---|---|
| | L(+)-lactate dehydrogenase from A. eutrophus | L(+)-lactate dehydrogenase from rabbit muscle | D(−)-lactate dehydrogenase from L. leichmanii |
| Glyoxylate | 8.7 | 23.9 | 5.0 |
| Pyruvate | 100.0 | 100.0 | 100.0 |
| 2-Oxobutyrate | 107.0 | 18.6 | 1.1 |
| 2-Oxovalerate | 125.0 | 0.7 | 0.0 |
| 3-Methyl-2-oxobutyrate | 28.5 | 0.0 | 0.0 |
| 3-Methyl-2-oxovalerate | 5.3 | 0.0 | 0.0 |
| 4-Methyl-2-oxopentanoate | 39.0 | 1.4 | 1.1 |
| Oxaloacetate | 0.0 | 33.1 | 23.1 |
| 2-Oxoglutarate | 79.6 | 0.0 | 0.0 |
| 3-Fluoropyruvate | 33.6 | 74.3 | 40.0 |

Oxidoreductases that can convert 2-oxoacids to their acyl-CoA counterparts (1.2.1) have been shown to accept multiple substrates as well. For example, branched-chain 2-keto-acid dehydrogenase complex (BCKAD), also known as 2-oxoisovalerate dehydrogenase (1.2.1.25), participates in branched-chain amino acid degradation pathways, converting 2-keto acids derivatives of valine, leucine and isoleucine to their acyl-CoA derivatives and $CO_2$. In some organisms including Rattus norvegicus (Paxton et al., Biochem. J. 234:295-303 (1986)) and Saccharomyces cerevisiae (Sinclair et al., Biochem. Mol. Biol. Int. 32:911-922 (1993), this complex has been shown to have a broad substrate range that includes linear oxo-acids such as 2-oxobutanoate and alpha-ketoglutarate, in addition to the branched-chain amino acid precursors.

Members of yet another class of enzymes, namely aminotransferases (2.6.1), have been reported to act on multiple substrates. Aspartate aminotransferase (aspAT) from Pyrococcus fursious has been identified, expressed in E. coli and the recombinant protein characterized to demonstrate that the enzyme has the highest activities towards aspartate and alpha-ketoglutarate but lower, yet significant activities towards alanine, glutamate and the aromatic amino acids (Ward et al., Archaea 133-141 (2002)). In another instance, an aminotransferase identified from Leishmania mexicana and expressed in E. coli (Vernal et al., FEMS Microbiol. Lett. 229:217-222 (2003)) was reported to have a broad substrate specificity towards tyrosine (activity considered 100% on tyrosine), phenylalanine (90%), tryptophan (85%), aspartate (30%), leucine (25%) and methionine (25%), respectively (Vernal et al., Mol. Biochem. Parasitol 96:83-92 (1998)). Similar broad specificity has been reported for a tyrosine aminotransferase from Trypanosoma cruzi, even though both of these enzymes have a sequence homology of only 6%. The latter enzyme can accept leucine, methionine as well as tyrosine, phenylalanine, tryptophan and alanine as efficient amino donors (Nowicki et al., Biochim. Biophys. Acta 1546: 268-281 (2001)).

CoA transferases (2.8.3) have been demonstrated to have the ability to act on more than one substrate. Specifically, a CoA transferase was purified from Clostridium acetobutylicum and was reported to have the highest activities on acetate, propionate, and butyrate. It also had significant activities with valerate, isobutyrate, and crotonate (Wiesenborn et al., Appl. Environ. Microbiol. 55:323-329 (1989)). In another study, the E. coli enzyme acyl-CoA:acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink, App. Environm. Microbiol. 58:1435-1439 (1992)), valerate (Vanderwinkel et al., Biochem. Biophys. Res Commun. 33:902-908 (1968b)) and butanoate (Vanderwinkel et al., Biochem. Biophys. Res Commun. 33:902-908 (1968a)).

Another class of enzymes useful in 14-BDO and GBL pathways is the acid-thiol ligases (6.2.1). Like enzymes in other classes, certain enzymes in this class have been determined to have broad substrate specificity. For example, acyl CoA ligase from Pseudomonas putida has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., Appl. Environ. Microbiol. 59:1149-1154 (1993)). A related enzyme, malonyl CoA synthetase (6.3.4.9) from Rhizobium trifolii could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., J. Am. Chem. Soc. 123:5822-5823 (2001)). Similarly, decarboxylases (4.1.1) have also been found with broad substrate ranges. Pyruvate decarboxylase (PDC), also termed keto-acid decarboxylase, is a key enzyme in alcoholic fermentation, catalyzing the decarboxylation of pyruvate to acetaldehyde. The enzyme isolated from Saccharomyces cerevisiae has a broad substrate range for aliphatic 2-keto acids including 2-ketobutyrate, 2-ketovalerate, and 2-phenylpyruvate (Li and Jordan, Biochemistry 38:10004-10012 (1999)). Similarly, benzoylformate decarboxylase has a broad substrate range and has been the target of enzyme engineering studies. The enzyme from Pseudomonas putida has been extensively studied and crystal structures of this enzyme are available (Polovnikova et al., Biochemistry 42:1820-1830 (2003); Hasson et al., Biochemistry 37:9918-9930 (1998)). Branched chain alpha-ketoacid decarboxylase (BCKA) has been shown to act on a variety of compounds varying in chain length from 3 to 6 carbons (Oku and Kaneda, J. Biol. Chem. 263:18386-18396 (1998); Smit et al., Appl. Environ. Microbiol. 71:303-311 (2005b)). The enzyme in Lactococcus lactis has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., Appl. Environ. Microbiol. 71:303-311 (2005a).

Interestingly, enzymes known to have one dominant activity have also been reported to catalyze a very different function. For example, the cofactor-dependent phosphoglycerate mutase (5.4.2.1) from Bacillus stearothermophilus and Bacillus subtilis is known to function as a phosphatase as well (Rigden et al., Protein Sci. 10:1835-1846 (2001)). The enzyme from B. stearothermophilus is known to have activity on several substrates, including 3-phosphoglycerate, alpha-napthylphosphate, p-nitrophenylphosphate, AMP, fructose-6-phosphate, ribose-5-phosphate and CMP.

The non-naturally occurring microbial organisms of the invention can be produced by introducing expressible nucleic acids encoding one or more of the enzymes or proteins participating in one or more 14-BDO or GBL biosynthetic pathways. Depending on the host microbial organism chosen for biosynthesis, nucleic acids for some or all of a particular 14-BDO or GBL biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve 14-BDO and GBL biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 14-BDO or GBL.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli*, *Klebsiella oxytoca*, *Anaerobiospirillum succiniciproducens*, *Actinobacillus succinogenes*, *Mannheimia succiniciproducens*, *Rhizobium etli*, *Bacillus subtilis*, *Corynebacterium glutamicum*, *Gluconobacter oxydans*, *Zymomonas mobilis*, *Lactococcus lactis*, *Lactobacillus plantarum*, *Streptomyces coelicolor*, *Clostridium acetobutylicum*, *Pseudomonas fluorescens*, and *Pseudomonas putida*. Exemplary yeasts or fungi include species selected from *Saccharomyces cerevisiae*, *Schizosaccharomyces pombe*, *Kluyveromyces lactis*, *Kluyveromyces marxianus*, *Aspergillus terreus*, *Aspergillus niger*, *Pichia pastoris*, *Rhizopus arrhizus*, *Rhizobus oryzae*, and the like. *E. coli* is a particularly useful host organisms since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the 14-BDO and GBL biosynthetic pathway constituents of a selected host microbial organism, the non-naturally occurring microbial organisms of the invention will include at least one exogenously expressed 14-BDO or GBL pathway-encoding nucleic acid and up to all encoding nucleic acids for one or more 14-BDO and GBL biosynthetic pathway. For example, 14-BDO and GBL biosynthesis can be established in a host deficient in a pathway enzyme or protein through exogenous expression of the corresponding encoding nucleic acid. In a host deficient in all enzymes or proteins of a 14-BDO or GBL pathway, exogenous expression of all enzymes or proteins in the pathway can be included, although it is understood that all enzymes or proteins of a pathway can be expressed even if the host contains at least one of the pathway enzymes or proteins. For example, exogenous expression of all enzymes or proteins in a pathway for production of 14-BDO and GBL can be included, such as a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase (or succinyl-CoA ligase), a glutamate dehydrogenase, a glutamate transaminase, a glutamate decarboxylase, a 4-aminobutyrate dehydrogenase, a 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase (or 4-hydroxybutyryl-CoA ligase), a 4-hydroxybutyryl-CoA reductase (alcohol forming), an alpha-ketoglutarate reductase, a 5-hydroxy-2-oxopentanoate dehydrogenase, a 5-hydroxy-2-oxopentanoate decarboxylase, a 5-hydroxy-2-oxopentanoate dehydrogenase (decarboxylation) or a 4-hydroxybutyrate lactonase.

Given the teachings and guidance provided herein, those skilled in the art will understand that the number of encoding nucleic acids to introduce in an expressible form will, at least, parallel the 14-BDO and GBL pathway deficiencies of the selected host microbial organism. Therefore, a non-naturally occurring microbial organism of the invention can have one, two, three, four, five, six, seven or eight up to all nucleic acids encoding the enzymes or proteins constituting a 14-BDO or GBL biosynthetic pathway disclosed herein. In some embodiments, the non-naturally occurring microbial organisms also can include other genetic modifications that facilitate or optimize 14-BDO and GBL biosynthesis or that confer other useful functions onto the host microbial organism. One such other functionality can include, for example, augmentation of the synthesis of one or more of the 14-BDO or GBL pathway precursors such as succinate, succinyl-CoA or alpha-ketoglutarate.

Generally, a host microbial organism is selected such that it produces the precursor of a 14-BDO or GBL pathway, either as a naturally produced molecule or as an engineered product that either provides de novo production of a desired precursor or increased production of a precursor naturally produced by the host microbial organism. For example, succinate is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a 14-BDO or GBL pathway.

In some embodiments, a non-naturally occurring microbial organism of the invention is generated from a host that contains the enzymatic capability to synthesize 14-BDO and GBL and in some embodiments synthesizing 14-BDO and GBL at a predetermined ratio. In this specific embodiment it can be useful to increase the synthesis or accumulation of a 14-BDO or GBL pathway product to, for example, drive 14-BDO and GBL pathway reactions toward 14-BDO and GBL production. Increased synthesis or accumulation can be accomplished by, for example, overexpression of nucleic acids encoding one or more of the above-described 14-BDO or GBL pathway enzymes or proteins. Over expression of the enzyme or enzymes and/or protein or proteins of the 14-BDO or GBL pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 14-BDO and GBL, through overexpression of one, two, three, four, five, six, seven or eight, that is, up to all nucleic acids encoding 14-BDO or GBL biosynthetic pathway enzymes or proteins. In addition, a non-naturally occurring organism can be generated by mutagenesis of an endogenous gene that results in an increase in activity of an enzyme in the 14-BDO or GBL biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user, which can be used to produce a predetermined ratio of 14-BDO to GBL. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism. It is also understood that increasing the expression of an enzyme or protein can alter the ratio of 14-BDO to GBL produced by the non-naturally occurring microorganisms described herein by enzymatically converting one or more pathway intermediates, which are shared between the 14-BDO and GBL pathways, towards the production of one of the products. In this embodiment, the pool of intermediates for production of one product can be shifted toward the production of another product ultimately resulting in change in the ratio of 14-BDO and GBL produced by the microorganisms or methods described herein.

It is understood that, in methods of the invention, any of the one or more exogenous nucleic acids can be introduced into a microbial organism to produce a non-naturally occurring microbial organism of the invention. The nucleic acids can be introduced so as to confer, for example, a 14-BDO and GBL biosynthetic pathway onto the microbial organism. Alternatively, encoding nucleic acids can be introduced to produce an intermediate microbial organism having the biosynthetic capability to catalyze some of the required reactions to confer 14-BDO and GBL biosynthetic capability. For example, a non-naturally occurring microbial organism having 14-BDO and GBL biosynthetic pathways can comprise at least two exogenous nucleic acids encoding desired enzymes or proteins, such as the combination of a succinyl-CoA transferase and a 4-hydroxybutyrate kinase, or alternatively a 4-hydroxybutyrate lactonase and a 1,4-butanediol dehydrogenase, or alternatively a glutamate decarboxylase and a 5-hydroxy-2-oxopentanoate decarboxylase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a succinyl-CoA reductase (alcohol forming), a 4-hydroxybutyryl-CoA transferase and a 4-hydroxybutyrate lactonase, or alternatively a 5-hydroxy-2-oxopentanoate dehydrogenase (decarboxylation), a succinate reductase and a phosphotrans-4-hydroxybutyrylase, or alternatively an alpha-ketoglutarate reductase, a 1,4-butanediol dehydrogenase and a 4-hydroxybutyrate lactonase, and so forth, as desired, so long as the combination of enzymes and/or proteins of the desired biosynthetic pathway results in production of the corresponding desired product. Similarly, any combination of four, a succinate reductase, a 4-hydroxybutyrate dehydrogenase, a 4-hydroxybutyrate kinase and a 4-hydroxybutyryl-CoA reductase (alcohol forming), or alternatively a 4-hydroxybutyrate lactonase, a succinyl-CoA reductase (alcohol forming), a 4-hydroxybutyryl-CoA synthetase and a 4-hydroxybutyryl-CoA reductase (alcohol forming), or alternatively a 4-aminobutyrate dehydrogenase, a 4-hydroxybutyrate dehydrogenase, a 4-hydroxybutyrate lactonase and a 4-hydroxybutyryl-CoA reductase (aldehyde forming), or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of 14-BDO and GBL as described herein, the non-naturally occurring microbial organisms and methods of the invention also can be utilized in various combinations with each other and with other microbial organisms and methods well known in the art to achieve product biosynthesis by other routes. For example, one alternative to produce 14-BDO and GBL other than use of the 14-BDO and GBL producers is through addition of another microbial organism capable of converting a 14-BDO or GBL pathway intermediate to 14-BDO or GBL. One such procedure includes, for example, the fermentation of a microbial organism that produces a 14-BDO or GBL pathway intermediate. The 14-BDO or GBL pathway intermediate can then be used as a substrate for a second microbial organism that converts the 14-BDO or GBL pathway intermediate to 14-BDO and GBL. The 14-BDO or GBL pathway intermediate can be added directly to another culture of the second organism or the original culture of the 14-BDO or GBL pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 14-BDO and GBL. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final products are synthesized. For example, the biosynthesis of 14-BDO and GBL can be accomplished by constructing a microbial organism that contains biosynthetic pathways for conversion of one pathway intermediate to another pathway intermediate or the product. Alternatively, 14-BDO and GBL also can be biosynthetically produced from microbial organisms through co-culture or co-fermentation using two organisms in the same vessel, where the first microbial organism produces a 14-BDO or GBL intermediate and the second microbial organism converts the intermediate to 14-BDO and GBL.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 14-BDO and GBL.

Sources of encoding nucleic acids for a 14-BDO or GBL pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Acinetobacter* sp. Strain M-1, *Acetobacter pasteurians, Achromobacter denitrificans, Acidaminococcus fermentans, Acinetobacter baumanii, Acinetobacter baylyi, Acinetobacter calcoaceticus, Acinetobacter* sp. Strain M-1, *Aeropyrum pernix* K1, *Agrobacterium tumefaciens, Arabidopsis thaliana, Archaeoglobus fulgidus* DSM 4304, *Aspergillus niger, Bacillus cereus, Bacillus megaterium, Bacillus subtilis, Bos taurus, Bradyrhizobium japonicum,* butyrate producing bacterium L2-50, *Campylobacter jejuni, Candida albicans, Candida Antarctica, Chloroflexus aurantiacus, Clostridium acetobutylicum, Clostridium acetobutylicum* ATCC 824, *Clostridium aminobutyricum, Clostridium beijerinckii, Clostridium beijerinckii, Clostridium difficile, Clostridium kluyveri, Clostridium kluyveri* DSM 555, *Clostridium perfringens, Clostridium saccharoperbutylacetonicum, Clostridium tetani, Clostridium thermocellum, Corynebacterium glutamicum, Erythrobacter* sp. NAP1, *Escherichia coli* str. K12, *Euglena gracilis, Flavobacterium lutescens, Fusarium oxysporum, Fusobacterium nucleatum, Geobacillus stearothermophilus, Geobacillus thermoglucosidasius* M10EXG, *Haemophilus influenzae, Haloarcula marismortui* ATCC 43049, *Halobacterium salinarum, Haloferax mediterranei, Heliobacter pylori, Homo sapiens,* isolated from metalibrary of anaerobic sewage digester microbial consortia, *Klebsiella pneumonia* MGH78578, *Kluyveromyces lactis, Lachancea kluyveri, Lactococcus lactis, Leuconostoc mesenteroides,* marine gamma proteobacterium HTCC2080, *Mesorhizobium loti, Metallosphaera sedula, Mus musculus, Mycobacterium bovis* BCG, *Mycobacterium tuberculosis, Myxococcus xanthus, Nicotiana tabacum, Nocardia farcinica* IFM 10152, *Nocardia* iowensis (sp. NRRL 5646), *Oryctolagus cuniculus, Oryza sativa, Penicillium chrysogenum, Porphyromonas gingivalis, Porphyromonas gingivalis* W83, *Pseudomonas aeruginosa, Pseudomonas aeruginosa* PAO1, *Pseudomonas fluorescens, Pseudomonas putida, Pseudomonas putida* E23, *Pseudomonas putida* KT2440, *Pseudomonas* sp, *Pseudomonas stutzeri, Pyrobaculum aerophilum* str. IM2, *Ralstonia eutropha, Ralstonia eutropha* H16, *Rattus norvegicus, Rhodobacter spaeroides, Roseiflexus castenholzii, Saccharomyces cerevisiae, Salmonella typhimurium, Schizosaccharomyces pombe, Simmondsia chinensis, Streptomyces clavuligenus, Streptomyces griseus* subsp. *griseus* NBRC 13350, *Sulfolobus acidocaldarius, Sulfolobus solfataricus, Sulfolobus tokodaii, Sulfolobus tokodaii 7, Sus scrofa, Thermotoga maritime, Thermus thermophilus, Trichomonas vaginalis* G3, *Trypanosoma brucei,* Uncultured bacterium, *Vibrio cholera, Xanthomonas campestris, Zymomonas mobilis,* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 14-BDO or GBL biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 14-BDO and GBL described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 14-BDO or GBL biosynthetic pathway exists in an unrelated species, 14-BDO or GBL biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 14-BDO and GBL.

Methods for constructing and testing the expression levels of a non-naturally occurring 14-BDO and GBL co-producing host can be performed, for example, by recombinant and detection methods well known in the art. Such methods can be found described in, for example, Sambrook et al., *Molecular Cloning: A Laboratory Manual,* Third Ed., Cold Spring Harbor Laboratory, New York (2001); and Ausubel et al., *Current Protocols in Molecular Biology,* John Wiley and Sons, Baltimore, Md. (1999).

Exogenous nucleic acid sequences involved in a pathway for production of 14-BDO and GBL can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 14-BDO or GBL biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In one embodiment, the invention provides a method for producing 14-BDO and GBL that includes culturing a non-naturally occurring microbial organism, including a microbial organism having a 14-BDO pathway and a GBL pathway, said 14-BDO pathway comprising at least one exogenous nucleic acid encoding a 14-BDO pathway enzyme expressed in a sufficient amount to produce 14-BDO, said 14-BDO pathway comprising a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase, a 4-hydroxybutyryl-CoA reductase (alcohol forming), an alpha-ketoglutarate reductase, a 5-hydroxy-2-oxopentanoate dehydrogenase, a 5-hydroxy-2-oxopentanoate decarboxylase or a 5-hydroxy-2-oxopentanoate dehydrogenase (decarboxylation) (see FIG. 1, steps A, B, C, D, E, F, G, H, I, J, K, L, M, N, O, P, Q, R, S, T, U, V, W, X, Y, Z, AA), said GBL pathway comprising at least one exogenous nucleic acid encoding an GBL pathway enzyme expressed in a sufficient amount to produce GBL, said GBL pathway comprising a succinyl-CoA reductase (aldehyde forming), an alpha-ketoglutarate decarboxylase, a 4-hydroxybutyrate dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a succinyl-CoA reductase (alcohol forming) or a 4-hydroxybutyrate lactonase (see FIG. 1, steps A, B, C, F, G, H, I, J, K, L, M, N, S, AB).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, A, C, O, P, Q, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase (see FIG. 1, steps G/H/I, A, C, O, R, E).

In a further aspect of the above embodiment, the method includes a microbial organism having a 14-BDO pathway comprising a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, A, C, T/U/V, Q, E).

In a further aspect of the above embodiment, the method includes a microbial organism having a 14-BDO pathway comprising a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, A, C, T/U/V, W).

In a further aspect of the above embodiment, the method includes a microbial organism having a 1,4-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps G/H/I, A, C, O, P, W).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase (see FIG. 1, steps G/H/I, S, D, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, S, O, P, Q, E).

In a further aspect of the above embodiment, the method includes a microbial organism having a 14-BDO pathway comprising a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase (see FIG. 1, steps G/H/I, S, O, R, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, S, T/U/V, Q, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, S, T/U/V, W).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming) (see FIG. 1, steps G/H/I, S, O, P, W).

In a further aspect of the above embodiment, the method includes a microbial organism having a 14-BDO pathway comprising a succinate reductase; a 4-hydroxybutyrate dehydrogenase; a 4-hydroxybutyrate reductase; and 1,4-butanediol dehydrogenase (see FIG. 1, steps F, C, D, E).

In a further aspect of the above embodiment, the method includes a microbial organism having a 14-BDO pathway comprising a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps F, C, O, P, Q, E).

In a further aspect of the above embodiment, the method includes a microbial organism having a 14-BDO pathway comprising a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps F, C, O, P, W).

In a further aspect of the above embodiment, the method includes a microbial organism having a 14-BDO pathway comprising a succinate reductase; a 4-hydroxybutyrate dehydrogenase; a 4-hydroxybutyrate kinase; a 4-hydroxybutyryl-phosphate reductase; and 1,4-butanediol dehydrogenase (see FIG. 1, steps F, C, O, R, E).

In a further aspect of the above embodiment, the method includes a microbial organism having a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase (see FIG. 1, steps F, C, T/U/V, Q, E).

In a further aspect of the above embodiment, the method includes a microbial organism having a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps F, C, T/U/V, W).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate reductase; and 1,4-butanediol dehydrogenase (see FIG. 1, steps B, C, D, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps B, C, O, P, Q, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming) (see FIG. 1, steps B, C, O, P, W).

In a further aspect of the above embodiment, the method includes a microbial organism having a 14-BDO pathway comprising. an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps B, C, O, R, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase (see FIG. 1, steps B, C, T/U/V, Q, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming) (see FIG. 1, steps B, C, T/U/V, W).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase (see FIG. 1, steps J/K, L, M/N, C, D, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase (see FIG. 1, steps J/K, L, M/N, C, O, P, Q, E).

In a further aspect of the above embodiment, the method includes a microbial organism having a 14-BDO pathway comprising a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming), (see FIG. 1, steps J/K, L, M/N, C, O, P, W)

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps J/K, L, M/N, C, O, R, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps J/K, L, M/N, C, T/U/V, Q, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps J/K, L, M/N, C, T/U/V, W).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase (see FIG. 1, steps X, Y, AA, Q, E).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming) (FIG. 1, steps X, Y, AA, and W).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate decarboxylase; and a 1,4-butanediol dehydrogenase (see FIG. 1, steps X, Y, Z, E).

In a further aspect of the above embodiment, the method includes a microbial organism having a GBL pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyrate lactonase (see FIG. 1, steps G/H/I, A, C, AB).

In a further aspect of the above embodiment, the method includes a microbial organism having a GBL pathway comprising a succinyl-CoA transferase, a succinyl-CoA hydrolase and a succinyl-CoA synthetase; a succinyl-CoA reductase (alcohol forming); and a 4-hydroxybutyrate lactonase, (see FIG. 1, steps G/H/I, S, AB)

In a further aspect of the above embodiment, the method includes a microbial organism having a GBL pathway comprising a succinate reductase; a 4-hydroxybutyrate dehydrogenase; and a 4-hydroxybutyrate lactonase (see FIG. 1, steps F, C, AB).

In a further aspect of the above embodiment, the method includes a microbial organism having a GBL pathway comprising an alpha-ketoglutarate decarboxylase, a 4-hydroxybutyrate dehydrogenase and a 4-hydroxybutyrate lactonase (see FIG. 1, steps B, C, AB).

In a further aspect of the above embodiment, the method includes a microbial organism having a GBL pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; and a 4-hydroxybutyrate lactonase (see FIG. 1, steps J/K, L, M/N, C, AB).

In one embodiment, the invention provides a method for producing 14-BDO and GBL that includes culturing a non-naturally occurring microbial organism, including a microbial organism having a 1,4-butanediol (14-BDO) pathway and a gamma-butyrolactone (GBL) pathway, said 14-BDO pathway comprising a first set of exogenous nucleic acids encoding 14-BDO pathway enzymes expressed in a sufficient amount to produce 14-BDO, wherein said first set is selected from the group consisting of: [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase)] (see FIG. 1, steps G/H/I, A, C, D, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, A, C, O, P, Q, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps G/H/I, A, C, O, R, E); [a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, A, C, T/U/V, Q, E); [a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, A, C, T/U/V, W); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps G/H/I, A, C, O, P, W); [a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase] (see FIG. 1, steps G/H/I, S, D, E); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, S, O, P, Q, E); [a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase] (see FIG. 1, steps G/H/I, S, O, R, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, S, T/U/V, Q, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, S, T/U/V, W); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming)] (see FIG. 1, steps G/H/I, S, O, P, W); [a succinate reductase; a 4-hydroxybutyrate dehydrogenase; a 4-hydroxybutyrate reductase; and 1,4-butanediol dehydrogenase] (see FIG. 1, steps F, C, D, E); [a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps F, C, O, P, Q, E); [a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps F, C, O, P, W); [a succinate reductase; a 4-hydroxybutyrate dehydrogenase; a 4-hydroxybutyrate kinase; a 4-hydroxybutyryl-phosphate reductase; and 1,4-butanediol dehydrogenase] (see FIG. 1, steps F, C, O, R, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase] (see FIG. 1, steps F, C, T/U/V, Q, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps F, C, T/U/V, W); [an alpha-ketoglutarate decarboxylase; a 4-hydroxybutyrate dehydrogenase; a 4-hydroxybutyrate reductase; and 1,4-butanediol dehydrogenase] (see FIG. 1, steps B, C, D, E); [an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps B, C, O, P, Q, E); [an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming)] (see FIG. 1, steps B, C, O, P, W); [an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps B, C, O, R, E); [an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase] (see FIG. 1, steps B, C, T/U/V, Q, E); [an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming)] (see FIG. 1, steps B, C, T/U/V, W); [a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase] (see FIG. 1, steps J/K, L, M/N, C, D, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase] (see FIG. 1, steps J/K, L, M/N, C, O, P, Q, E); [a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps J/K, L, M/N, C, O, P, W); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase]; (see FIG. 1, steps J/K, L, M/N, C, O, R, E) [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps J/K, L, M/N, C, T/U/V, Q, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps J/K, L, M/N, C, T/U/V, W); [an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase] (see FIG. 1, steps X, Y, AA, Q, E); [an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming)] (see FIG. 1, steps X, Y, AA, and W); and [an alpha-ketoglutarate reductase; a 5-hydroxy-2-oxopentanoate dehydrogenase; a 5-hydroxy-2-oxopentanoate decarboxylase; and a 1,4-butanediol dehydrogenase] (see FIG. 1, steps X, Y, Z, E), said GBL pathway comprising a second set of exogenous nucleic acid encoding an GBL pathway enzyme expressed in a sufficient amount to produce GBL, said second set is selected from the group consisting of [a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyrate lactonase] (see FIG. 1, steps G/H/I, A, C, AB); [a succinyl-CoA transferase, a succinyl-CoA hydrolase and a succinyl-CoA synthetase; a succinyl-CoA reductase (alcohol forming); and a 4-hydroxybutyrate lactonase] (see FIG. 1, steps G/H/I, S, AB); [a succinate reductase; a 4-hydroxybutyrate dehydrogenase; and a 4-hydroxybutyrate lactonase] (see FIG. 1, steps F, C, AB); [an alpha-ketoglutarate decarboxylase, a 4-hydroxybutyrate dehydrogenase and a 4-hydroxybutyrate lactonase] (see FIG. 1, steps B, C, AB); and [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; and a 4-hydroxybutyrate lactonase] (see FIG. 1, steps J/K, L, M/N, C, AB).

In a further aspect of each of the above embodiments, the exogenous nucleic acid is a heterologous nucleic acid.

In a further aspect of each of the above embodiments, the conditions include substantially anaerobic culture conditions.

In a further aspect of each of the above embodiments, the 14-BDO and GBL products are produced at a predetermined ratio. In some aspects of the invention, the predetermined ratio of 14-BDO to GBL is 1:1, or alternatively 1:2, or alternatively 1:3, or alternatively 1:4, or alternatively 1:5, or alternatively 1:6, or alternatively 1:7, or alternatively 1:8, or alternatively 1:9, or alternatively 1:10, or alternatively 1:15, or alternatively about 1:20, or alternatively 1:25, or alternatively 1:30, or alternatively 1:35, or alternatively 1:40, or alternatively 1:45, or alternatively about 1:50, or alternatively 1:60, or alternatively 1:70, or alternatively 1:80, or alternatively 1:90, or alternatively 1:100. In some aspects of the invention, the predetermined ratio of 14-BDO to GBL is 2:1, or alternatively 3:1, or alternatively 4:1, or alternatively 5:1, or alternatively 6:1, or alternatively 7:1, or alternatively 8:1, or alternatively 9:1, or alternatively 10:1, or alternatively 15:1, or alternatively about 20:1, or alternatively 25:1, or alternatively 30:1, or alternatively 35:1, or alternatively 40:1, or alternatively 45:1, or alternatively about 50:1, or alternatively 60:1, or alternatively 70:1, or alternatively 80:1, or alternatively 90:1, or alternatively 100:1.

In one embodiment, the invention provides a method for producing 14-BDO and GBL that includes culturing a non-naturally occurring microbial organism under conditions and for a sufficient period of time to produce 14-BDO and 4-hydroxybutyryl-phosphate followed by spontaneous lactonization of 4-hydroxybutyryl-phosphate to form GBL, wherein said non-naturally occurring microbial organism comprise a microbial organism having a 14-BDO pathway and a 4-hydroxybutyryl-phosphate pathway, said 14-BDO pathway comprising at least one exogenous nucleic acid encoding a 14-BDO pathway enzyme expressed in a sufficient amount to produce 14-BDO, said 14-BDO pathway comprising a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase, a 4-hydroxybutyryl-CoA reductase (alcohol forming), an alpha-ketoglutarate reductase, a 5-hydroxy-2-oxopentanoate dehydrogenase, a 5-hydroxy-2-oxopentanoate decarboxylase or a 5-hydroxy-2-oxopentanoate dehydrogenase (decarboxylation) (see FIG. 1, steps A, B, C, D, E, F, G, H, I, J, K, L, M, N, O, P, Q, R, S, T, U, V, W, X, Y, Z, AA), said 4-hydroxybutyryl-phosphate pathway comprising at least one exogenous nucleic acid encoding an 4-hydroxybutyryl-phosphate pathway enzyme expressed in a sufficient amount to produce 4-hydroxybutyryl-phosphate, said 4-hydroxybutyryl-phosphate pathway comprising a succinyl-CoA reductase (aldehyde forming), an alpha-ketoglutarate decarboxylase, a 4-hydroxybutyrate dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, a 4-aminobutyrate dehydrogenase, a 4-aminobutyrate transaminase, a 4-hydroxybutyrate kinase or a succinyl-CoA reductase (alcohol forming) (see FIG. 1, steps A, B, C, F, G, H, I, J, K, L, M, N, O, S).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase (see FIG. 1, steps G/H/I, A, C, D, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, A, C, O, P, Q, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase (see FIG. 1, steps G/H/I, A, C, O, R, E).

In a further aspect of the above embodiment, the method includes a microbial organism having a 14-BDO pathway comprising a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, A, C, T/U/V, Q, E).

In a further aspect of the above embodiment, the method includes a microbial organism having a 14-BDO pathway comprising a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, A, C, T/U/V, W).

In a further aspect of the above embodiment, the method includes a microbial organism having a 1,4-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps G/H/I, A, C, O, P, W).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase (see FIG. 1, steps G/H/I, S, D, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, S, O, P, Q, E).

In a further aspect of the above embodiment, the method includes a microbial organism having a 14-BDO pathway comprising a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase (see FIG. 1, steps G/H/I, S, O, R, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, S, T/U/V, Q, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, S, T/U/V, W).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming) (see FIG. 1, steps G/H/I, S, O, P, W).

In a further aspect of the above embodiment, the method includes a microbial organism having a 14-BDO pathway comprising a succinate reductase; a 4-hydroxybutyrate dehydrogenase; a 4-hydroxybutyrate reductase; and 1,4-butanediol dehydrogenase (see FIG. 1, steps F, C, D, E).

In a further aspect of the above embodiment, the method includes a microbial organism having a 14-BDO pathway comprising a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps F, C, O, P, Q, E).

In a further aspect of the above embodiment, the method includes a microbial organism having a 14-BDO pathway comprising a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps F, C, O, P, W).

In a further aspect of the above embodiment, the method includes a microbial organism having a 14-BDO pathway comprising a succinate reductase; a 4-hydroxybutyrate dehydrogenase; a 4-hydroxybutyrate kinase; a 4-hydroxybutyryl-phosphate reductase; and 1,4-butanediol dehydrogenase (see FIG. 1, steps F, C, O, R, E).

In a further aspect of the above embodiment, the method includes a microbial organism having a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase (see FIG. 1, steps F, C, T/U/V, Q, E).

In a further aspect of the above embodiment, the method includes a microbial organism having a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps F, C, T/U/V, W).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate reductase; and 1,4-butanediol dehydrogenase (see FIG. 1, steps B, C, D, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps B, C, O, P, Q, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming) (see FIG. 1, steps B, C, O, P, W).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps B, C, O, R, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase (see FIG. 1, steps B, C, T/U/V, Q, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming) (see FIG. 1, steps B, C, T/U/V, W).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase (see FIG. 1, steps J/K, L, M/N, C, D, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl- CoA reductase (aldehyde forming); and E) 1,4-butanediol dehydrogenase (see FIG. 1, steps J/K, L, M/N, C, O, P, Q, E).

In a further aspect of the above embodiment, the method includes a microbial organism having a 14-BDO pathway comprising a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps J/K, L, M/N, C, O, P, W).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps J/K, L, M/N, C, O, R, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps J/K, L, M/N, C, T/U/V, Q, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps J/K, L, M/N, C, T/U/V, W).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase (see FIG. 1, steps X, Y, AA, Q, E).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming) (see FIG. 1, steps X, Y, AA, and W).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate decarboxylase; and a 1,4-butanediol dehydrogenase (see FIG. 1, steps X, Y, Z, E).

In a further aspect of the above embodiment, the method includes a microbial organism having a 4-hydroxybutyryl-phosphate pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; and 4-hydroxybutyrate kinase (see FIG. 1, steps G/H/I, A, C, O).

In a further aspect of the above embodiment, the method includes a microbial organism having a 4-hydroxybutyryl-phosphate pathway comprising a succinyl-CoA transferase, a succinyl-CoA hydrolase or a succinyl-CoA synthetase; a succinyl-CoA reductase (alcohol forming); and a 4-hydroxybutyrate kinase (see FIG. 1, steps G/H/I, S, O).

In a further aspect of the above embodiment, the method includes a microbial organism having a 4-hydroxybutyryl-phosphate pathway comprising a succinate reductase; a 4-hydroxybutyrate dehydrogenase; and a 4-hydroxybutyrate kinase (see FIG. 1, steps F, C, O).

In a further aspect of the above embodiment, the method includes a microbial organism having a 4-hydroxybutyryl-phosphate pathway comprising an alpha-ketoglutarate decarboxylase; a 4-hydroxybutyrate dehydrogenase; and a 4-hydroxybutyrate kinase (FIG. 1, steps B, C, O).

In a further aspect of the above embodiment, the method includes a microbial organism having a 4-hydroxybutyryl-phosphate pathway comprising a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; and a 4-hydroxybutyrate kinase (see FIG. 1, steps J/K, L, M/N, C, O).

In one embodiment, the invention provides a method for producing 14-BDO and GBL that includes culturing a non-naturally occurring microbial organism under conditions and for a sufficient period of time to produce 14-BDO and 4-hydroxybutyryl-phosphate followed by spontaneous lactonization of 4-hydroxybutyryl-phosphate to form GBL, wherein said non-naturally occurring microbial organism comprise a microbial organism having a 14-BDO pathway and a 4-hydroxybutyryl-phosphate pathway, said 14-BDO pathway comprising a first set of exogenous nucleic acids encoding 14-BDO pathway enzymes expressed in a sufficient amount to produce 14-BDO, said first set is selected from the group consisting of [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase] (see FIG. 1, steps G/H/I, A, C, D, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, A, C, O, P, Q, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps G/H/I, A, C, O, R, E); [a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, A, C, T/U/V, Q, E); [a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (FIG. 1, steps G/H/I, A, C, T/U/V, W); [a succinyl-CoA transferase, a succinyl-CoA hydrolase or a succinyl-CoA synthetase; a succinyl- CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps G/H/I, A, C, O, P, W); [a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase] (see FIG. 1, steps G/H/I, S, D, E); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, S, O, P, Q, E]; [a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase] (see FIG. 1, steps G/H/I, S, O, R, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, S, T/U/V, Q, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, S, T/U/V, W); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming)] (see FIG. 1, steps G/H/I, S, O, P, W); [a succinate reductase; a 4-hydroxybutyrate dehydrogenase; a 4-hydroxybutyrate reductase; and 1,4-butanediol dehydrogenase] (see FIG. 1, steps F, C, D, E); [a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps F, C, O, P, Q, E); [a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps F, C, O, P, W); [a succinate reductase; a 4-hydroxybutyrate dehydrogenase; a 4-hydroxybutyrate kinase; a 4-hydroxybutyryl-phosphate reductase; and 1,4-butanediol dehydrogenase] (see FIG. 1, steps F, C, O, R, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase] (see FIG. 1, steps F, C, T/U/V, Q, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps F, C, T/U/V, W); [an alpha-ketoglutarate decarboxylase; a 4-hydroxybutyrate dehydrogenase; a 4-hydroxybutyrate reductase; and 1,4-butanediol dehydrogenase] (see FIG. 1, steps B, C, D, E); [an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps B, C, O, P, Q, E); [an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming)] (see FIG. 1, steps B, C, O, P, W); [an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps B, C, O, R, E); [an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase] (see FIG. 1, steps B, C, T/U/V, Q, E); [an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming)] (see FIG. 1, steps B, C, T/U/V, W); [a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase] (see FIG. 1, steps J/K, L, M/N, C, D, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase] (see FIG. 1, steps J/K, L, M/N, C, O, P, Q, E); [a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps J/K, L, M/N, C, O, P, W); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps J/K, L, M/N, C, O, R, E] [Pathway 26: FIG. 1, steps J/K, L, M/N, C, O, R, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps J/K, L, M/N, C, T/U/V, Q, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps J/K, L, M/N, C, T/U/V, W); [an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase] (see FIG. 1, steps X, Y, AA, Q, E); [an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming)] (see FIG. 1, steps X, Y, AA, and W); and [an alpha-ketoglutarate reductase; a 5-hydroxy-2- oxopentanoate dehydrogenase; a 5-hydroxy-2-oxopentanoate decarboxylase; and a 1,4-butanediol dehydrogenase] (see FIG. 1, steps X, Y, Z, E), said 4-hydroxybutyryl-phosphate pathway comprising a second set of exogenous nucleic acids encoding 4-hydroxybutyryl-phosphate pathway enzymes expressed in a sufficient amount to produce 4-hydroxybutyryl-phosphate, said second set selected from the group consisting of [a succinyl-CoA transferase, a succinyl-CoA hydrolase or a succinyl-CoA synthetase; a succinyl-CoA reductase (aldehyde forming); a 4-hydroxybutyrate dehydrogenase; and 4-hydroxybutyrate kinase] (see FIG. 1, steps G/H/I, A, C, O); [a succinyl-CoA transferase, a succinyl-CoA hydrolase or a succinyl-CoA synthetase; a succinyl-CoA reductase (alcohol forming); and a 4-hydroxybutyrate kinase]; (see FIG. 1, steps G/H/I, S, O) [a succinate reductase; a 4-hydroxybutyrate dehydrogenase; and a 4-hydroxybutyrate kinase] (see FIG. 1, steps F, C, O); [an alpha-ketoglutarate decarboxylase; a 4-hydroxybutyrate dehydrogenase; and a 4-hydroxybutyrate kinase] (see FIG. 1, steps B, C, O); and [a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; and a 4-hydroxybutyrate kinase] (see FIG. 1, steps J/K, L, M/N, C, O).

In a further aspect of each of the above embodiments, the exogenous nucleic acid is a heterologous nucleic acid.

In a further aspect of each of the above embodiments, the conditions include substantially anaerobic culture conditions.

In a further aspect of each of the above embodiments, the 14-BDO and GBL products are produced at a predetermined ratio. In some aspects of the invention, the predetermined ratio of 14-BDO to GBL is 1:1, or alternatively 1:2, or alternatively 1:3, or alternatively 1:4, or alternatively 1:5, or alternatively 1:6, or alternatively 1:7, or alternatively 1:8, or alternatively 1:9, or alternatively 1:10, or alternatively 1:15, or alternatively about 1:20, or alternatively 1:25, or alternatively 1:30, or alternatively 1:35, or alternatively 1:40, or alternatively 1:45, or alternatively about 1:50, or alternatively 1:60, or alternatively 1:70, or alternatively 1:80, or alternatively 1:90, or alternatively 1:100. In some aspects of the invention, the predetermined ratio of 14-BDO to GBL is 2:1, or alternatively 3:1, or alternatively 4:1, or alternatively 5:1, or alternatively 6:1, or alternatively 7:1, or alternatively 8:1, or alternatively 9:1, or alternatively 10:1, or alternatively 15:1, or alternatively about 20:1, or alternatively 25:1, or alternatively 30:1, or alternatively 35:1, or alternatively 40:1, or alternatively 45:1, or alternatively about 50:1, or alternatively 60:1, or alternatively 70:1, or alternatively 80:1, or alternatively 90:1, or alternatively 100:1.

In one embodiment, the invention provides a method for producing 14-BDO and GBL that includes culturing a non-naturally occurring microbial organism under conditions and for a sufficient period of time to produce 14-BDO and 4-hydroxybutyryl-CoA followed by spontaneous lactonization of 4-hydroxybutyryl-phosphate to form GBL, wherein said non-naturally occurring microbial organism comprise a microbial organism having a 14-BDO pathway and a 4-hydroxybutyryl-CoA pathway, said 14-BDO pathway comprising at least one exogenous nucleic acid encoding a 14-BDO pathway enzyme expressed in a sufficient amount to produce 14-BDO, said 14-BDO pathway comprising a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase, a 4-hydroxybutyryl-CoA reductase (alcohol forming), an alpha-ketoglutarate reductase, a 5-hydroxy-2-oxopentanoate dehydrogenase, a 5-hydroxy-2-oxopentanoate decarboxylase or a 5-hydroxy-2-oxopentanoate dehydrogenase (decarboxylation), said 4-hydroxybutyryl-CoA pathway comprising at least one exogenous nucleic acid encoding an 4-hydroxybutyryl-CoA pathway enzyme expressed in a sufficient amount to produce 4-hydroxybutyryl-CoA, (see FIG. 1, steps A, B, C, D, E, F, G, H, I, J, K, L, M, N, O, P, Q, R, S, T, U, V, W, X, Y, Z, AA) said 4-hydroxybutyryl-CoA pathway comprising a succinyl-CoA reductase (aldehyde forming), an alpha-ketoglutarate decarboxylase, a 4-hydroxybutyrate dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, a 4-aminobutyrate dehydrogenase, a 4-aminobutyrate transaminase, a 4-hydroxybutyrate kinase, a phosphotrans-4-hydroxybutyrylase, a succinyl-CoA reductase (alcohol forming), a 4-hydroxybutyryl-CoA transferase, a 4-hydroxybutyryl-CoA hydrolase, a 4-hydroxybutyryl-CoA synthetase, an alpha-ketoglutarate reductase, a 5-hydroxy-2-oxopentanoate dehydrogenase, or a 5-hydroxy-2-oxopentanoate dehydrogenase (decarboxylation) (see FIG. 1, steps A, B, C, F, G, H, I, J, K, L, M, N, O, P, S, T, U, V, X, Y, AA).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase (see FIG. 1, steps G/H/I, A, C, D, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, A, C, O, P, Q, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase (see FIG. 1, steps G/H/I, A, C, O, R, E).

In a further aspect of the above embodiment, the method includes a microbial organism having a 14-BDO pathway comprising a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, A, C, T/U/V, Q, E).

In a further aspect of the above embodiment, the method includes a microbial organism having a 14-BDO pathway comprising a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, A, C, T/U/V, W).

In a further aspect of the above embodiment, the method includes a microbial organism having a 1,4-BDO pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps G/H/I, A, C, O, P, W).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase (see FIG. 1, steps G/H/I, S, D, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps G/H/I, S, O, P, Q, E).

In a further aspect of the above embodiment, the method includes a microbial organism having a 14-BDO pathway comprising a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase (see FIG. 1, steps G/H/I, S, O, R, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps G/H/I, S, T/U/V, Q, E).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps G/H/I, S, T/U/V, W).

In a further aspect of the above embodiment, the method includes a microbial organism having a 14-BDO pathway comprising a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming) (see FIG. 1, steps G/H/I, S, O, P, W).

In a further aspect of the above embodiment, the method includes a microbial organism having a 14-BDO pathway comprising a succinate reductase; a 4-hydroxybutyrate dehydrogenase; a 4-hydroxybutyrate reductase; and 1,4-butanediol dehydrogenase (see FIG. 1, steps F, C, D, E).

In a further aspect of the above embodiment, the method includes a microbial organism having a 14-BDO pathway comprising a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps F, C, O, P, Q, E).

In a further aspect of the above embodiment, the method includes a microbial organism having a 14-BDO pathway comprising a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps F, C, O, P, W).

In a further aspect of the above embodiment, the method includes a microbial organism having a 14-BDO pathway comprising a succinate reductase; a 4-hydroxybutyrate dehydrogenase; a 4-hydroxybutyrate kinase; a 4-hydroxybutyryl-phosphate reductase; and 1,4-butanediol dehydrogenase (see FIG. 1, steps F, C, O, R, E).

In a further aspect of the above embodiment, the method includes a microbial organism having a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase (see FIG. 1, steps F, C, T/U/V, Q, E).

In a further aspect of the above embodiment, the method includes a microbial organism having a 14-BDO pathway comprising a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps F, C, T/U/V, W).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate reductase; and 1,4-butanediol dehydrogenase (see FIG. 1, steps B, C, D, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase (see FIG. 1, steps B, C, O, P, Q, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming) (see FIG. 1, steps B, C, O, P, W).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps B, C, O, R, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase (see FIG. 1, steps B, C, T/U/V, Q, E).

In a further aspect of the above embodiment, the method includes a microbial organism having a 14-BDO pathway comprising an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming) (see FIG. 1, steps B, C, T/U/V, W).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase (see FIG. 1, steps J/K, L, M/N, C, D, E].

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase (see FIG. 1, steps J/K, L, M/N, C, O, P, Q, E).

In a further aspect of the above embodiment, the method includes a microbial organism having a 14-BDO pathway comprising a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming) (see FIG. 1, steps J/K, L, M/N, C, O, P, W)

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase (see FIG. 1, steps J/K, L, M/N, C, O, R, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase (see FIG. 1, steps J/K, L, M/N, C, T/U/V, Q, E).

In a further aspect of the above embodiment, the method includes a microbial organism having a 14-BDO pathway comprising a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming) (see FIG. 1, steps J/K, L, M/N, C, T/U/V, W).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase (see FIG. 1, steps X, Y, AA, Q, E).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming) (see FIG. 1, steps X, Y, AA, and W).

In a further aspect of the above embodiment, the method includes a microbial organism having a 14-BDO pathway comprising an alpha-ketoglutarate reductase; a 5-hydroxy-2-oxopentanoate dehydrogenase; a 5-hydroxy-2-oxopentanoate decarboxylase; and a 1,4-butanediol dehydrogenase (see FIG. 1, steps X, Y, Z, E).

In a further aspect of the above embodiment, the method includes a microbial organism having a 14-BDO pathway comprising comprises a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; and a phosphotrans-4-hydroxybutyrylase (see FIG. 1, steps G/H/I, A, C, O, P).

In a further aspect of the above embodiment, the method includes a microbial organism having a 4-hydroxybutyryl-CoA pathway comprising a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyryl-CoA transferase, a 4-hydroxybutyryl-CoA hydrolase or a 4-hydroxybutyryl-CoA synthetase (see FIG. 1, steps G/H/I, A, C, T/U/V).

In a further aspect of the above embodiment, the method includes a microbial organism having a 4-hydroxybutyryl-CoA pathway comprising a succinyl-CoA transferase, a succinyl-CoA hydrolase or a succinyl-CoA synthetase; a succinyl-CoA reductase (alcohol forming); a 4-hydroxybutyrate kinase; and a phosphotrans-4-hydroxybutyrylase (see FIG. 1, steps G/H/I, S, O, P).

In a further aspect of the above embodiment, the method includes a microbial organism having a 4-hydroxybutyryl-CoA pathway comprising a succinyl-CoA transferase, a succinyl-CoA hydrolase or a succinyl-CoA synthetase; a succinyl-CoA reductase (alcohol forming); and a 4-hydroxybutyryl-CoA transferase, a 4-hydroxybutyryl-CoA hydrolase or a 4-hydroxybutyryl-CoA synthetase (see FIG. 1, steps G/H/I, S, T/U/V).

In a further aspect of the above embodiment, the method includes a microbial organism having a 4-hydroxybutyryl-CoA pathway comprising a succinate reductase; a 4-hydroxybutyrate dehydrogenase; a 4-hydroxybutyrate kinase and a phosphotrans-4-hydroxybutyrylase (see FIG. 1, steps F, C, O, P).

In a further aspect of the above embodiment, the method includes a microbial organism having a 4-hydroxybutyryl-CoA pathway comprising a succinate reductase; a 4-hydroxybutyrate dehydrogenase; and a 4-hydroxybutyryl-CoA transferase, a 4-hydroxybutyryl-CoA hydrolase or a 4-hydroxybutyryl-CoA synthetase (see FIG. 1, steps F, C, T/U/V).

In a further aspect of the above embodiment, the method includes a microbial organism having a 4-hydroxybutyryl-CoA pathway comprising an alpha-ketoglutarate decarboxylase; a 4-hydroxybutyrate dehydrogenase; a 4-hydroxybutyrate kinase; and a phosphotrans-4-hydroxybutyrylase (see FIG. 1, steps B, C, O, P).

In a further aspect of the above embodiment, the method includes a microbial organism having a 4-hydroxybutyryl-CoA pathway comprising an alpha-ketoglutarate decarboxylase; a 4-hydroxybutyrate dehydrogenase; and a 4-hydroxybutyryl-CoA transferase, a 4-hydroxybutyryl-CoA hydrolase or a 4-hydroxybutyryl-CoA synthetase (see FIG. 1, steps B, C, T/U/V).

In a further aspect of the above embodiment, the method includes a microbial organism having a 4-hydroxybutyryl-CoA pathway comprising a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; a 4-hydroxybutyrate kinase; and a phosphotrans-4-hydroxybutyrylase (see FIG. 1, steps J/K, L, M/N, C, O, P).

In a further aspect of the above embodiment, the method includes a microbial organism having a 4-hydroxybutyryl-CoA pathway comprising a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; and a 4-hydroxybutyryl-CoA transferase, a 4-hydroxybutyryl-CoA hydrolase or a 4-hydroxybutyryl-CoA synthetase (see FIG. 1, steps J/K, L, M/N, C, T/U/V).

In a further aspect of the above embodiment, the method includes a microbial organism having a 4-hydroxybutyryl-CoA pathway comprising an alpha-ketoglutarate reductase; a 5-hydroxy-2-oxopentanoate dehydrogenase and a 5-hydroxy-2-oxopentanoate dehydrogenase (decarboxylation) (see FIG. 1, steps X, Y, AA).

In one embodiment, the invention provides a method for producing 14-BDO and GBL that includes culturing a non-naturally occurring microbial organism under conditions and for a sufficient period of time to produce 14-BDO and 4-hydroxybutyryl-CoA followed by spontaneous lactonization of 4-hydroxybutyryl-phosphate to form GBL, wherein said non-naturally occurring microbial organism comprise a microbial organism having a 14-BDO pathway and a 4-hydroxybutyryl-CoA pathway, said 14-BDO pathway comprising a first set of exogenous nucleic acids encoding 14-BDO pathway enzymes expressed in a sufficient amount to produce 14-BDO, said first set is selected from the group consisting of [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase] (see FIG. 1, steps G/H/I, A, C, D, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, A, C, O, P, Q, E); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps G/H/I, A, C, O, R, E); [a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, A, C, T/U/V, Q, E); [a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, A, C, T/U/V, W); [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps G/H/I, A, C, O, P, W); [a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase] (see FIG. 1, steps G/H/I, S, D, E); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps G/H/I, S, O, P, Q, E); [a succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase] (see FIG. 1, steps G/H/I, S, O, R, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps G/H/I, S, T/U/V, Q, E); [a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps G/H/I, S, T/U/V, W); [a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (alcohol forming)] (see FIG. 1, steps G/H/I, S, O, P, W); [a succinate reductase; a 4-hydroxybutyrate dehydrogenase; a 4-hydroxybutyrate reductase; and 1,4-butanediol dehydrogenase] (see FIG. 1, steps F, C, D, E); [a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps F, C, O, P, Q, E); [a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps F, C, O, P, W); [a succinate reductase; a 4-hydroxybutyrate dehydrogenase; a 4-hydroxybutyrate kinase; a 4-hydroxybutyryl-phosphate reductase; and 1,4-butanediol dehydrogenase] (see FIG. 1, steps F, C, O, R, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase] (see FIG. 1, steps F, C, T/U/V, Q, E); [a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps F, C, T/U/V, W); [an alpha-ketoglutarate decarboxylase; a 4-hydroxybutyrate dehydrogenase; a 4-hydroxybutyrate reductase; and 1,4-butanediol dehydrogenase] (see FIG. 1, steps B, C, D, E); [an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase] (see FIG. 1, steps B, C, O, P, Q, E); [an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming)] (see FIG. 1, steps B, C, O, P, W); [an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps B, C, O, R, E); [an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase] (see FIG. 1, steps B, C, T/U/V, Q, E]; [an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming)] (see FIG. 1, steps B, C, T/U/V, W); [a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase] (see FIG. 1, steps J/K, L, M/N, C, D, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and E) 1,4-butanediol dehydrogenase] (see FIG. 1, steps J/K, L, M/N, C, O, P, Q, E); [a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming)] (see FIG. 1, steps J/K, L, M/N, C, O, P, W); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase] (see FIG. 1, steps J/K, L, M/N, C, O, R, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase] (see FIG. 1, steps J/K, L, M/N, C, T/U/V, Q, E); [a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming)] (see FIG. 1, steps J/K, L, M/N, C, T/U/V, W); [an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase] (see FIG. 1, steps X, Y, AA, Q, E); [an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming)] (see FIG. 1, steps X, Y, AA, and W); and [an alpha-ketoglutarate reductase; a 5-hydroxy-2-oxopentanoate dehydrogenase; a 5-hydroxy-2-oxopentanoate decarboxylase; and a 1,4-butanediol dehydrogenase] (see FIG. 1, steps X, Y, Z, E), said 4-hydroxybutyryl-CoA pathway comprising a second set of exogenous nucleic acids encoding 4-hydroxybutyryl-CoA pathway enzymes expressed in a sufficient amount to produce 4-hydroxybutyryl-CoA, said second set selected from the group consisting of [a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; and a phosphotrans-4-hydroxybutyrylase] (see FIG. 1, steps G/H/I, A, C, O, P); [a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyryl-CoA transferase, a 4-hydroxybutyryl-CoA hydrolase or a 4-hydroxybutyryl-CoA synthetase] (see FIG. 1, steps G/H/I, A, C, T/U/V); [a succinyl-CoA transferase, a succinyl-CoA hydrolase or a succinyl-CoA synthetase; a succinyl-CoA reductase (alcohol forming); a 4-hydroxybutyrate kinase; and a phosphotrans-4-hydroxybutyrylase] (see FIG. 1, steps G/H/I, S, O, P); [a succinyl-CoA transferase, a succinyl-CoA hydrolase or a succinyl-CoA synthetase; a succinyl-CoA reductase (alcohol forming); and a 4-hydroxybutyryl-CoA transferase, a 4-hydroxybutyryl-CoA hydrolase or a 4-hydroxybutyryl-CoA synthetase] (see FIG. 1, steps G/H/I, S, T/U/V); [a succinate reductase; a 4-hydroxybutyrate dehydrogenase; a 4-hydroxybutyrate kinase and a phosphotrans-4-hydroxybutyrylase] (see FIG. 1, steps F, C, O, P); [a succinate reductase; a 4-hydroxybutyrate dehydrogenase; and a 4-hydroxybutyryl-CoA transferase, a 4-hydroxybutyryl-CoA hydrolase or a 4-hydroxybutyryl-CoA synthetase] (see FIG. 1, steps F, C, T/U/V); [an alpha-ketoglutarate decarboxylase; a 4-hydroxybutyrate dehydrogenase; a 4-hydroxybutyrate kinase; and a phosphotrans-4-hydroxybutyrylase] (see FIG. 1, steps B, C, O, P); [an alpha-ketoglutarate decarboxylase; a 4-hydroxybutyrate dehydrogenase; and a 4-hydroxybutyryl-CoA transferase, a 4-hydroxybutyryl-CoA hydrolase or a 4-hydroxybutyryl-CoA synthetase] (see FIG. 1, steps B, C, T/U/V); [a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; a 4-hydroxybutyrate kinase; and a phosphotrans-4-hydroxybutyrylase] (see FIG. 1, steps J/K, L, M/N, C, O, P); [a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; and a 4-hydroxybutyryl-CoA transferase, a 4-hydroxybutyryl-CoA hydrolase or a 4-hydroxybutyryl-CoA synthetase] (see FIG. 1, steps J/K, L, M/N, C, T/U/V); and [an alpha-ketoglutarate reductase; a 5-hydroxy-2-oxopentanoate dehydrogenase and a 5-hydroxy-2-oxopentanoate dehydrogenase (decarboxylation)] (see FIG. 1, steps X, Y, AA).

In a further aspect of each of the above embodiments, the exogenous nucleic acid is a heterologous nucleic acid.

In a further aspect of each of the above embodiments, the conditions include substantially anaerobic culture conditions.

In a further aspect of each of the above embodiments, the 14-BDO and GBL products are produced at a predetermined ratio. In some aspects of the invention, the predetermined ratio of 14-BDO to GBL is 1:1, or alternatively 1:2, or alternatively 1:3, or alternatively 1:4, or alternatively 1:5, or alternatively 1:6, or alternatively 1:7, or alternatively 1:8, or alternatively 1:9, or alternatively 1:10, or alternatively 1:15, or alternatively about 1:20, or alternatively 1:25, or alternatively 1:30, or alternatively 1:35, or alternatively 1:40, or alternatively 1:45, or alternatively about 1:50, or alternatively 1:60, or alternatively 1:70, or alternatively 1:80, or alternatively 1:90, or alternatively 1:100. In some aspects of the invention, the predetermined ratio of 14-BDO to GBL is 2:1, or alternatively 3:1, or alternatively 4:1, or alternatively 5:1, or alternatively 6:1, or alternatively 7:1, or alternatively 8:1, or alternatively 9:1, or alternatively 10:1, or alternatively 15:1, or alternatively about 20:1, or alternatively 25:1, or alternatively 30:1, or alternatively 35:1, or alternatively 40:1, or alternatively 45:1, or alternatively about 50:1, or alternatively 60:1, or alternatively 70:1, or alternatively 80:1, or alternatively 90:1, or alternatively 100:1.

In one embodiment, the invention provides a method for producing 14-BDO and GBL that includes culturing a non-naturally occurring microbial organism under conditions and for a sufficient period of time to produce 14-BDO and 4-hydroxybutyryl-phosphate followed by spontaneous lactonization of 4-hydroxybutyryl-phosphate to form GBL, wherein said non-naturally occurring microbial organism comprise a microbial organism having a 14-BDO pathway and a 4-hydroxybutyryl-phosphate pathway, said 14-BDO pathway comprising at least one exogenous nucleic acid encoding a 14-BDO pathway enzyme expressed in a sufficient amount to produce 14-BDO, wherein the 14-BDO pathway comprises an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and said 4-hydroxybutyryl-phosphate pathway comprising at least one exogenous nucleic acid encoding an 4-hydroxybutyryl-phosphate pathway enzyme expressed in a sufficient amount to produce 4-hydroxybutyryl-phosphate (see steps B, C, T/U/V, Q, E), said 4-hydroxybutyryl-phosphate pathway comprising an alpha-ketoglutarate decarboxylase; a 4-hydroxybutyrate dehydrogenase; and a 4-hydroxybutyrate kinase [see steps B, C, O).

In a further aspect of the above embodiment, the non-naturally occurring microbial organism does not comprise an exogenous nucleic acid encoding a phosphotrans-4-hydroxybutyrylase. In on aspect, the microbial organism comprises a gene disruption in a gene encoding a phosphotrans-4-hydroxybutyrylase, wherein the gene disruption confers production of a predetermined ratio of 14-BDO to GBL. In some aspects of the invention, the predetermined ratio is 1:1, or alternatively 1:2, or alternatively 1:3, or alternatively 1:4, or alternatively 1:5, or alternatively 1:6, or alternatively 1:7, or alternatively 1:8, or alternatively 1:9, or alternatively 1:10, or alternatively 1:15, or alternatively about 1:20, or alternatively 1:25, or alternatively 1:30, or alternatively 1:35, or alternatively 1:40, or alternatively 1:45, or alternatively about 1:50, or alternatively 1:60, or alternatively 1:70, or alternatively 1:80, or alternatively 1:90, or alternatively 1:100. In some aspects of the invention, the predetermined ratio of 14-BDO to GBL is 2:1, or alternatively 3:1, or alternatively 4:1, or alternatively 5:1, or alternatively 6:1, or alternatively 7:1, or alternatively 8:1, or alternatively 9:1, or alternatively 10:1, or alternatively 15:1, or alternatively about 20:1, or alternatively 25:1, or alternatively 30:1, or alternatively 35:1, or alternatively 40:1, or alternatively 45:1, or alternatively about 50:1, or alternatively 60:1, or alternatively 70:1, or alternatively 80:1, or alternatively 90:1, or alternatively 100:1.

In a further aspect of the above embodiment, the exogenous nucleic acid is a heterologous nucleic acid.

In a further aspect of the above embodiment, the conditions include substantially anaerobic culture conditions.

Embodiments described herein include the down stream compound that can be produced from the 14-BDO and GBL producing non-naturally occurring microbial organisms of the invention, for example, 14-BDO. This compound can be synthesized by, for example, chemical hydrogenation of GBL. Chemical hydrogenation reactions are well known in the art. One exemplary procedure includes the chemical reduction of GBL or a mixture of GBL and 14-BDO deriving from the culture using a heterogeneous or homogeneous hydrogenation catalyst together with hydrogen, or a hydride-based reducing agent used stoichiometrically or catalytically, to produce 14-BDO.

Other procedures well known in the art are equally applicable for the above chemical reaction and include, for example, WO No. 82/03854 (Bradley, et al.), which describes the hydrogenolysis of gamma-butyrolactone in the vapor phase over a copper oxide and zinc oxide catalyst. British Pat. No. 1,230,276, which describes the hydrogenation of gamma-butyrolactone using a copper oxide-chromium oxide catalyst. The hydrogenation is carried out in the liquid phase. Batch reactions also are exemplified having high total reactor pressures. Reactant and product partial pressures in the reactors are well above the respective dew points. British Pat. No. 1,314,126, which describes the hydrogenation of gamma-butyrolactone in the liquid phase over a nickel-cobalt-thorium oxide catalyst. Batch reactions are exemplified as having high total pressures and component partial pressures well above respective component dew points. British Pat. No. 1,344,557, which describes the hydrogenation of gamma-butyrolactone in the liquid phase over a copper oxide-chromium oxide catalyst. A vapor phase or vapor-containing mixed phase is indicated as suitable in some instances. A continuous flow tubular reactor is exemplified using high total reactor pressures. British Pat. No. 1,512,751, which describes the hydrogenation of gamma-butyrolactone to 1,4-butanediol in the liquid phase over a copper oxide-chromium oxide catalyst. Batch reactions are exemplified with high total reactor pressures and, where determinable, reactant and product partial pressures well above the respective dew points. U.S. Pat. No. 4,301,077, which describes the hydrogenation to 1,4-butanediol of gamma-butyrolactone over a Ru—Ni—Co—Zn catalyst. The reaction can be conducted in the liquid or gas phase or in a mixed liquid-gas phase. Exemplified are continuous flow liquid phase reactions at high total reactor pressures and relatively low reactor productivities. U.S. Pat. No. 4,048,196, which describes the production of 1,4-butanediol by the liquid phase hydrogenation of gamma-butyrolactone over a copper oxide-zinc oxide catalyst. Further exemplified is a continuous flow tubular reactor operating at high total reactor pressures and high reactant and product partial pressures. And U.S. Pat. No. 4,652,685, which describes the hydrogenation of lactones to glycols.

Suitable purification and/or assays to test for the production of 14-BDO and GBL can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The 14-BDO and GBL products can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

The 14-BDO and GBL can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the 14-BDO and GBL producers can be cultured for the biosynthetic production of 14-BDO and GBL.

For the production of 14-BDO and GBL, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 14-BDO and GBL.

In addition to renewable feedstocks such as those exemplified above, the 14-BDO and GBL microbial organisms of the invention also can be modified for growth on syngas as its source of carbon. In this specific embodiment, one or more proteins or enzymes are expressed in the 14-BDO and GBL producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

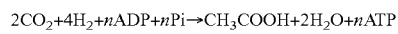

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a 14-BDO and GBL pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle is and/or hydrogenase activities can also be used for the conversion of CO, $CO_2$ and/or H2 to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or H2 by carbon monoxide dehydrogenase and hydrogenase are utilized to fix CO2 via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the 14-BDO or GBL precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a 14,BDO or GBL pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 14-BDO, GBL and any of the intermediate metabolites in the 14-BDO or GBL pathway. All that is required is to engineer in one or more of the required enzyme or protein activities to achieve biosynthesis of the desired compound or intermediate including, for example, inclusion of some or all of the 14-BDO and GBL biosynthetic pathways. Accordingly, the invention provides a non-naturally occurring microbial organism that produces and/or secretes 14-BDO and GBL when grown on a carbohydrate or other carbon source and produces and/or secretes any of the intermediate metabolites shown in the 14-BDO or GBL pathway when grown on a carbohydrate or other carbon source. The 14-BDO and GBL producing microbial organisms of the invention can initiate synthesis from an intermediate, for example, a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase (or succinyl-CoA ligase), a glutamate dehydrogenase, a glutamate transaminase, a glutamate decarboxylase, a 4-aminobutyrate dehydrogenase, a 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase (or 4-hydroxybutyryl-CoA ligase), a 4-hydroxybutyryl-CoA reductase (alcohol forming), an alpha-ketoglutarate reductase, a 5-hydroxy-2-oxopentanoate dehydrogenase, a 5-hydroxy-2-oxopentanoate decarboxylase, a 5-hydroxy-2-oxopentanoate dehydrogenase (decarboxylation) or a 4-hydroxybutyrate lactonase.

The non-naturally occurring microbial organisms of the invention are constructed using methods well known in the art as exemplified herein to exogenously express at least one nucleic acid encoding a 14-BDO and GBL pathway enzyme or protein in sufficient amounts to produce 14-BDO and GBL. It is understood that the microbial organisms of the invention are cultured under conditions sufficient to produce 14-BDO and GBL. Following the teachings and guidance provided herein, the non-naturally occurring microbial organisms of the invention can achieve biosynthesis of 14-BDO and GBL resulting in intracellular concentrations between about 0.1-200 mM or more. Generally, the intracellular concentration of 14-BDO and GBL is between about 0.01-1000 mM, particularly 3-150 mM, more particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the 14-BDO and GBL producers can synthesize 14-BDO and GBL at intracellular concentrations of 5-10 mM or more as well as all other concentrations exemplified herein. It is understood that, even though the above description refers to intracellular concentrations, 14-BDO and GBL producing microbial organisms can produce 14-BDO and GBL intracellularly and/or secrete the products into the culture medium.

In addition to the culturing and fermentation conditions disclosed herein, growth condition for achieving biosynthesis of 14-BDO and GBL can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 14-BDO and GBL includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 14-BDO and GBL. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 14-BDO and GBL. Generally, and as with non-continuous culture procedures, the continuous and/or near-continuous production of 14-BDO and GBL will include culturing a non-naturally occurring 14-BDO and GBL producing organism of the invention in sufficient nutrients and medium to sustain and/or nearly sustain growth in an exponential phase. Continuous culture under such conditions can be include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 14-BDO and GBL can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 14-BDO and GBL producers of the invention for continuous production of substantial quantities of 14-BDO and GBL, the 14-BDO and GBL producers also can be, for example, simultaneously subjected to chemical synthesis procedures to convert the product to other compounds or the product can be separated from the fermentation culture and sequentially subjected to chemical conversion to convert the product to other compounds, if desired.

In addition to the above fermentation procedures using the 14-BDO and GBL producers of the invention for continuous production of substantial quantities of 14-BDO and GBL, 14-BDO and 4-hydroxybutyryl-phosphate producers or 14-BDO and 4-hydroxybutyryl-CoA producers also can be, for example, simultaneously subjected to spontaneous lactonization procedures to convert the products 4-hydroxybutyryl-phosphate or 4-hydroxybutyryl-CoA to GBL as described herein. In some aspects, the spontaneous lactonization of 4-hydroxybutyryl-phosphate or 4-hydroxybutyryl-CoA to form GBL can occur intracellularly. Alternatively, if the products 4-hydroxybutyryl-phosphate or 4-hydroxybutyryl-CoA are secreted, the spontaneous lactonization of these products can occur extracellularly.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 14-BDO and GBL.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures.

The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a 14-BDO or GBL pathway can be introduced into a host organism. In some cases, it can be desirable to modify an activity of a 14-BDO or GBL pathway enzyme or protein to increase production of 14-BDO and GBL. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($k_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a 14-BDO or GBL pathway enzyme or protein. Such methods include, but are not limited to EpPCR, which introduces random point mutations by reducing the fidelity of DNA polymerase in PCR reactions (Pritchard et al., *J. Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol.* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE I

Pathways for Co-Production of 14-BDO and GBL from Succinate and Alpha-Ketoclutarate The 14-BDO and GBL coproduction pathways are exemplified in FIG. 1. As shown in FIG. 1A, central metabolism intermediates can be first channeled into alpha-ketoglutarate or succinate through the oxidative and/or the reductive branches of the TCA cycle. Alpha-ketoglutarate or succinate can then be converted to 4-hydroxybutyrate (4-HB) through different routes. When starting from alpha-ketoglutarate, it can be converted to succinic semialdehyde through a single transformation (Step B in FIG. 1A) or multiple-step conversions (Steps J or K plus Step L plus Steps M or N in FIG. 1B), and then succinic semialdehyde can be converted to 4-HB through Step C. When starting from succinate, it can be converted to succinyl-CoA (Steps G or H or I) then to succinic semialdehyde (Step A) then further to 4-HB (Step C). Alternatively, succinate can be directly converted to succinic semialdehyde (Step F) or succinyl-CoA can be directly converted to 4-HB (Step S).

4-HB is an important intermediate for both 14-BDO and GBL production. For 14-BDO production, 4-HB can be converted to 4-hydroxybutyrul-phosphate (Step O) then to 4-hydroxybutyryl-CoA (Step P) then to 4-hydroxybutanal (Step Q) and finally to 14-BDO (Step E). There are several possible alternative routes for the conversion from 4-HB to 14-BDO, such as the direct conversions from 4-HB to 4-hydroxybutanal (Step D), or from 4-hydroxybutyryl-phosphate to 4-hydroxylbutanal (Step R), or from 4-HB to 4-hydrobutyryl-CoA (Steps T or U or V), or from 4-hydrobutyryl-CoA to 14-BDO (Step W). Additionally, alpha-ketoglutarate can be converted to 2,5-dioxopentanoic acid (Step X), then to 5-hydroxy-2-oxopentanoic acid (Step Y), then further to 14-BDO (Step Z). An alternative route for this pathway will transform 5-hydroxy-2-oxopentanoic acid to 4-hydroxybutyryl-CoA (Step AA) that will be further converted to 14-BDO as described herein.

For GBL production, 4-HB can be directly converted to GBL through Step AB, or both 4-hydroxybutyryl-phosphate and 4-hydroxybutyryl-CoA can be converted to GBL by non-enzymatic transformations (Step AC and Step AD).

Under anaerobic growth conditions, the production of 14-BDO and GBL using the above describe pathways can be redox-balanced. The coproduction strain can produce both 14-BDO and GBL at different ratios based on the activities of pathways for 14-BDO and GBL, which can be adjust using metabolic engineering techniques. Therefore, the ratios of 14-BDO and GBL can be modified in engineered coproduction strains. The maximum theoretical yields of 14-BDO and GBL in a coproduction strain can be found based on the following equation:

$$\text{Glucose} \rightarrow 1.09a\,14\text{-BDO} + 1.33b\,\text{GBL} + (1.64a + 0.67b)\,CO_2 + (0.55a + 2b)H_2O$$

where a is the molar percentage of glucose converted to 14-BDO, and b is the percentage of glucose converted to GBL, and a+b=100%

For example, if 90% glucose is converted to 14-BDO and 10% glucose is converted to GBL, the maximum theoretical yields, in a coproduction strain, will be 0.981 moles 14-BDO and 0.133 moles GBL per mole glucose consumed. In another example, if 70% glucose is converted to 14-BDO and 30% glucose is converted to GBL, the maximum theoretical yields, in a coproduction strain, will be 0.763 moles 14-BDO and 0.4 moles GBL per mole glucose consumed.

For 14-BDO and GBL coproduction, all routes can lead to high theoretical yields for combined 14-BDO and GBL assuming glucose as the carbon source. Similar high theoretical yields can be obtained from additional substrates including sucrose, xylose, arabinose, synthesis gas, among many others.

EXAMPLE II

Enzyme Classification System for Co-Production of 14-BDO and GBL

This example describes the enzyme classification system for the exemplary pathways described in Example I for production of 1,4-butanediol (14-BDO) and gamma-butyrolactone (GBL). All transformations depicted in FIGS. 1A and 1B fall into the general categories of transformations shown in Table 5. Below is described a number of biochemically characterized genes in each category. Specifically listed are genes that can be applied to catalyze the appropriate transformations in FIGS. 1A and 1B when properly cloned and expressed.

Table 5 shows the enzyme types useful to convert common central metabolic intermediates into 14-BDO and GBL. The first three digits of each label correspond to the first three Enzyme Commission number digits which denote the general type of transformation independent of substrate specificity.

TABLE 5

Classes of Enzyme Transformations Depicted in FIG. 1

| LABEL | FUNCTION |
|---|---|
| 1.1.1.a | Oxidoreductase (oxo to alcohol) |
| 1.1.1.c | Oxidoreductase (2 step, acyl-CoA to alcohol) |
| 1.2.1.b | Oxidoreductase (acyl-CoA to aldehyde) |
| 1.2.1.c | Oxidoreductase (2-oxo acid to acyl-CoA, decarboxylation) |
| 1.2.1.d | Oxidoreductase (phosphonate reductase) |
| 1.2.1.e | Acid reductase |
| 1.4.1.a | Oxidoreductase (aminating) |
| 2.3.1.a | Acyltransferase (transferring phosphate group to CoA) |
| 2.6.1.a | Aminotransferase |
| 2.7.2.a | Phosphotransferase (carboxy acceptor) |
| 2.8.3.a | CoA transferase |

TABLE 5-continued

Classes of Enzyme Transformations Depicted in FIG. 1

| LABEL | FUNCTION |
|---|---|
| 3.1.1.a | Hydroxyacylhydrolase |
| 3.1.2.a | CoA hydrolase |
| 4.1.1.a | Carboxy-lyase |
| 6.2.1.a | CoA synthetase |

1.1.1.a Oxidoreductase (Oxo to Alcohol)

Aldehyde to alcohol. Three transformations described in FIG. 1 involve the conversion of an aldehyde to alcohol. These are 4-hydroxybutyrate dehydrogenase (Step C), 1,4-butanediol dehydrogenase (Step E), and 5-hydroxy-2-oxopentanoate dehydrogenase (Step Y). Exemplary genes encoding enzymes that catalyze the conversion of an aldehyde to alcohol, that is, alcohol dehydrogenase or equivalently aldehyde reductase, include alrA encoding a medium-chain alcohol dehydrogenase for C2-C14 (Tani et al. *Appl. Environ. Microbiol.* 66:5231-5235 (2000)), ADH2 from *Saccharomyces cerevisiae* (Atsumi et al. *Nature* 451:86-89 (2008)), yqhD from *E. coli* which has preference for molecules longer than C3 (Sulzenbacher et al. *Journal of Molecular Biology* 342:489-502 (2004)), and bdh I and bdh II from *C. acetobutylicum* which converts butyrylaldehyde into butanol (Walter et al. *Journal of Bacteriology* 174:7149-7158 (1992)). The protein sequences for each of these exemplary gene products, if available, can be found using the following GenBank accession numbers shown in Table 6.

TABLE 6

| Gene | Accession No. | GI No. | Organism |
|---|---|---|---|
| alrA | BAB12273.1 | 9967138 | *Acinetobacter* sp. Strain M-1 |
| ADH2 | NP_014032.1 | 6323961 | *Saccharymyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |

Enzymes exhibiting 4-hydroxybutyrate dehydrogenase activity (EC 1.1.1.61) also fall into this category. Such enzymes have been characterized in *Ralstonia eutropha* (Bravo et al. *J. Forensic Sci.* 49:379-387 (2004), *Clostridium kluyveri* (Wolff et al. *Protein Expr. Purif.* 6:206-212 (1995)) and *Arabidopsis thaliana* (Breitkreuz et al. *J. Biol. Chem.* 278:41552-41556 (2003)). The protein sequences for each of these exemplary gene products, if available, can be found using the following GenBank accession numbers shown in Table 7.

TABLE 7

| Gene | Accession No. | GI No. | Organism |
|---|---|---|---|
| 4hbd | YP_726053.1 | 113867564 | *Ralstonia eutropha* H16 |
| 4hbd | EDK35022.1 | 146348486 | *Clostridium kluyveri* DSM 555 |
| 4hbd | Q94B07 | 75249805 | *Arabidopsis thaliana* |

The adh1 gene from *Geobacillus thermoglucosidasius* M10EXG (Jeon et al., *J Biotechnol* 135:127-133 (2008)) was shown to exhibit high activity on both 4-hydroxybutanal and butanal as shown in Example VIII. Thus this enzyme exhibits 1,4-butanediol dehydrogenase activity. The protein sequence for the exemplary gene product, if available, can be found using the following GenBank accession numbers shown in Table 8.

TABLE 8

| Gene | Accession No. | GI No. | Organism |
| --- | --- | --- | --- |
| adh1 | AAR91477.1 | 40795502 | Geobacillus thermoglucosidasius M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al. *J Mol Biol* 352:905-17 (2005)). The reversibility of the human 3-hydroxyisobutyrate dehydrogenase was demonstrated using isotopically-labeled substrate (Manning et al. *Biochem J* 231:481-484 (1985)). Additional genes encoding this enzyme include 3hidh in *Homo sapiens* (Hawes et al. *Methods Enzymol.* 324:218-228 (2000)) and *Oryctolagus cuniculus* (Chowdhury et al. *Biosci. Biotechnol Biochem.* 60:2043-2047 (1996); Hawes et al. *Methods Enzymol.* 324:218-228 (2000)), mmsb in *Pseudomonas aeruginosa*, and dhat in *Pseudomonas putida* (Aberhart et al. *J Chem. Soc. [Perkin 1]* 6:1404-1406 (1979); Chowdhury et al. *Biosci. Biotechnol Biochem.* 67:438-441 (2003); Chowdhury et al. *Biosci. Biotechnol Biochem.* 60:2043-2047 (1996)). The protein sequences for each of these exemplary gene products, if available, can be found using the following GenBank accession numbers shown in Table 9.

TABLE 9

| Gene | Accession No. | GI No. | Organism |
| --- | --- | --- | --- |
| P84067 | P84067 | 75345323 | Thermus thermophilus |
| mmsb | P28811.1 | 127211 | Pseudomonas aeruginosa |
| dhat | Q59477.1 | 2842618 | Pseudomonas putida |
| 3hidh | P31937.2 | 12643395 | Homo sapiens |
| 3hidh | P32185.1 | 416872 | Oryctolagus cuniculus |

Several 3-hydroxyisobutyrate dehydrogenase enzymes have also been shown to convert malonic semialdehyde to 3-hydroxyproprionic acid (3-HP). Three gene candidates exhibiting this activity are mmsB from *Pseudomonas aeruginosa* PAO1 (62), mmsB from *Pseudomonas putida* KT2440 (Liao et al., US Publication 2005/0221466) and mmsB from *Pseudomonas putida* E23 (Chowdhury et al., *Biosci. Biotechnol. Biochem.* 60:2043-2047 (1996)). An enzyme with 3-hydroxybutyrate dehydrogenase activity in *Alcaligenes faecalis* M3A has also been identified (Gokam et al., U.S. Pat. No. 7,393,676; Liao et al., US Publication No. 2005/0221466). Additional gene candidates from other organisms including *Rhodobacter spaeroides* can be inferred by sequence similarity. The protein sequences for each of these exemplary gene products, if available, can be found using the following GenBank accession numbers shown in Table 10.

TABLE 10

| Gene | Accession No. | GI No. | Organism |
| --- | --- | --- | --- |
| mmsB | AAA25892.1 | 151363 | Pseudomonas aeruginosa |
| mmsB | NP_252259.1 | 15598765 | Pseudomonas aeruginosa PAO1 |
| mmsB | NP_746775.1 | 26991350 | Pseudomonas putida KT2440 |
| mmsB | JC7926 | 60729613 | Pseudomonas putida E23 |
| orfB1 | AAL26884 | 16588720 | Rhodobacter spaeroides |

The conversion of malonic semialdehyde to 3-HP can also be accomplished by two other enzymes: NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi, B. *Journal of Plant Pathology* 159:671-674 (2002); Stadtman, E. R. *J. Am. Chem. Soc.* 77:5765-5766 (1955)). This enzyme has not been associated with a gene in any organism to date. NADPH-dependent malonate semialdehyde reductase catalyzes the reverse reaction in autotrophic $CO_2$-fixing bacteria. Although the enzyme activity has been detected in *Metallosphaera sedula*, the identity of the gene is not known (Alber et al. *J. Bacteriol.* 188:8551-8559 (2006)).

1.1.1.c Oxidoreductase (2 Step, Acyl-CoA to Alcohol)

Steps S and W of FIG. 1 depict bifunctional reductase enzymes that can form 4-hydroxybutyrate and 1,4-butanediol from succinyl-CoA and 4-hydroxybutyryl-CoA, respectively. Exemplary 2-step oxidoreductases that convert an acyl-CoA to alcohol include those that transform substrates such as acetyl-CoA to ethanol (for example, adhE from *E. coli* (Kessler et al. FEBS. Lett. 281:59-63 (1991)) and butyryl-CoA to butanol (for example, adhE2 from *C. acetobutylicum* (Fontaine et al. J. Bacteriol. 184:821-830 (2002)). The *C. acetobutylicum* adhE2 gene was shown to convert 4-hydroxybutyryl-CoA to 1,4-butanediol, as described in Example IV. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al. J. Gen. Appl. Microbiol. 18:43-55 (1972); Koo et al. Biotechnol Lett. 27:505-510 (2005)). The protein sequences for each of these exemplary gene products, if available, can be found using the following GenBank accession numbers shown in Table 11.

TABLE 11

| Gene | Accession No. | GI No. | Organism |
| --- | --- | --- | --- |
| adhE | NP_415757.1 | 16129202 | Escherichia coli |
| adhE2 | AAK09379.1 | 12958626 | Clostridium acetobutylicum |
| adhE | AAV66076.1 | 55818563 | Leuconostoc mesenteroides |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii*, *Erythrobacter* sp. NAP1 and marine gamma proteobacterium HTCC2080 can be inferred by sequence similarity. The protein sequences for each of these exemplary gene products, if available, can be found using the following GenBank accession numbers shown in Table 12.

TABLE 12

| Gene | Accession No. | GI No. | Organism |
| --- | --- | --- | --- |
| mcr | AAS20429.1 | 42561982 | Chloroflexus aurantiacus |
| Rcas_2929 | YP_001433009.1 | 156742880 | Roseiflexus castenholzii |
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al. *Plant Physiology* 122:635-644) 2000)). The protein sequence for the exemplary gene product, if available, can be found using the following GenBank accession numbers shown in Table 13.

TABLE 13

| Gene | Accession No. | GI No. | Organism |
| --- | --- | --- | --- |
| FAR | AAD38039.1 | 5020215 | Simmondsia chinensis |

1.2.1.b Oxidoreductase (Acyl-CoA to Aldehyde)

Step A of FIG. 1 involves the conversion of succinyl-CoA to succinate semialdehyde by an aldehyde forming succinyl-CoA reductase. Step Q of FIG. 1 depicts the conversion of 4-hydroxybutyryl-CoA to 4-hydroxybutanal by an aldehyde-forming 4-hydroxybutyryl-CoA reductase. Several acyl-CoA dehydrogenases are capable of reducing an acyl-CoA to its corresponding aldehyde. Exemplary genes that encode such enzymes include the *Acinetobacter calcoaceticus* acyl encoding a fatty acyl-CoA reductase (Reiser and Somerville, *J. Bacteriology* 179:2969-2975 (1997)), the *Acinetobacter* sp. M-1 fatty acyl-CoA reductase (Ishige et al. *Appl. Environ. Microbiol.* 68:1192-1195 (2002)), and a CoA- and NADP-dependent succinate semialdehyde dehydrogenase encoded by the sucD gene in *Clostridium kluyveri* (Sohling and Gottschalk *J Bacteriol* 178:871-80 (1996); Sohling and Gottschalk *J. Bacteriol.* 178:871-880 (1996)). SucD of *P. gingivalis* is another aldehyde-forming succinyl-CoA reductase (Takahashi et al. *J. Bacteriol.* 182:4704-4710 (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al. *J Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., *Biotechnol Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol Biochem.* 71:58-68 (2007)). The protein sequences for each of these exemplary gene products, if available, can be found using the following GenBank accession numbers shown in Table 14.

TABLE 14

| Gene | Accession No. | GI No. | Organism |
| --- | --- | --- | --- |
| acr1 | YP_047869.1 | 50086359 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| sucD | P38947.1 | 730847 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| bld | AAP42563.1 | 31075383 | Clostridium saccharoperbutylacetonicum |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al. *Science* 318:1782-1786 (2007); Thauer, R. K. *Science* 318:1732-1733 (2007)). The enzyme utilizes NADPH as a cofactor and has been characterized in *Metallosphaera* and *Sulfolobus* spp (Alber et al. *J. Bacteriol.* 188:8551-8559 (2006); Hugler et al. *J. Bacteriol.* 184:2404-2410 (2002)). The enzyme is encoded by Msed_0709 in *Metallosphaera sedula* (Alber et al. *J. Bacteriol.* 188:8551-8559 (2006); Berg et al. *Science* 318:1782-1786 (2007)). A gene encoding a malonyl-CoA reductase from *Sulfolobus tokodaii* was cloned and heterologously expressed in *E. coli* (Alber et al. *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another candidate for CoA-acylating aldehyde dehydrogenase is the ald gene from *Clostridium beijerinckii* (Toth et al., *Appl Environ. Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., *Appl Environ. Microbiol* 65:4973-4980 (1999)). The protein sequences for each of these exemplary gene products, if available, can be found using the following GenBank accession numbers shown in Table 15.

TABLE 15

| Gene | Accession No. | GI No. | Organism |
| --- | --- | --- | --- |
| Msed_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |

TABLE 15-continued

| Gene | Accession No. | GI No. | Organism |
|---|---|---|---|
| eutE | AAA80209 | 687645 | Salmonella typhimurium |
| eutE | P77445 | 2498347 | Escherichia coli |

1.2.1.c Oxidoreductase (2-Oxo Acid to Acyl-CoA, Decarboxylation).

Step AA in FIG. 1 depicts the conversion of 5-hydroxy-2-oxopentanoic acid to 4-hydroxybutyryl-CoA. Candidate enzymes for this transformation include 1) branched-chain 2-keto-acid dehydrogenase, 2) alpha-ketoglutarate dehydrogenase, and 3) the pyruvate dehydrogenase multienzyme complex (PDHC). These enzymes are multi-enzyme complexes that catalyze a series of partial reactions which result in acylating oxidative decarboxylation of 2-keto-acids. Each of the 2-keto-acid dehydrogenase complexes occupies key positions in intermediary metabolism, and enzyme activity is typically tightly regulated (Fries et al. *Biochemistry* 42:6996-7002 (2003)). The enzymes share a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (that is, larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al. *Appl. Environ. Microbiol.* 73:1766-1771 (2007); Kim et al. *J. Bacteriol.* 190:3851-3858) 2008); Zhou et al. *Biotechnol. Lett.* 30:335-342 (2008)). For example, the inhibitory effect of NADH can be overcome by engineering an H322Y mutation in the E3 component (Kim et al. *J. Bacteriol.* 190:3851-3858 (2008)). Structural studies of individual components and how they work together in complex provide insight into the catalytic mechanisms and architecture of enzymes in this family (Aevarsson et al. *Nat. Struct. Biol.* 6:785-792 (1999); Zhou et al. *Proc. Natl. Acad. Sci. U.S.A.* 98:14802-14807 (2001)). The substrate specificity of the dehydrogenase complexes varies in different organisms, but generally branched-chain ketoacid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, R. G. *Curr. Top. Bioenerg.* 10:217-278 (1980)). Encoded by genes sucA, sucB and lpd in *E. coli*, AKGD gene expression is downregulated under anaerobic conditions and during growth on glucose (Park et al. *Mol. Microbiol.* 15:473-482 (1995)). Structural studies of the catalytic core of the E2 component pinpoint specific residues responsible for substrate specificity (Knapp et al. *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al. *Mol. Gen. Genet.* 234:285-296 (1992)). In yeast, the LPD1 gene encoding the E3 component is regulated at the transcriptional level by glucose (Roy and Dawes *J. Gen. Microbiol.* 133:925-933 (1987)). The E1 component, encoded by KGD1, is also regulated by glucose and activated by the products of HAP2 and HAP3 (Repetto and Tzagoloff *Mol. Cell. Biol.* 9:2695-2705 (1989)). The AKGD enzyme complex, inhibited by products NADH and succinyl-CoA, is well-studied in mammalian systems, as impaired function of has been linked to several neurological diseases (Tretter and dam-Vizi *Philos. Trans. R. Soc. Lond B Biol. Sci.* 360:2335-2345 (2005)). The protein sequences for each of these exemplary gene products, if available, can be found using the following GenBank accession numbers shown in Table 16.

TABLE 16

| Gene | Accession No. | GI No. | Organism |
|---|---|---|---|
| sucA | NP_415254.1 | 16128701 | Escherichia coli str. K12 |
| sucB | NP_415255.1 | 16128702 | Escherichia coli str. K12 |
| lpd | NP_414658.1 | 16128109 | Escherichia coli str. K12 |
| odhA | P23129.2 | 51704265 | Bacillus subtilis |
| odhB | P16263.1 | 129041 | Bacillus subtilis |
| pdhD | P21880.1 | 118672 | Bacillus subtilis |
| KGD1 | NP_012141.1 | 6322066 | Saccharomyces cerevisiae |
| KGD2 | NP_010432.1 | 6320352 | Saccharomyces cerevisiae |
| LPD1 | NP_116635.1 | 14318501 | Saccharomyces cerevisiae |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al. *Eur. J. Biochem.* 213:1091-1099 (1993)), *Rattus norvegicus* (Namba et al. *J. Biol. Chem.* 244: 4437-4447 (1969)) and *Pseudomonas putida* (Sokatch *J. Bacteriol.* 148:647-652 (1981)). In *Bacillus subtilis* the enzyme is encoded by genes pdhD (E3 component), bfmBB (E2 component), bfmBAA and bfmBAB (E1 component) (Wang et al. *Eur. J. Biochem.* 213:1091-1099 (1993)). In mammals, the complex is regulated by phosphorylation by specific phosphatases and protein kinases. The complex has been studied in rat hepatocytes (Chicco et al. *J. Biol. Chem.* 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al. *Nat. Struct. Biol.* 6:785-792 (1999); Mattevi *Science* 255:1544-1550 (1992)) and the enzyme complex has been studied (Sokatch et al. *J. Bacteriol.* 148:647-652 (1981)). Transcription of the *P. putida* BCKAD genes is activated by the gene product of bkdR (Hester et al. *Eur. J. Biochem.* 233:828-836 (1995)). In some organisms including *Rattus norvegicus* (Paxton et al. *Biochem. J.* 234:295-303 (1986)) and *Saccharomyces cerevisiae* (Sinclair et al. *Biochem. Mol. Bio. Int.* 31:911-922 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, *Biochemistry* 33:12879-12885 (1994)) The protein sequences for each of these exemplary gene products, if available, can be found using the following GenBank accession numbers shown in Table 17.

TABLE 17

| Gene | Accession No. | GI No. | Organism |
|---|---|---|---|
| bfmBB | NP_390283.1 | 16079459 | Bacillus subtilis |
| bfmBAA | NP_390285.1 | 16079461 | Bacillus subtilis |
| bfmBAB | NP_390284.1 | 16079460 | Bacillus subtilis |
| pdhD | P21880.1 | 118672 | Bacillus subtilis |
| lpdV | P09063.1 | 118677 | Pseudomonas putida |
| bkdB | P09062.1 | 129044 | Pseudomonas putida |
| bkdA1 | NP_746515.1 | 26991090 | Pseudomonas putida |
| bkdA2 | NP_746516.1 | 26991091 | Pseudomonas putida |
| Bckdha | NP_036914.1 | 77736548 | Rattus norvegicus |
| Bckdhb | NP_062140.1 | 158749538 | Rattus norvegicus |
| Dbt | NP_445764.1 | 158749632 | Rattus norvegicus |
| Dld | NP_955417.1 | 40786469 | Rattus norvegicus |

The pyruvate dehydrogenase complex, catalyzing the conversion of pyruvate to acetyl-CoA, has also been extensively studied. In the *E. coli* enzyme, specific residues in the E1 component are responsible for substrate specificity (Bisswanger, H. *J Biol. Chem.* 256:815-822 (1981); Bremer, J. *Eur. J Biochem.* 8:535-540 (1969); Gong et al. *J Biol. Chem.* 275:13645-13653 (2000)). As mentioned previously, enzyme engineering efforts have improved the *E. coli* PDH enzyme activity under anaerobic conditions (Kim et al. *Appl. Environ. Microbiol.* 73:1766-1771 (2007); Kim *J. Bacteriol.* 190:3851-3858 (2008); Zhou et al. *Biotechnol. Lett.* 30:335-342 (2008)). In contrast to the *E. coli* PDH, the *B. subtilis* complex is active and required for growth under anaerobic conditions (Nakano *J. Bacteriol.* 179:6749-6755 (1997)). The *Klebsiella pneumoniae* PDH, characterized during growth on glycerol, is also active under anaerobic conditions (Menzel et al. *J. Biotechnol.* 56:135-142 (1997)). Crystal structures of the enzyme complex from bovine kidney (Zhou et al. *Proc. Natl. Acad. Sci. U.S.A.* 98:14802-14807 (2001)) and the E2 catalytic domain from *Azotobacter vinelandii* are available (Mattevi et al. *Science* 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al. *Biochem. J.* 234:295-303 (1986)). The protein sequences for each of these exemplary gene products, if available, can be found using the following GenBank accession numbers shown in Table 18.

TABLE 18

| Gene | Accession No. | GI No. | Organism |
|---|---|---|---|
| aceE | NP_414656.1 | 16128107 | Escherichia coli str. K12 |
| aceF | NP_414657.1 | 16128108 | Escherichia coli str. K12 |
| lpd | NP_414658.1 | 16128109 | Escherichia coli str. K12 |
| pdhA | P21882.3 | 3123238 | Bacillus subtilis |
| pdhB | P21882.2 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumonia MGH78578 |
| aceF | YP_001333809.1 | 152968700 | Klebsiella pneumonia MGH78578 |
| lpdA | YP_001333810.1 | 152968701 | Klebsiella pneumonia MGH78578 |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodixin as electron acceptors in lieu of NAD(P)H. While most enzymes in this family are specific to pyruvate as a substrate (POR) some 2-ketoacid:ferredoxin oxidoreductases have been shown to accept a broad range of 2-ketoacids as substrates including alpha-ketoglutarate and 2-oxobutanoate (Fukuda and Wakagi *Biochim. Biophys. Acta* 1597:74-80 (2002); Zhang et al. *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi *Biochim. Biophys. Acta* 1597:74-80 (2002); Zhang et al. *J. Biochem.* 120:587-599 (1996)). A plasmid-based expression system has been developed for efficiently expressing this protein in *E. coli* (Fukuda et al. *Eur. J. Biochem.* 268:5639-5646 (2001)) and residues involved in substrate specificity were determined (Fukuda and Wakagi *Biochim. Biophys. Acta* 1597:74-80 (2002)). Two OFORs from *Aeropyrum pernix* str. K1 have also been recently cloned into *E. coli*, characterized, and found to react with a broad range of 2-oxoacids (Nishizawa et al. *FEBS Lett.* 579:2319-2322 (2005)). The gene sequences of these OFOR candidates are available, although they do not have GenBank identifiers assigned to date. There is bioinformatic evidence that similar enzymes are present in all archaea, some anaerobic bacteria and amitochondrial eukarya (Fukuda and Wakagi *Biochim. Biophys. Acta* 1597:74-80 (2005)). This class of enzyme is also interesting from an energetic standpoint, as reduced ferredoxin could be used to generate NADH by ferredoxin-NAD reductase (Petitdemange et al. *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment. The protein sequence for the exemplary gene product, if available, can be found using the following GenBank accession numbers shown in Table 19.

TABLE 19

| Gene | Accession No. | GI No. | Organism |
|---|---|---|---|
| ST2300 | NP_378302.1 | 15922633 | Sulfolobus tokodaii 7 |

1.2.1.d Oxidoreductase (Phosphonate Reductase)

The conversion of 4-hydroxybutyryl-phosphate to 4-hydroxybutanal (Step R) can be catalyzed by an oxidoreductase in the EC class 1.2.1. Aspartate semialdehyde dehydrogenase (ASD, EC 1.2.1.11) catalyzes the NADPH-dependent reduction of 4-aspartyl phosphate to aspartate-4-semialdehyde. ASD participates in amino acid biosynthesis and recently has been studied as an antimicrobial target (Hadfield et al., 40:14475-14483 (2001)). The *E. coli* ASD structure has been solved (Hadfield et al., 289:991-1002 (1999)) and the enzyme has been shown to accept the alternate substrate beta-3-methylaspartyl phosphate (Shames et al., 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); Blanco et al., *Acta Crystallogr. D. Biol. Crystallogr.* 60:1808-1815 (2004)). Other ASD candidates are found in *Mycobacterium tubercu-* losis (Shafiani et al., *J Appl Microbiol* 98:832-838 (2005)), *Methanococcus jannaschii* (Faehnle et al., 353:1055-1068 (2005)), and the infectious microorganisms *Vibrio cholera* and *Heliobacter pylori* (Moore et al., *Protein Expr. Purif.* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly et al., 140 (Pt 5):1023-1025 (1994)) and other organisms. The protein sequences for each of these exemplary gene products, if available, can be found using the following GenBank accession numbers shown in Table 20.

TABLE 20

| Gene | Accession No. | GI No. | Organism |
| --- | --- | --- | --- |
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Heliobacter pylori* |
| ARG5,6 | NP_010992.1 | 6320913 | *Saccharomyces cerevisiae* |
| argC | NP_389001.1 | 16078184 | *Bacillus subtilis* |

Other exemplary enzymes in this class include glyceraldehyde 3-phosphate dehydrogenase which converts glyceraldehyde-3-phosphate into D-glycerate 1,3-bisphosphate (e.g., *E. coli* gapA (Branlant et al., *Eur. J. Biochem.* 150:61-66 (1985))), N-acetyl-gamma-glutamyl-phosphate reductase which converts N-acetyl-L-glutamate-5-semialdehyde into N-acetyl-L-glutamyl-5-phosphate (e.g., *E. coli* argC (Parsot et al., *Gene.* 68:275-283 (1988))), and glutamate-5-semialdehyde dehydrogenase which converts L-glutamate-5-semialdehyde into L-glutamyl-5-phospate (e.g., *E. coli* proA (Smith et al., *J. Bacteriol.* 157:545-551 (1984a))). Genes encoding glutamate-5-semialdehyde dehydrogenase enzymes from *Salmonella typhimurium* (Mahan et al., *J Bacteriol.* 156:1249-1262 (1983)) and *Campylobacter jejuni* (Louie et al., 240:29-35 (1993)) were cloned and expressed in *E. coli*. The protein sequences for each of these exemplary gene products, if available, can be found using the following GenBank accession numbers shown in Table 21.

TABLE 21

| Gene | Accession No. | GI No. | Organism |
| --- | --- | --- | --- |
| gapA | P0A9B2.2 | 71159358 | *Escherichia coli* |
| argC | NP_418393.1 | 16131796 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

1.2.1.e Acid Reductase

Several steps in FIG. 1 depict the conversion of unactivated acids to aldehydes by an acid reductase. These include the conversion of 4-hydroxybutyrate to 4-hydroxybutanal (Step D), succinate to succinate semialdehyde (Step F), and alpha-ketoglutarate to 2,5-dioxopentanoate (Step X). One notable carboxylic acid reductase can be found in *Nocardia iowensis* which catalyzes the magnesium, ATP and NADPH-dependent reduction of carboxylic acids to their corresponding aldehydes (Venkitasubramanian et al., *J. Biol. Chem.* 282:478-485 (2007)). This enzyme is encoded by the car gene and was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid and the enzyme exhibits broad acceptance of aromatic and aliphatic substrates (Venkitasubramanian et al. "Biocatalytic Reduction of Carboxylic Acids: Mechanism and Applications" Chapter 15 in Biocatalysis in the Pharmaceutical and Biotechnology Industries, ed. R. N. Patel, CRC Press LLC, Boca Raton, Fla. (2006)). The protein sequences for each of these exemplary gene products, if available, can be found using the following GenBank accession numbers shown in Table 22.

TABLE 22

| Gene | Accession No. | GI No. | Organism |
| --- | --- | --- | --- |
| car | AAR91681.1 | 40796035 | *Nocardia iowensis* (sp. NRRL 5646) |
| npt | ABI83656.1 | 114848891 | *Nocardia iowensis* (sp. NRRL 5646) |

Additional car and npt genes can be identified based on sequence homology. The protein sequences for each of these exemplary gene products, if available, can be found using the following GenBank accession numbers shown in Table 23.

TABLE 23

| Gene | Accession No. | GI No. | Organism |
| --- | --- | --- | --- |
| fadD9 | YP_978699.1 | 121638475 | *Mycobacterium bovis* BCG |
| BCG 2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., J. Antibiot. 60 (6): 380-387 (2007)). Co-expression of griC and griD with SGR_665, an enzyme similar in sequence to the *Nocardia iowensis* npt, may be beneficial. The protein sequences for each of these exemplary gene products, if available, can be found using the following GenBank accession numbers shown in Table 24.

TABLE 24

| Gene | Accession No. | GI No. | Organism |
| --- | --- | --- | --- |
| griC | 182438036 | YP_01825755.1 | *Streptomyces griseus* subsp. *griseus* NBRC 13350 |
| griD | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., Gene 98:141-145 (1991)), *Candida albicans* (Guo et al., Mol. Genet. Genomics 269:271-279 (2003)), and *Schizosaccharomyces pombe* (Ford et al., Curr. Genet. 28:131-137 (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., J. Biol. Chem. 278:8250-8256 (2003)). The gene encoding the *P. chrysogenum* PPTase has not been identified to date and no high-confidence hits were identified by sequence comparison homology searching. The protein sequences for each of these exemplary gene products, if available, can be found using the following GenBank accession numbers shown in Table 25.

TABLE 25

| Gene | Accession No. | GI No. | Organism |
| --- | --- | --- | --- |
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

1.4.1.a Oxidoreductase (Aminating)

Glutamate dehydrogenase (Step J, FIG. 1B) and 4-aminobutyrate dehydrogenase (Step M, FIG. 1B) can be catalyzed by aminating oxidoreductases. Enzymes in this EC class catalyze the oxidative deamination of alpha-amino acids with NAD$^+$ or NADP$^+$ as acceptor, and the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al. J. Mol. Biol. 234:1270-1273 (1993); McPherson and Wootton Nucleic. Acids Res. 11:5257-5266 (1983)), gdh from *Thermotoga maritima* (Kort et al. Extremophiles 1:52-60 (1997); Lebbink, et al. J. Mol. Biol. 280:287-296 (1998)); Lebbink et al. J. Mol. Biol. 289:357-369 (1999)), and gdhAl from *Halobacterium salinarum* (Ingoldsby et al. Gene 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula Biotechnol Bioeng. 68:557-562 (2000); Stoyan et al. J. Biotechnol 54:77-80 (1997)). The nadX gene from *Thermotoga maritime* encoding for the aspartate dehydrogenase is involved in the biosynthesis of NAD (Yang et al. J. Biol. Chem. 278:8804-8808 (2003)). The protein sequences for each of these exemplary gene products, if available, can be found using the following GenBank accession numbers shown in Table 26.

TABLE 26

| Gene | Accession No. | GI No. | Organism |
| --- | --- | --- | --- |
| gdhA | P00370 | 118547 | *Escherichia coli* |
| gdh | P96110.4 | 6226595 | *Thermotoga maritima* |
| gdhA1 | NP_279651.1 | 15789827 | *Halobacterium salinarum* |
| ldh | P0A393 | 61222614 | *Bacillus cereus* |
| nadX | NP_229443.1 | 15644391 | *Thermotoga maritima* |

Additional glutamate dehydrogenase gene candidates are found in *Bacillus subtilis* (Khan et al., Biosci. Biotechnol Biochem. 69:1861-1870 (2005)), *Nicotiana tabacum* (Purnell et al., Planta 222:167-180 (2005)), *Oryza sativa* (Abiko et al., Plant Cell Physiol 46:1724-1734 (2005)), *Haloferax mediterranei* (Diaz et al., Extremophiles. 10:105-115 (2006)) and *Halobactreium salinarum* (Hayden et al., FEMS Microbiol Lett. 211:37-41 (2002)). The *Nicotiana tabacum* enzyme is composed of alpha and beta subunits encoded by gdh1 and gdh2 (Purnell et al., Planta 222:167-180 (2005)). Overexpression of the NADH-dependent glutamate dehydrogenase was found to improve ethanol production in engineered strains of *S. cerevisiae* (Roca et al., Appl Environ. Microbiol 69:4732-4736 (2003)). The protein sequences for each of these exemplary gene products, if available, can be found using the following GenBank accession numbers shown in Table 27.

TABLE 27

| Gene | Accession No. | GI No. | Organism |
| --- | --- | --- | --- |
| rocG | NP_391659.1 | 16080831 | *Bacillus subtilis* |
| gdh1 | AAR11534.1 | 38146335 | *Nicotiana tabacum* |
| gdh2 | AAR11535.1 | 38146337 | *Nicotiana tabacum* |
| GDH | Q852M0 | 75243660 | *Oryza sativa* |
| GDH | Q977U6 | 74499858 | *Haloferax mediterranei* |
| GDH | P29051 | 118549 | *Halobactreium salinarum* |
| GDH2 | NP_010066.1 | 6319986 | *Saccharomyces cerevisiae* |

An exemplary enzyme for catalyzing the conversion of aldehydes to their corresponding primary amines is lysine 6-dehydrogenase (EC 1.4.1.18), encoded by the lysDH genes. The lysine 6-dehydrogenase (deaminating), encoded by lysDH gene, catalyze the oxidative deamination of the E-amino group of L-lysine to form 2-aminoadipate-6-semialdehyde, which in turn nonenzymatically cyclizes to form Δ1-piperideine-6-carboxylate (Misono and Nagasaki J. Bacteriol. 150:398-401 (1982)). The lysDH gene from *Geobacillus stearothermophilus* encodes a thermophilic NAD-dependent lysine 6-dehydrogenase (Heydari et al. Appl Environ. Microbiol 70:937-942 (2004)). The lysDH gene from *Aeropyrum pernix* K1 is identified through homology from genome projects. Additional enzymes can be found in *Agrobacterium tumefaciens* (Hashimoto et al., J Biochem. 106:76-80 (1989); Misono et al., J Bacteriol. 150:398-401 (1982)) and *Achromobacter denitrificans* (Ruldeekulthamrong et al., BMB. Rep. 41:790-795 (2008)). The protein sequences for each of these exemplary gene products, if available, can be found using the following GenBank accession numbers shown in Table 28.

TABLE 28

| Gene | Accession No. | GI No. | Organism |
| --- | --- | --- | --- |
| lysDH | BAB39707 | 13429872 | *Geobacillus stearothermophilus* |
| lysDH | NP_147035.1 | 14602185 | *Aeropyrum pernix* K1 |
| lysDH | NP_353966 | 15888285 | *Agrobacterium tumefaciens* |
| lysDH | AAZ94428 | 74026644 | *Achromobacter denitrificans* |

An enzyme that converts 3-oxoacids to 3-amino acids is 3,5-diaminohexanoate dehydrogenase (EC 1.4.1.11), an enzyme found in organisms that ferment lysine. The gene encoding this enzyme, kdd, was recently identified in *Fusobacterium nucleatum* (Kreimeyer et al., 282:7191-7197 (2007)). The enzyme has been purified and characterized in other organisms (Baker et al., 247:7724-7734 (1972); Baker et al., 13:292-299 (1974)) but the genes associated with these enzymes are not known. Candidates in *Myxococcus xanthus, Porphyromonas gingivalis* W83 and other sequenced organisms can be inferred by sequence homology. The protein sequences for each of these exemplary gene products, if available, can be found using the following GenBank accession numbers shown in Table 29.

TABLE 29

| Gene | Accession No. | GI No. | Organism |
|---|---|---|---|
| kdd | AAL93966.1 | 19713113 | *Fusobacterium nucleatum* |
| mxan_439 | ABF87267.1 | 108462082 | *Myxococcus xanthus* |
| pg_1069 | AAQ66183.1 | 34397119 | *Porphyromonas gingivalis* |

2.3.1.a Acyltransferase (Transferring Phosphate Group to CoA)

Step P of FIG. 1 depicts the transformation of 4-hydroxybutyryl-CoA to 4-hydroxybutyryl-phosphate. Exemplary phosphate transferring acyltransferases include phosphotransacetylase, encoded by pta, and phosphotransbutyrylase, encoded by ptb. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Similarly, the ptb gene from *C. acetobutylicum* encodes an enzyme that can convert butyryl-CoA into butyryl-phosphate (Walter et al. *Gene* 134 (1): p. 107-11 (1993)); Huang et al. *J Mol Microbiol Biotechnol* 2 (1): p. 33-38 (2000). Additional ptb genes can be found in butyrate-producing bacterium L2-50 (Louis et al. *J. Bacteriol.* 186:2099-2106 (2004)) and *Bacillus megaterium* (Vazquez et al. *Curr. Microbiol* 42:345-349 (2001)). The protein sequences for each of these exemplary gene products, if available, can be found using the following GenBank accession numbers shown in Table 30.

TABLE 30

| Gene | Accession No. | GI No. | Organism |
|---|---|---|---|
| pta | NP_416800.1 | 16130232 | *Escherichia coli* |
| ptb | NP_349676 | 15896327 | *Clostridium acetobutylicum* |
| ptb | AAR19757.1 | 38425288 | butyrate-producing bacterium L2-50 |
| ptb | CAC07932.1 | 10046659 | *Bacillus megaterium* |

2.6.1.a Aminotransferase

Steps K and N in FIG. 1 can be catalyzed by aminotransferases that reversibly convert an aldehyde or ketone to an amino group. Common amino donor/acceptor combinations include glutamate/alpha-ketoglutarate, alanine/pyruvate, and aspartate/oxaloacetate. Several enzymes have been shown to convert aldehydes to primary amines, and vice versa. Lysine-6-aminotransferase (EC 2.6.1.36) is one exemplary enzyme capable of forming a primary amine. This enzyme function, converting lysine to alpha-aminoadipate semialdehyde, has been demonstrated in yeast and bacteria. Candidates from *Candida utilis* (Hammer et al., *J Basic Microbiol* 32:21-27 (1992)), *Flavobacterium lutescens* (Fujii et al., *J Biochem.* 128:391-397 (2000)) and *Streptomyces clavuligenus* (Romero et al., *J. Ind. Microbiol Biotechnol* 18:241-246 (1997)) have been characterized. A recombinant lysine-6-aminotransferase from *S. clavuligenus* was functionally expressed in *E. coli* (Tobin et al., *J. Bacteriol.* 173:6223-6229 (1991)). The *F. lutescens* enzyme is specific to alpha-ketoglutarate as the amino acceptor (Soda et al., 7:4110-4119 (1968)). Other enzymes which convert aldehydes to terminal amines include the dat gene product in *Acinetobacter baumanii* encoding 2,4-diaminobutanoate:2-ketoglutarate 4-transaminase (Ikai et al., *J. Bacteriol.* 179:5118-5125 (1997)). In addition to its natural substrate, 2,4-diaminobutyrate, DAT transaminates the terminal amines of lysine, 4-aminobutyrate and ornithine. The protein sequences for each of these exemplary gene products, if available, can be found using the following GenBank accession numbers shown in Table 31.

TABLE 31

| Gene | Accession No. | GI No. | Organism |
|---|---|---|---|
| lat | BAB13756.1 | 10336502 | *Flavobacterium lutescens* |
| lat | AAA26777.1 | 153343 | *Streptomyces clavuligenus* |
| dat | P56744.1 | 6685373 | *Acinetobacter baumanii* |

The conversion of an aldehyde to a terminal amine can also be catalyzed by gamma-aminobutyrate transaminase (GABA transaminase or 4-aminobutyrate transaminase). This enzyme naturally interconverts succinic semialdehyde and glutamate to 4-aminobutyrate and alpha-ketoglutarate and is known to have a broad substrate range (Schulz et al., 56:1-6 (1990); Liu et al., 43:10896-10905 (2004)). The two GABA transaminases in *E. coli* are encoded by gabT (Bartsch et al., *J. Bacteriol.* 172:7035-7042 (1990)) and puuE (Kurihara et al., *J. Biol. Chem.* 280:4602-4608 (2005)). GABA transaminases in *Mus musculus, Pseudomonas fluorescens*, and *Sus scrofa* have been shown to react with a range of alternate substrates including 6-aminocaproic acid (Cooper, 113:80-82 (1985); SCOTT et al., 234:932-936 (1959)). The protein sequences for each of these exemplary gene products, if available, can be found using the following GenBank accession numbers shown in Table 32.

TABLE 32

| Gene | Accession No. | GI No. | Organism |
|---|---|---|---|
| gabT | NP_417148.1 | 16130576 | *Escherichia coli* |
| puuE | NP_415818.1 | 16129263 | *Escherichia coli* |
| Abat | NP_766549.2 | 37202121 | *Mus musculus* |
| gabT | YP_257332.1 | 70733692 | *Pseudomonas fluorescens* |
| abat | NP_999428.1 | 47523600 | *Sus scrofa* |

Additional enzyme candidates for interconverting aldehydes and primary amines are putrescine transminases or other diamine aminotransferases. The *E. coli* putrescine aminotransferase is encoded by the ygjG gene and the purified enzyme also was able to transaminate cadaverine and spermidine (Samsonova et al., *BMC. Microbiol* 3:2 (2003)). In addition, activity of this enzyme on 1,7-diaminoheptane and with amino acceptors other than 2-oxoglutarate (e.g., pyruvate, 2-oxobutanoate) has been reported (Samsonova et al., *BMC. Microbiol* 3:2 (2003); KIM, 239:783-786 (1964)). A putrescine aminotransferase with higher activity with pyruvate as the amino acceptor than alpha-ketoglutarate is the spuC gene of *Pseudomonas aeruginosa* (Lu et al., *J. Bacteriol.* 184:3765-3773 (2002)). The protein sequences for each of these exemplary gene products, if available, can be found using the following GenBank accession numbers shown in Table 33.

TABLE 33

| Gene | Accession No. | GI No. | Organism |
|---|---|---|---|
| ygjG | NP_417544 | 145698310 | Escherichia coli |
| spuC | AAG03688 | 9946143 | Pseudomonas aeruginosa |

Enzymes that transaminate 3-oxoacids include GABA aminotransferase (described above), beta-alanine/alpha-ketoglutarate aminotransferase and 3-amino-2-methylpropionate aminotransferase. Beta-alanine/alpha-ketoglutarate aminotransferase (WO08027742) reacts with beta-alanine to form malonic semialdehyde, a 3-oxoacid. The gene product of SkPYD4 in *Saccharomyces kluyveri* was shown to preferentially use beta-alanine as the amino group donor (Andersen et al., *Gene* 124:105-109 (1993)). SkUGA1 encodes a homologue of *Saccharomyces cerevisiae* GABA aminotransferase, UGA1 (Ramos et al., *Eur. J. Biochem.* 149:401-404 (1985)), whereas SkPYD4 encodes an enzyme involved in both beta-alanine and GABA transamination (Andersen and Hansen, *Gene* 124:105-109 (1993)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Tamaki et al., 324:376-389 (2000); Kakimoto et al., 156:374-380 (1968)). The protein sequences for each of these exemplary gene products, if available, can be found using the following GenBank accession numbers shown in Table 34.

TABLE 34

| Gene | Accession No. | GI No. | Organism |
|---|---|---|---|
| SkyPYD4 | ABF58893.1 | 98626772 | Lachancea kluyveri |
| SkUGA1 | ABF58894.1 | 98626792 | Lachancea kluyveri |
| UGA1 | NP_011533.1 | 6321456 | Saccharomyces cerevisiae |
| Abat | P50554.3 | 122065191 | Rattus norvegicus |
| Abat | P80147.2 | 120968 | Sus scrofa |

Several aminotransferases transaminate the amino groups of amino acids to form 2-oxoacids. Aspartate aminotransferase is an enzyme that naturally transfers an oxo group from oxaloacetate to glutamate, forming alpha-ketoglutarate and aspartate. Aspartate is similar in structure to OHED and 2-AHD. Aspartate aminotransferase activity is catalyzed by, for example, the gene products of aspC from *Escherichia coli* (Yagi et al., 100:81-84 (1979); Yagi et al., 113:83-89 (1985)), AAT2 from *Saccharomyces cerevisiae* (Yagi et al., 92:35-43 (1982)) and ASPS from *Arabidopsis thaliana* (Kwok et al., 55:595-604 (2004); de la et al., 46:414-425 (2006); Wilkie et al., *Protein Expr. Purif.* 12:381-389 (1998)). The enzyme from *Rattus norvegicus* has been shown to transaminate alternate substrates such as 2-aminohexanedioic acid and 2,4-diaminobutyric acid (Recasens et al., 19:4583-4589 (1980)). Aminotransferases that work on other amino-acid substrates may also be able to catalyze this transformation. Valine aminotransferase catalyzes the conversion of valine and pyruvate to 2-ketoisovalerate and alanine The *E. coli* gene, avtA, encodes one such enzyme (Whalen et al., *J. Bacteriol.* 150: 739-746 (1982)). This gene product also catalyzes the transamination of alpha-ketobutyrate to generate α-aminobutyrate, although the amine donor in this reaction has not been identified (Whalen et al., *J. Bacteriol.* 158:571-574 (1984)).

The gene product of the *E. coli* serC catalyzes two reactions, phosphoserine aminotransferase and phosphohydroxythreonine aminotransferase (Lam et al., *J. Bacteriol.* 172:6518-6528 (1990)), and activity on non-phosphorylated substrates could not be detected (Drewke et al., *FEBS. Lett.* 390:179-182 (1996)). The protein sequences for each of these exemplary gene products, if available, can be found using the following GenBank accession numbers shown in Table 35.

TABLE 35

| Gene | Accession No. | GI No. | Organism |
|---|---|---|---|
| aspC | NP_415448.1 | 16128895 | Escherichia coli |
| AAT2 | P23542.3 | 1703040 | Saccharomyces cerevisiae |
| ASP5 | P46248.2 | 20532373 | Arabidopsis thaliana |
| Got2 | P00507 | 112987 | Rattus norvegicus |
| avtA | YP_026231.1 | 49176374 | Escherichia coli |
| serC | NP_415427.1 | 16128874 | Escherichia coli |

Another enzyme candidate is alpha-aminoadipate aminotransferase (EC 2.6.1.39), an enzyme that participates in lysine biosynthesis and degradation in some organisms. This enzyme interconverts 2-aminoadipate and 2-oxoadipate, using alpha-ketoglutarate as the amino acceptor. Gene candidates are found in *Homo sapiens* (Okuno et al., *Enzyme Protein* 47:136-148 (1993)) and *Thermus thermophilus* (Miyazaki et al., 150:2327-2334 (2004)). The *Thermus thermophilus* enzyme, encoded by lysN, is active with several alternate substrates including oxaloacetate, 2-oxoisocaproate, 2-oxoisovalerate, and 2-oxo-3-methylvalerate. The protein sequences for each of these exemplary gene products, if available, can be found using the following GenBank accession numbers shown in Table 36.

TABLE 36

| Gene | Accession No. | GI No. | Organism |
|---|---|---|---|
| lysN | BAC76939.1 | 31096548 | Thermus thermophilus |
| AadAT-II | Q8N5Z0.2 | 46395904 | Homo sapiens |

2.7.2.a Phosphotransferase (Carboxy Acceptor)

Step O of FIG. 1 involves the conversion of 4-hydroxybutyrate to 4-hydroxybutyryl-phosphate by the phosphotransferase enzymes in the EC class 2.7.2 that transform carboxylic acids to phosphonic acids with concurrent hydrolysis of one ATP. Butyrate kinase (EC 2.7.2.7) carries out the reversible conversion of butyryl-phosphate to butyrate during acidogenesis in *C. acetobutylicum* (Cary et al., 56:1576-1583 (1990)). This enzyme is encoded by either of the two buk gene products (Huang et al., *J Mol. Microbiol Biotechnol* 2:33-38 (2000)). Other butyrate kinase enzymes are found in *C. butyricum* and *C. tetanomorphum* (TWAROG et al., *J. Bacteriol.* 86:112-117 (1963)). Related enzyme isobutyrate kinase from *Thermotoga maritima* has also been expressed in *E. coli* and crystallized (Diao et al., *J. Bacteriol.* 191:2521-2529 (2009); Diao et al., *Acta Crystallogr. D. Biol. Crystallogr.* 59:1100-1102 (2003)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng et al., 335:73-81 (1996)). Two additional kinases in *E. coli* are also good candidates: acetate kinase and gamma-glutamyl kinase. The *E. coli* acetate kinase, encoded by ackA (Skarstedt et al., *J. Biol. Chem.* 251:6775-6783 (1976)), phosphorylates propionate in addition to acetate (Hesslinger et al., *Mol. Microbiol* 27:477-

492 (1998)). The *E. coli* gamma-glutamyl kinase, encoded by proB (Smith et al., *J. Bacteriol.* 157:545-551 (1984b)), phosphorylates the gamma carbonic acid group of glutamate. The protein sequences for each of these exemplary gene products, if available, can be found using the following GenBank accession numbers shown in Table 37.

TABLE 37

| Gene | Accession No. | GI No. | Organism |
|---|---|---|---|
| buk1 | NP_349675 | 15896326 | *Clostridium acetobutylicum* |
| buk2 | Q97111 | 20137415 | *Clostridium acetobutylicum* |
| buk2 | Q9X278.1 | 6685256 | *Thermotoga maritima* |
| lysC | NP_418448.1 | 16131850 | *Escherichia coli* |
| ackA | NP_416799.1 | 16130231 | *Escherichia coli* |
| proB | NP_414777.1 | 16128228 | *Escherichia coli* |

Acetylglutamate kinase phosphorylates acetylated glutamate during arginine biosynthesis. This enzyme is not known to accept alternate substrates; however, several residues of the *E. coli* enzyme involved in substrate binding and phosphorylation have been elucidated by site-directed mutagenesis (Marco-Marin et al., 334:459-476 (2003); Ramon-Maiques et al., *Structure.* 10:329-342 (2002)). The enzyme is encoded by argB in *Bacillus subtilis* and *E. coli* (Parsot et al., *Gene* 68:275-283 (1988)), and ARG5,6 in *S. cerevisiae* (Pauwels et al., *Eur. J Biochem.* 270:1014-1024 (2003)). The ARG5,6 gene of *S. cerevisiae* encodes a polyprotein precursor that is matured in the mitochondrial matrix to become acetylglutamate kinase and acetylglutamylphosphate reductase. The protein sequences for each of these exemplary gene products, if available, can be found using the following GenBank accession numbers shown in Table 38.

TABLE 38

| Gene | Accession No. | GI No. | Organism |
|---|---|---|---|
| argB | NP_418394.3 | 145698337 | *Escherichia coli* |
| argB | NP_389003.1 | 16078186 | *Bacillus subtilis* |
| ARG5,6 | NP_010992.1 | 6320913 | *Saccharomyces cerevisiae* |

2.8.3.a CoA transferase

Steps G and T in FIG. 1 involve CoA transferase activities. The gene products of cat1, cat2, and cat3 of *Clostridium kluyveri* have been shown to exhibit succinyl-CoA, 4-hydroxybutyryl-CoA, and butyryl-CoA acetyltransferase activities (Seedorf et al. *Proc Natl Acad Sci U.S.A.* 105 (6): 2128-2133 (2008); Sohling and Gottschalk *J Bacteriol* 178 (3):871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). The protein sequences for each of these exemplary gene products, if available, can be found using the following GenBank accession numbers shown in Table 39.

TABLE 39

| Gene | Accession No. | GI No. | Organism |
|---|---|---|---|
| cat1 | P38946.1 | 729048 | *Clostridium kluyveri* |
| cat2 | P38942.2 | 1705614 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

An additionally useful enzyme for this type of transformation is acyl-CoA: acetate-CoA transferase, also known as acetate-CoA transferase (EC 2.8.3.8), which has been shown to transfer the CoA moiety to acetate from a variety of branched and linear acyl-CoA substrates, including isobutyrate (Matthies and Schink *Appl Environ Microbiol* 58:1435-1439 (1992)), valerate (Vanderwinkel et al. *Biochem. Biophys. Res Commun.* 33:902-908 (1968)) and butanoate (Vanderwinkel, supra (1968)). This enzyme is encoded by atoA (alpha subunit) and atoD (beta subunit) in *E. coli* sp. K12 (Korolev et al. *Acta Crystallogr. D Biol Crystallogr.* 58:2116-2121 (2002); Vanderwinkel, supra (1968)). Similar enzymes exist in *Corynebacterium glutamicum* ATCC 13032 (Duncan et al., 68:5186-5190 (2002)), *Clostridium* saccharoperbutylacetonicum (Kosaka et al., *Biosci. Biotechnol Biochem.* 71:58-68 (2007)), and *Clostridium acetobutylicum* (Cary et al., 56:1576-1583 (1990); Wiesenborn et al., 55:323-329 (1989)). The protein sequences for each of these exemplary gene products, if available, can be found using the following GenBank accession numbers shown in Table 40.

TABLE 40

| Gene | Accession No. | GI No. | Organism |
|---|---|---|---|
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* |
| cg0592 | YP_224801.1 | 62389399 | *Corynebacterium glutamicum* |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack and Buckel *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al. *Eur. J. Biochem.* 118: 315-321 (1981)). The enzyme has been cloned and expressed in *E. coli* (Mac et al. *Eur. J. Biochem.* 226:41-51 (1994)). The protein sequences for each of these exemplary gene products, if available, can be found using the following GenBank accession numbers shown in Table 41.

TABLE 41

| Gene | Accession No. | GI No. | Organism |
|---|---|---|---|
| gctA | CAA57199.1 | 559392 | *Acidaminococcus fermentans* |
| gctB | CAA57200.1 | 559393 | *Acidaminococcus fermentans* |

3.1.1.a Hydroxyacylhydrolase

Step AB in FIG. 1 is the transformation of 4-hydroxybutyrate to GBL. This step can be catalyzed by enzymes in the 3.1.1 family that act on carboxylic ester bonds molecules for the interconversion between cyclic lactones and the open chain hydroxycarboxylic acids. The 1,4-lacton hydroxyacylhydrolase (EC 3.1.1.25), also known as 1,4-lactonase or gamma-lactonase, is specific for 1,4-lactones with 4-8 carbon atoms. It does not hydrolyze simple aliphatic esters, acetylcholine, or sugar lactones. The gamma lactonase in human blood and rat liver microsomes was purified (Fishbein et al., *J Biol Chem* 241:4835-4841 (1966)) and the lactonase activity was activated and stabilized by calcium ions (Fishbein et al., *J Biol Chem* 241:4842-4847 (1966)). The optimal lactonase activities were observed at pH 6.0, whereas high pH resulted in hydrolytic activities (Fishbein and Bessman, *J Biol Chem* 241:4842-4847 (1966)). The following genes have been annotated as 1,4-lactonase and can be utilized to catalyze the transformation of 4-hydroxybutyrate to GBL, including a lactonase from *Fusarium oxysporum* (Zhang et al., *Appl Microbiol Biotechnol* 75:1087-1094 (2007)). The protein sequences for each of these exemplary gene products, if available, can be found using the following GenBank accession numbers shown in Table 42.

TABLE 42

| Gene | Accession No. | GI No. | Organism |
| --- | --- | --- | --- |
| xccb100_2516 | YP_001903921.1 | 188991911 | *Xanthomonas campestris* |
| An16g06620 | CAK46996.1 | 134083519 | *Aspergillus niger* |
| BAA34062 | BAA34062.1 | 3810873 | *Fusarium oxysporum* |

Additionally, it has been reported that lipases such as *Candida antarctica* lipase B can catalyze the lactonization of 4-hydroxybutyrate to GBL (Efe et al., *Biotechnol Bioeng* 99:1392-1406 (2008)). Therefore, the following genes coding for lipases can also be utilized for Step AB in FIG. 1. The protein sequences for each of these exemplary gene products, if available, can be found using the following GenBank accession numbers shown in Table 43.

TABLE 43

| Gene | Accession No. | GI No. | Organism |
| --- | --- | --- | --- |
| calB | P41365.1 | 1170790 | *Candida antarctica* |
| lipB | P41773.1 | 1170792 | *Pseudomonas fluorescens* |
| estA | P37957.1 | 7676155 | *Bacillus subtilis* |

3.1.2.a CoA Hydrolase

Steps H and U in FIG. 1 involve enzymes in the 3.1.2 family that hydrolyze acyl-CoA molecules to their corresponding acids. Nevertheless, perhaps such enzymes can be modified to embark CoA-ligase or synthetase functionality if coupled to an energy source such as a proton pump or direct ATP hydrolysis. Several eukaryotic acetyl-CoA hydrolases (EC 3.1.2.1) have broad substrate specificity. For example, the enzyme from *Rattus norvegicus* brain (Robinson, Jr. et al., 71:959-965 (1976)) can react with butyryl-CoA, hexanoyl-CoA and malonyl-CoA. Though its sequence has not been reported, the enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). The acetyl-CoA hydrolase, ACH1, from *S. cerevisiae* represents another candidate hydrolase (Buu et al., *J. Biol. Chem.* 278:17203-17209 (2003)). The protein sequences for each of these exemplary gene products, if available, can be found using the following GenBank accession numbers shown in Table 44.

TABLE 44

| Gene | Accession No. | GI No. | Organism |
| --- | --- | --- | --- |
| acot12 | NP_570103.1 | 18543355 | *Rattus norvegicus* |
| ACH1 | NP_009538 | 6319456 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., 280:38125-38132 (2005)) and the closest *E. coli* homolog, tesB, which can also hydrolyze a broad range of CoA thioesters (Naggert et al., 266:11044-11050 (1991)). A similar enzyme has also been characterized in the rat liver (Deana, *Biochem. Int.* 26:767-773 (1992)). Other potential *E. coli* thioester hydrolases include the gene products of tesA (Bonner et al., 247:3123-3133 (1972)), ybgC (Kuznetsova et al., *FEMS Microbiol Rev* 29:263-279 (2005); Zhuang et al., 516:161-163 (2002)), paaI (Song et al., 281:11028-11038 (2006)), and ybdB (Leduc et al., *J Bacteriol.* 189:7112-7126 (2007)). The protein sequences for each of these exemplary gene products, if available, can be found using the following GenBank accession numbers shown in Table 45.

TABLE 45

| Gene | Accession No. | GI No. | Organism |
| --- | --- | --- | --- |
| acot8 | CAA15502 | 3191970 | *Homo sapiens* |
| tesB | NP_414986 | 16128437 | *Escherichia coli* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA:acetyl-CoA transferases may also serve as candidates for this reaction step but would require certain mutations to change their function. The protein sequences for each of these exemplary gene products, if available, can be found using the following GenBank accession numbers shown in Table 46.

TABLE 46

| Gene | Accession No. | GI No. | Organism |
| --- | --- | --- | --- |
| gctA | CAA57199.1 | 559392 | *Acidaminococcus fermentans* |
| gctB | CAA57200.1 | 559393 | *Acidaminococcus fermentans* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol. Chem.* 269:14248-14253 (1994)). Genes encoding this enzyme include hibch of *Rattus norvegicus* (Shimomura et al., supra; Shimomura et al., *Methods Enzymol.* 324:229-240 (2000)) and *Homo sapiens* (Shimomura et al., supra). Candidate genes by sequence homology include hibch of *Saccharomyces cerevisiae* and BC_2292 of *Bacillus cereus*. The protein sequences for each of these exemplary gene products, if available, can be found using the following GenBank accession numbers shown in Table 47.

TABLE 47

| Gene | Accession No. | GI No. | Organism |
| --- | --- | --- | --- |
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |

4.1.1.a Carboxy-Lyase

Alpha-ketoglutarate decarboxylase (Step B), glutamate decarboxylase (Step L), and 5-hydroxy-2-oxopentanoic acid decarboxylase (Step Z) in FIG. 1 all involve the decarboxylation of an alpha-ketoacid. The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase.

Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (22). This enzyme has been extensively studied, engineered for altered activity, and functionally expressed in *E. coli* (Killenberg-Jabs et al., 268:1698-1704 (2001); Li et al., *Biochemistry*. 38:10004-10012 (1999); ter Schure et al., *Appl. Environ. Microbiol.* 64:1303-1307 (1998)). The PDC from *Zymomonas mobilus*, encoded by pdc, also has a broad substrate range and has been a subject of directed engineering studies to alter the affinity for different substrates (Siegert et al., 18:345-357 (2005)). The crystal structure of this enzyme is available (Killenberg-Jabs et al., 268:1698-1704 (2001)). Other well-characterized PDC candidates include the enzymes from *Acetobacter pasteurians* (Chandra et al., 176:443-451 (2001)) and *Kluyveromyces lactis* (Krieger et al., 269:3256-3263 (2002)). The protein sequences for each of these exemplary gene products, if available, can be found using the following GenBank accession numbers shown in Table 48.

TABLE 48

| Gene | Accession No. | GI No. | Organism |
| --- | --- | --- | --- |
| pdc | P06672.1 | 118391 | *Zymomonas mobilus* |
| pdc1 | P06169 | 30923172 | *Saccharomyces cerevisiae* |
| pdc | AM21208 | 20385191 | *Acetobacter pasteurians* |
| pdc1 | Q12629 | 52788279 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Polovnikova et al., 42:1820-1830 (2003); Hasson et al., 37:9918-9930 (1998)). Site-directed mutagenesis of two residues in the active site of the *Pseudomonas putida* enzyme altered the affinity (Km) of naturally and non-naturally occurring substrates (Siegert et al., 18:345-357 (2005)). The properties of this enzyme have been further modified by directed engineering (Lingen et al., *Chembiochem*. 4:721-726 (2003); Lingen et al., *Protein Eng* 15:585-593 (2002)). The enzyme from *Pseudomonas aeruginosa*, encoded by mdlC, has also been characterized experimentally (Barrowman et al., 34:57-60 (1986)). Additional gene candidates from *Pseudomonas stutzeri, Pseudomonas fluorescens* and other organisms can be inferred by sequence homology or identified using a growth selection system developed in *Pseudomonas putida* (Henning et al., *Appl. Environ. Microbiol.* 72:7510-7517 (2006)). The protein sequences for each of these exemplary gene products, if available, can be found using the following GenBank accession numbers shown in Table 49.

TABLE 49

| Gene | Accession No. | GI No. | Organism |
| --- | --- | --- | --- |
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian et al., 102:10670-10675 (2005)) has been cloned and functionally expressed in other internal projects at Genomatica. However, it is not an ideal candidate for strain engineering because it is large (~130 kDa) and GC-rich. KDC enzyme activity has been detected in several species of rhizobia including *Bradyrhizobium japonicum* and *Mesorhizobium loti* (Green et al., 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka et al., 288:22-28 (1991)). The first twenty amino acids starting from the N-terminus were sequenced MTYKAPVKDVKFLLD-KVFKV (SEQ ID NO: 3) (Shigeoka and Nakano, 288:22-28 (1991)). The gene could be identified by testing candidate genes containing this N-terminal sequence for KDC activity. The protein sequences for each of these exemplary gene products, if available, can be found using the following GenBank accession numbers shown in Table 50.

TABLE 50

| Gene | Accession No. | GI No. | Organism |
| --- | --- | --- | --- |
| kgd | O50463.4 | 160395583 | *Mycobacterium tuberculosis* |
| kgd | NP_767092.1 | 27375563 | *Bradyrhizobium japonicum* |
| kgd | NP_105204.1 | 13473636 | *Mesorhizobium loti* |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku et al., 263:18386-18396 (1988); Smit et al., 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., 71:303-311 (2005)). The enzyme has been structurally characterized (Berg et al., 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., 18:345-357 (2005)), so this enzyme would be a promising candidate for directed engineering. Decarboxylation of alpha-ketoglutarate by a BCKA was detected in *Bacillus subtilis*; however, this activity was low (5%) relative to activity on other branched-chain substrates (Oku and Kaneda, 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. The protein sequence for the exemplary gene product, if available, can be found using the following GenBank accession numbers shown in Table 51.

TABLE 51

| Gene | Accession No. | GI No. | Organism |
|------|---------------|--------|----------|
| kdcA | AAS49166.1 | 44921617 | Lactococcus lactis |

Recombinant branched chain alpha-keto acid decarboxylase enzymes derived from the E1 subunits of the mitochondrial branched-chain keto acid dehydrogenase complex from Homo sapiens and Bos taurus have been cloned and functionally expressed in E. coli (Davie et al., 267:16601-16606 (1992); Wynn et al., 267:12400-12403 (1992); Wynn et al., 267:1881-1887 (1992)). In these studies, the authors found that co-expression of chaperonins GroEL and GroES enhanced the specific activity of the decarboxylase by 500-fold (Wynn et al., 267:12400-12403 (1992)). These enzymes are composed of two alpha and two beta subunits. The protein sequences for each of these exemplary gene products, if available, can be found using the following GenBank accession numbers shown in Table 52.

TABLE 52

| Gene | Accession No. | GI No. | Organism |
|------|---------------|--------|----------|
| BCKDHB | NP_898871.1 | 34101272 | Homo sapiens |
| BCKDHA | NP_000700.1 | 11386135 | Homo sapiens |
| BCKDHB | P21839 | 115502434 | Bos taurus |
| BCKDHA | P11178 | 129030 | Bos taurus |

6.2.1.a CoA Synthetase

Step I of FIG. 1 involves CoA synthetase or ligase reactions for succinate or 4-hydroxybutyrate as the substrates. Exemplary genes encoding enzymes likely to carry out these transformations include the sucCD genes of E. coli which naturally form a succinyl-CoA synthetase complex. This enzyme complex naturally catalyzes the formation of succinyl-CoA from succinate with the concaminant consumption of one ATP, a reaction which is reversible in vivo (Buck et al., Biochem. 24:6245-6252 (1985)). The protein sequences for each of these exemplary gene products, if available, can be found using the following GenBank accession numbers shown in Table 53.

TABLE 53

| Gene | Accession No. | GI No. | Organism |
|------|---------------|--------|----------|
| sucC | NP_415256.1 | 16128703 | Escherichia coli |
| sucD | AAC73823.1 | 1786949 | Escherichia coli |

Additional exemplary CoA-ligases include the rat dicarboxylate-CoA ligase for which the sequence is yet uncharacterized (Vamecq et al., Biochemical Journal 230:683-693 (1985)), either of the two characterized phenylacetate-CoA ligases from P. chrysogenum (Lamas-Maceiras et al., Biochem. J. 395:147-155 (2005); Wang et al., Biochem Biophy Res Commun 360 (2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from Bacillus subtilis (Bower et al., J. Bacteriol. 178 (14):4122-4130 (1996)). Additional candidate enzymes are acetoacetyl-CoA synthetases from Mus musculus (Hasegawa et al., Biochim Biophys Acta 1779:414-419 (2008)) and Homo sapiens (Ohgami et al., Biochem Pharmacol 65:989-994 (2003)) which naturally catalyze the ATP-dependant conversion of acetoacetate into acetoacetyl-CoA. 4-hydroxybutyryl-CoA synthetase activity has been demonstrated in Metallosphaera sedula (Berg et al., Science 318: 1782-1786 (2007)). This function has been tentatively assigned to the Msed_1422 gene. The protein sequences for each of these exemplary gene products, if available, can be found using the following GenBank accession numbers shown in Table 54.

TABLE 54

| Gene | Accession No. | GI No. | Organism |
|------|---------------|--------|----------|
| phl | CAJ15517.1 | 77019264 | Penicillium chrysogenum |
| phlB | ABS19624.1 | 152002983 | Penicillium chrysogenum |
| paaF | AAC24333.2 | 22711873 | Pseudomonas putida |
| bioW | NP_390902.2 | 50812281 | Bacillus subtilis |
| AACS | NP_084486.1 | 21313520 | Mus musculus |
| AACS | NP_076417.2 | 31982927 | Homo sapiens |
| Msed_1422 | YP_001191504 | 146304188 | Metallosphaera sedula |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from Archaeoglobus fulgidus, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., J Bacteriol 184:636-644 (2002)). The enzyme from Haloarcula marismortui (annotated as a succinyl-CoA synthetase) accepts propionate, butyrate, and branched-chain acids (isovalerate and isobutyrate) as substrates, and was shown to operate in the forward and reverse directions (Brasen et al., Arch Microbiol 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen et al., supra). The enzymes from A. fulgidus, H. marismortui and P. aerophilum have all been cloned, functionally expressed, and characterized in E. coli (Musfeldt et al., supra; Brasen et al., supra). The protein sequences for each of these exemplary gene products, if available, can be found using the following GenBank accession numbers shown in Table 55.

TABLE 55

| Gene | Accession No. | GI No. | Organism |
|------|---------------|--------|----------|
| AF1211 | NP_070039.1 | 11498810 | Archaeoglobus fulgidus DSM 4304 |
| scs | YP_135572.1 | 55377722 | Haloarcula marismortui ATCC 43049 |
| PAE3250 | NP_560604.1 | 18313937 | Pyrobaculum aerophilum str. IM2 |

EXAMPLE III

Biosynthesis of 4-Hydroxybutanoic Acid (4-HB)

This example describes exemplary biochemical pathways for 4-HB production. 4-HB is the common intermediate for both 14-BDO and GBL productions.

Previous reports of 4-HB synthesis in microbes have focused on this compound as an intermediate in production of the biodegradable plastic poly-hydroxyalkanoate (PHA) (U.S. Pat. No. 6,117,658). The use of 4-HB/3-hydroxybutyrate (3-HB) copolymers over poly-3-hydroxybutyrate polymer (PHB) can result in plastic that is less brittle (Saito and Doi, Intl. J. Biol. Macromol. 16:99-104 (1994)). The production of monomeric 4-HB described herein is a fundamentally distinct process for several reasons: (1) the product is secreted, as opposed to PHA which is produced intracellularly and remains in the cell; (2) for organisms that produce hydroxybutanoate polymers, free 4-HB is not produced, but rather the Coenzyme A derivative is used by the polyhydroxyalkanoate synthase; (3) in the case of the polymer, formation of the granular product changes thermodynamics; and (4) extracellular pH is not an issue for production of the polymer, whereas it will affect whether 4-HB is present in the free acid or conjugate base state, and also the equilibrium between 4-HB and GBL.

4-HB can be produced in two enzymatic reduction steps from succinate, a central metabolite of the TCA cycle, with succinic semialdehyde as the intermediate (FIG. 1). The first of these enzymes, succinic semialdehyde dehydrogenase, is native to many organisms including E. coli, in which both NADH- and NADPH-dependent enzymes have been found (Donnelly and Cooper, Eur. J. Biochem. 113:555-561 (1981); Donnelly and Cooper, J. Bacteriol. 145:1425-1427 (1981); Marek and Henson, J. Bacteriol. 170:991-994 (1988)). There is also evidence supporting succinic semialdehyde dehydrogenase activity in S. cerevisiae (Ramos et al., Eur. J. Biochem. 149:401-404 (1985)), and a putative gene has been identified by sequence homology. However, most reports indicate that this enzyme proceeds in the direction of succinate synthesis (Donnelly and Cooper, supra; Lutke-Eversloh and Steinbuchel, FEMS Microbiol. Lett. 181:63-71 (1999)), participating in the degradation pathway of 4-HB and gamma-aminobutyrate. Succinic semialdehyde also is natively produced by certain microbial organisms such as E. coli through the TCA cycle intermediate α-ketogluterate via the action of two enzymes: glutamate: succinic semialdehyde transaminase and glutamate decarboxylase. An alternative pathway, used by the obligate anaerobe Clostridium kluyveri to degrade succinate, activates succinate to succinyl-CoA, then converts succinyl-CoA to succinic semialdehyde using an alternative succinic semialdehyde dehydrogenase which is known to function in this direction (Sohling and Gottschalk, Eur. J. Biochem. 212:121-127 (1993)). However, this route has the energetic cost of ATP required to convert succinate to succinyl-CoA.

The second enzyme of the pathway, 4-hydroxybutanoate dehydrogenase, is not native to E. coli or yeast but is found in various bacteria such as C. kluyveri and Ralstonia eutropha (Lutke-Eversloh et al., FEMS Microbiol Lett. 181:63-71 (1999); Sohling et al., J. Bacteriol. 178:871-880 (1996); Wolff et al., Protein Expr. Purif. 6:206-212 (1995); Valentin et al., Eur. J Biochem. 227:43-60 (1995)). These enzymes are known to be NADH-dependent, though NADPH-dependent forms also exist. An additional pathway to 4-HB from alpha-ketoglutarate was demonstrated in E. coli resulting in the accumulation of poly(4-HB) (Song et al., Wei Sheng Wu Xue. Bao. 45:382-386 (2005)). The recombinant strain required the overexpression of three heterologous genes, PHA synthase (R. eutropha), 4-hydroxybutyrate dehydrogenase (R. eutropha) and 4-hydroxybutyrate:CoA transferase (C. kluyveri), along with two native E. coli genes: glutamate: succinic semialdehyde transaminase and glutamate decarboxylase. Alpha-ketoglutarate can be directly converted to succinic semialdehyde by an alpha-ketoglutarate decarboxylase such as the one identified in Euglena gracilis (Shigeoka et al., Arch. Biochem. Biophys. 288:22-28 (1991); Shigeoka et al., Biochem. J. 282 (Pt 2):319-323 (1992); Shigeoka et al., Biochem. J. 292 (Pt 2):463-467 (1993)). However, this enzyme has not previously been applied to impact the production of 4-HB or related polymers in any organism.

The microbial production capabilities of 4-HB were explored in two microbes, E. coli and S. cerevisiae, using in silico metabolic models of each organism. Potential pathways to 4-HB proceed via a succinate, succinyl-CoA, or alpha-ketoglutarate intermediate as shown in FIG. 1.

A first step in the 4-HB production pathway from succinate involves the conversion of succinate to succinic semialdehyde via an NADH- or NADPH-dependant succinic semialdehyde dehydrogenase. In E. coli, gabD is an NADP-dependant succinic semialdehyde dehydrogenase and is part of a gene cluster involved in 4-aminobutyrate uptake and degradation (Schneider et al., J. Bacteriol. 184:6976-6986 (2002); Niegemann et al., Arch. Microbiol 160:454-460 (1993)). sad is believed to encode the enzyme for NAD-dependant succinic semialdehyde dehydrogenase activity (Marek et al., J. Bacteriol. 170:991-994 (1988)). S. cerevisiae contains only the NADPH-dependant succinic semialdehyde dehydrogenase, putatively assigned to UGA2, which localizes to the cytosol (Huh et al., 425:686-691 (2003)). The maximum yield calculations assuming the succinate pathway to 4-HB in both E. coli and S. cerevisiae require only the assumption that a non-native 4-HB dehydrogenase has been added to their metabolic networks.

The pathway from succinyl-CoA to 4-hydroxybutyrate was described in U.S. Pat. No. 6,117,658 as part of a process for making polyhydroxyalkanoates comprising 4-hydroxybutyrate monomer units. Clostridium kluyveri is one example organism known to possess CoA-dependant succinic semialdehyde dehydrogenase activity (Sohling et al., Eur. J. Biochem. 212:121-127 (1993); Sohling and Gottschalk, J Bacteriol. 178:871-880 (1996)). In this study, it is assumed that this enzyme, from C. kluyveri or another organism, is expressed in E. coli or S. cerevisiae along with a non-native or heterologous 4-HB dehydrogenase to complete the pathway from succinyl-CoA to 4-HB. The pathway from alpha-ketoglutarate to 4-HB was demonstrated in E. coli resulting in the accumulation of poly(4-hydroxybutyric acid) to 30% of dry cell weight (Song et al., Wei Sheng Wu Xue. Bao. 45:382-386 (2005)). As E. coli and S. cerevisiae natively or endogenously possess both glutamate:succinic semialdehyde transaminase and glutamate decarboxylase (Coleman et al., J Biol. Chem. 276:244-250 (2001)), the pathway from alpha-ketoglutarate to 4-HB can be completed in both organisms by assuming only that a non-native 4-HB dehydrogenase is present.

EXAMPLE IV

Biosynthesis of 1,4-Butanediol from Succinate and Alpha-Ketoglutarate

This example illustrates the construction and biosynthetic production of 4-HB and 14-BDO from microbial organisms. Pathways for 4-HB and 14-BDO are disclosed herein.

There are several alternative enzymes that can be utilized in the pathway described above. The native or endogenous enzyme for conversion of succinate to succinyl-CoA can be replaced by a CoA transferase such as that encoded by the cat1 gene C. kluyveri (Sohling and Gottschalk, Eur. J Biochem. 212:121-127 (1993)), which functions in a similar manner to the conversion of 4-HB to 4-hydroxybutyryl-CoA.

However, the production of acetate by this enzyme may not be optimal, as it might be secreted rather than being converted back to acetyl-CoA. In this respect, it also can be beneficial to eliminate acetate formation. As one alternative to this CoA transferase, a mechanism can be employed in which the 4-HB is first phosphorylated by ATP and then converted to the CoA derivative, similar to the acetate kinase/phosphotransacetylase pathway in E. coli for the conversion of acetate to acetyl-CoA. The net cost of this route is one ATP, which is the same as is required to regenerate acetyl-CoA from acetate. The enzymes phosphotransbutyrylase (ptb) and butyrate kinase (bk) are known to carry out these steps on the non-hydroxylated molecules for butyrate production in C. acetobutylicum (Cary et al., Appl Environ Microbiol 56:1576-1583 (1990); Valentine, R. C. and R. S. Wolfe, J Biol. Chem. 235:1948-1952 (1960)). These enzymes are reversible, allowing synthesis to proceed in the direction of 4-HB.

14-BDO also can be produced via alpha-ketoglutarate in addition to or instead of through succinate. As described herein, one pathway to accomplish product biosynthesis is with the production of succinic semialdehyde via alpha-ketoglutarate using the endogenous enzymes. An alternative is to use an alpha-ketoglutarate decarboxylase that can perform this conversion in one step (Tian et al., Proc Natl Acad Sci US.A 102:10670-10675 (2005)).

For the construction of different strains of 14-BDO-producing microbial organisms, a list of applicable genes was assembled for corroboration. Briefly, one or more genes within the 4-HB and/or 14-BDO biosynthetic pathways were identified for each step of the complete 14-BDO-producing pathway shown in FIG. 1, using available literature resources, the NCBI genetic database, and homology searches. The genes cloned and assessed in this study are presented below in Table 56, along with the appropriate references and gene accession and GI numbers to the polypeptide sequence. As discussed further below, some genes were synthesized for codon optimization while others were cloned via PCR from the genomic DNA of the native or wild-type organism. For some genes both approaches were used, and in this case the native genes are indicated by an "n" suffix to the gene identification number when used in an experiment. Note that only the DNA sequences differ; the proteins are identical.

TABLE 56

Genes expressed in host 14-BDO-producting microbial organisms.

| Gene ID number | Reaction (FIG. 1) | Gene name | Source organism | Enzyme name | GI number | Reference |
|---|---|---|---|---|---|---|
| 0001 | T | Cat2 | Clostridium kluyveri DSM 555 | 4-hydroxybutyrate coenzyme A transferase | 1228100 | 1 |
| 0002 | Q/E | adhE | Clostridium acetobutylicum ATCC 824 | Aldehyde/alcohol dehydrogenase | 15004739 | 2 |
| 0003 | Q/E | adhE2 | Clostridium acetobutylicum ATCC 824 | Aldehyde/alcohol dehydrogenase | 15004865 | 2 |
| 0004 | G | Cat1 | Clostridium kluyveri DSM 555 | Succinate coenzyme A transferase | 1228100 | 1 |
| 0008 | A | sucD | Clostridium kluyveri DSM 555 | Succinic semialdehyde dehydrogenase (CoA-dependent) | 1228100 | 1 |
| 0009 | C | 4-HBd | Ralstonia eutropha H16 | 4-hydroxybutyrate dehydrogenase (NAD-dependent) | 113867564 | 2 |
| 0010 | C | 4-HBd | Clostridium kluyveri DSM 555 | 4-hydroxybutyrate dehydrogenase (NAD-dependent) | 1228100 | 1 |
| 0011 | Q/E | adhE | E. coli | Aldehyde/alcohol dehydrogenase | 16129202 | |
| 0012 | Q/E | yqhD | E. coli | Aldehyde/alcohol dehydrogenase | 1630909 | |
| 0013 | E | bdhB | Clostridium acetobutylicum ATCC 824 | Butanol dehydrogenase II | 1586542 | 2 |
| 0020 | P | ptb | Clostridium acetobutylicum ATCC 824 | Phosphotransbutyrylase | 15896327 | 2 |
| 0021 | O | buk1 | Clostridium acetobutylicum ATCC 824 | Butyrate kinase I | 20137334 | 2 |
| 0022 | O | buk2 | Clostridium acetobutylicum ATCC 824 | Butyrate kinase II | 20137415 | 2 |
| 0023 | E | adhEm | isolated from metalibrary of anaerobic sewage digester microbial consortia | Alcohol dehydrogenase | | 8 |
| 0024 | E | adhE | Clostridium thermocellum | Alcohol dehydrogenase | 125972944 | |
| 0025 | E | ald | Clostridium beijerinckii | Coenzyme A-acylating aldehyde dehydrogenase | 49036681 | 9 |

TABLE 56-continued

Genes expressed in host 14-BDO-producting microbial organisms.

| Gene ID number | Reaction (FIG. 1) | Gene name | Source organism | Enzyme name | GI number | Reference |
|---|---|---|---|---|---|---|
| 0026 | E | bdhA | *Clostridium acetobutylicum* ATCC 824 | Butanol dehydrogenase | 15896543 | 2 |
| 0027 | Q | bld | *Clostridium saccharoperbutylacetonicum* | Butyraldehyde dehydrogenase | 31075383 | 4 |
| 0028 | E | bdh | *Clostridium saccharoperbutylacetonicum* | Butanol dehydrogenase | 124221917 | 4 |
| 0029 | Q/E | adhE | *Clostridium tetani* | Aldehyde/alcohol dehydrogenase | 28211045 | |
| 0030 | Q/E | adhE | *Clostridium perfringens* | Aldehyde/alcohol dehydrogenase | 18311513 | |
| 0031 | Q/E | adhE | *Clostridium difficile* | Aldehyde/alcohol dehydrogenase | 126700586 | |
| 0032 | B | sucA | *Mycobacterium bovis* BCG, Pasteur | alpha-ketoglutarate decarboxylase | 121637177 | 5 |
| 0033 | T | cat2 | *Clostridium aminobutyricum* | 4-hydroxybutyrate coenzyme A transferase | 6249316 | |
| 0034 | T | cat2 | *Porphyromonas gingivalis* W83 | 4-hydroxybutyrate coenzyme A transferase | 34541558 | |
| 0035 | A | sucD | *Porphyromonas gingivalis* W83 | Succinic semialdehyde dehydrogenase (CoA-dependent) | 34540484 | |
| 0036 | C | 4-HBd | *Porphyromonas gingivalis* W83 | NAD-dependent 4-hydroxybutyrate dehydrogenase | 34540485 | |
| 0037 | C | gbd | Uncultured bacterium | 4-hydroxybutyrate dehydrogenase | 5916168 | 6 |
| 0038 | G | sucCD | *E. coli* | Succinyl-CoA synthetase | 16128703 and 16128704 | |

1 Sohling and Gottschalk, *Eur. J. Biochem.* 212: 121-127 (1993); Sohling and Gottschalk, *J. Bacterial.* 178: 871-880 (1996)
2 Nolling et al., J., *J. Bacterial.* 183: 4823-4838 (2001)
[3]Pohlmann et al., *Nat. Biotechnol.* 24: 1257-1262 (2006)
4 Kosaka et al., *Biosci. Biotechnol. Biochem.* 71: 58-68 (2007)
5 Brosch et al., *Proc. Natl. Acad. Sci. U.S.A.* 104: 5596-5601 (2007)
6 Henne et al., *Appl. Environ. Microbiol.* 65: 3901-3907 (1999)
[7](Fontaine et al., *J Bacteriol.* 184: 821-830 (2002))
8 (Wexler et al., *Environ Microbiol* 7: 1917-1926 (2005))
9 (Toth et al., *Appl Environ Microbiol* 65: 4973-4980 (1999))

Expression Vector Construction for 14-BDO Pathway.

Vector backbones and some strains were obtained from Dr. Rolf Lutz of Expressys. The vectors and strains are based on the pZ Expression System developed by Dr. Rolf Lutz and Prof. Hermann Bujard (Lutz, R. and H. Bujard, *Nucleic Acids Res* 25:1203-1210 (1997)). Vectors obtained were pZE13luc, pZA33luc, pZS*13luc and pZE22luc and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

```
lacZalpha-RI
                                      (SEQ ID NO: 4)
5'GACGAATTCGCTAGCAAGAGGAGAAGTCGACATGTCCAATTCACTGG
CCGTCGTTTTAC3' lacZalpha 3'BB
                                      (SEQ ID NO: 5)
5'-GACCCTAGGAAGCTTTCTAGAGTCGACCTATGCGGCATCAGAGCA
GA-3'.
```

This generated a fragment with a 5' end of EcoRI site, NheI site, a Ribosomal Binding Site, a SalI site and the start codon. On the 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a NheI/XbaI non-site that is not digested by either enzyme), the genes cloned into the vectors could be "Biobricked" together. Briefly, this method allows joining an unlimited number of genes into the vector using the same 2 restriction sites (as long as the sites do not appear internal to the genes), because the sites between the genes are destroyed after each addition.

All vectors have the pZ designation followed by letters and numbers indication the origin of replication, antibiotic resistance marker and promoter/regulatory unit. The origin of replication is the second letter and is denoted by E for ColE1, A for p15A and S for pSC101-based origins. The first number represents the antibiotic resistance marker (1 for Ampicillin, 2 for Kanamycin, 3 for Chloramphenicol, 4 for Spectinomycin and 5 for Tetracycline). The final number defines the promoter that regulated the gene of interest (1 for $P_{LtetO-1}$, 2 for $P_{LlacO-1}$, 3 for $P_{AllacO-1}$, and 4 for $P_{lac/ara-1}$). The MCS and the gene of interest follows immediately after. For the work discussed here we employed two base vectors, pZA33 and pZE13, modified for the biobricks insertions as discussed above. Once the gene(s) of interest have been cloned into them, resulting plasmids are indicated using the four digit gene codes given in Table 56; e.g., pZA33-XXXX-YYYY- . . . .

Host Strain Construction.

The parent strain in all studies described here is *E. coli* K-12 strain MG1655. Markerless deletion strains in adhE, gabD, and aldA were constructed under service contract by a third party using the redET method (Datsenko, K. A. and B. L. Wanner, *Proc Natl Acad Sci USA* 97:6640-6645 (2000)). Subsequent strains were constructed via bacteriophage P1 mediated transduction (Miller, J. Experiments in Molecular Genetics, Cold Spring Harbor Laboratories, New York (1973)). Strain C600Z1 (lacI$^q$, PN25-tetR, Sp$^R$, lacY1, leuB6, mcrB+, supE44, thi-1, thr-1, tonA21) was obtained from Expressys and was used as a source of a lacIq allele for P1 transduction. Bacteriophage P1vir was grown on the C600Z1 *E. coli* strain, which has the spectinomycin resistance gene linked to the lacI$^q$. The P1 lysate grown on C600Z1 was used to infect MG1655 with selection for spectinomycin resistance. The spectinomycin resistant colonies were then screened for the linked lacI$^q$ by determining the ability of the transductants to repress expression of a gene linked to a $P_{AllacO-1}$ promoter. The resulting strain was designated MG1655 lacI$^q$. A similar procedure was used to introduce lacI$^Q$ into the deletion strains.

Production of 4-HB from Succinate.

For construction of a 4-HB producer from succinate, genes encoding steps from succinate to 4-HB and 4-HB-CoA (Steps G, A, C, O in FIG. 1) were assembled onto the pZA33 and pZE13 vectors as described below. Various combinations of genes were assessed, as well as different constructs bearing incomplete pathways as controls (Tables 2 and 3). The plasmids were then transformed into host strains containing lacI$^Q$, which allow inducible expression by addition of isopropyl β-D-1-thiogalactopyranoside (IPTG). Both wild-type and hosts with deletions in genes encoding the native succinic semialdehyde dehydrogenase were tested.

Activity of the heterologous enzymes were first tested in in vitro assays, using strain MG1655 lacI$^Q$ as the host for the plasmid constructs containing the pathway genes. Cells were grown aerobically in LB media (Difco) containing the appropriate antibiotics for each construct, and induced by addition of IPTG at 1 mM when the optical density (OD600) reached approximately 0.5. Cells were harvested after 6 hours, and enzyme assays conducted as discussed below.

In Vitro Enzyme Assays.

To obtain crude extracts for activity assays, cells were harvested by centrifugation at 4,500 rpm (Beckman-Coulter, Allegera X-15R) for 10 min. The pellets were resuspended in 0.3 mL BugBuster (Novagen) reagent with benzonase and lysozyme, and lysis proceeded for 15 minutes at room temperature with gentle shaking Cell-free lysate was obtained by centrifugation at 14,000 rpm (Eppendorf centrifuge 5402) for 30 min at 4° C. Cell protein in the sample was determined using the method of Bradford et al., *Anal. Biochem.* 72:248-254 (1976), and specific enzyme assays conducted as described below. Activities are reported in Units/mg protein, where a unit of activity is defined as the amount of enzyme required to convert 1 μmol of substrate in 1 min. at room temperature. In general, reported values are averages of at least 3 replicate assays.

Succinyl-CoA transferase (Cat1) activity was determined by monitoring the formation of acetyl-CoA from succinyl-CoA and acetate, following a previously described procedure Sohling and Gottschalk, *J. Bacteriol.* 178:871-880 (1996). Succinyl-CoA synthetase (SucCD) activity was determined by following the formation of succinyl-CoA from succinate and CoA in the presence of ATP. The experiment followed a procedure described by Cha and Parks, *J. Biol. Chem.* 239: 1961-1967 (1964). CoA-dependent succinate semialdehyde dehydrogenase (SucD) activity was determined by following the conversion of NAD to NADH at 340 nm in the presence of succinate semialdehyde and CoA (Sohling and Gottschalk, *Eur. J. Biochem.* 212:121-127 (1993)). 4-HB dehydrogenase (4-HBd) enzyme activity was determined by monitoring the oxidation of NADH to NAD at 340 nm in the presence of succinate semialdehyde. The experiment followed a published procedure Gerhardt et al. *Arch. Microbiol.* 174:189-199 (2000). 4-HB CoA transferase (Cat2) activity was determined using a modified procedure from Scherf and Buckel, *Appl. Environ. Microbiol.* 57:2699-2702 (1991). The formation of 4-HB-CoA or butyryl-CoA formation from acetyl-CoA and 4-HB or butyrate was determined using HPLC.

Alcohol (ADH) and aldehyde (ALD) dehydrogenase was assayed in the reductive direction using a procedure adapted from several literature sources (Durre et al., *FEMS Microbiol. Rev.* 17:251-262 (1995); Palosaari and Rogers, *J. Bacteriol.* 170:2971-2976 (1988) and Welch et al., *Arch. Biochem. Biophys.* 273:309-318 (1989)). The oxidation of NADH is followed by reading absorbance at 340 nM every four seconds for a total of 240 seconds at room temperature. The reductive assays were performed in 100 mM MOPS (adjusted to pH 7.5 with KOH), 0.4 mM NADH, and from 1 to 50 μl of cell extract. The reaction is started by adding the following reagents: 100 μl of 100 mM acetaldehyde or butyraldehyde for ADH, or 100 μl of 1 mM acetyl-CoA or butyryl-CoA for ALD. The Spectrophotometer is quickly blanked and then the kinetic read is started. The resulting slope of the reduction in absorbance at 340 nM per minute, along with the molar extinction coefficient of NAD(P)H at 340 nM (6000) and the protein concentration of the extract, can be used to determine the specific activity.

The enzyme activity of PTB is measured in the direction of butyryl-CoA to butyryl-phosphate as described in Cary et al. *J. Bacteriol.* 170:4613-4618 (1988). It provides inorganic phosphate for the conversion, and follows the increase in free CoA with the reagent 5,5'-dithiobis-(2-nitrobenzoic acid), or DTNB. DTNB rapidly reacts with thiol groups such as free CoA to release the yellow-colored 2-nitro-5-mercaptobenzoic acid (TNB), which absorbs at 412 nm with a molar extinction coefficient of 14,140 M cm$^{-1}$. The assay buffer contained 150 mM potassium phosphate at pH 7.4, 0.1 mM DTNB, and 0.2 mM butyryl-CoA, and the reaction was started by addition of 2 to 50 μL cell extract. The enzyme activity of BK is measured in the direction of butyrate to butyryl-phosphate formation at the expense of ATP. The procedure is similar to the assay for acetate kinase previously described Rose et al., *J. Biol. Chem.* 211:737-756 (1954). However we have found another acetate kinase enzyme assay protocol provided by Sigma to be more useful and sensitive. This assay links conversion of ATP to ADP by acetate kinase to the linked conversion of ADP and phosphoenol pyruvate (PEP) to ATP and pyruvate by pyruvate kinase, followed by the conversion of pyruvate and NADH to lactate and $NAD^+$ by lactate dehydrogenase. Substituting butyrate for acetate is the only major modification to allow the assay to follow BK enzyme activity. The assay mixture contained 80 mM triethanolamine buffer at pH 7.6, 200 mM sodium butyrate, 10 mM $MgCl_2$, 0.1 mM NADH, 6.6 mM ATP, 1.8 mM phosphoenolpyruvate. Pyruvate kinase, lactate dehydrogenase, and myokinase were added according to the manufacturer's instructions. The reaction was started by adding 2 to 50 μL cell extract, and the reaction was monitored based on the decrease in absorbance at 340 nm indicating NADH oxidation.

Analysis of CoA Derivatives by HPLC.

An HPLC based assay was developed to monitor enzymatic reactions involving coenzyme A (CoA) transfer. The developed method allowed enzyme activity characterization by quantitative determination of CoA, acetyl CoA (AcCoA), butyryl CoA (BuCoA) and 4-hydroxybutyrate CoA (4-HB-CoA) present in in-vitro reaction mixtures. Sensitivity down to low μM was achieved, as well as excellent resolution of all the CoA derivatives of interest.

Chemical and sample preparation was performed as follows. Briefly, CoA, AcCoA, BuCoA and all other chemicals, were obtained from Sigma-Aldrich. The solvents, methanol and acetonitrile, were of HPLC grade. Standard calibration curves exhibited excellent linearity in the 0.01-1 mg/mL concentration range. Enzymatic reaction mixtures contained 100 mM Tris HCl buffer (pH 7), aliquots were taken at different time points, quenched with formic acid (0.04% final concentration) and directly analyzed by HPLC.

HPLC analysis was performed using an Agilent 1100 HPLC system equipped with a binary pump, degasser, thermostated autosampler and column compartment, and diode array detector (DAD), was used for the analysis. A reversed phase column, Kromasil 100 Sum C18, 4.6×150 mm (Peeke Scientific), was employed. 25 mM potassium phosphate (pH 7) and methanol or acetonitrile, were used as aqueous and organic solvents at 1 mL/min flow rate. Two methods were developed: a short one with a faster gradient for the analysis of well-resolved CoA, AcCoA and BuCoA, and a longer method for distinguishing between closely eluting AcCoA and 4-HBCoA. Short method employed acetonitrile gradient (0 min—5%, 6 min—30%, 6.5 min—5%, 10 min—5%) and resulted in the retention times 2.7, 4.1 and 5.5 min for CoA, AcCoA and BuCoA, respectively. In the long method methanol was used with the following linear gradient: 0 min—5%, 20 min—35%, 20.5 min—5%, 25 min—5%. The retention times for CoA, AcCoA, 4-HBCoA and BuCoA were 5.8, 8.4, 9.2 and 16.0 min, respectively. The injection volume was 5 μL, column temperature 30° C., and UV absorbance was monitored at 260 nm.

The results demonstrated activity of each of the four pathway steps (Table 57), though activity is clearly dependent on the gene source, position of the gene in the vector, and the context of other genes with which it is expressed. For example, gene 0035 encodes a succinic semialdehyde dehydrogenase that is more active than that encoded by 0008, and 0036 and 0010n are more active 4-HB dehydrogenase genes than 0009. There also seems to be better 4-HB dehydrogenase activity when there is another gene preceding it on the same operon.

TABLE 57

In vitro enzyme activities in cell extracts from MG1655 lacI$^Q$ containing the plasmids expressing genes in the 4-HB-CoA pathway. Activities are reported in Units/mg protein, where a unit of activity is defined as the amount of enzyme required to convert 1 μmol of substrate in 1 min. at room temperature.

| Sample # | pZE13 (a) | pZA33 (b) | OD600 | Cell Prot (c) | Cat1 | SucD | 4HBd | Cat2 |
|---|---|---|---|---|---|---|---|---|
| 1 | cat1 (0004) | | 2.71 | 6.43 | 1.232 | 0.00 | | |
| 2 | cat1 (0004)-sucD (0035) | | 2.03 | 5.00 | 0.761 | 2.57 | | |
| 3 | cat1 (0004)-sucD (0008) | | 1.04 | 3.01 | 0.783 | 0.01 | | |
| 4 | sucD (0035) | | 2.31 | 6.94 | | 2.32 | | |
| 5 | sucD (0008) | | 1.10 | 4.16 | | 0.05 | | |
| 6 | | 4hbd (0009) | 2.81 | 7.94 | 0.003 | | 0.25 | |
| 7 | | 4hbd (0036) | 2.63 | 7.84 | | | 3.31 | |
| 8 | | 4hbd (0010n) | 2.00 | 5.08 | | | 2.57 | |
| 9 | cat1 (0004)-sucD (0035) | 4hbd (0009) | 2.07 | 5.04 | 0.600 | 1.85 | 0.01 | |
| 10 | cat1 (0004)-sucD (0035) | 4hbd (0036) | 2.08 | 5.40 | 0.694 | 1.73 | 0.41 | |
| 11 | cat1 (0004)-sucD (0035) | 4hbd (0010n) | 2.44 | 4.73 | 0.679 | 2.28 | 0.37 | |
| 12 | cat1 (0004)-sucD (0008) | 4hbd (0009) | 1.08 | 3.99 | 0.572 | −0.01 | 0.02 | |
| 13 | cat1 (0004)-sucD (0008) | 4hbd (0036) | 0.77 | 2.60 | 0.898 | −0.01 | 0.04 | |
| 14 | cat1 (0004)-sucD (0008) | 4hbd (0010n) | 0.63 | 2.47 | 0.776 | 0.00 | 0.00 | |
| 15 | | cat2 (0034) | 2.56 | 7.86 | | | | 1.283 |
| 16 | | cat2(0034)-4hbd(0036) | 3.13 | 8.04 | | | 24.86 | 0.993 |
| 17 | | cat2(0034)-4hbd(0010n) | 2.38 | 7.03 | | | 7.45 | 0.675 |
| 18 | | 4hbd(0036)-cat2(0034) | 2.69 | 8.26 | | | 2.15 | 7.490 |
| 19 | | 4hbd(0010n)-cat2(0034) | 2.44 | 6.59 | | | 0.59 | 4.101 |

(a) Genes expressed from Plac on pZE13, a high-copy plasmid with colE1 origin and ampicillin resistance. Gene identification numbers are as given in Table 56.
(b) Genes expressed from Plac on pZA33, a medium-copy plasmid with pACYC origin and chloramphenicol resistance.
(c) Cell protein given as mg protein per mL extract.

Recombinant strains containing genes in the 4-HB pathway were then evaluated for the ability to produce 4-HB in vivo from central metabolic intermediates. Cells were grown anaerobically in LB medium to OD600 of approximately 0.4, then induced with 1 mM IPTG. One hour later, sodium succinate was added to 10 mM, and samples taken for analysis following an additional 24 and 48 hours. 4-HB in the culture broth was analyzed by GC-MS as described below. The results indicate that the recombinant strain can produce over 2 mM 4-HB after 24 hours, compared to essentially zero in the control strain (Table 58).

TABLE 58

Production of 4-HB from succinate in *E. coli* strains harboring plasmids expressing various combinations of 4-HB pathway genes.

| Sample # | Host Strain | pZE13 | pZA33 | 24 Hours OD600 | 24 Hours 4HB, µM | 24 Hours 4HB norm. (a) | 48 Hours OD600 | 48 Hours 4HB, µM | 48 Hours 4HB norm. (a) |
|---|---|---|---|---|---|---|---|---|---|
| 1 | MG1655 lacIq | cat1 (0004)-sucD (0035) | 4hbd (0009) | 0.47 | 487 | 1036 | 1.04 | 1780 | 1711 |
| 2 | MG1655 lacIq | cat1 (0004)-sucD (0035) | 4hbd (0027) | 0.41 | 111 | 270 | 0.99 | 214 | 217 |
| 3 | MG1655 lacIq | cat1 (0004)-sucD (0035) | 4hbd (0036) | 0.47 | 863 | 1835 | 0.48 | 2152 | 4484 |
| 4 | MG1655 lacIq | cat1 (0004)-sucD (0035) | 4hbd (0010n) | 0.46 | 956 | 2078 | 0.49 | 2221 | 4533 |
| 5 | MG1655 lacIq | cat1 (0004)-sucD (0008) | 4hbd (0009) | 0.38 | 493 | 1296 | 0.37 | 1338 | 3616 |
| 6 | MG1655 lacIq | cat1 (0004)-sucD (0008) | 4hbd (0027) | 0.32 | 26 | 81 | 0.27 | 87 | 323 |
| 7 | MG1655 lacIq | cat1 (0004)-sucD (0008) | 4hbd (0036) | 0.24 | 506 | 2108 | 0.31 | 1448 | 4672 |
| 8 | MG1655 lacIq | cat1 (0004)-sucD (0008) | 4hbd (0010n) | 0.24 | 78 | 324 | 0.56 | 233 | 416 |
| 9 | MG1655 lacIq gabD | cat1 (0004)-sucD (0035) | 4hbd (0009) | 0.53 | 656 | 1237 | 1.03 | 1643 | 1595 |
| 10 | MG1655 lacIq gabD | cat1 (0004)-sucD (0035) | 4hbd (0027) | 0.44 | 92 | 209 | 0.98 | 214 | 218 |
| 11 | MG1655 lacIq gabD | cat1 (0004)-sucD (0035) | 4hbd (0036) | 0.51 | 1072 | 2102 | 0.97 | 2358 | 2431 |
| 12 | MG1655 lacIq gabD | cat1 (0004)-sucD (0035) | 4hbd (0010n) | 0.51 | 981 | 1924 | 0.97 | 2121 | 2186 |
| 13 | MG1655 lacIq gabD | cat1 (0004)-sucD (0008) | 4hbd (0009) | 0.35 | 407 | 1162 | 0.77 | 1178 | 1530 |
| 14 | MG1655 lacIq gabD | cat1 (0004)-sucD (0008) | 4hbd (0027) | 0.51 | 19 | 36 | 1.07 | 50 | 47 |
| 15 | MG1655 lacIq gabD | cat1 (0004)-sucD (0008) | 4hbd (0036) | 0.35 | 584 | 1669 | 0.78 | 1350 | 1731 |
| 16 | MG1655 lacIq gabD | cat1 (0004)-sucD (0008) | 4hbd (0010n) | 0.32 | 74 | 232 | 0.82 | 232 | 283 |
| 17 | MG1655 lacIq | vector only | vector only | 0.8 | 1 | 2 | 1.44 | 3 | 2 |
| 18 | MG1655 lacIq gabD | vector only | vector only | 0.89 | 1 | 2 | 1.41 | 7 | 5 |

(a) Normalized 4-HB concentration, µM/OD600 units

An alternate to using a CoA transferase (cat1) to produce succinyl-CoA from succinate is to use the native *E. coli* sucCD genes, encoding succinyl-CoA synthetase. This gene cluster was cloned onto pZE13 along with candidate genes for the remaining steps to 4-HB to create pZE13-0038-0035-0036.

Production of 4-HB from Glucose.

Figure 2:
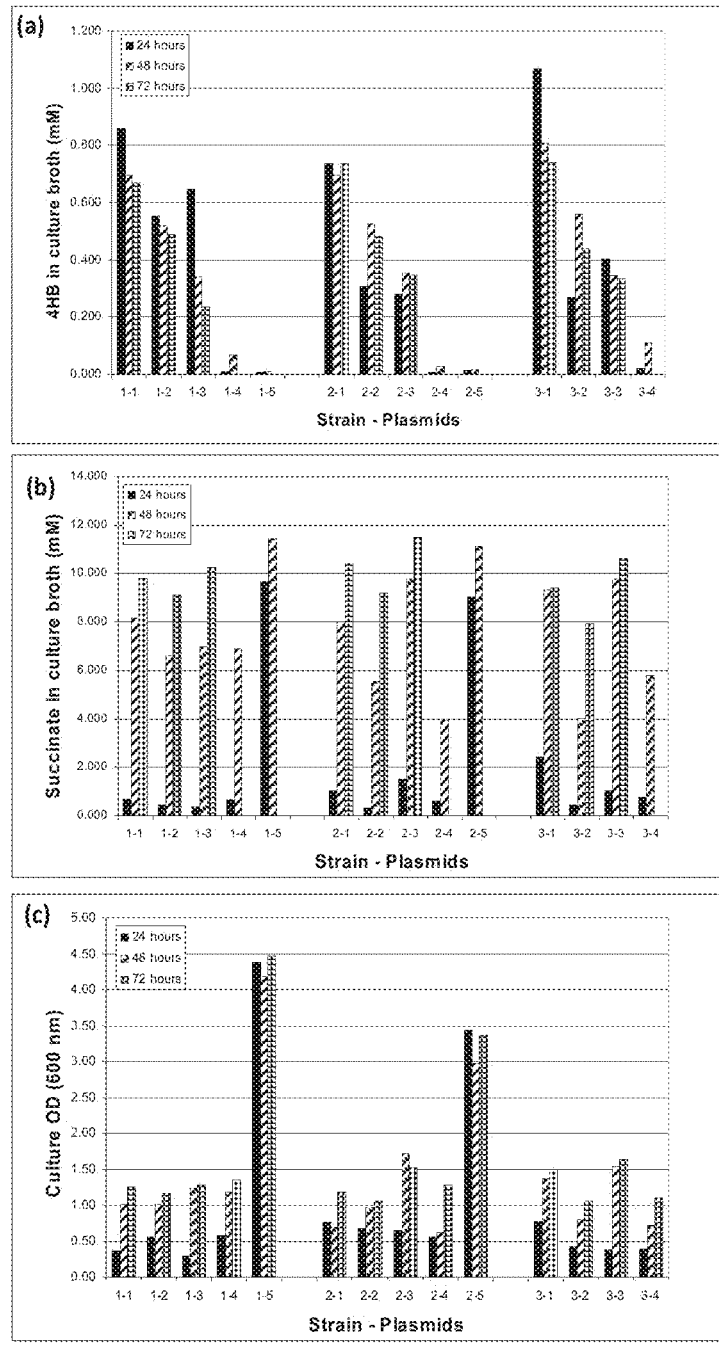
FIG. 2 shows the production of 4-HB in glucose minimal medium using *E. coli* strains harboring plasmids expressing various combinations of 4-HB pathway genes. (a) 4-HB concentration in culture broth; (b) succinate concentration in culture broth; (c) culture OD, measured at 600 nm. Clusters of bars represent the 24 hour, 48 hour, and 72 hour (if measured) timepoints. The codes along the x-axis indicate the strain/plasmid combination used. The first index refers to the host strain: 1, MG1655 lacI$^Q$; 2, MG1655 ΔgabD lacI$^Q$; 3, MG1655 ΔgabD ΔaldA lacI$^Q$. The second index refers to the plasmid combination used: 1, pZE13-0004-0035 and pZA33-0036; 2, pZE13-0004-0035 and pZA33-0010n; 3, pZE13-0004-0008 and pZA33-0036; 4, pZE13-0004-0008 and pZA33-0010n; 5, Control vectors pZE13 and pZA33.

Although the above experiments demonstrate a functional pathway to 4-HB from a central metabolic intermediate (succinate), an industrial process would require the production of chemicals from low-cost carbohydrate feedstocks such as glucose or sucrose. Thus, the next set of experiments was aimed to determine whether endogenous succinate produced by the cells during growth on glucose could fuel the 4-HB pathway. Cells were grown anaerobically in M9 minimal medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$) supplemented with 20 g/L glucose, 100 mM 3-(N-morpholino)propane-sulfonic acid (MOPS) to improve the buffering capacity, 10 µg/mL thiamine, and the appropriate antibiotics. 0.25 mM IPTG was added when OD600 reached approximately 0.2, and samples taken for 4-HB analysis every 24 hours following induction. In all cases 4-HB plateaued after 24 hours, with a maximum of about 1 mM in the best strains (FIG. 2a), while the succinate concentration continued to rise (FIG. 2b). This indicates that the supply of succinate to the pathway is likely not limiting, and that the bottleneck may be in the activity of the enzymes themselves or in NADH availability. Gens 0035 and 0036 are clearly the best candidates for CoA-dependent succinic semialdehyde dehydrogenase and 4-HB dehydrogenase, respectively. The elimination of one or both of the genes encoding known (gabD) or putative (aldA) native succinic semialdehyde dehydrogenases had little effect on performance. Finally, it should be noted that the cells grew to a much lower OD in the 4-HB-producing strains than in the controls (FIG. 2c).

Figure 3:
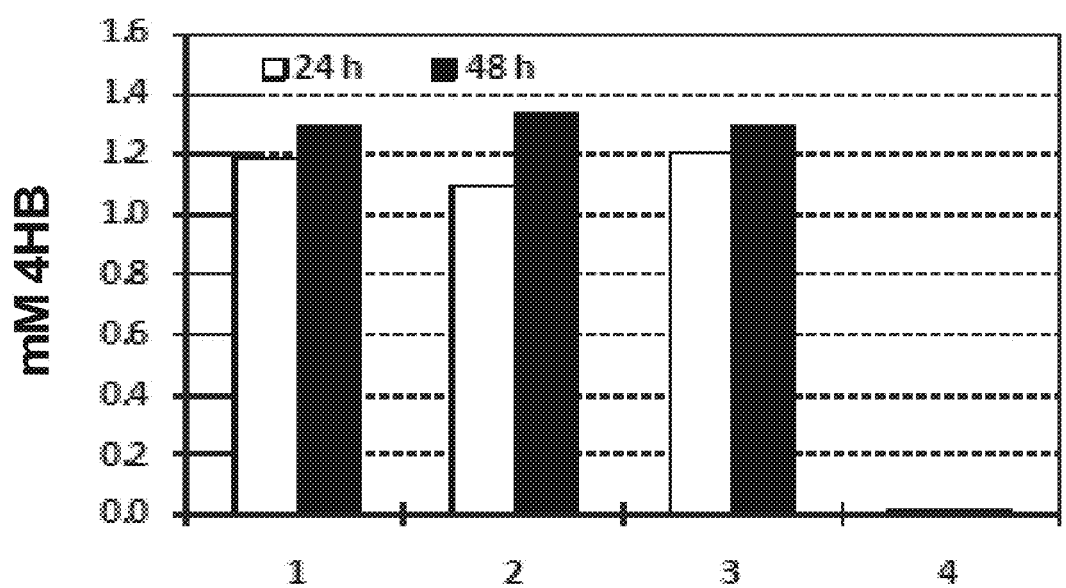
FIG. 3 shows the production of 4-HB from glucose in *E. coli* strains expressing α-ketoglutarate decarboxylase from *Mycobacterium tuberculosis*. Strains 1-3 contain pZE13-0032 and pZA33-0036. Strain 4 expresses only the empty vectors pZE13 and pZA33. Host strains are as follows: 1 and 4, MG1655 lacI$^Q$; 2, MG1655 ΔgabD lacI$^Q$; 3, MG1655 ΔgabD ΔaldA lacI$^Q$. The bars refer to concentration at 24 and 48 hours.

An alternate pathway for the production of 4-HB from glucose is via alpha-ketoglutarate. We explored the use of an alpha-ketoglutarate decarboxylase from *Mycobacterium tuberculosis* (Tian et al., Proc. Natl. Acad. Sci. USA 102: 10670-10675 (2005)) to produce succinic semialdehyde directly from alpha-ketoglutarate (Step B in FIG. 1). To demonstrate that this gene (0032) was functional in vivo, we expressed it on pZE13 in the same host as 4-HB dehydrogenase (gene 0036) on pZA33. This strain was capable of producing over 1.0 mM 4-HB within 24 hours following induction with 1 mM IPTG (FIG. 3). Since this strain does not express a CoA-dependent succinic semialdehyde dehydrogenase, the possibility of succinic semialdehyde production via succinyl-CoA is eliminated. It is also possible that the native genes responsible for producing succinic semialdehyde could function in this pathway; however, the amount of 4-HB produced when the pZE13-0032 plasmid was left out of the host is the negligible.

Production of 14-BDO from 4-HB.

The production of 14-14-BDO from 4-HB required two reduction steps, catalyzed by dehydrogenases. Alcohol and aldehyde dehydrogenases (ADH and ALD, respectively) are NAD+/H and/or NADP+/H-dependent enzymes that together can reduce a carboxylic acid group on a molecule to an alcohol group, or in reverse, can perform the oxidation of an alcohol to a carboxylic acid. This biotransformation has been demonstrated in wild-type *Clostridium acetobutylicum* (Jewell et al., Current Microbiology, 13:215-19 (1986)), but neither the enzymes responsible nor the genes responsible were identified. In addition, it is not known whether activation to 4-HB-CoA is first required (Step T in FIG. 1), or if the aldehyde dehydrogenase (Step Q) can act directly on 4-HB. We developed a list of candidate enzymes from *C. acetobutylicum* and related organisms based on known activity with the non-hydroxylated analogues to 4-HB and pathway intermediates, or by similarity to these characterized genes (Table 56). Since some of the candidates are multifunctional dehydrogenases, they could potentially catalyze both the NAD(P) H-dependent reduction of the acid (or CoA-derivative) to the aldehyde, and of the aldehyde to the alcohol. Before beginning work with these genes in *E. coli*, we first validated the result referenced above using *C. acetobutylicum* ATCC 824.

Cells were grown in Schaedler broth (Accumedia, Lansing, Mich.) supplemented with 10 mM 4-HB, in an anaerobic atmosphere of 10% $CO_2$, 10% $H_2$, and 80% $N_2$ at 30° C. Periodic culture samples were taken, centrifuged, and the broth analyzed for 14-BDO by GC-MS as described below. 14-BDO concentrations of 0.1 mM, 0.9 mM, and 1.5 mM were detected after 1 day, 2 days, and 7 days incubation, respectively. No 14-BDO was detected in culture grown without 4-HB addition. To demonstrate that the 14-BDO produced was derived from glucose, we grew the best 14-BDO producing strain MG1655 lacI$^Q$ pZE13-0004-0035-0002 pZA33-0034-0036 in M9 minimal medium supplemented with 4 g/L uniformly labeled $^{13}$C-glucose. Cells were induced at OD of 0.67 with 1 mM IPTG, and a sample taken after 24 hours. Analysis of the culture supernatant was performed by mass spectrometry.

Gene candidates for the 4-HB to 14-BDO conversion pathway were next tested for activity when expressed in the *E. coli* host MG1655 lacI$^Q$. Recombinant strains containing each gene candidate expressed on pZA33 were grown in the presence of 0.25 mM IPTG for four hours at 37° C. to fully induce expression of the enzyme. Four hours after induction, cells were harvested and assayed for ADH and ALD activity as described above. Since 4-HB-CoA and 4-hydroxybutyraldehyde are not available commercially, assays were performed using the non-hydroxylated substrates (Table 59). The ratio in activity between 4-carbon and 2-carbon substrates for *C. acetobutylicum* adhE2 (0002) and *E. coli* adhE (0011) were similar to those previously reported in the literature (Atsumi et al., *Biochim. Biophys. Acta.* 1207:1-11 (1994)).

due to the lower cell density achieved in anaerobic cultures. When normalized to cell OD, the 14-BDO production per unit biomass is higher in anaerobic conditions (Table 60).

TABLE 60

Absolute and normalized 14-BDO concentrations from cultures of cells expressing adhE2 from *C. acetobutylicum*, sucD from *C. kluyveri*, or sucD from *P. gingivalis*, as well as the negative control.

| Gene expressed | Conditions | 14-BDO (µM) | OD (600 nm) | 14-BDO/OD |
|---|---|---|---|---|
| none | Aerobic | 0 | 13.4 | 0 |
| none | Microaerobic | 0.5 | 6.7 | 0.09 |
| none | Anaerobic | 2.2 | 1.26 | 1.75 |
| 0002 | Aerobic | 138.3 | 9.12 | 15.2 |
| 0002 | Microaerobic | 48.2 | 5.52 | 8.73 |
| 0002 | Anaerobic | 54.7 | 1.35 | 40.5 |
| 0008n | Aerobic | 255.8 | 5.37 | 47.6 |
| 0008n | Microaerobic | 127.9 | 3.05 | 41.9 |
| 0008n | Anaerobic | 60.8 | 0.62 | 98.1 |
| 0035 | Aerobic | 21.3 | 14.0 | 1.52 |
| 0035 | Microaerobic | 13.1 | 4.14 | 3.16 |
| 0035 | Anaerobic | 21.3 | 1.06 | 20.1 |

As discussed above, it may be advantageous to use a route for converting 4-HB to 4-HB-CoA that does not generate acetate as a byproduct. To this aim, we tested the use of phosphotransbutyrylase (ptb) and butyrate kinase (bk) from *C. acetobutylicum* to carry out this conversion via Steps O and P in FIG. 1. The native ptb/bk operon from *C. acetobutylicum*

TABLE 59

In vitro enzyme activities in cell extracts from MG1655 lacI$^Q$ containing pZA33 expressing gene candidates for aldehyde and alcohol dehydrogenases. Activities are expressed in µmol min$^{-1}$ mg cell protein$^{-1}$. N.D., not determined.

| | | Aldehyde dehydrogenase | | Alcohol dehydrogenase | |
|---|---|---|---|---|---|
| Gene | Substrate | Butyryl-CoA | Acetyl-CoA | Butyraldehyde | Acetaldehyde |
| 0002 | | 0.0076 | 0.0046 | 0.0264 | 0.0247 |
| 0003n | | 0.0060 | 0.0072 | 0.0080 | 0.0075 |
| 0011 | | 0.0069 | 0.0095 | 0.0265 | 0.0093 |
| 0013 | | N.D. | N.D. | 0.0130 | 0.0142 |
| 0023 | | 0.0089 | 0.0137 | 0.0178 | 0.0235 |
| 0025 | | 0 | 0.0001 | N.D. | N.D. |
| 0026 | | 0 | 0.0005 | 0.0024 | 0.0008 |

Figure 4:
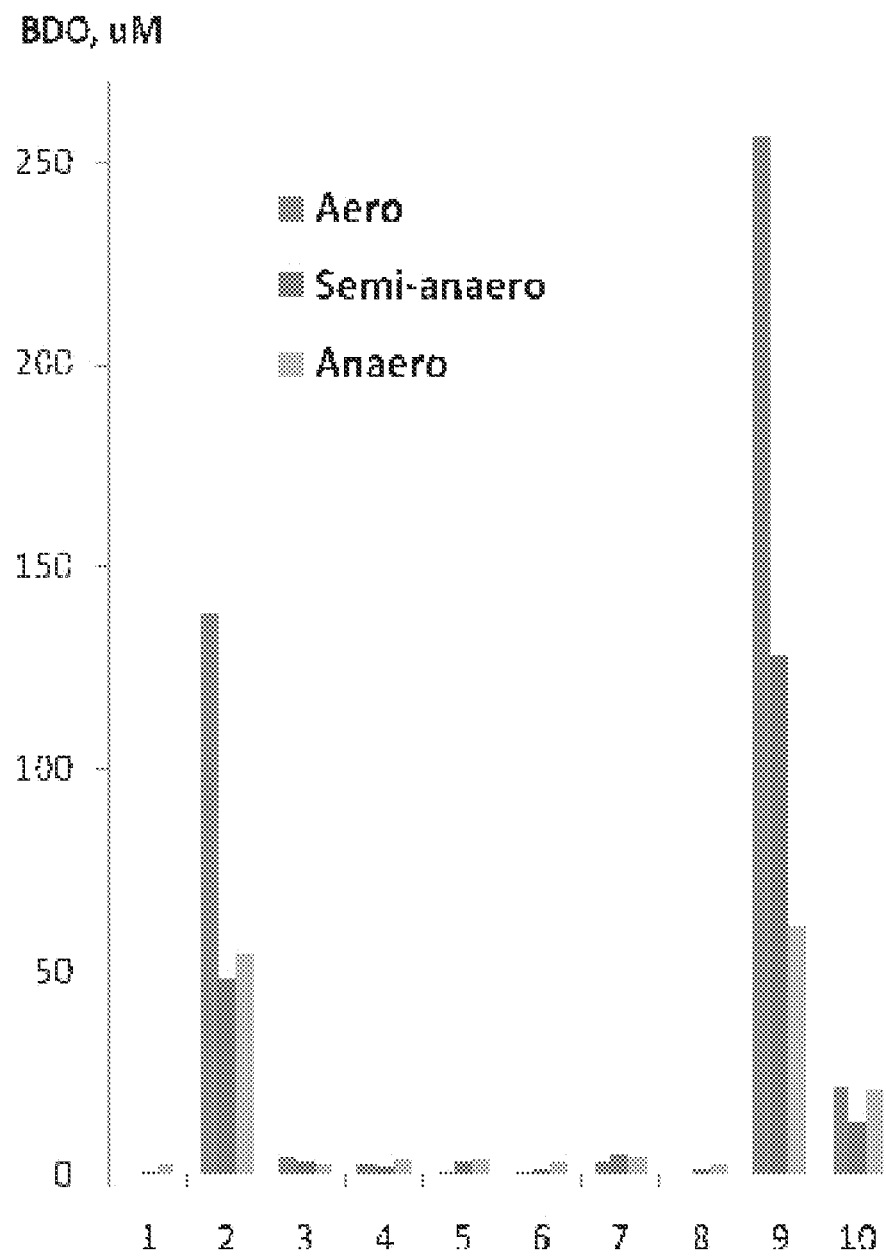
FIG. 4 shows the production of BDO from 10 mM 4-HB in recombinant *E. coli* strains. Numbered positions correspond to experiments with MG1655 lacI$^Q$ containing pZA33-0024, expressing cat2 from *P. gingivalis*, and the following genes expressed on pZE13: 1, none (control); 2, 0002; 3, 0003; 4, 0003n; 5, 0011; 6, 0013; 7, 0023; 8, 0025; 9, 0008n; 10, 0035. Gene numbers are defined in Table 56. For each position, the bars refer to aerobic, microaerobic, and anaerobic conditions, respectively. Microaerobic conditions were created by sealing the culture tubes but not evacuating them.
Figure 5:
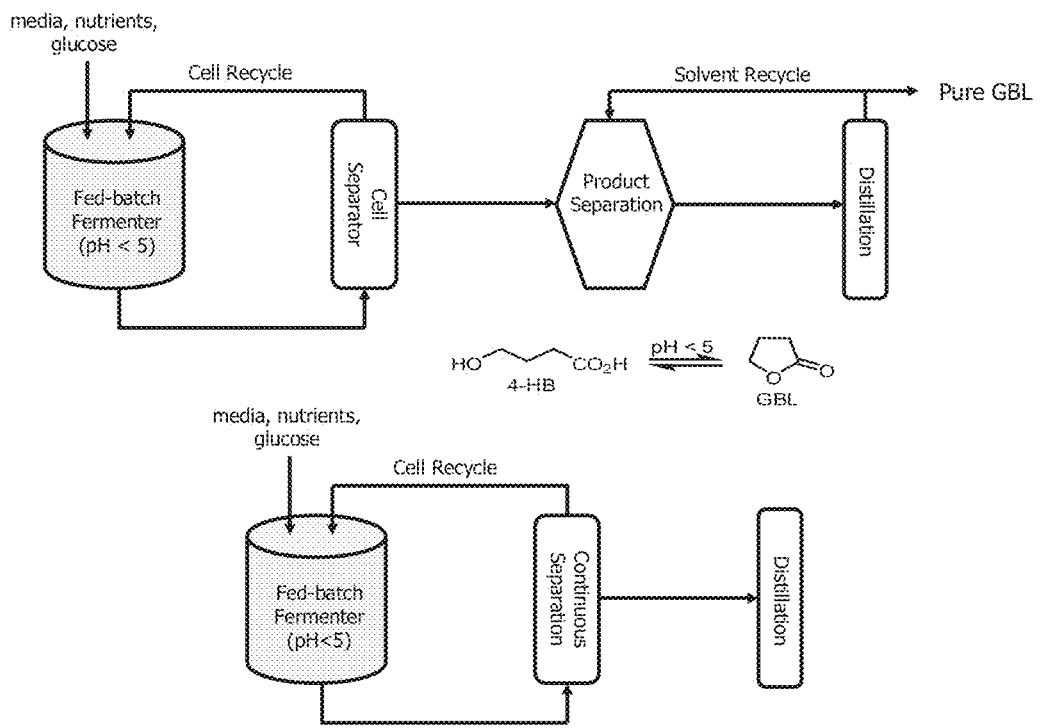
FIG. 5 is a schematic process flow diagram of bioprocesses for the production of γ-butyrolactone. Panel (a) illustrates fed-batch fermentation with batch separation and panel (b) illustrates fed-batch fermentation with continuous separation.

For the 14-BDO production experiments, cat2 from *Porphyromonas gingivalis* W83 (gene 0034) was included on pZA33 for the conversion of 4-HB to 4-HB-CoA, while the candidate dehydrogenase genes were expressed on pZE13. The host strain was MG1655 lacI$^Q$. Along with the alcohol and aldehyde dehydrogenase candidates, we also tested the ability of CoA-dependent succinic semialdehyde dehydrogenases (sucD) to function in this step, due to the similarity of the substrates. Cells were grown to an OD of about 0.5 in LB medium supplemented with 10 mM 4-HB, induced with 1 mM IPTG, and culture broth samples taken after 24 hours and analyzed for 14-BDO as described below. The best 14-BDO production occurred using adhE2 from *C. acetobutylicum*, sucD from *C. kluyveri*, or sucD from *P. gingivalis* (FIG. 4). Interestingly, the absolute amount of 14-BDO produced was higher under aerobic conditions; however, this is primarily (genes 0020 and 0021) was cloned and expressed in pZA33. Extracts from cells containing the resulting construct were taken and assayed for the two enzyme activities as described herein. The specific activity of BK was approximately 65 U/mg, while the specific activity of PTB was approximately 5 U/mg. One unit (U) of activity is defined as conversion of 1 µM substrate in 1 minute at room temperature. Finally, the construct was tested for participation in the conversion of 4-HB to 14-BDO. Host strains were transformed with the pZA33-0020-0021 construct described and pZE13-0002, and compared to use of cat2 in 14-BDO production using the aerobic procedure used above in FIG. 4. The BK/PTB strain produced 1 mM 14-BDO, compared to 2 mM when using cat2 (Table 61). Interestingly, the results were dependent on whether the host strain contained a deletion in the native adhE gene.

TABLE 61

Absolute and normalized 14-BDO concentrations from cultures of cells expressing adhE2 from *C. acetobutylicum* in pZE13 along with either cat2 from *P. gingivalis* (0034) or the PTB/BK genes from *C. acetobutylicum* on pZA33. Host strains were either MG1655 lacI$^Q$ or MG1655 ΔadhE lacI$^Q$.

| Genes | Host Strain | 14-BDO (μM) | OD (600 nm) | 14-BDO/OD |
|---|---|---|---|---|
| 0034 | MG1655 lacI$^Q$ | 0.827 | 19.9 | 0.042 |
| 0020 + 0021 | MG1655 lacI$^Q$ | 0.007 | 9.8 | 0.0007 |

μg/mL thiamine, and the appropriate antibiotics. 0.25 mM IPTG was added approximately 15 hours following inoculation, and culture supernatant samples taken for 14-BDO, 4-HB, and succinate analysis 24 and 48 hours following induction. The production of 14-BDO appeared to show a dependency on gene order (Table 62). The highest 14-BDO production, over 0.5 mM, was obtained with cat2 expressed first, followed by 4-HBd on pZA33, and cat1 followed by *P. gingivalis* sucD on pZE13. The addition of *C. acetobutylicum* adhE2 in the last position on pZE13 resulted in slight improvement. 4-HB and succinate were also produced at higher concentrations.

TABLE 62

Production of 14-BDO, 4-HB, and succinate in recombinant *E. coli* strains expressing combinations of 14-BDO pathway genes, grown in minimal medium supplemented with 20 g/L glucose. Concentrations are given in mM.

| Sample | pZE13 | pZA33 | Induction OD | 24 Hours OD600 nm | Su | 4HB | BDO | 48 Hours OD600 nm | Su | 4HB | BDO |
|---|---|---|---|---|---|---|---|---|---|---|---|
| 1 | cat1(0004)-sucD(0035) | 4hbd (0036)-cat2(0034) | 0.92 | 1.29 | 5.44 | 1.37 | 0.240 | 1.24 | 6.42 | 1.49 | 0.280 |
| 2 | cat1(0004)-sucD(0008N) | 4hbd (0036)-cat2(0034) | 0.36 | 1.11 | 6.90 | 1.24 | 0.011 | 1.06 | 7.63 | 1.33 | 0.011 |
| 3 | adhE(0002)-cat1(0004)-sucD(0035) | 4hbd (0036)-cat2(0034) | 0.20 | 0.44 | 0.34 | 1.84 | 0.050 | 0.60 | 1.93 | 2.67 | 0.119 |
| 4 | cat1(0004)-sucD(0035)-adhE(0002) | 4hbd (0036)-cat2(0034) | 1.31 | 1.90 | 9.02 | 0.73 | 0.073 | 1.95 | 9.73 | 0.82 | 0.077 |
| 5 | adhE(0002)-cat1(0004)-sucD(0008N) | 4hbd (0036)-cat2(0034) | 0.17 | 0.45 | 1.04 | 1.04 | 0.008 | 0.94 | 7.13 | 1.02 | 0.017 |
| 6 | cat1(0004)-sucD(0008N)-adhE(0002) | 4hbd (0036)-cat2(0034) | 1.30 | 1.77 | 10.47 | 0.25 | 0.004 | 1.80 | 11.49 | 0.28 | 0.003 |
| 7 | cat1(0004)-sucD(0035) | cat2(0034)-4hbd(0036) | 1.09 | 1.29 | 5.63 | 2.15 | 0.461 | 1.38 | 6.66 | 2.30 | 0.520 |
| 8 | cat1(0004)-sucD(0008N) | cat2(0034)-4hbd(0036) | 1.81 | 2.01 | 11.28 | 0.02 | 0.000 | 2.24 | 11.13 | 0.02 | 0.000 |
| 9 | adhE(0002)-cat1(0004)-sucD(0035) | cat2(0034)-4hbd(0036) | 0.24 | 1.99 | 2.02 | 2.32 | 0.106 | 0.89 | 4.85 | 2.41 | 0.186 |
| 10 | cat1(0004)-sucD(0035)-adhE(0002) | cat2(0034)-4hbd(0036) | 0.98 | 1.17 | 5.30 | 2.08 | 0.569 | 1.33 | 6.15 | 2.14 | 0.640 |
| 11 | adhE(0002)-cat1(0004)-sucD(0008N) | cat2(0034)-4hbd(0036) | 0.20 | 0.53 | 1.38 | 2.30 | 0.019 | 0.91 | 8.10 | 1.49 | 0.034 |
| 12 | cat1(0004)-sucD(0008N)-adhE(0002) | cat2(0034)-4hbd(0036) | 2.14 | 2.73 | 12.07 | 0.16 | 0.000 | 3.10 | 11.79 | 0.17 | 0.002 |
| 13 | vector only | vector only | 2.11 | 2.62 | 9.03 | 0.01 | 0.000 | 3.00 | 12.05 | 0.01 | 0.000 |

TABLE 61-continued

Absolute and normalized 14-BDO concentrations from cultures of cells expressing adhE2 from *C. acetobutylicum* in pZE13 along with either cat2 from *P. gingivalis* (0034) or the PTB/BK genes from *C. acetobutylicum* on pZA33. Host strains were either MG1655 lacI$^Q$ or MG1655 ΔadhE lacI$^Q$.

| Genes | Host Strain | 14-BDO (μM) | OD (600 nm) | 14-BDO/OD |
|---|---|---|---|---|
| 0034 | MG1655 ΔadhE lacI$^Q$ | 2.084 | 12.5 | 0.166 |
| 0020 + 0021 | MG1655 ΔadhE lacI$^Q$ | 0.975 | 18.8 | 0.052 |

Production of 14-BDO from Glucose.

The final step of pathway corroboration is to express both the 4-HB and 14-BDO segments of the pathway in *E. coli* and demonstrate production of 14-BDO in glucose minimal medium. New plasmids were constructed so that all the required genes fit on two plasmids. In general, cat1, adhE, and sucD genes were expressed from pZE13, and cat2 and 4-HBd were expressed from pZA33. Various combinations of gene source and gene order were tested in the MG1655 lacI$^Q$ background. Cells were grown anaerobically in M9 minimal medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$) supplemented with 20 g/L glucose, 100 mM 3-(N-morpholino)propanesulfonic acid (MOPS) to improve the buffering capacity, 10

Analysis of 14-BDO, 4-HB and Succinate by GCMS.

14-BDO, 4-HB and succinate in fermentation and cell culture samples were derivatized by silylation and quantitatively analyzed by GCMS using methods adapted from literature reports (Song et al., *Wei Sheng Wu Xue. Bao.* 45:382-386 (2005)). The developed method demonstrated good sensitivity down to 1 μM, linearity up to at least 25 mM, as well as excellent selectivity and reproducibility.

Sample preparation was performed as follows: 100 μL filtered (0.2 μm or 0.45 μm syringe filters) samples, e.g. fermentation broth, cell culture or standard solutions, were dried down in a SpeedVac Concentrator (Savant SVC-100H) for approximately 1 hour at ambient temperature, followed by the addition of 20 μL 10 mM cyclohexanol solution, as an internal standard, in dimethylformamide. The mixtures were vortexed and sonicated in a water bath (Branson 3510) for 15 min to ensure homogeneity. 100 μL silylation derivatization reagent, N,O-bis(trimethylsilyl)trifluoro-acetimide (BSTFA) with 1% trimethylchlorosilane, was added, and the mixture was incubated at 70° C. for 30 min. The derivatized samples were centrifuged for 5 min, and the clear solutions were directly injected into GCMS. All the chemicals and reagents were from Sigma-Aldrich, with the exception of 14-BDO which was purchased from J. T. Baker.

GCMS was performed on an Agilent gas chromatograph 6890N, interfaced to a mass-selective detector (MSD) 5973N operated in electron impact ionization (EI) mode has been used for the analysis. A DB-5MS capillary column (J&W Scientific, Agilent Technologies), 30 m×0.25 mm i.d.×0.25 μm film thickness, was used. The GC was operated in a split injection mode introducing 1 μL of sample at 20:1 split ratio. The injection port temperature was 250° C. Helium was used as a carrier gas, and the flow rate was maintained at 1.0 mL/min. A temperature gradient program was optimized to ensure good resolution of the analytes of interest and minimum matrix interference. The oven was initially held at 80° C. for 1 min, then ramped to 120° C. at 2° C./min, followed by fast ramping to 320° C. at 100° C./min and final hold for 6 min at 320° C. The MS interface transfer line was maintained at 280° C. The data were acquired using 'lowmass' MS tune settings and 30-400 m/z mass-range scan. The total analysis time was 29 min including 3 min solvent delay. The retention times corresponded to 5.2, 10.5, 14.0 and 18.2 min for BSTFA-derivatized cyclohexanol, 14-BDO, 4-HB and succinate, respectively. For quantitative analysis, the following specific mass fragments were selected (extracted ion chromatograms): m/z 157 for internal standard cyclohexanol, 116 for 14-BDO, and 147 for both 4-HB and succinate. Standard calibration curves were constructed using analyte solutions in the corresponding cell culture or fermentation medium to match sample matrix as close as possible. GCMS data were processed using Environmental Data Analysis ChemStation software (Agilent Technologies).

Figure 6F:
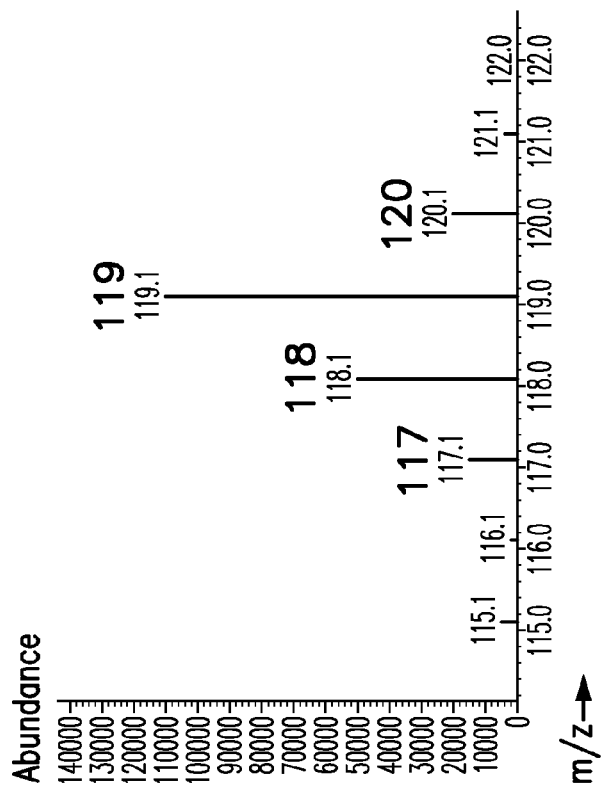
FIG. 6 shows the mass spectrum of 4-HB and BDO produced by MG1655 lacI$^Q$ pZE13-0004-0035-0002 pZA33-0034-0036 grown in M9 minimal medium supplemented with 4 g/L unlabeled glucose (a, c, e, and g) uniformly labeled $^{13}$C-glucose (b, d, f, and h). (a) and (b), mass 116 characteristic fragment of derivatized BDO, containing 2 carbon atoms; (c) and (d), mass 177 characteristic fragment of derivatized BDO, containing 1 carbon atom; (e) and (f), mass 117 characteristic fragment of derivatized 4-HB, containing 2 carbon atoms; (g) and (h), mass 233 characteristic fragment of derivatized 4-HB, containing 4 carbon atoms.
Figure 6E:
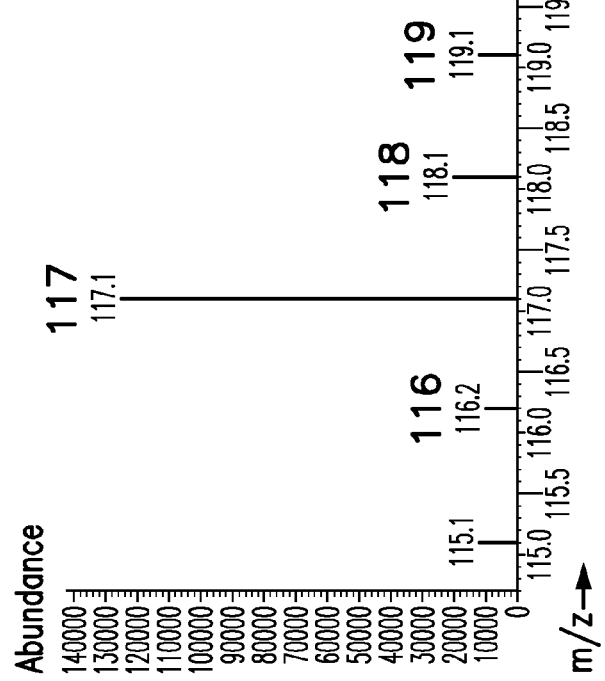

The results indicated that most of the 4-HB and 14-BDO produced were labeled with $^{13}C$ (FIG. 6, right-hand sides). Mass spectra from a parallel culture grown in unlabeled glucose are shown for comparison (FIG. 6, left-hand sides). Note that the peaks seen are for fragments of the derivatized molecule containing different numbers of carbon atoms from the metabolite. The derivatization reagent also contributes some carbon and silicon atoms that naturally-occurring label distribution, so the results are not strictly quantitative.

Production of 14-BDO from 4-HB Using Alternate Pathways.

The various alternate pathways were also tested for 14-BDO production. This includes use of the native E. coli SucCD enzyme to convert succinate to succinyl-CoA (Table 63, rows 2-3), use of alpha-ketoglutarate decarboxylase in the alpha-ketoglutarate pathway (Table 63, row 4), and use of PTB/BK as an alternate means to generate the CoA-derivative of 4-HB (Table 63, row 1). Strains were constructed containing plasmids expressing the genes indicated in Table 63, which encompass these variants. The results show that in all cases, production of 4-HB and 14-BDO occurred (Table 63).

TABLE 63

Production of 14-BDO, 4-HB, and succinate in recombinant E. coli strains genes for different 14-BDO pathway variants, grown anaerobically in minimal medium supplemented with 20 g/L glucose, and harvested 24 hours after induction with 0.1 mM IPTG. Concentrations are given in mM.

| Genes on pZE13 | Genes on pZA33 | Succinate | 4-HB | 14-BDO |
|---|---|---|---|---|
| 0002 + 0004 + 0035 | 0020n – 0021n – 0036 | 0.336 | 2.91 | 0.230 |
| 0038 + 0035 | 0034 – 0036 | 0.814 | 2.81 | 0.126 |

TABLE 63-continued

Production of 14-BDO, 4-HB, and succinate in recombinant E. coli strains genes for different 14-BDO pathway variants, grown anaerobically in minimal medium supplemented with 20 g/L glucose, and harvested 24 hours after induction with 0.1 mM IPTG. Concentrations are given in mM.

| Genes on pZE13 | Genes on pZA33 | Succinate | 4-HB | 14-BDO |
|---|---|---|---|---|
| 0038 + 0035 | 0036 – 0034 | 0.741 | 2.57 | 0.114 |
| 0035 + 0032 | 0034 – 0036 | 5.01 | 0.538 | 0.154 |

EXAMPLE V

Biosynthesis of GBL

This example describes exemplary biochemical pathways for GBL production.

As shown in FIG. 1, 4-HB can be biosynthesized from succinate or alpha-ketoglutarate. 4-HB, 4-hydroxybutyryl-phoaphate, and 4-hydroxybutyryl-CoA can all be converted into GBL (Steps AB, AC, and AD in FIG. 1).

Previous studies have demonstrated the transformation from 4-HB to GBL. The conversion from 4-HB to GBL can be catalyzed by either the 1,4-lacton hydroxyacylhydrolase (EC 3.1.1.25) or the lipases (Step AB in FIG. 1). In vitro activities of 1,4-lacton hydroxyacylhydrolase, or gamma lactonase on 4-HB has been described (Fishbein and Bessman, *J Biol Chem* 241:4835-4841 (1966)), (Fishbein and Bessman, *J Biol Chem* 241:4842-4847 (1966)). Additionally, lipases such as *Candida antarctica* lipase B has been tested to catalyze the lactonization of 4-hydroxybutyrate to GBL (Efe et al., *Biotechnol Bioeng* 99:1392-1406 (2008)).

The transformation from 4-hydroxybutyryl-phoaphate to GBL can be a non-enzymatic step (Step AC in FIG. 1). This is demonstrated by the following results. The hose strain used was E. coli strain MG1655. Cells were grown in bottles with M9 minimal medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$) supplemented with glucose under batch culture conditions. Gene expression was induced by 0.25 mM IPTG and culture supernatant samples were taken for 14-BDO, GBL, 4-HB, and other products analysis. When the 4-HB pathway was expressed in the host strain, the cells produced 4-HB from glucose. However, 4-HB was not converted to GBL or 14-BDO when no downstream gene presents (Table 64, row 1). When the 4-HB kinase (021) was expressed from the pZA335 plasmid, the cells were able to convert 4-HB to GBL through 4-hydroxybutyryl-phospate, whereas 14-BDO was not produced (Table 64, row 2). Thus, activated 4-hydroxybutyryl-phosphate can be converted to GBL through the non-enzymatic lactonization reaction (Step AC in FIG. 1). The high amount of GBL detected in this experiment was unexpected because, to our knowledge, the lactonization of 4-hydroxybutyryl-phosphate had never before been demonstrated. The conversion of 4-hydroxybutyrate to GBL is thermodynamically favored at a non-basic pH (Efe, et al., Biotechnol Bioeng 99:1392-1406 (2008)), though it requires a sufficient driving force to overcome the energy of activation (Perez-Prior, et al., Journal of Organic Chemistry, 70, 420-426 (2005)). It was not obvious beforehand that the phosphate group attached to 4-hydroxybutyrate would provide sufficient activation to enable GBL formation at such a high level. These results demonstrate the conversion of 4-hydroxybutyryl-phosphate to GBL through the non-enzymatic lactonization reaction.

droxybutyryl-CoA had never before been demonstrated. The conversion of 4-hydroxybutyrate to GBL is thermodynamically favored at a non-basic pH (Efe, et al., Biotechnol Bioeng 99:1392-1406 (2008)), though it requires a sufficient driving force to overcome the energy of activation (Perez-Prior, et al.,

TABLE 64

Transformation of 4-hydroxybutyryl-phosphate to GBL in recombinant *E. coli* strain.

| Host Strain | Genes | Enzyme Name | Source organism | Accession Number | Time (h) | OD 600 | 4-HB (mM) | GBL (mM) | 14-BDO (mM) |
|---|---|---|---|---|---|---|---|---|---|
| MG1655 + 4-HB pathway | None | — | — | — | 48 | 1.00 | 13.25 | 0 | 0 |
| MG1655 + 4-HB | pZA33-021 | butyrate kinase | *Clostridium acetobutylicum* | NP_349675 | 48 | 1.80 | 48.80 | 2.77 | 0 |

The transformation from 4-hydroxybutyryl-CoA to GBL through a non-enzymatic lactonization reaction (Step AD in FIG. 1) is demonstrated by the following results. The host strain used in the experiments was strain 432 (ΔadhE ΔldhA ΔpflB ΔlpdA::K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd). This strain contained the components of the 14-BDO pathway leading to 4HB integrated into the chromosome of *E. coli* at the fimD locus. It also contained additional genetic modifications to direct metabolic flux into the 4-HB pathway. Cells were grown in bottles with M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with glucose under batch culture conditions. Gene expression was induced by 0.25 mM IPTG and culture supernatant samples were taken for 14-BDO, GBL, 4-HB, and other products analysis. Cultured with glucose, strain 432 produced 4-HB but produced neither GBL nor 14-BDO (Table 65, row 1). When genes coding for the 4-hydroxybutyryl-CoA transferase (034) or the combined butyrate kinase/phosphotransbutyrylase (020/021) were expressed, the resulting enzymes allowed the engineered strain to convert 4-HB to 4-hydroxybutyryl-CoA. The activated 4-hydroxybutyryl-CoA resulted in the production of significant amount of GBL through the non-enzymatic lactonization reaction (Table 65, rows 2-3). In the case described by Table 65, row 3, there were no exogenous genes expressed to enable the production of the intermediate, 4-hydroxybutyryl-phosphate. 4-Hydroxybutyryl-CoA transferase enabled the production of 4-hydroxybutyryl-CoA from 4-hydroxybutyrate. Thus the experiment summarized in Table 65, row 3, demonstrated that 4-hydroxybutyryl-CoA is capable of undergoing non-enzymatic lactonization to form GBL. The high amount of GBL detected in this experiment was unexpected because, to our knowledge, the lactonization of 4-hy- Journal of Organic Chemistry, 70, 420-426 (2005)). It was not obvious beforehand that the CoA group attached to 4-hydroxybutyrate would provide sufficient activation to enable GBL formation at such a high level. Without downstream enzymes for 14-BDO biosynthesis, none or very little 14-BDO was produced. The little amount of 14-BDO that was produced was likely due to some residual endogenous aldehyde dehydrogenase activities. These results demonstrate the conversion of 4-hydroxybutyryl-CoA to GBL through the non-enzymatic lactonization reaction.

TABLE 65

Transformation of 4-hydroxybutyryl-CoA to GBL in recombinant *E. coli* strain.

| Host Strain | Genes | Enzyme Name | Source organism | Accession Number | Time (h) | OD 600 | 4-HB (mM) | GBL (mM) | 14-BDO (mM) |
|---|---|---|---|---|---|---|---|---|---|
| 432 | None | — | — | — | 48 | 1.06 | 4.41 | 0 | 0 |
| 432 | pZs*-2021C | butyrate kinase & phosphotransbutyrylase | *Clostridium acetobutylicum* | NP_349675 & NP_349676 | 48 | 1.13 | 3.60 | 1.35 | 0 |
| 432 | F'-034 | 4-hydroxybutyryl-CoA transferase | *Porphyromonas gingivalis* ATCC 33277 | YP_001928841 | 48 | 0.99 | 2.94 | 0.85 | 0.11 |

EXAMPLE VI

Control of the 14-BDO and GBL Ratio During Co-Production

One important aspect of coproduction of 14-BDO and GBL is to control the ratio between the two coproducts to match the market needs. Depending on different region, the local market needs for 14-BDO and GBL can be different, thus it is important to coproduce 14-BDO and GBL with tailored ratio to satisfy the market needs. In this example, we demonstrate a method to coproduce 14-BDO and GBL at different ratios.

To adjust the ratio of 14-BDO and GBL, several different methods can be employed. First, 4-hydroxybutyryl-CoA can be converted to GBL by the non-enzymatic lactonization reaction (Step AD in FIG. 1) or to BDO through 4-hydroxybutanal by an acyl-CoA reductase (aldehyde forming) plus 14-BDL dehydrogenase (Steps Q and E in FIG. 1). An acyl-CoA reductase (aldehyde forming) with high activity will convert more 4-hydroxybutyryl-CoA to 4-hydroxybutanal, which is subsequently converted to 14-BDO, therefore reducing the amount of GBL formed from 4-hydroxybutyryl-CoA. This will result in a higher 14-BDO to GBL ratio. Similarly, low activity of acyl-CoA reductase (aldehyde forming) may result in a lower 14-BDO to GBL ratio. Additionally, 4-hydroxybutyryl-CoA can be directly converted 14-BDO by an acyl-CoA reductase (alcohol forming) (Step W in FIG. 1), thus 14-BDO to GBL ratio can be adjusted by the acyl-CoA reductase (alcohol forming) activities. Third, 4-hydroxybutyryl-phosphate can be converted to GBL by the non-enzymatic lactonization reaction (Step AC in FIG. 1) or indirectly to 14-BDO through a phosphate transferring acyltransferases (Step P in FIG. 1) or an acyl-phosphate reductase (Step R in FIG. 1). Therefore, the activities of phosphate transferring acyltransferases or acyl-phosphate reductase in the 14-BDO production pathway can be utilized to adjust 14-BDO to GBL ratio. Finally, 4-HB can be directly converted to GBL by a hydroxyacylhydrolase (Step AB in FIG. 1) competing against reactions leading to 14-BDO including 4-HB kinase (Step O in FIG. 1), 4-HB reductase (Step D in FIG. 1), and/or 4-hydroxybutyryl-CoA transferase, hydrolase, or synthetase (Steps T, U, V, in FIG. 1). Therefore, activities of hydroxyacylhydrolase and other enzymes leading to 14-BDO production can be utilized to adjust 14BDO to GBL ratio in coproduction.

As described above, the activities of the acyl-CoA reductase (aldehyde forming) can be utilized to adjust the ratio of 14-BDO to GBL in coproduction. Different acyl-CoA reductases (aldehyde forming, also known as aldehyde dehydrogenase) were tested for their aldehyde dehydrogenase activities by in vivo transformation measurements. The host strain used in the experiments was strain 761 (ΔadhE ΔldhA ΔpflB Δsad ΔgabD ΔlpdA::K.p./pdA322 Δmdh ΔarcA gltAR163L fimD::E. coli sucCD, P. gingivalis sucD, P. gingivalis 4hbd fimD::M. bovis sucA, C. kluyveri 4hbd). This strain contained the components of the BDO pathway leading to 4HB integrated into the chromosome of E. coli at the fimD locus. It also contained additional genetic modifications to direct metabolic flux into the 4-HB pathway. The 4-hydroxybutyryl-CoA transferase (034) was expressed from the F' plasmid and allowed the engineered strains to convert 4-HB to 4-hydroxybutyryl-CoA. Genes encoding different aldehyde dehydrogenase were expressed from pZs* plasmid. Cells were grown in fermentor with M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with glucose under batch fermentation conditions. Gene expression of aldehyde dehydrogenases was induced by 0.25 mM IPTG and culture supernatant samples were taken for 14-BDO, GBL, and other products analysis. As shown in Table 66, aldehyde dehydrogenases from different organism results in different 14-BDO and GBL titers in the fermentation broth and different ratios between the 14-BDO and GBL coproducts. Among the aldehyde dehydrogenase tested, gene 704 encoding the *Salmonella enterica Typhimurium* aldehyde dehydrogenase resulted in the lowest 14-BDO to GBL ratio at 0.5, allowing two moles of GBL produced for every mole of 14-BDO produced. On the other hand, gene 025B encoding the *Clostridium beijerinckii* NCIMB 8052 aldehyde dehydrogenase resulted in the highest 14-BDO to GBL ratio at 7.2. Several aldehyde dehydrogenases from different source organisms produced 14-BDO and GBL at ratios between 0.5 and 7.2 (Table 66). These genes can be utilized to generate coproduction strains with different 14-BDO to GBL ratio to meet the needs of different regional markets.

TABLE 66

Production of 14-BDO and GBL in recombinant *E. coli* strains with genes for different aldehyde dehydrogenase.

| Host Strain | Genes | Enzyme Name | Source organism | Accession Number | Time (h) | OD 600 | 14-BDO (mM) | GBL (mM) | 14-BDO: GBL |
|---|---|---|---|---|---|---|---|---|---|
| 761 | pZs*-704, F'-034 | Aldehyde dehydrogenase | *Salmonella enterica Typhimurium* | NP_460996 | 120 | 9.4 | 106 | 197 | 0.5 |
| 761 | pZs*-744, F'-034 | Aldehyde dehydrogenase | *Clostridium methylpentosum* DSM 5476 | ZP_03705305 | 120 | 8.6 | 166 | 131 | 1.3 |
| 761 | pZs*-707, F'-034 | Aldehyde dehydrogenase | *Lactobacillus brevis* ATCC 367 | YP_795711 | 120 | 11.4 | 132 | 50 | 2.6 |
| 761 | pZs*-778, F'-034 | Aldehyde dehydrogenase | *Bacillus selenitireducens* MLS10 | ZP_02169447 | 120 | 10.8 | 298 | 67 | 4.4 |
| 761 | pZs*-025B, F'-034 | Aldehyde dehydrogenase | *Clostridium beijerinckii* NCIMB 8052 | YP_001310903 | 144 | 10.3 | 384 | 53 | 7.2 |

EXAMPLE VII

Biosynthesis Coproduction of 1,4 BDO and GBL

This Example describes the biosynthetic coproduction of 14-BDO and GBL using fermentation and other bioprocesses.

Methods for the integration of the 4-HB fermentation step into a complete process for the coproduction of purified 14-BDO and GBL are described below. Since 4-HB and GBL are in equilibrium, the fermentation broth will contain both compounds. At low pH this equilibrium is shifted to favor GBL. Therefore, the fermentation can operate at pH 7.5 or less, generally pH 5.5 or less. After removal of biomass, the product stream enters into a separation step in which 14-BDO and GBL are removed and the remaining stream enriched in 4-HB is recycled. Finally, 14-BDO and GBL are distilled to remove any impurities. The process operates in one of three ways: 1) fed-batch fermentation and batch separation; 2) fed-batch fermentation and continuous separation; 3) continuous fermentation and continuous separation.

Fermentation Protocol to Coproduce 14-BDO and GBL (Batch):

The production organism is grown in a 10 L bioreactor sparged with an N$_2$/CO$_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until the total concentration of 14-BDO, GBL, and 4-HB reaches a concentration of between 20-200 g/L with a preferred ratio among the three coproducts, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a product separations unit. Isolation of 14-BDO and GBL is done by standard separations procedures employed in the art to separate organic products from dilute aqueous solutions, such as liquid-liquid extraction using a water immiscible organic solvent (e.g., toluene) to provide an organic solution of 14-BDO and GBL. The resulting solution is then subjected to standard distillation methods to remove and recycle the organic solvent and to provide GBL (boiling point 204° C.) and 14-BDO (boiling point 230° C.) which are distilled and isolated as purified liquids.

Fermentation Protocol to Coproduce 14-BDO/GBL (Fully Continuous):

The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The total concentration of 14-BDO, GBL, and 4-HB in the bioreactor remains constant at 30-40 g/L, with a preferred ratio among the three coproducts, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of coproducts concentrations. In continuous mode, fermenter contents are constantly removed as new feed medium is supplied. The exit stream, containing cells, medium, and coproducts 14-BDO, GBL, and 4-HB, is then subjected to a continuous product separations procedure, with or without removing cells and cell debris, and is done by standard continuous separations methods employed in the art to separate organic products from dilute aqueous solutions, such as continuous liquid-liquid extraction using a water immiscible organic solvent (e.g., toluene) to provide an organic solution of 14-BDO and GBL. The resulting solution is subsequently subjected to standard continuous distillation methods to remove and recycle the organic solvent and to provide GBL (boiling point 204° C.) and 14-BDO (boiling point 230° C.) which are distilled and isolated as purified liquids.

EXAMPLE VIII

Expression of Heterologous Genes Encoding BDO Pathway Enzymes

This example describes the expression of various non-native pathway enzymes to provide improved production of 14-BDO.

4-Hydroxybutanal Reductase.

4-hydroxybutanal reductase activity of adh1 from *Geobacillus thermoglucosidasius* (M10EXG) was utilized. This led to improved 14-BDO production by increasing 4-hydroxybutanal reductase activity over endogenous levels.

Multiple alcohol dehydrogenases were screened for their ability to catalyze the reduction of 4-hydroxybutanal to 14-BDO. Most alcohol dehydrogenases with high activity on butyraldehyde exhibited far lower activity on 4-hydroxybutyraldehyde. One notable exception is the adh1 gene from *Geobacillus thermoglucosidasius* M10EXG (Jeon et al., *J. Biotechnol.* 135:127-133 (2008)) (GNM0084), which exhibits high activity on both 4-hydroxybutanal and butanal.

The native gene sequence and encoded protein sequence if the adh1 gene from *Geobacillus thermoglucosidasius* are shown in FIG. 7. The *G. thermoglucosidasius* ald1 gene was expressed in *E. coli*.

Figures 8, 9:
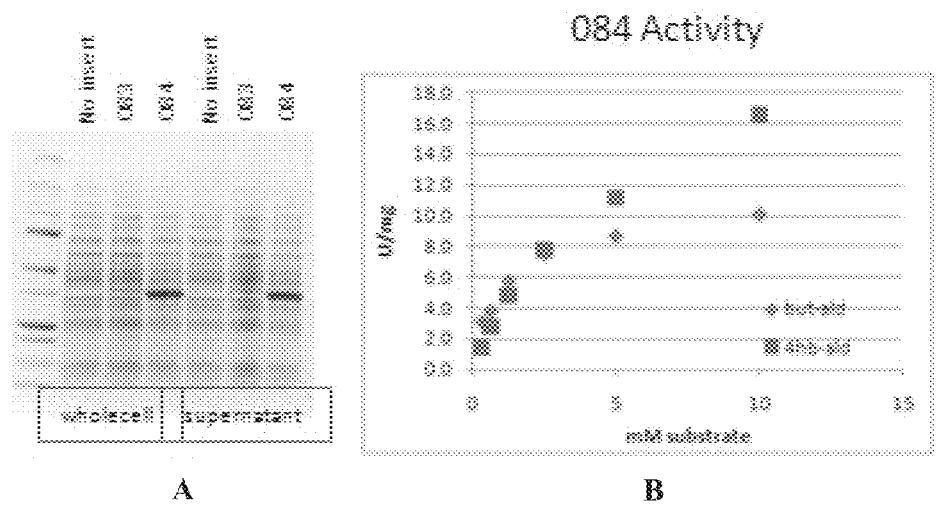
FIG. 9 shows the production of 14-BDO in various strains: plasmid with no insert; 025B, 025B-026n; 025B-026A; 025B-026B; 025B-026C; 025B-050; 025B-052; 025B-053; 025B-055; 025B-057; 025B-058; 025B-071; 025B-083; 025B-084; PTSlacO-025B; PTSlacO-025B-026n.

The Adh1 enzyme (084) expressed very well from its native gene in *E. coli* (see FIG. 8A). In ADH enzyme assays, the *E. coli* expressed enzyme showed very high reductive activity when butyraldehyde or 4HB-aldehyde were used as the substrates (see FIG. 8B). The Km values determined for these substrates were 1.2 mM and 4.0 mM, respectively. These activity values showed that the Adh1 enzyme was the most active on reduction of 4HB-aldehyde of all the candidates tested.

The 084 enzyme was tested for its ability to boost 14-BDO production when coupled with the *C. beijerinckii* ald. The 084 gene was inserted behind the *C. beijerinckii* ald variant 025B gene to create a synthetic operon that results in coupled expression of both genes. Similar constructs linked 025B with other ADH candidate genes, and the effect of including each ADH with 025B on 14-BDO production was tested. The host strain used was ECKh-459 (ΔadhE ldhA ΔpflB ΔlpdA::fnr-pflB6-K.p.lpdA322 Δmdh ΔarcA gltAR163L fimD::*E. coli* sucCD, *P. gingivalis* sucD, *P. gingivalis* 4hbd fimD::*M. bovis* sucA, *C. kluyveri* 4hbd fimD::*C. acetobutylicum* buk1, *C. acetobutylicum* ptb), which contains the remainder of the 14-BDO pathway on the chromosome. The 084 ADH expressed in conjunction with 025B showed the highest amount of 14-BDO (right arrow in FIG. 9) when compared with 025B only (left arrow in FIG. 9) and in conjunction with endogenous ADH functions. It also produced more 14-BDO than did other ADH enzymes when paired with 025B, indicated as follows: 026A-C, codon-optimized variants of *Clostridium acetobutylicum* butanol dehydrogenase; 050, *Zymomonas mobilis* alcohol dehydrogenase 1; 052, *Citrobacter freundii* 1,3-propanediol dehydrogenase; 053, *Lactobacillus brevis* 1,3-propanediol dehydrogenase; 057, *Bacteroides fragilis* lactaldehyde reductase; 058, *E. coli* 1,3-propanediol dehydrogenase; 071, *Bacillus subtilis* 168 alpha-ketoglutarate semialdehyde dehydrogenase. The constructs labeled "PT5lacO" are those in which the genes are driven by the PT5lacO promoter. In all other cases, the PA1lacO-1 promoter was used. This shows that inclusion of the 084 ADH in the 14-BDO pathway increased 14-BDO production.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for producing a fermentation broth comprising a non-naturally occurring microbial organism in which the intracellular concentration of 1,4-butanediol (14-BDO) is at least 1M and in which the intracellular concentration of gamma-butyrolactone (GBL) is between 0.001 and 10 mM, comprising:
- a) culturing the non-naturally occurring microbial organism for a sufficient period of time to produce 14-BDO and 4-hydroxybutyryl-CoA followed by spontaneous lactonization of 4-hydroxybutyryl-CoA to form GBL, wherein said 14-BDO is produced at an intracellular concentration of at least 1 M, wherein said GBL is produced at an intracellular concentration of between 0.001 mM and 10 mM, wherein said non-naturally occurring microbial organism comprises a 14-BDO pathway and a 4-hydroxybutyryl-CoA pathway, said 14-BDO pathway comprising at least one exogenous nucleic acid encoding a 14-BDO pathway enzyme expressed in a sufficient amount to produce 14-BDO, said 14-BDO pathway comprising:
  - i) a 4-hydroxybutyryl-CoA reductase (alcohol forming), a succinyl-CoA reductase (aldehyde forming), an alpha-ketoglutarate decarboxylase, a 4-hydroxybutyrate dehydrogenase, a 4-hydroxybutyrate reductase, a 1,4-butanediol dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, an 4-aminobutyrate dehydrogenase, an 4-aminobutyrate transaminase, a 4-hydroxybutyrate kinase, a phosphotrans-4-hydroxybutyrylase, a 4-hydroxybutyryl-CoA reductase (aldehyde forming), a 4-hydroxybutyryl-phosphate reductase, a succinyl-CoA reductase (alcohol forming), a 4-hydroxybutyryl-CoA transferase, a 4-hydroxybutyryl-CoA hydrolase, a 4-hydroxybutyryl-CoA synthetase, an alpha-ketoglutarate reductase, a 5-hydroxy-2-oxopentanoate dehydrogenase, a 5-hydroxy-2-oxopentanoate decarboxylase or a 5-hydroxy-2-oxopentanoate dehydrogenase (decarboxylation), said 4-hydroxybutyryl-CoA pathway comprising at least one exogenous nucleic acid encoding an 4-hydroxybutyryl-CoA pathway enzyme expressed in a sufficient amount to produce 4-hydroxybutyryl-CoA, and said 4-hydroxybutyryl-CoA pathway comprising:
  - ii) a 4-hydroxybutyryl-CoA transferase, a succinyl-CoA reductase (aldehyde forming), an alpha-ketoglutarate decarboxylase, a 4-hydroxybutyrate dehydrogenase, a succinate reductase, a succinyl-CoA transferase, a succinyl-CoA hydrolase, a succinyl-CoA synthetase, a glutamate dehydrogenase, a glutamate transaminase, a glutamate decarboxylase, a 4-aminobutyrate dehydrogenase, a 4-aminobutyrate transaminase, a 4-hydroxybutyrate kinase, a phosphotrans-4-hydroxybutyrylase, a succinyl-CoA reductase (alcohol forming), a 4-hydroxybutyryl-CoA hydrolase, a 4-hydroxybutyryl-CoA synthetase, an alpha-ketoglutarate reductase, a 5-hydroxy-2-oxopentanoate dehydrogenase, or a 5-hydroxy-2-oxopentanoate dehydrogenase (decarboxylation).

2. The method of claim 1, wherein the 14-BDO pathway comprises a pathway selected from the group consisting of:
(i) a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate reductase; and a 1,4-butanediol dehydrogenase;
(ii) a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase;
(iii) a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase;
(iv) a succinyl-CoA transferase, a succinyl-CoA hydrolase, or a succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase;
(v) a succinyl-CoA transferase, a succinyl-CoA hydrolase or succinyl-CoA synthetase; a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming);
(vi) a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; a phosphotrans-4-hydroxybutyrylase; and a 4-hydroxybutyryl-CoA reductase (alcohol forming);
(vii) a succinyl-CoA transferase, a succinyl-CoA hydrolase or a succinyl-CoA synthetase; a succinyl-CoA reductase (alcohol forming); a 4-hydroxybutyrate reductase; and 1,4-butanediol dehydrogenase;
(viii) a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; a 4-hydroxybutyryl-CoA reductase (aldehyde forming); and a 1,4-butanediol dehydrogenase;
(ix) succinyl-CoA transferase, a succinyl-CoA hydrolase or succinyl-CoA synthetase; a succinyl-CoA reductase (alcohol forming), a 4-hydroxybutyrate kinase, a 4-hydroxybutyryl-phosphate reductase; and a 1,4-butanediol dehydrogenase;
(x) a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase;

(xi) a succinyl-CoA transferase, a succinyl-CoA hydrolase or a succinyl-CoA synthetase; a succinyl-CoA reductase (alcohol forming); a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming);

(xii) a succinyl-CoA transferase, a succinyl-CoA hydrolase or a succinyl-CoA synthetase; a succinyl-CoA reductase (alcohol forming); a 4-hydroxybutyrate kinase; a phosphotrans-4-hydroxybutyrylase; and a 4-hydroxybutyryl-CoA reductase (alcohol forming);

(xiii) a succinate reductase; a 4-hydroxybutyrate dehydrogenase; a 4-hydroxybutyrate reductase; and 1,4-butanediol dehydrogenase;

(xiv) a succinate reductase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase;

(xv) a succinate reductase; a 4-hydroxybutyrate dehydrogenase; a 4-hydroxybutyrate kinase; a phosphotrans-4-hydroxybutyrylase; and a 4-hydroxybutyryl-CoA reductase (alcohol forming);

(xvi) a succinate reductase; a 4-hydroxybutyrate dehydrogenase; a 4-hydroxybutyrate kinase; a 4-hydroxybutyryl-phosphate reductase; and 1,4-butanediol dehydrogenase;

(xvii) a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and 1,4-butanediol dehydrogenase;

(xviii) a succinate reductase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming);

(xix) an alpha-ketoglutarate decarboxylase; a 4-hydroxybutyrate dehydrogenase; a 4-hydroxybutyrate reductase; and 1,4-butanediol dehydrogenase;

(xx) an alpha-ketoglutarate decarboxylase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase;

(xxi) an alpha-ketoglutarate decarboxylase; a 4-hydroxybutyrate dehydrogenase; a 4-hydroxybutyrate kinase; a phosphotrans-4-hydroxybutyrylase and 4-hydroxybutyryl-CoA reductase (alcohol forming);

(xxii) an alpha-ketoglutarate decarboxylase; a 4-hydroxybutyrate dehydrogenase; a 4-hydroxybutyrate kinase; a 4-hydroxybutyryl-phosphate reductase; and a 1,4-butanediol dehydrogenase;

(xxiii) an alpha-ketoglutarate decarboxylase; a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase;

(xxiv) an alpha-ketoglutarate decarboxylase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming);

(xxv) a glutamate dehydrogenase or a glutamate transaminase; a glutamate decarboxylase; a 4-aminobutyrate dehydrogenase or 4-aminobutyrate transaminase; a 4-hydroxybutyrate dehydrogenase; a 4-hydroxybutyrate reductase; and a 1,4-butanediol dehydrogenase;

(xxvi) a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase;

(xxvii) a glutamate dehydrogenase or glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a phosphotrans-4-hydroxybutyrylase; and a 4-hydroxybutyryl-CoA reductase (alcohol forming);

(xxviii) a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyrate kinase; a 4-hydroxybutyryl-phosphate reductase; and a 1,4-butanediol dehydrogenase;

(xxix) a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; a 4-hydroxybutyryl-CoA reductase (aldehyde forming); and a 1,4-butanediol dehydrogenase;

(xxx) a glutamate dehydrogenase or a glutamate transaminase; a glutamate decarboxylase; a 4-aminobutyrate dehydrogenase or a 4-aminobutyrate transaminase; a 4-hydroxybutyrate dehydrogenase; a 4-hydroxybutyryl-CoA transferase, a 4-hydroxybutyryl-CoA hydrolase or a 4-hydroxybutyryl-CoA synthetase; and a 4-hydroxybutyryl-CoA reductase (alcohol forming);

(xxxi) an alpha-ketoglutarate reductase; a 5-hydroxy-2-oxopentanoate dehydrogenase; a 5-hydroxy-2-oxopentanoate dehydrogenase (decarboxylation); a 4-hydroxybutyryl-CoA reductase (aldehyde forming); and a 1,4-butanediol dehydrogenase;

(xxxii) an alpha-ketoglutarate reductase; a 5-hydroxy-2-oxopentanoate dehydrogenase; a 5-hydroxy-2-oxopentanoate dehydrogenase (decarboxylation); and a 4-hydroxybutyryl-CoA reductase (alcohol forming); and (xxxiii) an alpha-ketoglutarate reductase; a 5-hydroxy-2-oxopentanoate dehydrogenase; a 5-hydroxy-2-oxopentanoate decarboxylase; and a 1,4-butanediol dehydrogenase;

(xxxiv) a succinyl-CoA reductase (aldehyde forming); a 4-hydroxybutyrate dehydrogenase; a 4-hydroxybutyrate reductase; and 1,4-butanediol dehydrogenase;

(xxxv) a succinyl-CoA reductase (aldehyde forming); a 4-hydroxybutyrate dehydrogenase; a 4-hydroxybutyrate kinase; a phosphotrans-4-hydroxybutyrylase; a 4-hydroxybutyryl-CoA reductase (aldehyde forming); and a 1,4-butanediol dehydrogenase;

(xxxvi) a succinyl-CoA reductase (aldehyde forming); a 4-hydroxybutyrate dehydrogenase; a 4-hydroxybutyrate kinase; a phosphotrans-4-hydroxybutyrylase and 4-hydroxybutyryl-CoA reductase (alcohol forming);

(xxxvii) a succinyl-CoA reductase (aldehyde forming); a 4-hydroxybutyrate dehydrogenase; a 4-hydroxybutyrate kinase; a 4-hydroxybutyryl-phosphate reductase; and a 1,4-butanediol dehydrogenase;

(xxxviii) a succinyl-CoA reductase (aldehyde forming); a 4-hydroxybutyrate dehydrogenase; a 4-hydroxybutyryl-CoA transferase, a 4-hydroxybutyryl-CoA hydrolase or 4-hydroxybutyryl-CoA synthetase; a 4-hydroxybutyryl-CoA reductase (aldehyde forming); and a 1,4-butanediol dehydrogenase; and (xxxix) a succinyl-CoA reductase (aldehyde forming); a 4-hydroxybutyrate dehydrogenase; a 4-hydroxybutyryl-CoA transferase, a 4-hydroxybutyryl-CoA hydrolase or a 4-hydroxybutyryl-CoA synthetase; and 4-hydroxybutyryl-CoA reductase (alcohol forming).

3. The method of claim 1, wherein the 4-hydroxybutyryl-CoA pathway comprises a pathway selected from the group consisting of:

(i) a succinyl-CoA transferase, a succinyl-CoA hydrolase or a succinyl-CoA synthetase; a succinyl-CoA reductase (aldehyde forming); a 4-hydroxybutyrate dehydrogenase; a 4-hydroxybutyrate kinase; and a phosphotrans-4-hydroxybutyrylase;

(ii) a succinyl-CoA transferase, a succinyl-CoA hydrolase or a succinyl-CoA synthetase; a succinyl-CoA reductase (aldehyde forming); a 4-hydroxybutyrate dehydrogenase; and a 4-hydroxybutyryl-CoA transferase, a 4-hydroxybutyryl-CoA hydrolase or a 4-hydroxybutyryl-CoA synthetase;

(iii) a succinyl-CoA transferase, a succinyl-CoA hydrolase or a succinyl-CoA synthetase; a succinyl-CoA reductase (alcohol forming); a 4-hydroxybutyrate kinase; and a phosphotrans-4-hydroxybutyrylase;

(iv) a succinyl-CoA transferase, a succinyl-CoA hydrolase or a succinyl-CoA synthetase; a succinyl-CoA reductase (alcohol forming); and a 4-hydroxybutyryl-CoA transferase, a 4-hydroxybutyryl-CoA hydrolase or a 4-hydroxybutyryl-CoA synthetase;

(v) a succinate reductase; a 4-hydroxybutyrate dehydrogenase; a 4-hydroxybutyrate kinase and a phosphotrans-4-hydroxybutyrylase;

(vi) a succinate reductase; a 4-hydroxybutyrate dehydrogenase; and a 4-hydroxybutyryl-CoA transferase, a 4-hydroxybutyryl-CoA hydrolase or a 4-hydroxybutyryl-CoA synthetase;

(vii) an alpha-ketoglutarate decarboxylase; a 4-hydroxybutyrate dehydrogenase; a 4-hydroxybutyrate kinase; and a phosphotrans-4-hydroxybutyrylase;

(viii) an alpha-ketoglutarate decarboxylase; a 4-hydroxybutyrate dehydrogenase; and a 4-hydroxybutyryl-CoA transferase, a 4-hydroxybutyryl-CoA hydrolase or a 4-hydroxybutyryl-CoA synthetase;

(ix) a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; a 4-hydroxybutyrate kinase; and a phosphotrans-4-hydroxybutyrylase;

(x) a glutamate dehydrogenase or a glutamate transaminase; a glutamate decarboxylase; an 4-aminobutyrate dehydrogenase or an 4-aminobutyrate transaminase; a 4-hydroxybutyrate dehydrogenase; and a 4-hydroxybutyryl-CoA transferase, a 4-hydroxybutyryl-CoA hydrolase or a 4-hydroxybutyryl-CoA synthetase;

(xi) an alpha-ketoglutarate reductase; a 5-hydroxy-2-oxopentanoate dehydrogenase and a 5-hydroxy-2-oxopentanoate dehydrogenase (decarboxylation);

(xii) a succinyl-CoA reductase (aldehyde forming); a 4-hydroxybutyrate dehydrogenase; and a phosphotrans-4-hydroxybutyrylase; and (xiii) a succinyl-CoA reductase (aldehyde forming); a 4-hydroxybutyrate dehydrogenase; and a 4-hydroxybutyryl-CoA transferase, a 4-hydroxybutyryl-CoA hydrolase or 4-hydroxybutyryl-CoA synthetase.

4. The method of claim 1, wherein said culturing is performed under substantially anaerobic culture conditions.

5. The method of claim 1, wherein said exogenous nucleic acid is a heterologous nucleic acid.

6. The method of claim 1, wherein said microbial organism comprises one, two, three, four, five, six, seven or eight exogenous nucleic acids each encoding a 14-BDO or 4-hydroxybutyryl-CoA pathway enzyme.

7. A method of making 1,4-butanediol (14-BDO), comprising:
a) performing the culturing step of claim 1; and
b) separating the 14-BDO from other components in the culture.

8. The method of claim 7, wherein the separating comprises extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

* * * * *